(12) United States Patent
Lee et al.

(10) Patent No.: US 7,109,339 B2
(45) Date of Patent: Sep. 19, 2006

(54) SUBSTITUTED TRICYCLIC GAMMA-CARBOLINES AS SEROTONIN RECEPTOR AGONISTS AND ANTAGONISTS

(75) Inventors: Taekyu Lee, Doylestown, PA (US); Wenting Chen, Langhorne, PA (US); Wei Deng, Lexington, MA (US); Albert J. Robichaud, Ringoes, NJ (US); Ruth R. Wexler, Belle Mead, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 133 days.

(21) Appl. No.: 10/743,449

(22) Filed: Dec. 19, 2003

(65) Prior Publication Data

US 2004/0180875 A1    Sep. 16, 2004

Related U.S. Application Data

(60) Provisional application No. 60/434,760, filed on Dec. 19, 2002.

(51) Int. Cl.
*C07D 417/00*    (2006.01)
*C07D 471/04*    (2006.01)
(52) U.S. Cl. .......................... 546/86; 344/60; 344/128
(58) Field of Classification Search ................ 546/86; 544/60, 128
See application file for complete search history.

(56) References Cited

U.S. PATENT DOCUMENTS

| | | | |
|---|---|---|---|
| 3,914,421 A | 10/1975 | Rajagopalan | |
| 4,013,652 A | 3/1977 | Rajagopalan | |
| 4,115,577 A | 9/1978 | Rajagopalan | |
| 4,183,936 A | 1/1980 | Rajagopalan | |
| 4,219,550 A | 8/1980 | Rajagopalan | |
| 4,238,607 A | 12/1980 | Rajagopalan | |
| 6,057,325 A * | 5/2000 | Kennis et al. | 514/259.2 |
| 6,548,493 B1 | 4/2003 | Robichaud et al. | |
| 6,552,017 B1 | 4/2003 | Robichaud et al. | |
| 6,849,640 B1 * | 2/2005 | Ennis et al. | 514/292 |

FOREIGN PATENT DOCUMENTS

| | | |
|---|---|---|
| EP | 0 473 550 | 3/1992 |
| WO | WO 00/35922 | 6/2000 |
| WO | WO 00/77001 | 12/2000 |
| WO | WO 00/77002 | 12/2000 |
| WO | WO 00/77010 | 12/2000 |
| WO | WO 02/059129 | 8/2002 |
| WO | WO 03/014118 | 2/2003 |

OTHER PUBLICATIONS

Chojnacka-Wójcik, E. et al., "Involvement of 5-$HT_{2C}$ Receptors in the m-CPP-Induced Antinociception in Mice", Pol. J. Pharmacol., vol. 46, pp. 423-428 (1994).

Cryan, J.F. et al., "Antidepressant-Like Behavorial Effects Mediated by 5-Hydroxytrepamine$_{2C}$ Receptors", The Journal of Pharmacology and Experimental Therapeutics, vol. 295, No. 3, pp. 1120-1126 (2000).

Grottick, A.J. et al., "Activation of 5-$HT_{2C}$ receptors reduces the locomotor and rewarding effects of nicotine", Psychopharmacology, vol. 157, pp. 292-298 (2001).

Grottick, A.J. et al., "Studies to Investigate the Role of 5-$HT_{2C}$ Receptors on Cocaine- and Food- Maintained Behavior", The Journal of Pharmacology and Experimental Therapeutics, vol. 293, No. 3, pp. 1183-1191 (200).

Hoffman, B.J. et al., "Distribution of serotonin 5-$HT_{1C}$ receptor mRNA in adult rat brain", FEBS Letters, vol. 247, No. 2, pp. 453-462 (1989).

Hoyer, D. et al., "VII. International Union of Pharmacology Classification of Receptors for 5-Hydroxytryptamine (Serotonin)", Pharmacological Reviews, vol. 46, No. 2, pp. 157-203 (1994).

Kinbara, K. et al., "Chiral discrimination upon crystallization of the disastereomeric salts of 1- arylethylamines with mandelic acid or *p*-methoxymandelic acid: interpretation of the resolution efficiencies on the basis of the crystal structures", J. Chem. Soc., Perkin Trans. 2, pp. 2615-2622 (1996).

(Continued)

Primary Examiner—D. Margaret Seaman
(74) Attorney, Agent, or Firm—Sammy G. Duncan, Jr.

(57) ABSTRACT

The present invention is directed to novel compounds represented by structural Formula (I):

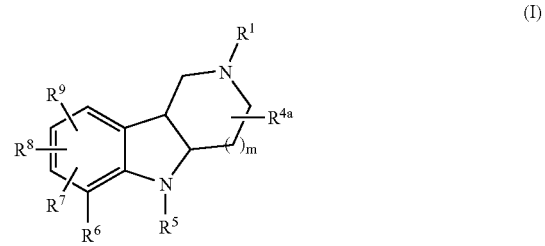

(I)

or a pharmaceutically acceptable salt thereof, wherein $R^1$, $R^{4a}$, $R^5$, $R^6$, $R^7$, $R^8$, $R^9$, and m, are defined herein. The invention is also concerned with pharmaceutical formulations comprising these novel compounds as active ingredients and the use of the novel compounds and their formulations in the treatment of certain central nervous system disorders. The compounds of this invention are serotonin receptor modulators, in particular 5$HT_{2C}$ receptor agonists and antagonists, and are useful in the control or prevention of central nervous system disorders including obesity, anorexia, bulemia, depression, anxiety, psychosis, schizophrenia, migraine, addictive behavior, obsessive-compulsive disorder, and sexual disorders.

5 Claims, No Drawings

OTHER PUBLICATIONS

Mazzola-Pomietto, P. et al., "Evidance that *m*-chlorophenylpiperazine-induced hyperthermia in rats is mediated by stimulation of 5-HT$_{2C}$ receptors", Psychopharmacology, vol. 123, pp. 333-339 (1996).

Millan, M.J. et al., "5-HT$_{2C}$ receptors mediate penile erections in rats: actions of novel and selective agonists and antagonists", European Journal of Pharmacology, vol. 325, pp. 9-12 (1997).

Nonogaki, K. et al., "Leptin-independent hyperphagia and type 2 diabetes in mice with a mutated serotonin 5-HT$_{2C}$ receptor gene", Nature Medicine, vol. 4, No. 10, pp. 1152-1156 (1998).

Rittenhouse, P.A. et al., "Evidence that ACTH Secretion Is Regulated by Serotonin$_{2A/2C}$ (5-HT$_{2A/2C}$) Receptors", The Journal of Pharmacology and Experimental Therapeutics, vol. 271, No. 3, pp. 1647-1655 (1994).

Sharpley, A.L. et al., "Slow Wave Sleep in Humans: Role of 5-HT$_{2A}$ and 5-HT$_{2C}$ Receptors", Neuropharmacology, vol. 33, No. 3/4, pp. 467-471 (1994).

Sundberg, R.J., Indoles, Academic Press Limited, publ., p. v (table of contents) (1996).

Tomori, H. et al., "Facile Optical Resolution of a Dibenzopyrazinoazepine Derivative and the Nature of Molecular Recognition of Amines by Chiral 2,3-Di-O-(arylcarbonyl)tartaric Acids", Bull. Chem. Soc. Jpn., vol. 69, No. 12, pp. 3581-3590 (1996).

Vickers, S.P. et al., "Comparative effects of continuous infusion of mCPP, Ro 60-0175 and d-fenfluramine on food intake, water intake, body weight and locomotor activity in rats", British Journal of Pharmacology, vol. 130, pp. 1305-1314 (2000).

Vickers, S.P. et al., "Evidence that hypophagia induced by d-fenfluramine and d-nonfenfluramine in the rat is mediated by 5-HT$_{2C}$ receptors", Neuropharmacology, vol. 41, pp. 200-209 (2001).

Vickers, S.P. et al., "Reduced satiating effect of *d*-fenlurnmine in serotonin 5-HT$_{2C}$ receptor mutant mice", Psychopharmacology, vol. 143, pp. 309-314 (1999).

DiMatteo, V., et al., "Role of 5-HT$_{2C}$ receptors in the control of central dopamine function", Trends in Pharmacological Sciences, vol. 22, No. 5, pp. 229-232, May 2001.

Database Caplus on STN, AN 1989:497120, Marko et al. "Synthesis of tritium-labeled stobadin, a new cardioprotective agent", abstract, Journal of Labeled Compounds and Radiopharmaceuticals, 1989, 27(1), 35-43.

Database Caplus on STN, AN 1975:508140, Barkov et al. "Relation between the chemical structure and pharmacological activity of carboline derivatives", abstract, Khimiko-Farmatsevticheskii Zhurnal (1975), 9(4), 6-10.

\* cited by examiner

SUBSTITUTED TRICYCLIC GAMMA-CARBOLINES AS SEROTONIN RECEPTOR AGONISTS AND ANTAGONISTS

RELATED APPLICATIONS

This application claims priority benefit under Title 35 § 119(e) of U.S. provisional Application No. 60/434,760, filed Dec. 19, 2002, the contents of which are herein incorporated by reference.

FIELD OF THE INVENTION

The present invention is directed to novel compounds represented by structural Formula (I):

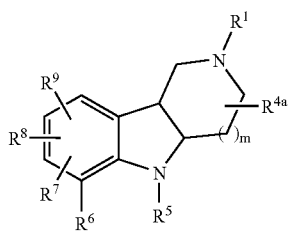

(I)

or a pharmaceutically acceptable salt thereof, wherein $R^1$, $R^{4a}$, $R^5$, $R^6$, $R^7$, $R^8$, $R^9$, and m, are defined herein. The invention is also concerned with pharmaceutical formulations comprising these novel compounds as active ingredients and the use of the novel compounds and their formulations in the treatment of certain central nervous system disorders. The compounds of this invention are serotonin receptor modulators, in particular $5HT_{2C}$ receptor agonists and antagonists, and are useful in the control or prevention of central nervous system disorders including obesity, anorexia, bulimia, depression, anxiety, psychosis, schizophrenia, migraine, addictive behavior, obsessive-compulsive disorder, and sexual disorders.

BACKGROUND OF THE INVENTION

The neurotransmitter/hormone serotonin (5-hydroxytryptamine, 5-HT) regulates many physiological processes via a group of at least 14 distinct receptors that are organized into 7 subfamilies (Hoyer, D., et al., Pharmacol. Rev., 46, 1994). The $5\text{-}HT_2$ subfamily is composed of the $5\text{-}HT_{2A}$, $5\text{-}HT_{2B}$, and $5\text{-}HT_{2C}$ receptors as determined by gene homology and pharmacological properties. There exists a substantial correlation for the relationship between $5\text{-}HT_2$ receptor modulation and a variety of diseases and therapies. Prior to the early 1990's the $5\text{-}HT_{2C}$ and $5\text{-}HT_{2A}$ receptors were referred to as $5\text{-}HT_{1C}$ and $5\text{-}HT_2$, respectively.

The direct or indirect agonism or antagonism of $5\text{-}HT_2$ receptors, either selectively or non-selectively, has been associated with the treatment of various central nervous system (CNS) disorders including obesity, depression, schizophrenia and bi-polar disorders. In the recent past the contribution of serotonergic activity to the mode of action of anti-obesity drugs has been well documented. Compounds that increase the overall basal tone of serotonin in the CNS have been successfully developed as anorectic drugs. The serotonin releasing agents, such as fenfluramine, function by increasing the amount of serotonin present in the nerve synapse. These breakthrough treatments, however, are not without side effects. Due to the mechanism of action of serotonin releasing agents, they effect the activity of a number of serotonin receptor subtypes in a wide variety of organs including those not associated with the desired mechanism of action. This non-specific modulation of the serotonin family of receptors most likely plays a significant role in the side effect profile. In addition, these compounds or their metabolites often have a high affinity for a number of the serotonin receptors as well as a multitude of other monoamine neurotransmitters and nuisance receptors. Removing some of the receptor cross reactivity would allow for the examination and possible development of potent therapeutic ligands with an improved side effect profile.

The $5\text{-}HT_{2C}$ receptor is a G-protein coupled receptor. It is almost exclusively expressed in the central nervous system including the hypothalamus, hippocampus, amygdala, nucleus of the solitary tract, spinal cord, cortex, olfactory bulb, ventral tegmental area (VTA), nucleus accumbens and choroid plexus (Hoffman, B. and Mezey, E., FEBS Lett., 247, 1989). There is ample evidence to support the role of selective $5\text{-}HT_{2C}$ receptor ligands in a number of disease therapies. $5\text{-}HT_{2C}$ knockout mice develop a late stage obesity syndrome that is not reversed by fenfluramine or other direct acting $5\text{-}HT_{2C}$ agonists such as mCPP (Nonogaki, K., et al., Nature Med., 4, 1998; Vickers, S., et. al., Psychopharmacology, 143, 1999). Administration of selective $5\text{-}HT_{2C}$ agonists to rats causes a reduction in food intake and corresponding reduction in body weight (Vickers, S., et al., Br. J. Pharmacol., 130, 2000) and these responses can be blocked by administration of selective $5\text{-}HT_{2C}$ antagonists (Vicker, S., et al., Neuropharmacol., 41, 2001). $5\text{-}HT_{2C}$ receptor modulation in the hypothalamus can also influence thermoregulation (Mazzola-Pomietto, P., et al., Psychopharmacology, 123, 1996), sleep (Sharpley, A., et al., Neuropharmacology, 33, 1994), sexual behavior and neuroendocrine function (Rittenhouse, P. et al., J. Pharmacol. Exp. Ther., 271, 1994). Activation of $5\text{-}HT_{2C}$ receptors in the VTA modulates the activity of dopaminergic neurons that are involved in aspects of depression (Di Matteo, V. et al., Trends Pharmacol. Sci., 22, 2001) and $5\text{-}HT_{2C}$ receptor agonists such as WAY 161503, RO 60-0175 and RO 60-0332 are active in rodent models of depression (Cryan, J. and Lucki, I., J. Pharmacol. Exp. Ther., 295, 2000). $5\text{-}HT_{2C}$ agonists have been reported to reduce the rewarding effects of nicotine administration in rats (Grottick, A., et al., Psychopharmacology, 157, 2001) and influences rodent responses to cocaine administration (Grottick, A., et al., J. Pharmacol. Exp. Ther., 295, 2000). Modulation of $5\text{-}HT_{2C}$ receptors in the spinal cord can influence pain perception (Chojnacka-Wojcik, E., et al., Pol. J. Pharmacol., 46, 1994). There is also data indicating that the $5\text{-}HT_{2C}$ receptor agonists mCPP and RO 60-0175 mediate penile erections in rats (Millan, M., et al., Eur J. Pharmacol. 325, 1997).

Compounds reported to bind to and activate $5\text{-}HT_{2C}$ receptors are disclosed in the following documents. U.S. Pat. Nos. 3,914,421; 4,013,652; 4,115,577; 4,183,936; and 4,238,607 disclose pyridopyrrolobenz-heterocycles of formula:

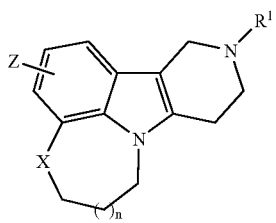

where X is O, S, S(=O), or SO₂; n is 0 or 1; $R^1$ is various carbon substituents, and Z is a monosubstituent of H, methyl, or chloro.

U.S. Pat. No. 4,219,550 discloses pyridopyrrolo-benzheterocycles of formula:

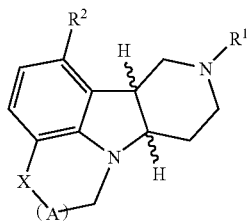

where X is O or S; $R^1$ is $C_{1-4}$ alkyl or cyclopropyl; $R^2$ is H, CH₃, OCH₃, Cl, Br, F, or CF₃; and (A) is —CH₂—, —CH(CH₃)—, or —CH₂CH₂—.

European Patent Application EP 473,550 A1 discloses indolonaphthyridines of formula:

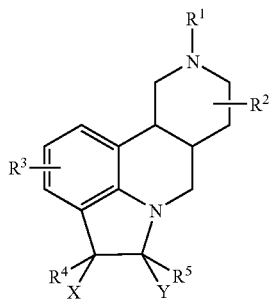

wherein X and Y are H or a simple ring, $R^1$, is H, alkyl, alkylcarbonylalkyl, arylcarbonylalkyl, aralkyl, or a mono or disubstituted carbamoylalkyl; and $R^3$, $R^4$, and $R^5$ are H, halogen, alkyl, alkoxy, alkylthio or trifluoromethyl.

PCT International Patent Application WO 00/35922 discloses tetrahydro-1H-pyrazino(1,2-A-quinoxalin-5(6H)one derivatives of formula:

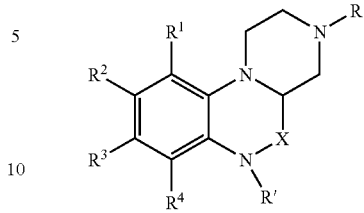

as being 5HT$_{2C}$ agonists; wherein X is CR⁵R⁶ or carbonyl; R is H or alkyl; R' is H, alkyl, acyl, or aroyl; and $R^1$, $R^2$, $R^3$, and $R^4$ are independently, H, alkyl, alkoxy, halogen, trifluoroalkyl, cyano, alkylsulfonamide, alkyl amide, amino, alkylamino, dialkylamino, trifluoroalkoxy, acyl, or aryl.

U.S. Pat. Nos. 6,552,017, 6,548,493 PCT International Patent Application WO 00/77001, WO 00/77002, and WO 00/77010 discloses substituted heterocycle fused gamma-carbolines of formula:

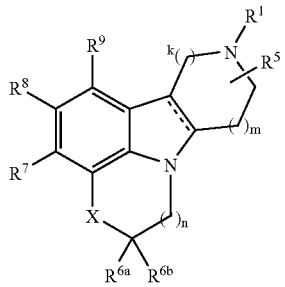

wherein X is CHR, C(=O), O, S, S(=O), SO₂, NR, C(=O)NR, or NRC(=O); n is 0, 1 or 2; m is 0, 1, 2 or 3; k is 1 or 2: $R^1$ is H, alkyl, alkenyl, alkynyl, cycloalkyl, acyl, or aryl; $R^5$ is H or alkyl, $R^{6a}$ and $R^{6b}$ are independently H, OH, alkyl, alkenyl, alkynyl, cycloalkyl, alkoxy, trifluoroalkyl, alkylamino, trifluoroalkoxy, acyl, or aryl; and $R^7$, $R^8$, and $R^9$ are independently, H, alkyl, alkenyl, alkynyl, cycloalkyl, alkoxy, halogen, trifluoroalkyl, cyano, alkylsulfonamide, alkyl amide, amino, alkylamino, dialkylamino, trifluoroalkoxy, acyl, aryl, or heterocyclic ring.

Patent Application WO 02/59129 discloses substituted pyridoindoles of formula:

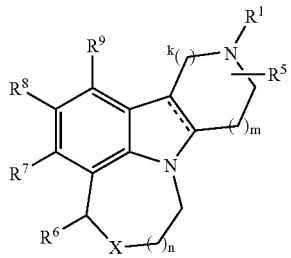

wherein X is O, S, S(=O), SO₂, or NR; n is 1 or 2; k is 1 or 2: R¹ is H, alkyl, alkenyl, alkynyl, cycloalkyl, acyl, or aryl; R⁵ and R⁶ are independently H, or alkyl: and R⁷, R⁸, and R⁹ are independently, H, alkyl, alkenyl, alkynyl, cycloalkyl, alkoxy, halogen, trifluoroalkyl, cyano, alkylsulfonamide, alkyl amide, amino, alkylamino, dialkylamino, trifluoroalkoxy, acyl, aryl, or heterocyclic ring.

PTC International Patent Application WO 03/14118 discloses 1H-pyrido[4,3-b]indoles of formula:

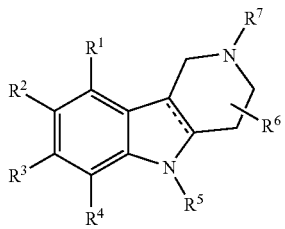

wherein $R^1$, $R^2$, $R^3$ and $R^4$ are independently, H, halo, $CF_3$, $OCF_3$, CN, $NO_2$, alkyl, alkenyl, alkynyl, cycloalkyl, cycloalkenyl, alkoxy, thioalkyl, C(=O)Ar, aryl, or alkyleneAr, provided that at least one of $R^1$, $R^2$, $R^3$ or $R^4$ is aryl; and $R^5$, $R^6$ and $R^7$ are independently H, or various carbon substituents.

None of the above references suggest or disclose the compounds of the present invention. There remains a need to discover new compounds useful as serotonin receptor modulators, i.e. selective agonists and antagonists, which are useful in the control or prevention of central nervous system disorders. As such, the present invention discloses novel compounds which are useful as serotonin agonists and antagonists, and provide good in vitro potency.

SUMMARY OF THE INVENTION

One object of the present invention is to provide novel compounds which are useful as agonists of the 5-HT2C receptor, or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating central nervous system disorders including obesity, anorexia, bulemia, depression, anxiety, psychosis, schizophrenia, migraine, addictive behavior, obsessive-compulsive disorder, and sexual disorders comprising administering to a host in need of such treatment a therapeutically effective amount of at least one of the compounds of the present invention or a pharmaceutically acceptable salt or prodrug form thereof. More specifically, the present invention provides a method for treating obesity.

These and other objects, which will become apparent during the following detailed description, have been achieved by the inventors' discovery that compounds of Formula (I):

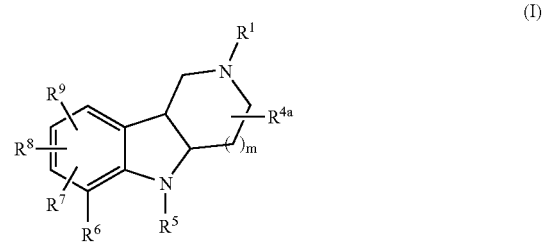

or pharmaceutically acceptable salt or prodrug forms thereof, wherein $R^1$, $R^{4a}$, $R^5$, $R^6$, $R^7$, $R^8$, $R^9$ and m are defined below, are effective agonists of the 5-HT2C receptor.

DETAILED DESCRIPTION OF THE EMBODIMENTS

Thus, in a first embodiment, the present invention provides a novel compound of Formula (I):

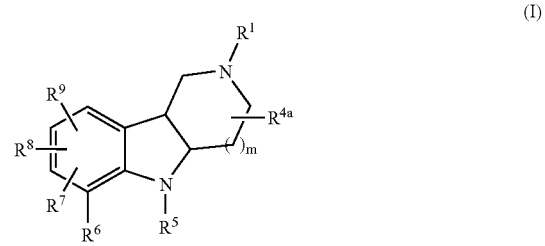

or a stereoisomer or a pharmaceutically acceptable salt form thereof, wherein:

$R^1$ is selected from H, C(=O)$R^{2a}$, C(=O)O$R^{2a}$, S(=O)$R^{2a}$, S(=O)$_2R^{2a}$, $C_{3-7}$ cycloalkyl, $C_{1-4}$ alkyl substituted with 0–3 $R^2$, $C_{2-4}$ alkenyl substituted with 0–2 $R^2$, $C_{2-4}$ alkynyl substituted with 0–2 $R^2$, aryl substituted with 0–5 $R^{42}$;

$C_{3-10}$ carbocyclic residue substituted with 0–3 $R^{41}$, and

5–6 membered heterocyclic ring system containing from 1–4 heteroatoms selected from the group consisting of N, O, and S substituted with 0–3 $R^{41}$;

$R^2$, at each occurrence, is independently selected from halo, $C_{1-3}$ haloalkyl, $C_{1-4}$ alkoxy, $C_{1-4}$ alkyl, $C_{2-4}$ alkenyl, $C_{2-4}$ alkynyl, $C_{3-6}$ cycloalkyl, aryl substituted with 0–5 $R^{42}$;

$C_{3-10}$ carbocyclic residue substituted with 0–3 $R^{41}$, and

5–6 membered heterocyclic ring system containing from 1–4 heteroatoms selected from the group consisting of N, O, and S substituted with 0–3 $R^{41}$;

$R^{2a}$ is H, $C_{1-4}$ alkyl, (aryl)$C_{1-4}$ alkyl-, or ($C_{3-6}$ cycloalkyl) $C_{1-4}$ alkyl-;

$R^{4a}$ is H or $C_{1-4}$ alkyl;

$R^5$ is H, $C_{1-4}$ alkyl substituted with 0–2 $R^{20}$, —C(=O)($C_{1-4}$ alkyl), —C(=O)O($C_{1-4}$ alkyl), or $C_{1-4}$ haloalkyl;

$R^6$ is selected from
halo, —CF₃, —OCF₃, —CN, —NO₂, —OCH₃, —SCH₃, —CF₂CF₃, —O—$R^{11}$, —OCF₂CF₃, —OCF₂H, —OCF₂CH₃, —S—$R^{11}$, —S(=O)—$R^{11}$, —S(=O)₂—$R^{11}$, —S(=O)—$NR^{10}$—$R^{11}$, —S(=O)₂—$NR^{10}$—$R^{11}$, —$NR^{10}$—$R^{11}$, —CH₂O—

$R^{11}$, —$CH_2S$—$R^{11}$, —$CH_2S(=O)$—$R^{11}$, —$CH_2S(=O)_2$-$R^{11}$, —$CH_2NR^{10}$—$R^{11}$, —$C(=O)NR^{10}$—$R^{11}$ $C_{1-4}$ haloalkyl, ($C_{1-14}$ haloalkyl)oxy; $C_{1-4}$ alkyl substituted with 0–2 $R^{20}$, $C_{2-4}$ alkenyl substituted with 0–2 $R^{20}$, $C_{2-4}$ alkynyl substituted with 0–1 $R^{20}$, and $C_{3-6}$ carbocyclic residue substituted with 0–3 $R^{21}$, $R^7$ and $R^9$ are independently selected from
H, F, Cl, Br, —$CF_3$, —$OCF_3$, —OH, —CN, —$NO_2$, —$CF_2CF_3$, $C_{1-4}$ alkyl, $C_{2-4}$ alkenyl, $C_{2-4}$ alkynyl, $C_{1-4}$ haloalkyl, $C_{1-4}$ alkoxy, and ($C_{1-4}$ haloalkyl)oxy;

$R^8$ is selected from
halo, —$CF_3$, —$OCF_3$, —OH, —CN, —$NO_2$, —$OCH_3$, —$SCH_3$, —$CF_2CF_3$, —$OR^{12}$, —$SR^{12}$, —$NR^{12}R^{13}$, —C(O)H, —$C(O)R^{12}$, —$C(O)NR^{12}R^{13}$, —$NR^{14}C(O)R^{12}$, —$C(O)OR^{12}$, —$OC(O)R^{12}$, —$OC(O)OR^{12}$, —$S(O)R^{12}$, —$S(O)_2R^{12}$, —$S(O)NR^{12}R^{13}$, —$S(O)_2NR^{12}R^{13}$, —$NR^{14}S(O)R^{12}$, —$NR^{14}S(O)_2R^{12}$, —$NR^{12}C(O)R^{15}$, —$NR^{12}C(O)OR^{15}$, —$NR^{12}S(O)_2R^{15}$, —$NR^{12}C(O)NHR^{15}$; $C_{1-6}$ alkyl substituted with 0–2 $R^{8a}$, $C_{2-6}$ alkenyl substituted with 0–2 $R^{8a}$, $C_{2-6}$ alkynyl substituted with 0–2 $R^{8a}$, $C_{3-6}$ cycloalkyl substituted with 0–2 $R^{8a}$, $C_{3-10}$ carbocyclic residue substituted with 0–3 $R^{33}$;

$R^{8a}$, at each occurrence, is independently selected from
halo, —$CF_3$, —$OCF_3$, —OH, —CN, —$NO_2$, —$CF_2CF_3$, methyl, ethyl, n-propyl, i-propyl, n-butyl, i-butyl, s-butyl, t-butyl, —$OR^{12}$, —$SR^{12}$, —$NR^{12}R^{13}$, —C(O)H, —$C(O)R^{12}$, —$C(O)NR^{12}R^{13}$, —$NR^{14}C(O)R^{12}$, —$C(O)OR^{12}$, —$OC(O)R^{12}$, —$OC(O)OR^{12}$, —$S(O)R^{12}$, —$S(O)_2R^{12}$, —$S(O)NR^{12}R^{13}$, —$S(O)_2NR^{12}R^{13}$, —$NR^{14}S(O)R^{12}$, —$NR^{14}S(O)_2R^{12}$, —$NR^{12}C(O)R^{15}$, —$NR^{12}C(O)OR^{15}$, —$NR^{12}S(O)_2R^{15}$, —$NR^{12}C(O)NHR^{15}$;
phenyl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{33}$;

$R^{10}$ is H or $C_{1-4}$ alkyl;

$R^{11}$ is selected from
$C_{1-6}$ alkyl substituted with 0–2 $R^{20}$, $C_{2-6}$ alkenyl substituted with 0–2 $R^{20}$, $C_{2-6}$ alkynyl substituted with 0–1 $R^{20}$, $C_{3-10}$ carbocyclic residue substituted with 0–3 $R^{21}$, aryl substituted with 0–5 $R^{23}$, and
5–10 membered heterocyclic ring system containing from 1–4 heteroatoms selected from the group consisting of N, O, and S substituted with 0–3 $R^{21}$;

alternatively, $R^{10}$ and $R^{11}$ join to form a 5- or 6-membered ring optionally substituted with —O— or —$N(R^{14})$—;

alternatively, $R^{10}$ and $R^{11}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{12}$ is selected from H,
$C_{1-6}$ alkyl substituted with 0–2 $R^{12a}$, $C_{2-6}$ alkenyl substituted with 0–2 $R^{12a}$, $C_{2-6}$ alkynyl substituted with 0–2 $R^{12a}$, $C_{3-6}$ cycloalkyl substituted with 0–3 $R^{33}$, aryl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{33}$;

$R^{12a}$, at each occurrence, is independently selected from
H, halo, —OH, —CN, —$NO_2$, —$CO_2H$, —$SO_2R^{45}$, —$SOR^{45}$, —$SR^{45}$, —$NR^{46}SO_2R^{45}$, —$NR^{46}COR^{45}$, —$NR^{46}R^{47}$, —$SO_2NR^{46}R^{47}$, —$CONR^{46}R^{47}$, —$OR^{45}$, =O, $C_{1-4}$ alkyl, $C_{2-6}$ alkenyl, $C_{2-6}$ alkynyl, phenyl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{33}$;

$R^{13}$, at each occurrence, is independently selected from H, $C_{14}$ alkyl, $C_{24}$ alkenyl, and $C_{24}$ alkynyl;

alternatively, $R^{12}$ and $R^{13}$ join to form a 5- or 6-membered ring optionally substituted with —O— or —$N(R^{14})$—;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H and $C_{1-4}$ alkyl;

$R^{15}$, at each occurrence, is independently selected from H, $C_{1-4}$ alkyl, $C_{2-4}$ alkenyl, and $C_{2-4}$ alkynyl;

$R^{16}$, at each occurrence, is independently selected from
H, OH, halo, CN, $NO_2$, $CF_3$, $SO_2R^{45}$, $NR^{46}R^{47}$, —C(=O)H, $C_{1-4}$ alkyl, $C_{2-4}$ alkenyl, $C_{2-4}$ alkynyl, $C_{1-4}$ haloalkyl, $C_{1-3}$ haloalkyl-oxy-, and $C_{1-3}$ alkyloxy-;

$R^{20}$ is selected from
H, halo, —OH, —$CF_3$, —CN, —$NO_2$, —$CO_2H$, —$SO_2R^{45}$, —$SOR^{45}$, —$SR^{45}$, —$NR^{46}SO_2R^{45}$, —$NR^{46}COR^{45}$, —$NR^{46}R^{47}$, $C_{1-4}$ alkyl, $C_{2-6}$ alkenyl, $C_{2-6}$ alkynyl, $C_{1-4}$ alkoxy, $C_{1-4}$ haloalkyl;
$C_{3-10}$ carbocyclic residue substituted with 0–3 $R^{21}$;
aryl substituted with 0–5 $R^{23}$; and
5–10 membered heterocyclic ring system containing from 1–4 heteroatoms selected from the group consisting of N, O, and S substituted with 0–3 $R^{21}$;

$R^{21}$, at each occurrence, is independently selected from
H, OH, halo, $CF_3$, $SO_2R^{45}$, $NR^{46}R^{47}$, CN, $NO_2$, =O, $C_{1-4}$ alkyl, $C_{1-4}$ alkoxy, and ($C_{1-4}$ haloalkyl)oxy;

$R^{23}$, at each occurrence, is independently selected from
H, OH, halo, $CF_3$, $SO_2R^{45}$, $NR^{46}R^{47}$, CN, $NO_2$, $C_{1-4}$ alkyl, $C_{1-4}$ alkoxy, and ($C_{1-4}$ haloalkyl)oxy;

$R^{33}$, at each occurrence, is independently selected from
H, OH, halo, —CN, —$NO_2$, —$CF_3$, —$OCF_3$, —$SO_2R^{35}$, —$S(=O)R^{35}$, —$SR^{35}$, —$NR^{36}R^{37}$, —$NHC(=O)R^{35}$, —$C(=O)NR^{36}R^{37}$, —C(=O)H, —$C(=O)R^{35}$, —$C(=O)OR^{35}$, —$OC(=O)R^{35}$, —$OR^{35}$, $C_{1-6}$ alkyl, $C_{2-6}$ alkenyl, $C_{2-6}$ alkynyl, $C_{1-4}$ haloalkyl, $C_{1-4}$ alkoxy, ($C_{1-4}$ haloalkyl)oxy, $C_{3-6}$ cycloalkyl, phenyl, aryl substituted with 0–2 $R^{34}$, $C_{1-6}$ alkyl substituted with $R^{34}$, and $C_{2-6}$ alkenyl substituted with $R^{34}$;

$R^{34}$, at each occurrence, is independently selected from
OH, $C_{1-14}$ alkoxy, —$SO_2R^{35}$, —$NR^{36}R^{37}$, $NR^{36}R^{37}C(=O)$—, and ($C_{1-4}$ alkyl)$CO_2$—;

$R^{35}$, at each occurrence, is independently selected from
$C_{1-4}$ alkyl, $C_{1-4}$ haloalkyl, $C_{3-6}$ cycloalkyl, ($C_{3-6}$ cycloalkyl)methyl-, and ($C_{3-6}$ cycloalkyl)ethyl-;

$R^{36}$, at each occurrence, is independently selected from H and $C_{1-4}$ alkyl;

$R^{37}$, at each occurrence, is independently selected from H, $C_{1-4}$ alkyl, —$C(=O)NH(C_{1-4}$ alkyl), —$SO_2(C_{1-4}$ alkyl), —$C(=O)O(C_{1-4}$ alkyl), —$C(=O)(C_{1-4}$ alkyl), and —C(=O)H;

$R^{41}$, at each occurrence, is independently selected from

H, $CF_3$, halo, OH, $CO_2H$, $SO_2R^{45}$, $NR^{46}R^{47}$, $NO_2$, CN, =O, $C_{1-4}$ alkyl, $C_{2-8}$ alkenyl, $C_{2-8}$ alkynyl, $C_{1-4}$ alkoxy, and $C_{1-4}$ haloalkyl;

$R^{42}$, at each occurrence, is independently selected from
H, $CF_3$, halo, OH, $CO_2H$, $SO_2R^{45}$, $SOR^{45}$, $SR^{45}$, $NR^{46}SO_2R^{45}$, $NR^{46}COR^{45}$, $NR^{46}R^{47}$, $NO_2$, CN, $C_{1-4}$ alkyl, $C_{2-6}$ alkenyl, $C_{2-6}$ alkynyl, $C_{1-4}$ alkoxy, and $C_{1-4}$ haloalkyl;

$R^{45}$ is $C_{1-4}$ alkyl;

$R^{46}$, at each occurrence, is independently selected from H and $C_{1-4}$ alkyl;

$R^{47}$, at each occurrence, is independently selected from H, $C_{1-4}$ alkyl, —C(=O)NH($C_{1-4}$ alkyl), —SO$_2$($C_{1-4}$ alkyl), —C(=O)O($C_{1-4}$ alkyl), —C(=O)($C_{1-4}$ alkyl), and —C(=O)H;

m is 1 or 2;

provided that when $R^{11}$ is $C_{1-6}$ alkyl, then $R^1$ is not a $C_{1-4}$ alkyl substituted by a) an unsubstituted 3H-pyrimidine-4-one moiety, b) a substituted 3H-pyrimidine-4-one moiety, c) an unsubstituted bicyclic derivative of 3H-pyrimidine-4-one, or d) a substituted bicyclic derivative of 3H-pyrimidine-4-one;

provided that when $R^6$ is —O—$R^{11}$ and $R^6$ is $C_{1-6}$ alkyl; then $R^{8a}$ is not a substituted or unsubstituted indole moiety.

In another embodiment, the present invention provides a novel compound of Formula (Ia) wherein:

(Ia)

or a stereoisomer or a pharmaceutically acceptable salt form thereof, wherein:

$R^1$ is selected from
H, $C_{1-3}$ haloalkyl, $C_{3-6}$ cycloalkyl, $C_{1-4}$ alkyl substituted with 0–2 $R^2$, $C_{2-4}$ alkenyl substituted with 0–2 $R^2$, and $C_{2-4}$ alkynyl substituted with 0–2 $R^2$;

$R^2$, at each occurrence, is independently selected from
halo, $C_{1-3}$ haloalkyl, $C_{1-4}$ alkoxy, $C_{1-4}$ alkyl, $C_{3-6}$ cycloalkyl, and phenyl substituted with 0–5 $R^{42}$;

$R^{4a}$ is H or $C_{1-4}$ alkyl;

$R^5$ is H, $C_{1-4}$ alkyl substituted with 0–2 $R^{20}$, or $C_{1-4}$ haloalkyl;

$R^6$ is selected from
halo, —$CF_3$, —$OCF_3$, —CN, —$NO_2$, —$OCH_3$, —$SCH_3$, —$CF_2CF_3$, —O—$R^{11}$, —$OCF_2CF_3$, —$OCF_2H$, —$OCF_2CH_3$, —S—$R^{11}$, —S(=O)—$R^{11}$, —S(=O)$_2$—$R^{11}$, —$NR^{10}$—$R^{11}$, —$CH_2O$—$R^{11}$, —$CH_2S$—$R^{11}$, $CH_2S$(=O)—$R^{11}$, $CH_2S$(=O)$_2$—$R^{11}$, —$CH_2NR^{10}$—$R^{11}$, $C_{1-4}$ haloalkyl, ($C_{1-4}$ haloalkyl)oxy;
$C_{1-4}$ alkyl substituted with 0–2 $R^{20}$, $C_{2-4}$ alkenyl substituted with 0–2 $R^{20}$, $C_{2-4}$ alkynyl substituted with 0–1 $R^{20}$, and $C_{3-6}$ carbocyclic residue substituted with 0–3 $R^{21}$;

$R^7$ and $R^9$ are independently selected from
H, F, Cl, Br, —$CF_3$, —$OCF_3$, —OH, —CN, —$NO_2$, —$CF_2CF_3$, $C_{1-4}$ alkyl, $C_{2-4}$ alkenyl, $C_{2-4}$ alkynyl, $C_{1-4}$ haloalkyl, $C_{1-4}$ alkoxy, and ($C_{1-4}$ haloalkyl)oxy;

$R^8$ is selected from
halo, —$CF_3$, —$OCF_3$, —OH, —CN, —$NO_2$, —$OCH_3$, —$SCH_3$, —$CF_2CF_3$, —$OR^{12}$, —$SR^{12}$, —$NR^{12}R^{13}$, —C(O)H, —C(O)$R^{12}$, —C(O)$NR^{12}R^{13}$, —$NR^{14}$C(O) $R^{12}$, —C(O)$OR^{12}$, —OC(O)$R^{12}$, —OC(O)$OR^{12}$, —S(O)$R^{12}$, —S(O)$_2R^{12}$, —S(O)$NR^{12}R^{13}$, —S(O)$_2NR^{12}R^{13}$, —$NR^{14}$S(O)$R^{12}$, —$NR^{14}$S(O)$_2R^{12}$, —$NR^{12}$C(O)$R^{15}$, —$NR^{12}$C(O)$OR^{15}$, —$NR^{12}$S(O)$_2R^{15}$, —$NR^{12}$C(O)$NHR^{15}$;
$C_{1-6}$ alkyl substituted with 0–2 $R^{8a}$, $C_{2-6}$ alkenyl substituted with 0–2 $R^{8a}$, $C_{2-6}$ alkynyl substituted with 0–2 $R^{8a}$, $C_{3-6}$ cycloalkyl substituted with 0–2 $R^{8a}$, and $C_{3-10}$ carbocyclic residue substituted with 0–3 $R^{33}$;

$R^{8a}$, at each occurrence, is independently selected from
halo, —$CF_3$, —$OCF_3$, —OH, —CN, —$NO_2$, —$CF_2CF_3$, methyl, ethyl, n-propyl, i-propyl, n-butyl, i-butyl, s-butyl, t-butyl, —$OR^{12}$, —$SR^{12}$, —$NR^{12}R^{13}$, —C(O)H, —C(O)$R^{12}$, —C(O)$NR^{12}R^{13}$, —$NR^{14}$C(O)$R^{12}$, —C(O)$OR^{12}$, —OC(O)$R^{12}$, —OC(O)$OR^{12}$, —S(O) $R^{12}$, —S(O)$_2R^{12}$, —S(O)$NR^{12}R^{13}$, —S(O)$_2NR^{12}R^{13}$, —$NR^{14}$S(O)$R^{12}$, —$NR^{14}$S(O)$_2R^{12}$, —$NR^{12}$C(O)$R^{15}$, —$NR^{12}$C(O)$OR^{15}$, —$NR^{12}$S(O)$_2R^{15}$, —$NR^{12}$C(O) $NHR^{15}$;
phenyl substituted with 0–5 $R^{33}$;
$C_{3-10}$ carbocyclic residue substituted with 0–3 $R^{33}$, and
5–6 membered heterocyclic ring system containing from 1–4 heteroatoms selected from the group consisting of N, O, and S substituted with 0–3 $R^{33}$;

$R^{10}$ is H or $C_{1-4}$ alkyl;

$R^{11}$ is selected from
$C_{1-6}$ alkyl substituted with 0–2 $R^{20}$, $C_{2-6}$ alkenyl substituted with 0–2 $R^{20}$, $C_{2-6}$ alkynyl substituted with 0–1 $R^{20}$, $C_{3-10}$ carbocyclic residue substituted with 0–3 $R^{21}$, aryl substituted with 0–5 $R^{23}$, and
5–10 membered heterocyclic ring system containing from 1–4 heteroatoms selected from the group consisting of N, O, and S substituted with 0–3 $R^{21}$;
alternatively, $R^{10}$ and $R^{11}$ join to form a 5- or 6-membered ring optionally substituted with —O— or —N($R^{14}$)—;
alternatively, $R^{10}$ and $R^{11}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{12}$ is selected from H,
$C_{1-6}$ alkyl substituted with 0–2 $R^{12a}$, $C_{2-6}$ alkenyl substituted with 0–2 $R^{12a}$, $C_{2-6}$ alkynyl substituted with 0–2 $R^{12a}$, $C_{3-6}$ cycloalkyl substituted with 0–3 $R^{33}$, aryl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{33}$;

$R^{12a}$, at each occurrence, is independently selected from
H, halo, —OH, —CN, —$NO_2$, —$CO_2H$, —$SO_2R^{45}$, —$SOR^{45}$, —$SR^{45}$, —$NR^{46}SO_2R^{45}$, —$NR^{46}COR^{45}$, —$NR^{46}R^{47}$, —$SO_2NR^{46}R^{47}$, —$CONR^{46}R^{47}$, —$OR^{45}$, =O, $C_{1-4}$ alkyl, $C_{2-6}$ alkenyl, $C_{2-6}$ alkynyl, phenyl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{33}$;

$R^{13}$, at each occurrence, is independently selected from
H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H and $C_{1-4}$ alkyl;

$R^{15}$, at each occurrence, is independently selected from H, $C_{1-4}$ alkyl, $C_{2-4}$ alkenyl, and $C_{2-4}$ alkynyl;

$R^{16}$, at each occurrence, is independently selected from H, OH, halo, CN, $NO_2$, $CF_3$, $SO_2R^{45}$, $NR^{46}R^{47}$, —C(=O)H, $C_{1-4}$ alkyl, $C_{2-4}$ alkenyl, $C_{2-4}$ alkynyl, $C_{1-4}$ haloalkyl, $C_{1-3}$ haloalkyl-oxy-, and $C_{1-3}$ alkyloxy-;

$R^{20}$ is selected from
H, halo, —OH, —$CF_3$, —CN, —$NO_2$, —$CO_2H$, —$SO_2R^{45}$, —$SOR^{45}$, —$SR^{45}$, —$NR^{46}SO_2R^{45}$, —$NR^{46}COR^{45}$, —$NR^{46}R^{47}$, $C_{1-4}$ alkyl, $C_{2-6}$ alkenyl, $C_{2-6}$ alkynyl, $C_{1-4}$ alkoxy, $C_{1-4}$ haloalkyl;
$C_{3-10}$ carbocyclic residue substituted with 0–3 $R^{21}$;
aryl substituted with 0–5 $R^{23}$; and
5–10 membered heterocyclic ring system containing from 1–4 heteroatoms selected from the group consisting of N, O, and S substituted with 0–3 $R^{21}$;

$R^{21}$, at each occurrence, is independently selected from H, OH, halo, $CF_3$, $SO_2R^{45}$, $NR^{46}R^{47}$, CN, $NO_2$, =O, $C_{1-4}$ alkyl;
$C_{1-4}$ alkoxy, and ($C_{1-4}$ haloalkyl)oxy;

$R^{23}$, at each occurrence, is independently selected from H, OH, halo, $CF_3$, $SO_2R^{45}$, $NR^{46}R^{47}$, CN, $NO_2$, $C_{1-4}$ alkyl;
$C_{1-4}$ alkoxy, and ($C_{1-4}$ haloalkyl)oxy;

$R^{33}$, at each occurrence, is independently selected from H, OH, halo, —CN, —$NO_2$, —$CF_3$, —$OCF_3$, —$SO_2R^{35}$, —S(=O)$R^{35}$, —$SR^{35}$, —$NR^{36}R^{37}$, —NHC(=O)$R^{35}$, —C(=O)$NR^{36}R^{37}$, —C(=O)H, —C(=O)$R^{35}$, —C(=O)$OR^{35}$, —OC(=O)$R^{35}$, —$OR^{35}$, $C_{1-6}$ alkyl, $C_{2-6}$ alkenyl, $C_{2-6}$ alkynyl, $C_{1-4}$ haloalkyl, $C_{1-4}$ alkoxy, ($C_{1-4}$ haloalkyl)oxy, $C_{3-6}$ cycloalkyl, phenyl, aryl substituted with 0–2 $R^{34}$, $C_{1-6}$ alkyl substituted with $R^{34}$, and $C_{2-6}$ alkenyl substituted with $R^{34}$;

$R^{34}$, at each occurrence, is independently selected from OH, $C_{1-4}$ alkoxy, —$SO_2R^{35}$, —$NR^{36}R^{37}$, —$NR^{36}R^{37}C$(=O)—, and ($C_{1-4}$ alkyl)$CO_2$—;

$R^{35}$, at each occurrence, is independently selected from $C_{1-4}$ alkyl, $C_{1-4}$ haloalkyl, $C_{3-6}$ cycloalkyl, ($C_{3-6}$ cycloalkyl)methyl-, and ($C_{3-6}$ cycloalkyl)ethyl-;

$R^{36}$, at each occurrence, is independently selected from H and $C_{1-4}$ alkyl;

$R^{37}$, at each occurrence, is independently selected from H, $C_{1-4}$ alkyl, —C(=O)NH($C_{1-4}$ alkyl), —$SO_2$($C_{1-4}$ alkyl), —C(=O)O($C_{1-4}$ alkyl), —C(=O)($C_{1-4}$ alkyl), and —C(=O)H;

$R^{41}$, at each occurrence, is independently selected from H, $CF_3$, halo, OH, $CO_2H$, $SO_2R^{45}$, $NR^{46}R^{47}$, $NO_2$, CN, =O, $C_{1-4}$ alkyl, $C_{2-8}$ alkenyl, $C_{2-8}$ alkynyl, $C_{1-4}$ alkoxy, and $C_{1-4}$ haloalkyl;

$R^{42}$, at each occurrence, is independently selected from H, $CF_3$, halo, OH, $CO_2H$, $SO_2R^{45}$, $SOR^{45}$, $SR^{45}$, $NR^{46}SO_2R^{45}$, $NR^{46}COR^{45}$, $NR^{46}R^{47}$, $NO_2$, CN, $C_{1-4}$ alkyl, $C_{2-6}$ alkenyl, $C_{2-6}$ alkynyl, $C_{1-4}$ alkoxy, and $C_{1-4}$ haloalkyl;

$R^{45}$ is $C_{1-4}$ alkyl;

$R^{46}$, at each occurrence, is independently selected from H and $C_{1-4}$ alkyl;

$R^{47}$, at each occurrence, is independently selected from H, $C_{1-4}$ alkyl, —C(=O)NH($C_{1-4}$ alkyl), —$SO_2$($C_{1-4}$ alkyl), —C(=O)O($C_{1-4}$ alkyl), —C(=O)($C_{1-4}$ alkyl), and —C(=O)H;

m is 1 or 2.

In another embodiment, the present invention provides a novel compound of Formula (Ia) wherein:

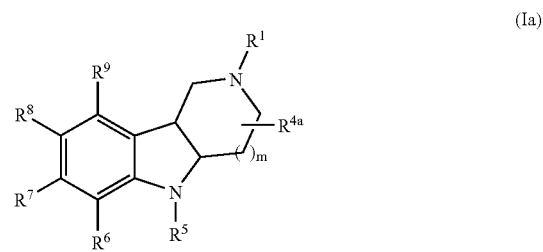

(Ia)

or a stereoisomer or a pharmaceutically acceptable salt form thereof, wherein:

$R^1$ is selected from
H, $CF_3$, methyl, ethyl, cyclopropyl, cyclobutyl, cyclopentyl, cyclohexyl, $C_{1-4}$ alkyl substituted with 0–1 $R^2$, $C_{2-4}$ alkenyl substituted with 0–1 $R^2$, and $C_{2-4}$ alkynyl substituted with 0–1 $R^2$;

$R^2$ is selected from
F, Cl, $CH_2F$, $CHF_2$, $CF_3$, methyl, ethyl, cyclopropyl, cyclobutyl, cyclopentyl, cyclohexyl, and phenyl;

$R^{4a}$ is H or methyl;

$R^5$ is H, methyl, or ethyl;

$R^6$ is selected from
F, Cl, —$CF_3$, —$OCF_3$, —$CF_2CF_3$, —$OCF_2CF_3$, —$OCF_2H$, —$OCF_2CH_3$, —CN, —$NO_2$, —O—$R^{11}$, —S—$R^{11}$, —S(=O)—$R^{11}$, —S(=O)$_2$—$R^{11}$, —$CH_2$O—$R^{11}$, —$CH_2$S—$R^{11}$, $CH_2$S(=O)—$R^{11}$, —$CH_2$S(=O)$_2$—$R^{11}$, methyl, ethyl, n-propyl, i-propyl, n-butyl, i-butyl, and s-butyl;

$R^7$ and $R^9$ are independently selected from
H, F, Cl, —$CH_3$, —$OCH_3$, —$CF_3$, —$OCF_3$, —CN, and —$NO_2$;

$R^8$ is selected from —$OR^{12}$, —$SR^{12}$, —$NR^{12}R^{13}$, —C(O)$R^{12}$, —S(O)$R^{12}$, —S(O)$_2R^{12}$, $C_{1-6}$ alkyl substituted with 0–2 $R^{8a}$, $C_{2-6}$ alkenyl substituted with 0–2 $R^{8a}$, $C_{2-6}$ alkynyl substituted with 0–2 $R^{8a}$, $C_{3-6}$ cycloalkyl substituted with 0–2 $R^{8a}$, and $C_{3-10}$ carbocyclic residue substituted with 0–3 $R^{33}$;

$R^{8a}$, at each occurrence, is independently selected from
halo, —$CF_3$, —$OCF_3$, —OH, —CN, —$NO_2$, —$CF_2CF_3$, methyl, ethyl, n-propyl, i-propyl, n-butyl, i-butyl, s-butyl, t-butyl, —$OR^{12}$, —$SR^{12}$, —$NR^{12}R^{13}$, —C(O)H, —C(O)$R^{12}$, —C(O)$NR^{12}R^{13}$, —$NR^{14}$C(O)$R^{12}$, —C(O)$OR^{12}$, —OC(O)$R^{12}$, —OC(O)$OR^{12}$, —S(O)$R^{12}$, —S(O)$_2R^{12}$, —S(O)$NR^{12}R^{13}$, —S(O)$_2NR^{12}R^{13}$, —$NR^{14}$S(O)$R^{12}$, —$NR^{14}$S(O)$_2R^{12}$, —$NR^{12}$C(O)$R^{15}$, —$NR^{12}$C(O)$OR^{15}$, —$NR^{12}$S(O)$_2R^{15}$, —$NR^{12}$C(O)$NHR^{15}$;
phenyl substituted with 0–5 $R^{33}$;
$C_{3-10}$ carbocyclic residue substituted with 0–3 $R^{33}$, and
5–6 membered heterocyclic ring system containing from 1–4 heteroatoms selected from the group consisting of N, O, and S substituted with 0–3 $R^{33}$;

R¹¹ is selected from
    methyl, ethyl, propyl, and phenyl substituted with 0–5 R²³;
R¹² is selected from
    $C_{1-6}$ alkyl substituted with 0–2 $R^{12}a$ $C_{2-6}$ alkenyl substituted with 0–2 $R^{12a}$, $C_{2-6}$ alkynyl substituted with 0–2 $R^{12a}$, $C_{3-6}$ cycloalkyl substituted with 0–3 $R^{33}$, aryl substituted with 0–5 $R^{33}$;
    $C_{3-10}$ carbocyclic residue substituted with 0–3 $R^{33}$, and
    5–10 membered heterocyclic ring system containing from 1–4 heteroatoms selected from the group consisting of N, O, and S substituted with 0–3 $R^{33}$;
$R^{12a}$, at each occurrence, is independently selected from
    H, halo, —OH, —CN, —NO₂, —CO₂H, —SO₂R⁴⁵, —SOR⁴⁵, —SR⁴⁵, —NR⁴⁶SO₂R⁴⁵, —NR⁴⁶COR⁴⁵, —NR⁴⁶R⁴⁷, —SO₂NR⁴⁶R⁴⁷, —CONR⁴⁶R⁴⁷, —OR⁴⁵, =O, $C_{1-4}$ alkyl, $C_{2-6}$ alkenyl, $C_{2-6}$ alkynyl, phenyl substituted with 0–5 $R^{33}$;
    $C_{3-10}$ carbocyclic residue substituted with 0–3 $R^{33}$, and
    5–10 membered heterocyclic ring system containing from 1–4 heteroatoms selected from the group consisting of N, O, and S substituted with 0–3 $R^{33}$;
$R^{13}$, at each occurrence, is independently selected from
    H, $C_{1-4}$ alkyl, $C_{2-4}$ alkenyl, and $C_{2-4}$ alkynyl;
alternatively, $R^{12}$ and $R^{13}$ join to form a 5- or 6-membered ring selected from pyrrolyl, pyrrolidinyl, imidazolyl, piperidinyl, piperizinyl, methylpiperizinyl, and morpholinyl;
alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, and benztriazolyl; wherein said bicyclic heterocyclic ring system is substituted with 0–1 $R^{16}$;
$R^{14}$ is H, methyl, ethyl, propyl, or butyl;
$R^{15}$ is H, methyl, ethyl, propyl, or butyl;
$R^{16}$, at each occurrence, is independently selected from
    H, OH, F, Cl, CN, NO₂, methyl, ethyl, methoxy, ethoxy, trifluoromethyl, and trifluoromethoxy;
$R^{23}$, at each occurrence, is independently selected from
    H, OH, F, Cl, CF₃, SO₂R⁴⁵, NR⁴⁶R⁴⁷, CN, NO₂, methyl, ethyl, propyl, and butyl;
$R^{33}$, at each occurrence, is independently selected from
    H, OH, halo, —CN, —NO₂, —CF₃, —OCF₃, —SO₂R³⁵, —S(=O)R³⁵, —SR³⁵, —NR³⁶R³⁷, —NHC(=O)R³⁵, —C(=O)NR³⁶R³⁷, —C(=O)H, —C(=O)R³⁵, —C(=O)OR³⁵, —OC(=O)R³⁵, —OR³⁵, $C_{1-6}$ alkyl, $C_{2-6}$ alkenyl, $C_{2-6}$ alkynyl, $C_{1-4}$ haloalkyl, $C_{1-4}$ alkoxy, ($C_{1-4}$ haloalkyl)oxy, $C_{3-6}$ cycloalkyl, phenyl, aryl substituted with 0–2 $R^{34}$, $C_{1-6}$ alkyl substituted with $R^{34}$, and $C_{2-6}$ alkenyl substituted with $R^{34}$;
$R^{34}$, at each occurrence, is independently selected from
    OH, $C_{1-4}$ alkoxy, —SO₂R³⁵, —NR³⁶R³⁷, NR³⁶R³⁷C(=O)—, and ($C_{1-4}$ alkyl)CO₂—;
$R^{35}$, at each occurrence, is independently selected from
    $C_{1-4}$ alkyl, $C_{1-4}$ haloalkyl, $C_{3-6}$ cycloalkyl, ($C_{3-6}$ cycloalkyl)methyl-, and ($C_{3-6}$ cycloalkyl)ethyl-;
$R^{36}$, at each occurrence, is independently selected from H and $C_{1-4}$ alkyl;
$R^{37}$, at each occurrence, is independently selected from H, $C_{1-4}$ alkyl, —C(=O)NH($C_{1-4}$ alkyl), —SO₂($C_{1-4}$ alkyl), —C(=O)O($C_{1-4}$ alkyl), —C(=O)($C_{1-4}$ alkyl), and —C(=O)H;
$R^{45}$ is $C_{1-4}$ alkyl;
$R^{46}$, at each occurrence, is independently selected from H and $C_{1-4}$ alkyl;

$R^{47}$, at each occurrence, is independently selected from H, $C_{1-4}$ alkyl, —C(=O)NH($C_{1-4}$ alkyl), —SO₂($C_{1-4}$ alkyl), —C(=O)O($C_{1-4}$ alkyl), —C(=O)($C_{1-4}$ alkyl), and —C(=O)H;
m is 1 or 2.

In another embodiment, the present invention provides a novel compound of Formula (Ib) wherein:

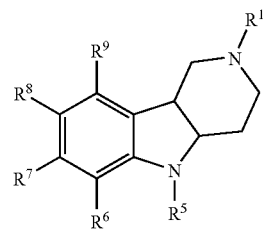

(Ib)

or a stereoisomer or a pharmaceutically acceptable salt form thereof, wherein:
$R^1$ is selected from H, methyl, and ethyl;
$R^5$ is H, methyl, or ethyl;
$R^6$ is selected from —F, —Cl, —CF₃, —OCF₃, —CF₂CF₃, —OCF₂CF₃, —OCF₂H, —OCF₂CH³, —CN, —NO₂, —OCH₃, —OCH₂CH₃, —SCH₃, —SCH₂CH₃, —S(=O)CH₃, —S(=O)₂CH₃, methyl, ethyl, n-propyl, i-propyl, n-butyl, i-butyl, and s-butyl;
$R^7$ is H, F, or Cl;
$R^8$ is selected from —OR¹², —SR¹², —NR¹²R¹³, —C(O)R¹², —S(O)R¹², —S(O)₂R¹², $C_{1-6}$ alkyl substituted with 0–2 $R^{8a}$, $C_{3-6}$ cycloalkyl substituted with 0–2 $R^{8a}$, and $C_{3-10}$ carbocyclic residue substituted with 0–3 $R^{33}$;
$R^{8a}$, at each occurrence, is independently selected from
    H, F, Cl, Br, methyl, ethyl, n-propyl, i-propyl, n-butyl, i-butyl, s-butyl, t-butyl, —OH, methoxy, ethoxy, n-propoxy, i-propoxy, —CF₃, —OCF₃, —CN, —NO₂, —CF₂CF₃, —SCH₃, —SCH₂CH₃, —SO₂CH₃, —NH₂, —CH₂NH(CH₃), —CH₂N(CH₃)₂, —NH(CH₃), —N(CH₃)₂, —CO(CH₃), —CO(OCH₃), —NHCO(CH₃), —CONH₂, —C(=O)H, —CH(OH)CH₃, —CH₂OH, —CH₂CH₂OH, —CH₂OCH₃, —CH₂CH₂OCH₃, —CH₂OCH₂CH₃, phenyl substituted with 0–5 $R^{33}$ and pyridyl substituted with 0–5 $R^{33}$
$R^9$ is H;
$R^{12}$ is selected from
    $C_{1-6}$ alkyl substituted with 0–2 $R^{12a}$, cyclopropyl substituted with 0–2 $R^{33}$, cyclobutyl substituted with 0–2 $R^{33}$, cyclopentyl substituted with 0–2 $R^{33}$, cyclohexyl substituted with 0–2 $R^{33}$, bicyclo[3.1.1]heptane substituted with 0–2 $R^{33}$, bicyclo[2.2.1]heptane substituted with 0–2 $R^{33}$, phenyl substituted with 0–3 $R^{33}$; and pyridyl substituted with 0–3 $R^{33}$;
$R^{12a}$, at each occurrence, is independently selected from
    H, F, Cl, —OH, methyl, ethyl, cyclopropyl substituted with 0–2 $R^{33}$, cyclobutyl substituted with 0–2 $R^{33}$, cyclopentyl substituted with 0–2 $R^{33}$, cyclohexyl substituted with 0–2 $R^{33}$, bicyclo[3.1.1]heptane substituted with 0–2 $R^{33}$, bicyclo[2.2.1]heptane substituted with 0–2 $R^{33}$, and phenyl substituted with 0–3 $R^{33}$;
$R^{13}$ is H, methyl, or ethyl;
$R^{33}$, at each occurrence, is independently selected from
    H, F, Cl, Br, methyl, ethyl, n-propyl, i-propyl, n-butyl, i-butyl, s-butyl, t-butyl, —OH, methoxy, ethoxy, n-propoxy, i-propoxy, —SCH₃, —SCH₂CH₃, —SO₂CH₃, —CF₃, —OCF₃, —CF₂CF₃, —CN, —NO₂, —NH₂, —CH₂NH(CH₃), —CH₂N(CH₃)₂, —NH(CH₃), —N(CH₃)₂, —CO(CH₃), —CO(OCH₃), —NHCO(CH₃), —CONH₂, —C(=O)H, —CH(OH)CH₃, —CH₂OH, —CH₂CH₂OH, —CH₂OCH₃, —CH₂CH₂OCH₃, and —CH₂OCH₂CH₃.

In another embodiment, the present invention provides a novel compound of Formula (Ib):

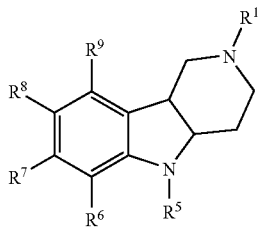
(Ib)

or a stereoisomer or a pharmaceutically acceptable salt form thereof, wherein:

$R^1$ is H or methyl;

$R^5$ is H or methyl;

$R^6$ is selected from —F, —Cl, —CF₃, —CF₂CF₃, —OCF₃, —OCF₂CF₃, —OCF₂H, —OCF₂CH³, —CN, —OCH₃, —SCH₃, —S(=O)CH₃, —S(=O)₂CH₃, or methyl;

$R^7$ is H, F, or Cl;

$R^8$ is selected from —OR¹², —SR¹², —NR¹²R¹³, $C_{1-6}$ alkyl substituted with 0–2 $R^{8a}$, and $C_{3-6}$ cycloalkyl substituted with 0–2 $R^{8a}$, $R^{8a}$, at each occurrence, is independently selected from H, F, Cl, Br, methyl, ethyl, n-propyl, i-propyl, n-butyl, i-butyl, s-butyl, t-butyl, —OH, methoxy, ethoxy, n-propoxy, i-propoxy, —CF₃, —OCF₃, —CN, —CF₂CF₃, —SCH₃, —SCH₂CH₃, —CH₂NH(CH₃), —CH₂N(CH₃)², —NH(CH₃), —N(CH₃)₂, —CO(CH₃), —CO(OCH₃), —NHCO(CH₃), —CONH₂, —CH(OH)CH₃, —CH₂OH, —CH₂CH₂OH, —CH₂OCH₃, —CH₂CH₂OCH₃, —CH₂OCH₂CH₃. phenyl substituted with 0–5 $R^{33}$, and pyridyl substituted with 0–5 $R^{33}$ $R^9$ is H;

$R^{12}$ is selected from methyl, ethyl, propyl, butyl, pentyl, hexyl, cyclopropyl, cyclobutyl, cyclopentyl, cyclohexyl, bicyclo[3.1.1]heptane, bicyclo[2.2.1]heptane, methyl substituted with $R^{12a}$;
ethyl substituted with $R^{12a}$;
propyl substituted with $R^{12a}$;
phenyl substituted with 0–2 $R^{33}$; and
pyridyl substituted with 0–2 $R^{33}$;

$R^{12a}$ is selected from cyclopropyl, cyclobutyl, cyclopentyl, cyclohexyl, bicyclo[3.1.1]heptane, bicyclo[2.2.1]heptane, and phenyl substituted with 0–2 $R^{33}$;

$R^{13}$ is H, methyl, or ethyl;

$R^{33}$, at each occurrence, is independently selected from

H, F, Cl, Br, methyl, ethyl, n-propyl, i-propyl, n-butyl, i-butyl, s-butyl, t-butyl, —OH, methoxy, ethoxy, n-propoxy, i-propoxy, —SCH₃, —SCH₂CH₃, —SO₂CH₃, —CF₃, —OCF₃, —CN, —NO₂, —NH₂, —CH₂NH(CH₃), —CH₂N(CH₃)₂, —NH(CH₃), —N(CH₃)₂, —CO(CH₃), —CO(OCH₃), —NHCO(CH₃), —CONH₂, —C(=O)H, —CH(OH)CH₃, —CH₂OH, —CH₂CH₂OH, —CH₂OCH₃, —CH₂CH₂OCH₃, and —CH₂OCH₂CH₃.

In another embodiment, the present invention provides a novel compound of Formula (Ic):

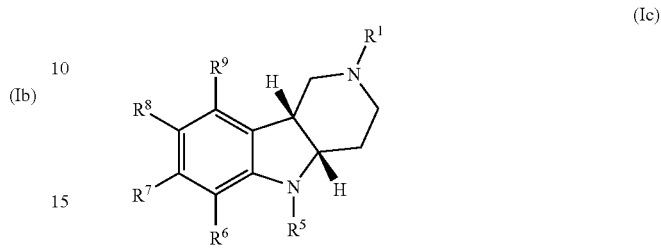
(Ic)

or a pharmaceutically acceptable salt thereof.

In an even further more preferred embodiment of the present invention, are compounds of Formula (1) selected from disclosed Examples 1–212.

In another embodiment $R^1$ is H or methyl.
In another embodiment $R^1$ is methyl.
In another embodiment $R^1$ is H.
In another embodiment $R^5$ is H or methyl.
In another embodiment $R^5$ is methyl.
In another embodiment $R^5$ is H.
In another embodiment $R^6$ is —CF₃, —OCF₃, —CN, —OCH₃, —SCH₃, —S(=O)CH₃, —S(=O)₂CH₃, or methyl.
In another embodiment $R^6$ is —CF₃.
In another embodiment $R^6$ is —CN.
In another embodiment $R^6$ is —OCH₃.
In another embodiment $R^6$ is —SCH₃.
In another embodiment $R^6$ is methyl.
In another embodiment $R^7$ is H.
In another embodiment $R^9$ is H.
In another embodiment $R^8$ is —OR¹², —SR¹², —NR¹²R¹³, $C_{1-6}$ alkyl substituted with 0–2 $R^{8a}$, or $C_{3-6}$ cycloalkyl substituted with 0–2 $R^{8a}$.
In another embodiment $R^8$ is —OR¹².
In another embodiment $R^8$ is —SR¹².
In another embodiment $R^8$ is —NR¹²R¹³.
In another embodiment $R^8$ is $C_{1-6}$ alkyl substituted with 0–2 $R^{8a}$.
In another embodiment $R^8$ is $C_{3-6}$ cycloalkyl substituted with 0–2 $R^{8a}$.
In another embodiment $R^{8a}$, at each occurrence, is independently selected from H, F, Cl, Br, methyl, ethyl, n-propyl, i-propyl, n-butyl, i-butyl, s-butyl, t-butyl, —OH, methoxy, ethoxy, n-propoxy, i-propoxy, —CF₃, —OCF₃, —CN, —CF₂CF₃, —SCH₃, —SCH₂CH₃, —CH₂NH(CH₃), —CH₂N(CH₃)₂, —NH(CH₃), —N(CH₃)₂, —CO(CH₃), —CO(OCH₃), —NHCO(CH₃), —CONH₂, —CH(OH)CH₃, —CH₂OH, —CH₂CH₂OH, —CH₂OCH₃, —CH₂CH₂OCH₃, —CH₂OCH₂CH₃, phenyl substituted with 0–5 $R^{33}$, and pyridyl substituted with 0–5 $R^{33}$ In another embodiment $R^{12}$ is selected from methyl substituted with $R^{12a}$; ethyl substituted with $R^{12a}$; propyl substituted with $R^{12a}$; and phenyl substituted with 0–2 $R^{33}$.

In another embodiment $R^{12}$ is phenyl substituted with 0–3 $R^{33}$.

In another embodiment $R^{12}$ is phenyl substituted with 0–2 $R^{33}$.

In another embodiment $R^{33}$, at each occurrence, is independently selected from H, F, Cl, Br, methyl, ethyl, n-propyl, i-propyl, n-butyl, i-butyl, s-butyl, t-butyl, —OH, methoxy, ethoxy, n-propoxy, i-propoxy, —SCH$_3$, —SCH$_2$CH$_3$, —SO$_2$CH$_3$, —SO$_2$CH$_2$CH$_3$, —CF$_3$, —OCF$_3$, —CN, —NO$_2$, —NH$_2$, —CH$_2$NH(CH$_3$), —CH$_2$N(CH$_3$)$_2$, —NH (CH$_3$), —N(CH$_3$)$_2$, —CO(CH$_3$), —CO(OCH$_3$), —NHCO (CH$_3$), —CONH$_2$, —C(=O)H, —CH(OH)CH$_3$, —CH$_2$OH, —CH$_2$CH$_2$OH, —CH$_2$OCH$_3$, —CH$_2$CH$_2$OCH$_3$, and —CH$_2$OCH$_2$CH$_3$.

In a second embodiment, the present invention provides a pharmaceutical composition comprising a compound of Formula (I) and a pharmaceutically acceptable carrier.

In a third embodiment, the present invention provides a method for the treatment a central nervous system disorder comprising administering to a host in need of such treatment a therapeutically effective amount of a compound of Formula (I), or a pharmaceutically acceptable salt thereof, wherein the compound is a 5HT$_{2C}$ agonist.

In a more preferred embodiment the present invention provides a method for the treatment central nervous system disorders including obesity, anorexia, bulemia, depression, anxiety, psychosis, schizophrenia, migraine, addictive behavior, obsessive-compulsive disorder, and sexual disorders comprising administering to a host in need of such treatment a therapeutically effective amount of a compound of Formula (I).

In a further preferred embodiment the central nervous system disorder comprises obesity.

In another further preferred embodiment the central nervous system disorder comprises schizophrenia.

In another further preferred embodiment the central nervous system disorder comprises depression.

In another further preferred embodiment the central nervous system disorder comprises anxiety.

In another further preferred embodiment the central nervous system disorder sexual disorders.

In another further preferred embodiment the central nervous system disorder addictive behaviors.

In a fourth embodiment the present invention provides novel compounds of Formula (I) or pharmaceutically acceptable salt forms thereof for use in therapy.

In a fifth embodiment the present invention provides the use of novel compounds of Formula (I) or pharmaceutically acceptable salt forms thereof for the manufacture of a medicament for the treatment of central nervous system disorders including obesity, anorexia, bulemia, depression, anxiety, psychosis, schizophrenia, migraine, addictive behavior, obsessive-compulsive disorder, and sexual disorders.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted", as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g. $R^2$, $R^{23}$, $R^{33}$ etc.) occurs more than one time in any constituent or formula for a compound, its definition at each occurrence is independent of its definition at every other occurrence. Thus, for example, if a group is shown to be substituted with 0–2 $R^2$, then said group may optionally be substituted zero, one or two $R^2$ groups and $R^2$ at each occurrence is selected independently from the definition of $R^2$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms; for example, "C$_1$–C$_6$ alkyl" or "C$_{1-6}$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl. Unless otherwise specified, preferred alkyl are methyl, ethyl, n-propyl, i-propyl, n-butyl, i-butyl, sec-butyl, and t-butyl.

"Alkenyl" or "alkenylene" is intended to include hydrocarbon chains of either a straight or branched configuration having the specified number of carbon atoms, for example "C$_{2-6}$ alkenyl", and one or more unsaturated carbon-carbon bonds which may occur in any stable point along the chain. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like. Unless otherwise specified, preferred alkenyl are ethenyl, 1-propenyl, 2-propenyl, 2-butenyl, and 3-butenyl.

"Alkynyl" or "alkynylene" is intended to include hydrocarbon chains of either a straight or branched configuration, having the specified number of carbon atoms, for example "C$_{2-6}$ alkynyl", and one or more carbon-carbon triple bonds which may occur in any stable point along the chain, such as ethynyl, propynyl, butynyl, pentynyl, hexynyl and the like. Unless otherwise specified, preferred alkynyl are ethynyl and propynyl.

"Cycloalkyl" is intended to include saturated ring groups, having the specified number of carbon atoms. For example, "C$_3$–C$_6$ cycloalkyl" denotes such as cyclopropyl, cyclobutyl, cyclopentyl, or cyclohexyl.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Unless otherwise specified, preferred alkoxy are methoxy, ethoxy, n-propoxy, and i-propoxy.

Similarly, "alkylthio" is represents an alkyl group as defined above with the indicated number of carbon atoms attached through a sulpher bridge. Unless otherwise specified, preferred alkylthio are methylthio and ethylthio.

"Halo" or "halogen" as used herein refers to fluoro, chloro, bromo, and iodo. Preferred halo are fluoro and chloro.

"Counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$, where v=1 to 3 and w=1 to (2v+1)). Examples of haloalkyl include, but are not limited to, trifluoromethyl, difluoromethyl, fluoromethyl, trichloromethyl, pentafluoroethyl, pentachloroethyl, 2,2,2-trifluoroethyl, heptafluoropropyl, and heptachloropropyl. Unless otherwise specified, preferred haloalkyl are trifluoromethyl, difluoromethyl, and fluoromethyl.

As used herein, "carbocycle" or "carbocyclic residue" or "carbocyclic moiety" is intended to mean any stable 3- to 7-membered monocyclic or bicyclic or 7- to 13-membered bicyclic or tricyclic, any of which may be saturated or partially unsaturated. Examples of such carbocycles include, but are not limited to, cyclopropyl, cyclobutyl, cyclopentyl, cyclohexyl, cycloheptyl, cyclooctyl, cyclopentenyl, cyclohexenyl, bicyclo[3.1.1.]heptane, bicyclo[2.2.1]heptane, [3.3.0]bicyclooctane, [4.3.0]bicyclononane, [4.4.0]bicyclodecane (decalin), [2.2.2]bicyclooctane, indanyl, adamantyl, or tetrahydronaphthyl (tetralin).

As used herein, the term "heterocycle" or "heterocyclic ring" or "heterocyclic ring system" is intended to mean a stable 5- to 7-membered monocyclic or bicyclic or 7- to 14-membered bicyclic heterocyclic ring which is saturated, partially unsaturated, or unsaturated, and which consists of carbon atoms and 1, 2, 3 or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds one, then these heteroatoms are not adjacent to one another. It is preferred that the total number of S and O atoms in the heterocycle is not more than one.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b] tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred 5 to 10 membered heterocycles include, but are not limited to, pyridinyl, pyrimidinyl, triazinyl, furanyl, thienyl, thiazolyl, pyrrolyl, pyrazolyl, pyrazinyl, piperazinyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, benzoxazolyl, benzthiazolyl, benzisothiazolyl, isatinoyl, isoxazolopyridinyl, isothiazolopyridinyl, thiazolopyridinyl, oxazolopyridinyl, imidazolopyridinyl, pyrazolopyridinyl, quinolinyl, and isoquinolinyl. Preferred 5 to 6 membered heterocycles include, but are not limited to, pyridinyl, pyrimidinyl, triazinyl, furanyl, thienyl, thiazolyl, pyrrolyl, pyrazinyl, piperazinyl, piperidinyl, pyrazolyl, imidazolyl, oxazolyl, isoxazolyl, tetrazolyl, and oxazolidinyl; more preferred 5 to 6 membered heterocycles include, but are not limited to, pyridinyl, pyrimidinyl, triazinyl, furanyl, thienyl, thiazolyl, piperazinyl, piperidinyl, pyrazolyl, imidazolyl, and tetrazolyl. Also included are fused ring and spiro compounds containing, for example, the above heterocycles.

As used herein, the term "aryl", or aromatic residue, is intended to mean an aromatic moiety containing six to ten carbon atoms, such as phenyl and naphthyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

"Prodrugs" are intended to include any covalently bonded carriers which release the active parent drug according to Formula (I) in vivo when such prodrug is administered to a mammalian subject. Prodrugs of a compound of Formula (I) are prepared by modifying functional groups present in the compound in such a way that the modifications are cleaved, either in routine manipulation or in vivo, to the parent compound. Prodrugs include compounds of Formula (I) wherein a hydroxy, amino, or sulfhydryl group is bonded to any group that, when the prodrug or compound of Formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of Formula (I), and the like.

"Stable compound" and "stable structure" are meant to indicate a compound that is sufficiently robust to survive isolation to a useful degree of purity from a reaction mixture, and formulation into an efficacious therapeutic agent.

Synthesis

Throughout the details of the invention, the following abbreviations are used with the following meanings:

| Reagents: | |
|---|---|
| DIBAL | diisobutyl aluminum hydride |
| Et$_3$N | triethylamine |
| TFA | trifluoroacetic acid |
| LAH | lithium aluminum hydride |
| NBS | N-bromosuccinimide |
| Red-Al | Sodium bis(2-methoxyethoxy)aluminum hydride |
| Pd$_2$dba$_3$ | Tris(dibenzylideneacetone)dipalladium(0) |
| ACE-Cl | 2-chloroethylchloroformate |
| Solvents: | |
| THF | tetrahydrofuran |
| MeOH | methanol |
| EtOH | ethanol |
| EtOAc | ethyl acetate |
| HOAc | acetic acid |
| DMF | dimethyl formamide |
| DMSO | dimethyl sulfoxide |
| DME | dimethoxyethane |
| Et$_2$O | diethylether |
| iPrOH | isopropanol |
| Others: | |
| Ar | aryl |
| Ph | phenyl |
| Me | methyl |
| Et | ethyl |
| NMR | nuclear magnetic resonance |
| MHz | megahertz |
| BOC | tert-butoxycarbonyl |
| CBZ | benzyloxycarbonyl |
| Bn | benzyl |
| Bu | butyl |
| Pr | propyl |
| cat. | catalytic |
| mL | milliliter |
| nM | nanometer |
| ppm | part per million |
| mmol | millimole |
| mg | milligram |
| g | gram |
| kg | kilogram |
| TLC | thin layer chromatography |
| HPLC | high pressure liquid chromatography |
| rt | room temperature |
| aq. | aqueous |
| sat. | saturated |

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagent and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the regents and reactions proposed. Such restrictions to the substituents which are compatible with the reaction conditions will be readily apparent to one skilled in the art and alternate methods must then be used.

The preparation of compounds of Formula (I) of the present invention may be carried out in a convergent or sequential synthetic manner. Detailed synthetic preparations of the compounds of Formula (I) are shown in the following reaction schemes. The skills required in preparation and purification of the compounds of Formula (I) and the intermediates leading to these compounds are known to those in the art. Purification procedures include, but are not limited to, normal or reverse phase chromatography, crystallization, and distillation.

Several methods for the preparation of the compounds of the present invention are illustrated in the schemes and examples shown below. The substitutions are as described and defined above.

Compounds of Formula (I) of this invention may be prepared as shown in Scheme 1. Thus, preparation of an aryl hydrazine (II) is accomplished, for example, by treatment of a corresponding substituted aniline with $NaNO_2$ followed by reduction of the N-nitroso intermediate with $SnCl_2$ in conc. HCl. Assembly of the core indole intermediate (IV) is accomplished by Fischer indole cyclization of the aryl hydrazine and a suitably substituted ketone (i.e. (III)) by methods described by, but not limited to, R. J. Sundberg, "Indoles, Best Synthetic Methods" 1996, Academic Press, San Diego, Calif. For example, treatment of the aryl hydrazine (II) as the free base or the corresponding mineral acid salt with the ketone (III) ($R^1$=H, Bn, CBZ, $CO_2Et$, etc) in an alcoholic solvent in the presence of mineral acid affords the indoles (IV) as the free bases (after treatment with aq. NaOH). Reduction of the indoles to the corresponding cis or trans substituted indolines is accomplished by, for example, treatment with hydrogen in the presence of a catalyst such as platinum oxide or palladium on carbon, or with a metal such as zinc and a mineral acid such as hydrochloric acid, or with sodium and liquid ammonia, or with borane-amine complex such as borane-triethylamine in tetrahydrofuran, or preferably by treatment with triethylsilane or $NaCNBH_3$ in an acid such as acetic or trifluoroacetic acid.

SCHEME 1

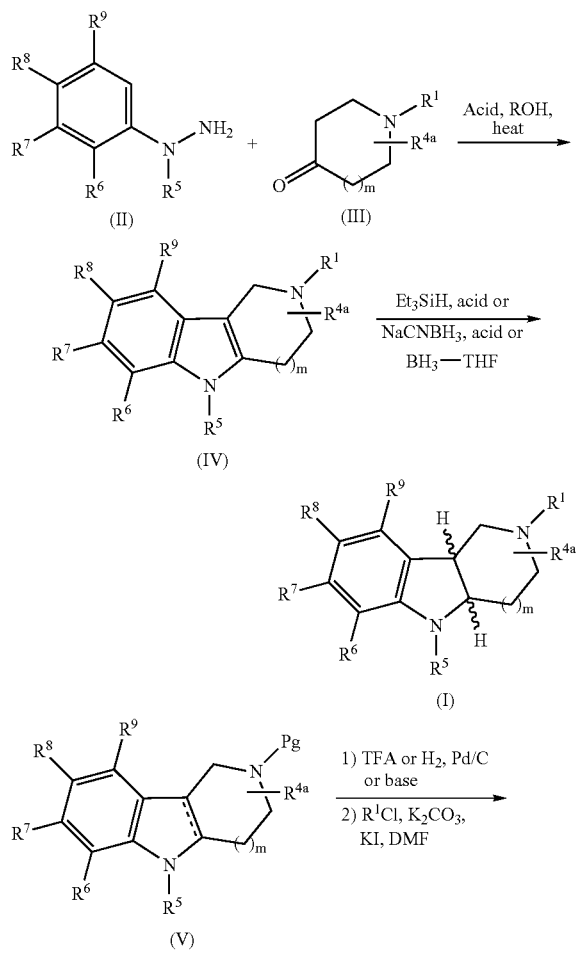

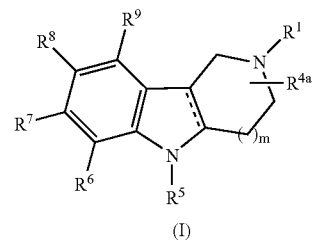

(I)

The corresponding enantiomers can be isolated by separation of the racemic mixture of (I) on a chiral stationary phase column utilizing normal or reverse phase HPLC techniques, the details of which are described in the examples. Alternatively, a diastereomeric mixture of (I) can be prepared by treatment of (I, $R^2$=H) with an appropriate chiral acid (or suitably activated derivative), for example dibenzoyl tartrate or the like (see, for example, Kinbara, K., et. al., *J. Chem. Soc., Perkin Trans.* 2, 1996, 2615; and Tomori, H., et. al., *Bull. Chem. Soc. Jpn.*, 1996, 3581). The diastereomers would then be separated by traditional techniques (i.e. silica chromatography, crystallization, HPLC, etc) followed by removal of the chiral auxiliary to afford enantiomerically pure (I).

In the cases where the carboline nitrogen has been protected (V) (i.e. Pg=Boc, Bn, CBZ, $CO_2R$), it may be removed under a variety of conditions as described in Greene, T. W., Wuts, P. G. W., "Protective Groups in Organic Synthesis, 2nd Edition", John Wiley and Sons, Inc., New York, pages 309–405, 1991. The free secondary amine could then be alkylated, for example, by treatment with a suitably substituted alkyl halide ($R^1Cl$, $R^1Br$ or $R^1I$) and a base to afford additional compounds of type (I), as described, for example, by Glennon, R. A., et. al., *Med. Chem. Res.*, 1996, 197.

Compounds of Formula (II) can be prepared as described in Scheme 2. Formation of the aryl amine (VII) may be accomplished by reduction of the corresponding aryl nitro compound (VI). The reduction may be accomplished with a variety of reducing agents, for example, LAH, $SnCl_2$, $NaBH_4$, $N_2H_4$, etc. or with hydrogen in the presence of a suitable catalyst, such as palladium on carbon, or platinum oxide, etc., (see Hudlicky, M., "Reductions in Organic Chemistry", Ellis Horwood, Ltd., Chichester, UK, 1984). Formation of the aryl hydrazine (II) may then be performed as previously described in Scheme 1 or more directly by treatment of the aniline (VII) with aq. hydrochloric acid, stannous chloride and $NaNO_2$ at room temperature (see, Buck, J. S., Ide, W. S., *Org. Syn., Coll.* Vol., 2, 1943, 130). This latter procedure is especially important when initiating the synthesis with halogenated arylamines (VII). The necessity for preparation of the hydrazine intermediate without the use of strong reductive conditions is critical in these such examples.

SCHEME 2

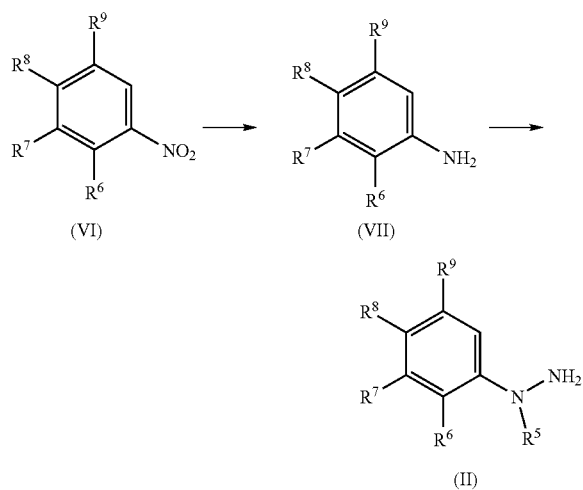

Another related route to hydrazines of Formula (II) is shown in Scheme 3. When an aromatic substitution pattern containing a sulfur moiety is desired the following route may be employed. Displacement of a halogen (Cl, F) of a suitably substituted aryl nitro derivative (VIII) by the prerequisite nucleophile under basic conditions affords intermediates of type (IX). Reduction of the nitro moiety followed by elaboration of the resultant amine to the substituted or unsubstituted hydrazine (X) is as described above.

SCHEME 3

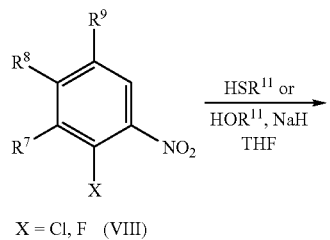

X = Cl, F  (VIII)

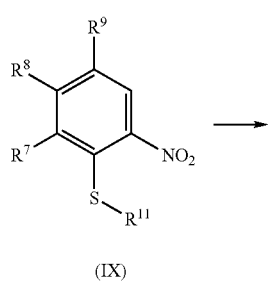

(IX)

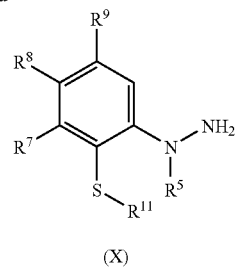

(X)

Initiating the synthesis with a nitrobenzene derivative such as (VIII), this approach allows for a variety of derivatization. More highly substituted nitrobenzenes can be obtained by traditional synthetic manipulation (i.e aromatic substitution) and are known by those in the art (see Larock, R. C., *Comprehensive Organic Transformations*, VCH Publishers, New York, 1989).

An alternate, more direct approach to differentially substituted analogs is shown in Scheme 4. Initiating the preparation of compounds of type (I) with an aryl iodide expands the versatility of this approach. The preparation of an intermediate which can be functionalized at a later stage is a more efficient approach to some of the substitution types. Fischer indole cyclization of the iodide (XI) with the ketone (III) as described previously, followed by protection of the amine with $Boc_2O$, affords the iodo indole (XII). Alkylation of the indole nitrogen under basic conditions followed by removal of the Boc protecting group and a second alkylation of the carboline nitrogen affords the selective differentially substituted carboline indoles (XIII). Usual reduction of the indole to indoline is carried out without any loss of the aromatic halogen to afford the common aryliodide (XIV). Facile displacement of the iodide with a variety of sulfur nucleophiles under copper catalyzed conditions affords the diaryl sulfides (XV).

SCHEME 4

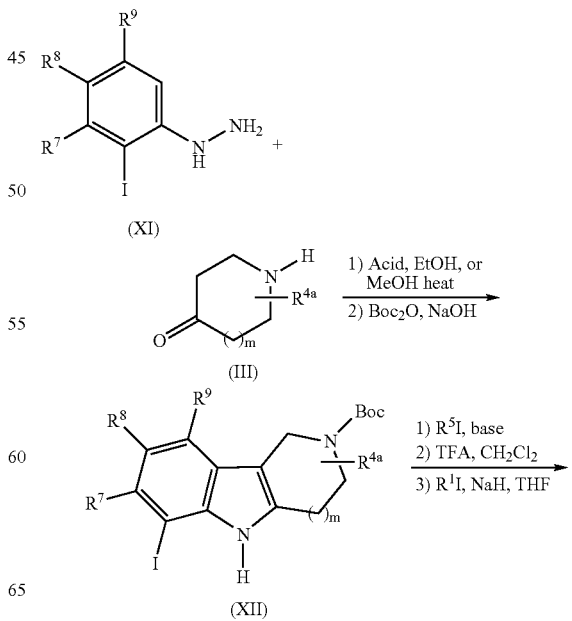

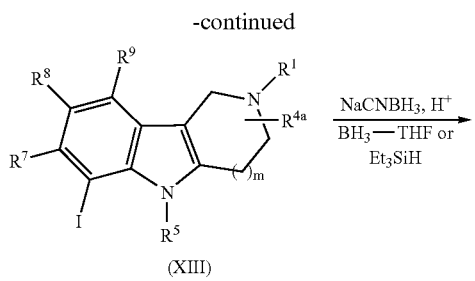

(XIII)

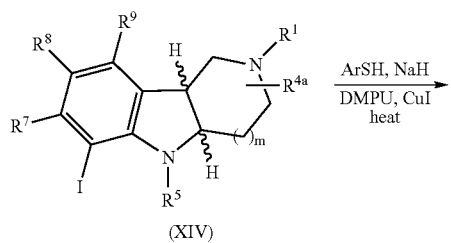

(XIV)

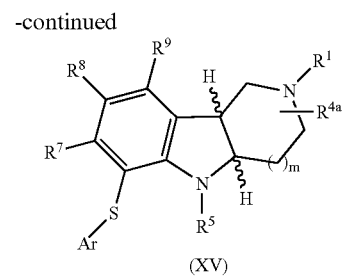

(XV)

Additional method of preparing differentially substituted analogs is shown in Scheme 5. Facile displacement of the iodo-group of indole (XII) with $Zn(CN)_2$ under Pd(0) catalyzed conditions affords the cyanoindole (XVI). Reduction of indole is achieved as described previously, followed by protection of the amine with $Boc_2O$ and alkylation of the indoline nitrogen under basic conditions affords the cyanoindoline (XVIII). Alternatively, iodoindole (XII) can be reduced and treated $Boc_2O$ to give iodoindoline (XVII) as described previously. Displacement of the iodide with $Zn(CN)_2$ catalyzed by Pd(0) under microwave condition followed by alkylation of the indoline nitrogen produces cyanoindoline (XVIII).

SCHEME 5

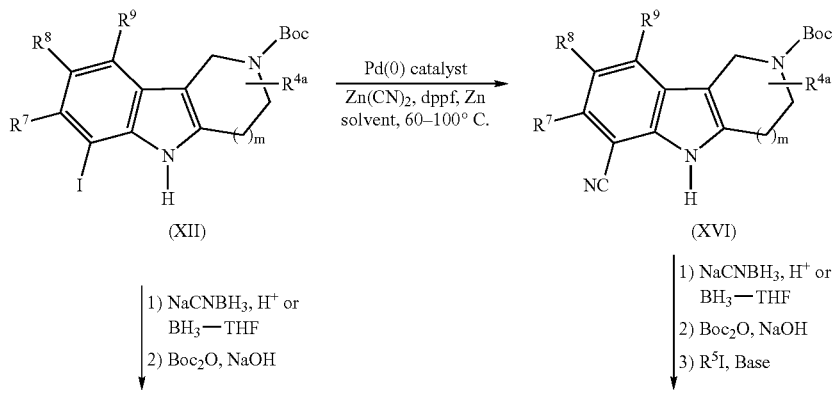

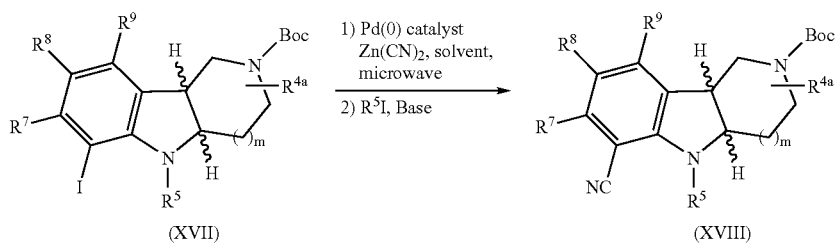

The preparation of compounds of Formula (I) with additional diversity of functionalization of the aromatic A ring of the tricycle is described here. Bromination of the indolines (I, $R^8$=H) when the amine is protected (with the Boc or CBZ protecting groups), with for example, NBS in DMF, affords the $R^8$ brominated derivatives (XIX). These activated aryl derivatives (XIX) act as excellent counterparts for a number of important synthetic transformations.

One example is described in Scheme 6, where the aromatic ring of Formula (I) is substituted with an arylamino group. Treatment of bromide (XIX) with a variety of anilines (XX) in the presence of a Pd(0) catalyst, such as $Pd_2(dba)_3$, $Pd(PPh_3)_4$ or $Pd(PPh_3)_2Cl_2$, and suitable ligand such BINAP or $PPh_3$, and a base such as NaOtBu or $CsCO_3$ in a suitable solvent such as DMF, toluene, THF, DME, or the like, affords the biaryl anilines (XXI).

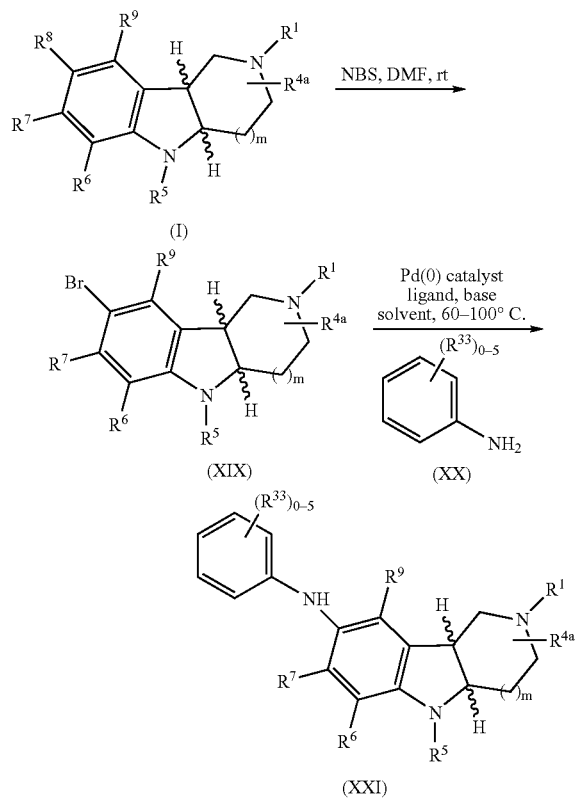

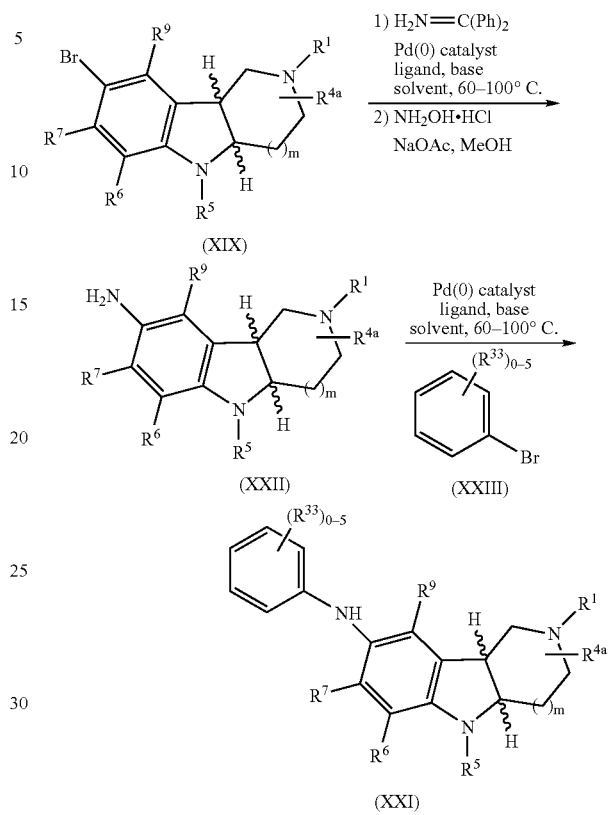

An alternate method for preparing biaryl anilines (XXI) is described in Scheme 7 and proceeds from brominated derivatives (XIX). Treatment of arylbromide derivatives of type (XIX) with diphenylmethyl imine in the presence of a Pd(0) catalyst, such as $Pd_2(dba)_3$, $Pd(PPh_3)_4$ or $Pd(PPh_3)_2Cl_2$, and suitable ligand such BINAP or $PPh_3$, and a base such as NaOtBu or $CsCO_3$ in a suitable solvent such as DMF, toluene, THF, DME, or the like, followed affords an imine intermediate. Basic hydrolysis (hydroxylamine, sodium acetate in methanol) affords the primary aniline derivative (XXII). Coupling of these anilines with various arylbromide (XXIII) under Pd(0) catalyzed condition described above affords the biaryl anilines (XXI).

Similarly arylamino coupling of the bromine derivatives (XXIV), readily obtained by the synthetic sequence exemplified in Scheme 2, (starting with the suitably functionalized bromo nitrobenzenes (VI), is shown in Scheme 8. This approach allows for the preparation of arylamino-indoles as well as the corresponding indoline derivatives. Protection of the amine functionality must be carried out if $R^1$, =H (see Greene et. al for protections of amines). This is readily accomplished, for example, by treatment of bromo derivatives (XXIV) with excess $(Boc)_2O$ in aqueous sodium hydroxide and dioxane. Subsequent coupling with a variety of aryl anilines is carried out as described above in Scheme 6, to afford the arylamino indoline adducts (XXV). This protocol is amenable to $R^a$, $R^b$, and $R^c$ bromide, iodide, triflates, and/or diazo derivatives. In addition, there exists a wide range of procedures and protocols for functionalizing haloaromatics, aryldiazonium and aryltriflate compounds. These procedures are well known by those in the art and described, for example (see Stanforth, S. P., *Tetrahedron*, 1998, 263; Buchwald, S. L., et. al., *J. Am. Chem. Soc.,* 1998, 9722; Stille, J. K., et. al., *J. Am. Chem. Soc.,* 1984, 7500). Among these procedures are biaryl couplings, alkylations, acylations, aminations, and amidations. The power of palladium catalyzed functionalization of aromatic cores has been explored in depth in the last decade. An excellent review of this field can be found in J. Tsuji, "Palladium Reagents and Catalysts, Innovations in Organic Synthesis", J. Wiley and Sons, New York, 1995.

SCHEME 8

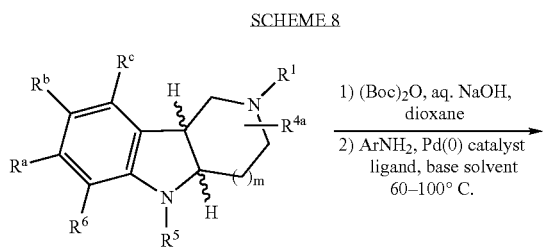

R$^a$, R$^b$, or R$^c$ = Br, I, OTf, N$_2$ (XXIV)

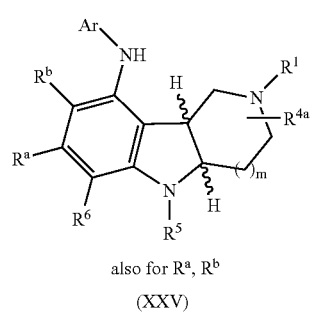

also for R$^a$, R$^b$ (XXV)

The aniline (XXII) can also react with an appropriate aldehyde (XXVII) in the presence a suitable reducing agent such as sodium triacetoxyborohydride or sodium cyanoborohydride under mild reaction conditions, such as in the presence of acetic acid, in a suitable solvent such as 1,2-dichloroethane, THF, methanol or acetonitrile to produce the variety of secondary aniline analogs (XXVI). In analogy of Scheme 8, the protocol described in Scheme 9 can also be applied to analogs of (XIX) where the R$^7$ or R$^9$ groups are NH$_2$, Br, I, OTf, etc., to afford analogs of (XXVI) where the alkylamino group is on the R$^7$ or R$^9$ position.

SCHEME 9

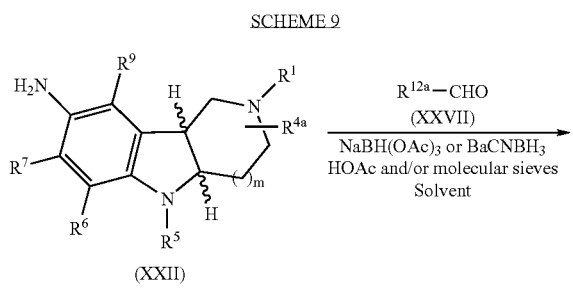

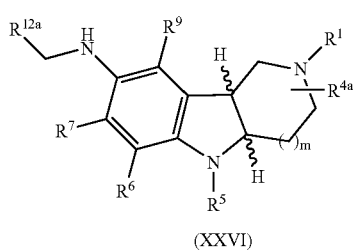

(XXVI)

The aniline (XXII) can react with 1 equivalent of various alkylhalides or alkylsulfonates (XXVII) in the presence a suitable base such as NaH, K$_2$CO$_3$, Na$_2$CO$_3$, CsCO$_3$, Et$_3$N or Et$_2$(i-Pr)N in a suitable solvent such as DMF, DMSO, toluene, THF, DME or the like, produce the variety of secondary aniline analogs (XXVIII) as shown in scheme 10. In analogy of Scheme 8, the protocol described in Scheme 10 can also be applied to analogs of (XIX) where the R$^7$ or R$^9$ groups are NH$_2$ to afford analogs of (XXVIII) where the alkylamino group is on the R$^7$ or R$^9$ position.

SCHEME 10

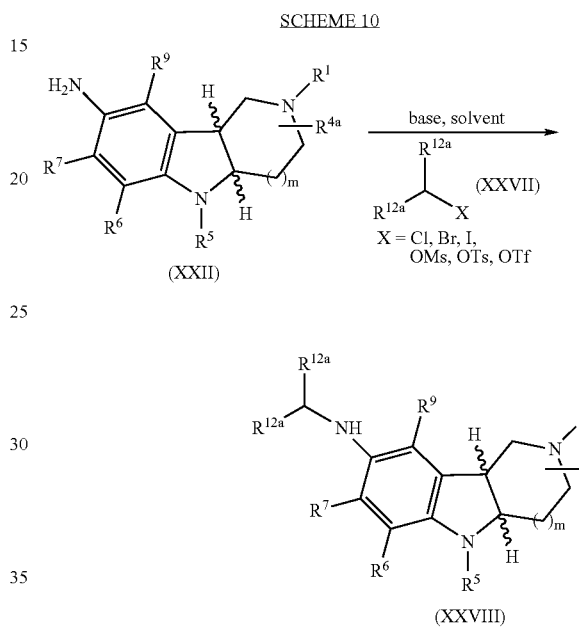

An alternate method for preparing secondary anilines (XXVI) or α-substituted secondary anilines (XXVIII) proceeds from bromides (XIX). Treatment of bromide (XIX) with a variety of alkyl or benzylamines (XXIX), which can be chiral if R$^{12a}$ and R$^{12a}$ are appropriate groups, in the presence of a Pd(0) catalyst, such as Pd$_2$(dba)$_3$, Pd(PPh$_3$)$_4$ or Pd(PPh$_3$)$_2$Cl$_2$, and suitable ligand such BINAP or PPh$_3$, and a base such as NaOtBu or CSCO$_3$ in a suitable solvent such as DMF, toluene, THF, DME, or the like, affords the anilines (XXVIII). In analogy of Scheme 8, the protocol described in Scheme 11 can also be applied to analogs of (XIX) where the R$^7$ or R$^9$ groups are Br, I, OTf, etc., to afford analogs of (XXX) or where the alkylamino group is on the R$^7$ or R$^9$ position.

SCHEME 11

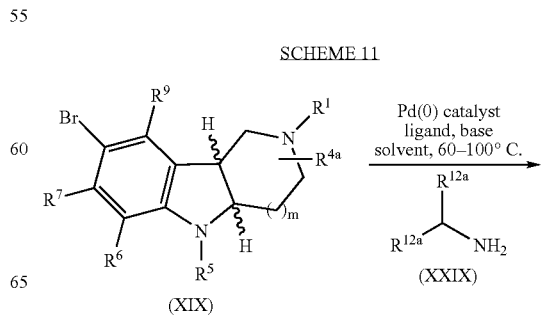

-continued

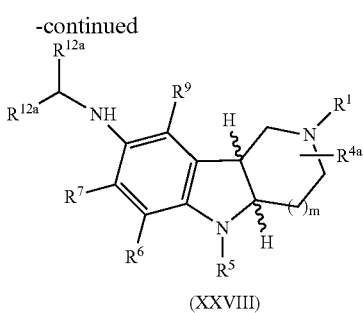

(XXVIII)

Scheme 12 shows another example for functionalizing arylbromides. Treatment of the arylbromide (XIX) with suitable base such as n-BuLi or t-BuLi followed by addition of $B(O\text{-}iPr)_3$ in a suitable solvent such as THF, DME, or the like, affords an aryl boronic ester intermediate. Treatment of the intermediate with suitable acid such as HOAc followed by oxidation with $H_2O_2$ affords the phenol derivatives (XXX). Coupling of these phenols (XXX) with various alkylhalides or alkylsulfonates (XXXI) in the presence of a suitable base such as NaH or KOH in a suitable solvent such as DMF, DMSO, toluene, THF, DME, or the like, affords the alkoxy indoline (XXXII). In analogy of Scheme 8, the protocol described in Scheme 12 can also be applied to analogs of (XIX) where the $R^7$ or $R^9$ groups are Br, I, OTf, etc., to afford analogs of (XXXII) where the alkoxy group is on the $R^7$ or $R^9$ position.

SCHEME 12

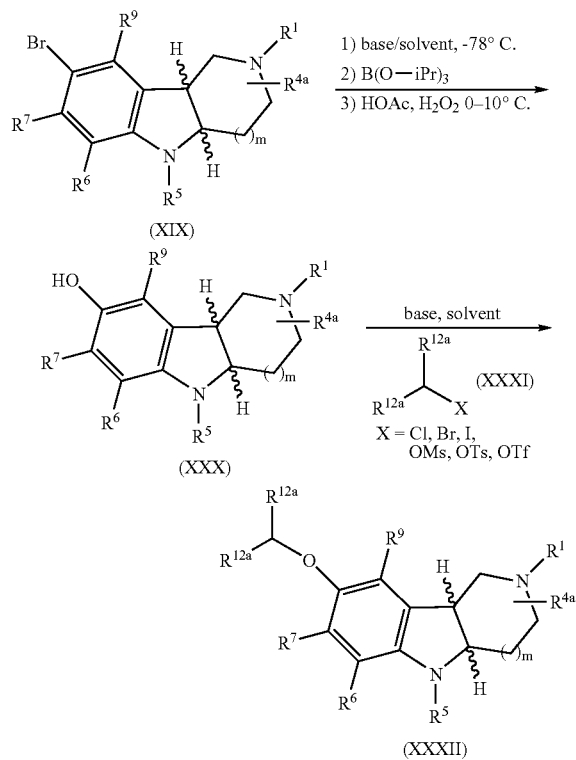

Alternatively, various alcohols (XXXIII) couple to the phenols (XXX) under Mitsunobu reaction condition (See Mitsunobu, O. *Synthesis* 1981, 1–28) in the presence of diethylazodicarboxylate (DEAD) with a suitable ligand such as $PPh_3$ or $Et_3P$ in a suitable solvent such as THF to afford the alkoxy indoline (XXXII) as shown in Scheme 13. In analogy of Scheme 8, the protocol described in Scheme 13 can also be applied to analogs of (XXX) where the $R^7$ or $R^9$ group is OH to afford analogs of (XXXII) or where the alkoxy group is on the $R^7$ or $R^9$ position.

SCHEME 13

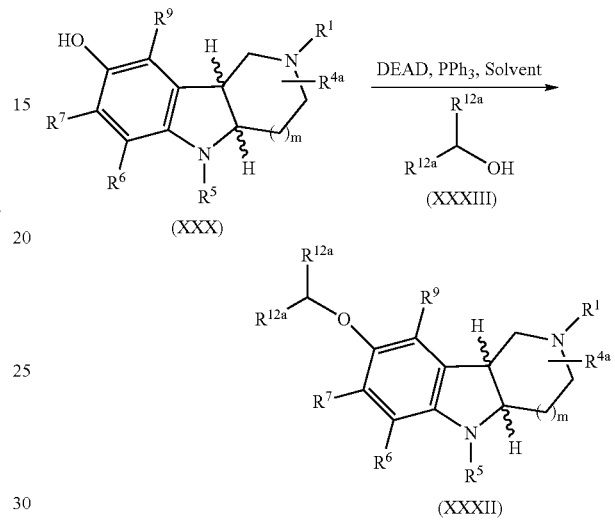

In addition, the phenols (XXX) also reacts with a functionalized aryl boronic acid (XXXIV) in the presence of Cu(II) species, such as $Cu(OAc)_2$ or $CuF_6(MeCN)_4$ and a base such as $NEt_3$ or $K_2CO_3$ in a suitable solvent such as $CH_2Cl_2$ to afford the aryloxy indoline (XXXV) as shown in Scheme 14. In analogy of Scheme 8, the protocol described in Scheme 14 can also be applied to analogs of (XXX) where the $R^7$ or $R^9$ group is OH to afford analogs of (XXXV) or where the aryloxy group is on the $R^7$ or $R^9$ position.

SCHEME 14

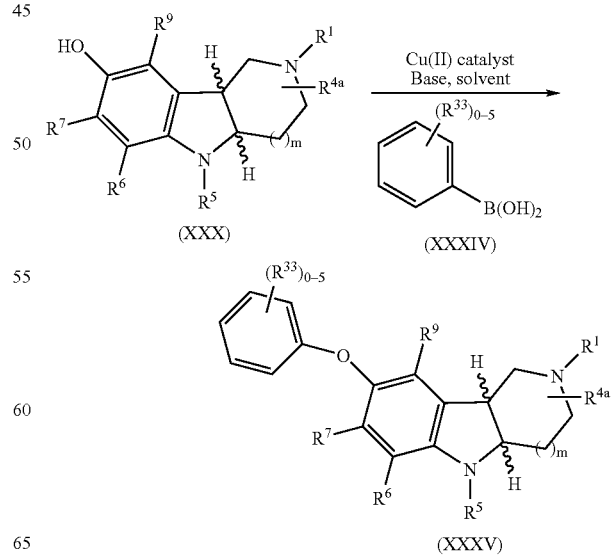

Similarly arylbromides can be converted to thiophenol derivatives as shown in Scheme 15. Treatment of the arylbromide (XIX) with suitable base such as n-BuLi or t-BuLi followed by addition of sulfur in a suitable solvent such as pentane, hexane, THF, DME, or the like, followed by aqueous work-up affords the thiophenol (XXXVI). Various alkylhalides or alkylsulfonates (XXXI) can be coupled to the thiophenol (XXXVI) in the presence of a suitable base such as $K_2CO_3$, $Na_2CO_3$, NaH or KOH in a suitable solvent such as DMF, DMSO, toluene, THF, DME, or the like, affords the sulfide derivatives (XXXVII). These sulfides (XXXV) can be oxidized by suitable oxidizers such as MCPBA, $NaIO_4$, $H_2O_2$, $KMnO_4$, or oxone in a suitable solvent such as $CH_2Cl_2$, $CHCl_3$, MeOH, EtOH, $H_2O$, or the like to give sulfoxides or sulfones (XXXVIII). In analogy of Scheme 8, the protocol described in Scheme 15 can also be applied to analogs of (XIX) where the $R^7$ or $R^9$ groups are Br, I, OTf, etc., to afford analogs of (XXXVII) and (XXXVIII) where the alkylthio, alkylsulfoxy or alkylsulfonyl group is on the $R^7$ or $R^9$ position.

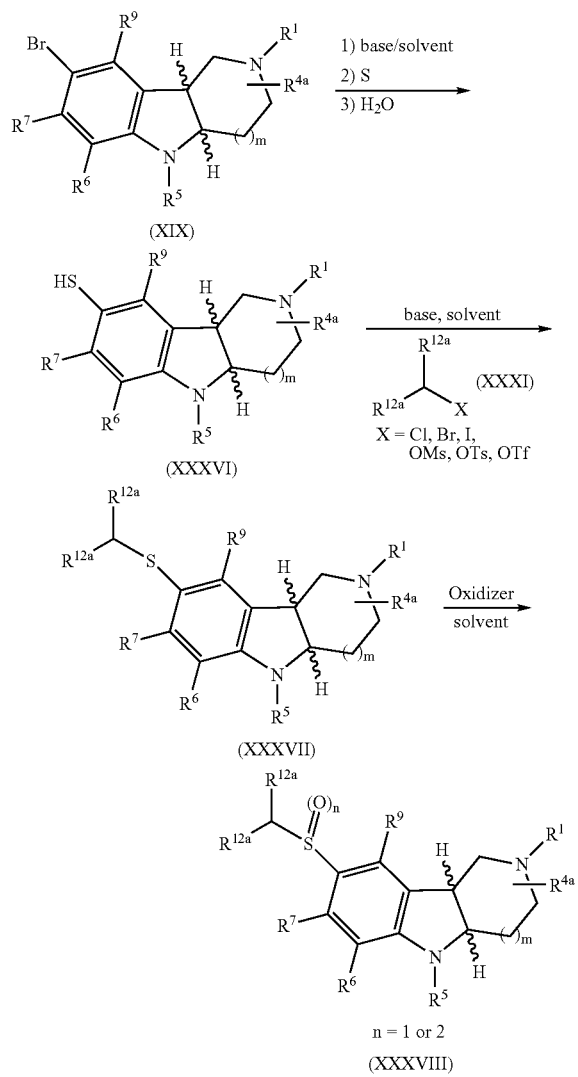

Another example is shown in Scheme 16. Treating bromide derivatives (XIX) with an appropriate alkyl zinc reagent (XXXIX), which can be generated from the corresponding alkyl halide, in the presence of Pd(0) catalyst such as $Pd_2(dba)_3$, $Pd(PPh_3)_4$ or $Pd(PPh_3)_2Cl_2$, and with or without a copper(I) salt, affords the derivatives (XL) where $R^8$ is a alkyl group (see Knochel, P., et. al. *Chem. Rev.* 1993, 93, 2117; and Weichert, A., et. al. *Syn. Lett.* 1996, 473). In analogy of Scheme 8, the protocol described in Scheme 16 can also be applied to analogs of (XIX) where the $R^7$ or $R^9$ groups are Br, I, OTf, etc., to afford analogs of (XL) where the alkoxy group is on the $R^7$ or $R^9$ position.

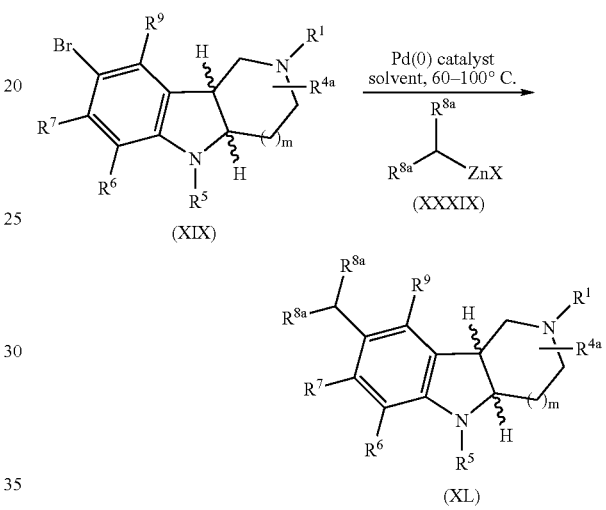

Furthermore, as an extension of this approach to a rapid preparation of a large array of biaryl indole and indoline derivatives, these bromide derivatives (XIX or XXIV) can be bound to a solid support and the arylamine couplings can be carried out on solid support as illustrated in Scheme 17. Towards that end treatment of indoline (XIX) with TFA in $CH_2Cl_2$, to remove the Boc protecting group, followed by extraction from aqueous base provides the free amine (XIX). The free amine can be loaded onto a suitable solid support such as (XLI) using conditions well known to those skilled in the art. Thus, p-nitrophenylchloroformate Wang resin (XLI) which can be obtained commercially from sources such as Novabiochem, Inc. is swollen in a suitable solvent such as N-methylpyrrolidinone and treated with 1.5 equiv. of amine to afford the functionalized resin (XLII). Arylamine couplings are then carried out in array format by treatment of resins (XLII) with a suitable palladium source such as $Pd_2(dba)_3$, $Pd(PPh_3)_4$, $Pd(dppf)Cl_2$ or $Pd(PPh_3)_2Cl_2$, and suitable ligand such BINAP or $PPh_3$, and a base such as NaOtBu or $CsCO_3$ with an excess (typically 5 equivalents) of an aniline. The coupling may be repeated to ensure complete conversion to the desired coupled product. Cleavage from the solid support by treatment with TFA affords the corresponding indoles and indolines (XLIII) as their TFA salts.

SCHEME 17

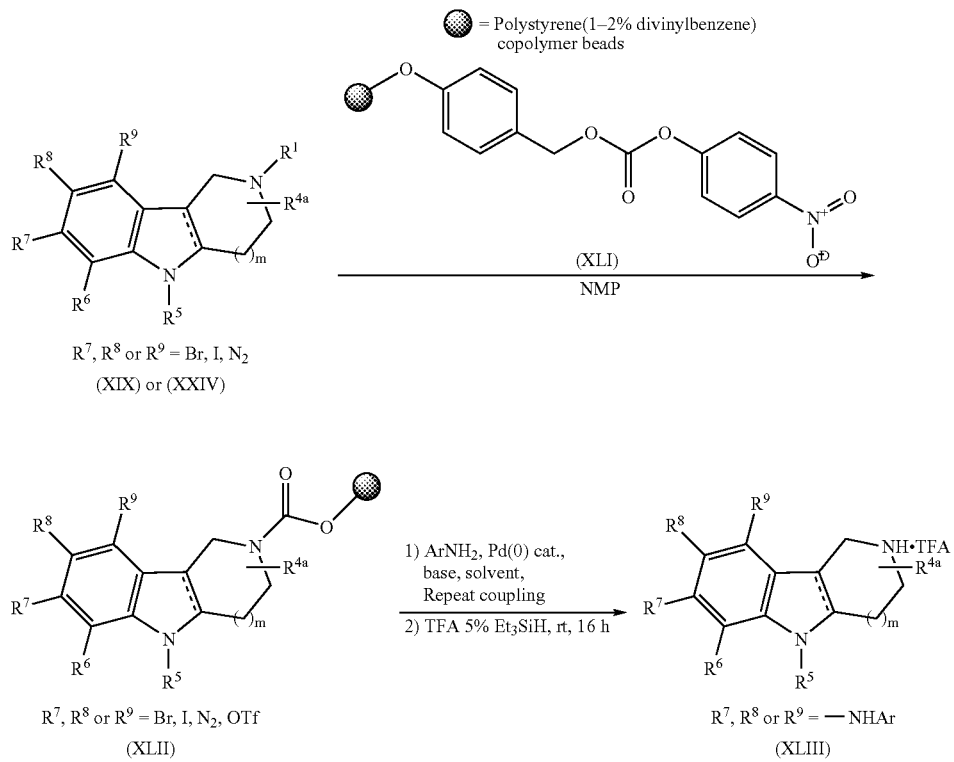

In addition, derivatives of type (I) can be alkylated with any number of functionalized alkyl sidechains. Typical procedures utilizing standard alkylation of a secondary amine with an alkylhalide under base catalyzed conditions are well known by those skilled in the art. For example, the secondary amino group of Formula (I) ($R^1$=H) can be alkylated with alkylhalides or alkylsulfonates in the presence of NaI or KI and a base such as $K_2CO_3$, $Na_2CO_3$, triethylamine, or the like, in dioxane or THF or other such solvent while heating (see Glennon, R. A., et. al., *Med. Chem. Res.*, 1996, 197) affords the $R^1$ alkylated indolines.

It is understood that the compounds of the present invention can be prepared in a number of ways well known to one skilled in the art of organic synthesis. The compounds of the present invention can be synthesized using the methods described herein, together with synthetic methods known in the art of synthetic organic chemistry, or variations thereon as appreciated by those skilled in the art. Additional methods include, but are not limited to, those described in U.S. Ser. No. 09/594,954 (filed Jun. 15, 2000); U.S. Ser. No. 09/595,250 (filed Jun. 15, 2000); U.S. Ser. No. 09/594,008 (filed Jun. 15, 2000); U.S. Ser. No. 10/026,793 (filed Dec. 19, 2001); U.S. Ser. No. 10/026,611 (filed Dec. 19, 2001); U.S. Ser. No. 10/026,404 (filed Dec. 19, 2001); wherein all references are hereby incorporated in their entirety herein by reference.

EXAMPLES

Example 1 cis-(4a,9b)-8-bromo-6-methylsulfanyl-2,3,4,4a,5,9b-hexahydro-1H-pyrido[4,3-b]indole

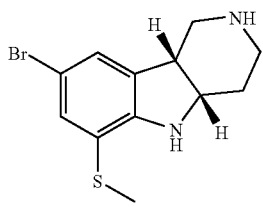

Step A. 2-Methylsulfanyl-phenylamine (23.6 g, 169.5 mmol) was suspended in conc. HCl (200 mL) and trifluoroacetic acid (130 mL), and cooled to 0° C. in an ice bath. Sodium nitrite (14.0 g, 203.4 mmol) was dissolved in water (45 mL) and added dropwise to the suspension over 45 min. After the addition, the reaction was stirred at 0° C. for 1 h. In a separate flask, tin(II) chloride (76 g, 338.4 mmol) was dissolved in conc. HCl (100 mL) and added slowly over 15 min to the reaction mixture. The resultant suspension was warmed to rt and stirred for 48 h. The reaction was filtered, washed with iso-propyl alcohol (15 mL), and dried to give 1-(2-methylsulfanyl-phenyl)hydrazine hydrochloride (30 g, 93%). $^1$H NMR (CD$_3$OD, 300 MHz) δ 7.44 (d, 1H, J=7.7 Hz), 7.32–7.26 (m, 1H), 7.08–7.00 (m, 2H), 2.39 (s, 3H) ppm.

Step B. 1-(2-Methylsulfanyl-phenyl)hydrazine hydrochloride (27 g, 141.9 mmol) and 4-piperidone monohydrate hydrochloride (21.8 g, 141.9 mmol) were dissolved in ethanol (350 mL) and heated at reflux for 45 min. Conc. HCl (30 mL) was added and heated at reflux for 12 h. The reaction was cooled to rt, filtered, washed with cold isopropyl alcohol (50 mL), and dried to give an off white solid, 6-methylsulfanyl-2,3,4,5-tetrahydro-1H-pyrido[4,3-b]indole hydrochloride (33 g, 92%).

$^1$H NMR (CD$_3$OD, 300 MHz) δ 7.24 (d, 1H, J=8.7 Hz), 7.08 (dd, 1H, J=0.7, 7.3 Hz), 6.93 (t, 1H, J=7.7 Hz), 3.29–3.27 (m, 2H), 3.17 (t, 2H, J=5.85 Hz), 2.85 (t, 2H, J=5.65 Hz), 2.44 (s, 3H) ppm.

Step C. 6-Methylsulfanyl-2,3,4,5-tetrahydro-1H-pyrido[4,3-b]indole hydrochloride (20 g, 78.74 mmol) was suspended in trifluoroacetic acid (562 mL) and cooled to 0° C. in an ice bath. NaCNBH$_3$ (19.53 g, 314.96 mmol) was added portion wise over 25 min and the mixture was stirred at 0° C. for 4 h. The reaction mixture was basified to pH 10 with conc. ammonium hydroxide and extracted with ethyl acetate (4×500 mL) and the organic layer separated. The organics were collected, dried over magnesium sulfate, and filtered to give cis-(4a,9b)-6-methylsulfanyl-2,3,4,4a,5,9b-hexahydro-1H-pyrido[4,3-b]indole. $^1$H NMR (CDCl$_3$, 300 MHz) δ 7.11 (d, 1H, J=7.7 Hz), 6.99 (d, 1H, J=7.3 Hz), 6.73 (t, 1H, J=5.7 Hz), 4.11 (s, 1H), 3.95–3.92 (m, 2H), 3.27–3.01 (m, 3H), 2.93–2.83 (m, 2H), 2.41 (s, 3H), 2.02–1.91 (m, 1H), 1.82–1.74 (m, 1H) ppm.

Step D. Cis-(4a,9b)-6-methylsulfanyl-2,3,4,4a,5,9b-hexahydro-1H-pyrido[4,3-b]indole (4 g, 18.2 mmol) was dissolved in CH$_2$Cl$_2$ (30 mL) and saturated potassium carbonate (25 mL) was added. This mixture was stirred vigorously and cooled to 0° C. in an ice bath. Di-tert-butyl dicarbonate (3.9 g, 18.2 mmol) and 4-dimethylamino-pyridine (10 mg, 0.082 mmol) in CH$_2$Cl$_2$ (20 mL) were added in 5 portions over 15 min. The mixture was stirred at 0° C. for 2 h. The organic layer was separated and aqueous layer was back extracted with CH$_2$Cl$_2$ (2×150 mL). The combined organics were dried over magnesium sulfate, filtered and concentrated under reduced pressure to give tert-butyl cis-(4a,9b)-6-methylsulfanyl-1,3,4,4a,5,9b-hexahydro-2H-pyrido[4,3-b]indole-2-carboxylate (4.84 g, 83%). $^1$H NMR (DMSO d$_6$ 300 MHz) δ 6.99 (d, 1H, J=7.8 Hz), 6.93 (dt, 1H, J=2.2, 7.4 Hz), 6.56 (t, 1H, J=7.6 Hz), 4.00–3.95 (m, 1H), 3.59 (dd, 1H, J=5.3, 8.3 Hz), 3.45–3.26 (m, 4H), 2.34 (s, 3H), 1.90–1.84 (m, 1H), 1.71–1.69 (m, 1H), 1.36 (s, 9H) ppm.

Step E. Tert-butyl cis-(4a,9b)-6-methylsulfanyl-1,3,4,4a,5,9b-hexahydro-2H-pyrido[4,3-b]indole-2-carboxylate (1 g, 3.13 mmol) was dissolved in DMF (4 mL) at rt, and cooled to 0° C. in an ice bath. In a separate flask N-bromosuccinimide (NBS) (0.56 g, 3.13 mmol) was dissolved in DMF (1.5 mL) and added slowly to the first solution over 5 min. The reaction mixture was stirred for 1 h at 0° C. The reaction was followed by thin layer chromatography until no more starting material was present. The reaction mixture was quenched with water (30 mL) and extracted with ethyl acetate (3×40 mL). The organic layers were collected and washed with brine (3×34 mL) and water (1×30 mL). The organic layer was dried over magnesium sulfate, filtered, and concentrated under reduced pressure to give an oil. The oil was purified by silica gel column chromatography, (15% ethyl acetate, hexanes) to afford tert-butyl cis-(4a,9b)-8-bromo-6-methylsulfanyl-1,3,4,4a,5,9b-hexahydro-2H-pyrido[4,3-b]indole-2-carboxylate as an oil (0.64 g, 51%). $^1$H NMR (CDCl$_3$, 300 MHz) δ 7.18 (d, 1H, J=1.9 Hz), 7.11 (s, 1H), 4.09–4.00 (m, 1H), 3.74–3.51 (m, 3H), 3.39–3.28 (m, 2H), 2.41 (s, 3H), 1.98–1.84 (m, 1H), 1.75–1.60 (m, 1H), 1.47 (s, 9H) ppm.

Step F. Tert-butyl cis-(4a,9b)-8-bromo-6-methylsulfanyl-1,3,4,4a,5,9b-hexahydro-2H-pyrido[4,3-b]indole-2-carboxylate (25 mg, 0.063 mmol) was dissolved in trifluoroacetic acid/chloroform (1:2, 1.5 mL) and stirred for 0.5 h. The solvent was evaporated under reduced pressure, and the residue was dissolved in water. The aqueous solution was basified with concentrated ammonium hydroxide to pH 12, and extracted with chloroform (3×10 mL). The organic solution was washed with brine, dried over magnesium sulfate, filtered and concentrated under reduced pressure to give the title compound as a yellow semi-solid (17.7 mg, 95%). $^1$H NMR (300 MHz, CD$_3$OD) δ7.27 (d, 1H, J=2.2 Hz), 7.18 (d, 1H, J=2.2 Hz), 3.50–3.10 (m, 3H), 3.11 (s, 3H), 2.68 (dd, 1H, J=12.9, 9.6 Hz), 2.38, (s, 3H), 2.28–2.05 (m, 2H) ppm MS (EI) 315.0 (M+H).

Example 2 cis-(4a,9b)-8-bromo-5-methyl-6-(methylsulfanyl)-2,3,4,4a,5,9b-hexahydro-1H-pyrido[4,3-b]indole

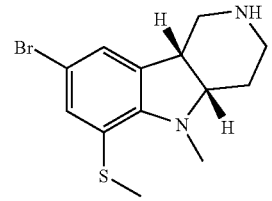

Step A. To a methylene chloride (300 mL) solution of 6-methylsulfanyl-2,3,4,5-tetrahydro-1H-pyrido[4,3-b]indole hydrochloride (from Example 1, Step B) (18.03 g, 71 mmol) was added triethylamine (14.3 g, 142 mmol) in one portion and resulted solution was stirred at rt for 10 min. The reaction was cooled to 0° C. in an ice bath then di-tert-butyl dicarbonate (18.6 g, 85 mmol) was added, and then reaction was allowed to warm slowly to rt and stir for 14 h. Reaction mixture was poured into water (300 mL) and then layers separated. The aqueous layer was extracted with chloroform (3×100 mL) and the organics collected, washed with brine (150 mL), dried over MgSO$_4$, and concentrated to dryness under reduced pressure. The resultant semi-solid was recrystalized from ethyl acetate to give tert-butyl 6-methylsulfanyl-1,3,4,5-tetrahydro-2H-pyrido[4,3-b]indole-2-carboxylate as sandy brown solid (7.2 g, 32%). $^1$H NMR (CDCl$_3$, 300 MHz) δ 8.19 (br s, 1H), 7.36 (d, 1H, J=8.0 Hz), 7.25 (d, 1H, J=6.9 Hz), 7.09 (t, 1H, J=7.7 Hz), 4.63 (br s, 2H), 3.82 (br s, 2H), 2.91–2.82 (m, 2H), 2.50 (s, 3H), 1.50 (s, 9H) ppm.

Step B. Tert-butyl 6-methylsulfanyl-1,3,4,5-tetrahydro-2H-pyrido[4,3-b]indole-2-carboxylate (7.2 g, 22.6 mmol), potassium hydroxide (6.3 g, 113 mmol), and iodomethane (32 g, 226 mmol) were combined with dry DME (110 mL) and stirred at rt for 10 h. The reaction was then filtered and the residue washed with chloroform. The filtrate was concentrated under reduced pressure to give tert-butyl 5-methyl-6-methylsulfanyl-1,3,4,5-tetrahydro-2H-pyrido[4,3-b]indole-2-carboxylate as an oily brown residue (7.7 g, 105%). $^1$H NMR (CDCl$_3$, 300 MHz) δ 7.32 (d, 1H, J=7.7 Hz), 7.12 (d, 1H, J=6.6 Hz), 7.03 (t, 1H, J=7.0 Hz), 4.61 (s, 2H), 4.08 (s, 3H), 3.85 (br s, 2H), 2.80 (br s, 2H), 2.49 (s, 3H), 1.49 (s, 9H) ppm Step C. Tert-butyl 5-methyl-6-methylsulfanyl-1,3,4,5-tetrahydro-2H-pyrido[4,3-b]indole-2-carboxylate (7.7 g, 23.9 mmol) was stirred in trifluoroacetic acid (120 mL) at 0° C. for 10 min, then sodium cyanoborohydride (8.25 g, 119 mmol) was added slowly while monitoring the internal reaction temperature to be below 5° C. during the addition. After the addition, the reaction was allowed to warm to rt under nitrogen and stir for 2 h. Ice chips were added and the reaction was cooled in an ice bath, and then basified to a pH~13 with 50% sodium hydroxide. The aqueous mixture was then extracted with chloroform (3×80 mL) and then the organics were collected, washed with brine (1×100 ml), dried over magnesium sulfate, and concentrated under reduced pressure to an oily residue. The residue was dissolved in chloroform (75 mL) and to this was added di-tert-butyl dicarbonate (3.2 g) and triethylamine (3.0 mL) the reaction was stirred for 2 h. The solvent evaporated under reduced pressure to give an oil. This oil was purified by silica gel column chromatography eluting with (5%, then 10%) ethyl acetate/hexanes, to give tert-butyl cis-(4a,9b)-5-methyl-6-methylsulfanyl-1,3,4,4a,5,9b-hexahydro-2H-pyrido[4,3-b]indole-2-carboxylate as a colorless oil (2.85 g, 36%) $^1$H NMR (CDCl$_3$, 300 MHz) δ 7.13 (dd, 1H, J=7.7, 1.1 Hz), 6.96 (d, 1H, J=7.4 Hz), 6.70 (t, 1H, J=7.3 Hz), 4.00–3.27 (m, 6H), 3.14 (s, 3H), 2.36 (s, 3H), 1.98–1.85 (m, 2H0, 1.42 (s, 9H) ppm.

Step D. Tert-butyl cis-(4a,9b)-5-methyl-6-methylsulfanyl-1,3,4,4a,5,9b-hexahydro-2H-pyrido[4,3-b]indole-2-carboxylate (60 mg, 0.19 mmol) was dissolved in anhydrous DMF (1 mL) at 0° C., to this was added NBS (33 mg, 0.19 mmol) in DMF (0.5 mL). This was stirred at 0° C. for 1 h. Then water (3 mL) was added and reaction partitioned over chloroform. Layers were separated and aqueous layer extracted with chloroform (3×5 mL). The organics were collected, washed with water (3×10 mL), dried over magnesium sulfate, and concentrated under reduced pressure to tert-butyl cis-(4a,9b)-8-bromo-5-methyl-6-methylsulfanyl-1,3,4,4a,5,9b-hexahydro-2H-pyrido[4,3-b]indole-2-carboxylate as a yellow solid (57 mg, 76%). $^1$H NMR (CDCl$_3$, 300 MHz) δ 7.19 (d, 1H, J=1.8 Hz), 7.02 (d, 1H, J=1.9 Hz), 3.60–3.20 (m, 6H), 3.10 (s, 3H), 2.36 (s, 3H), 1.94–1.80 (m, 2H), 1.43 (s, 9H) ppm.

Step E. Tert-butyl cis-(4a,9b)-8-bromo-5-methyl-6-methylsulfanyl-1,3,4,4a,5,9b-hexahydro-2H-pyrido[4,3-b]indole-2-carboxylate (20 mg, 0.048 mmol) was dissolved in trifluoroacetic acid/chloroform (1:2, 1.5 mL) and stirred for 0.5 h. The solvent was evaporated under reduced pressure to give the title compound as a yellow semi-solid (19 mg, 90%). $^1$H NMR (CD$_3$OD, 300 MHz) δ 7.27 (d, 1H, J=2.2 Hz), 7.17 (d, 1H, J=2.2 Hz), 3.50–3.30 (m, 3H), 3.28–3.12 (m, 2H), 3.11 (s, 3H), 2.69 (dd, 1H, J=9.6, 3.3 Hz), 2.38 (s, 3H), 2.28–2.00 (m, 2H) ppm. MS (CI, NH3) 315 (M+H).

Example 3 cis-(4a,9b)-6-methylsulfanyl-2,3,4,4a,5,9b-hexahydro-1H-pyrido[4,3-b]indol-8-amine

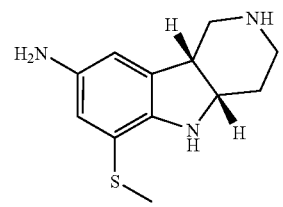

Step A. Tert-butyl cis-(4a,9b)-8-bromo-6-methylsulfanyl-1,3,4,4a,5,9b-2H-pyrido[4,3-b]indole-2-carboxylate (from Example 1 step E)(950 mg, 2.37 mmol) and di-tert-butyl dicarbonate (1.29 g, 5.92 mmol) were mixed together neat and heated at 86° C. for 6.5 h under nitrogen. The resultant residue was purified by silica gel column eluting with 7.5% ethylacetate/hexanes to give di(tert-butyl)cis-(4a,9b)-8-bromo-6-methylsulfanyl-3,4,4a,9b-tetrahydro-1H-pyrido[4,3-b]indole-2,5-dicarboxylate as a foam (1.13 g, 95%). $^1$H NMR (DMSO d$_6$, 300 MHz) δ 7.29 (s, 1H), 7.19 (s, 1H), 4.69–4.61 (m, 1H), 4.22–4.18 (m,1H), 3.71–3.62 (m,1H), 3.57–3.37 (m, 2H), 2.98–2.84 (m, 2H), 2.37 (s, 3H), 2.00–1.96 (m, 1H), 1.51 (s, 9H), 1.37 (s, 9H) ppm.

Step B. Di(tert-butyl)cis-(4a,9b)-8-bromo-6-methylsulfanyl-3,4,4a,9b-tetrahydro-1H-pyrido[4,3-b]indole-2,5-dicarboxylate (100 mg, 0.20 mmol), benzophenone imine (43 mg, 0.24 mmol), and sodium tert-butoxide (29 mg, 0.30 mmol) were dissolved/suspended in anhydrous toluene (1.5 mL) and then argon was bubbled through the reaction solution for 10 min. Then (R)-(+)-2,2'-bis(diphenylphosphino)-1,1'-binaphthyl (5 mg, 0.008 mmol) and tris(dibenzylideneacetone)dipalladium (0) (2 mg, 0.002 mmol) were added and then argon was bubbled through the reaction solution for 10 min, then heated at 90° C. for 5 h. Reaction mixture was cooled to rt, diluted with ethyl acetate (25 ml) and filtered. The filtrate was concentrated under reduced pressure to give a yellow colored oil. The oil was dissolved in methyl alcohol and to it added sodium acetate (33 mg, 0.40 mmol) and hydroxylamine hydrochloride (42 mg, 0.60 mmol) and stirred for 20 min at rt. Reaction was quenched with 6N sodium hydroxide to pH~12, and extracted with ethyl acetate (3×15 mL). Organic layer was separated, dried over magnesium sulfate, and concentrated under reduced. The oil residue was purified by silica gel column chromatography to give di(tert-butyl)cis-(4a,9b)-8-amino-6-methylsulfanyl-3,4,4a,9b-tetrahydro-1H-pyrido[4,3-b]indole-2,5-dicarboxylate as a foam (37 mg, 42%). $^1$H NMR (CDCl$_3$, 300 MHz) δ 6.46–6.36 (m, 2H), 4.69–4.59 (m, 1H), 4.38–4.24 (m, 1H), 3.91–3.82 (m, 1H), 3.72–3.20 (m, 4H), 3.00–2.78 (m, 2H), 2.40 (s, 3H), 2.05–1.92 (m, 1H), 1.60–1.34 (m, 18H) ppm.

Step C. Di(tert-butyl)cis(4a,9b)-8-amino-6-methylsulfanyl-3,4,4a,9b-tetrahydro-1H-pyrido[4,3-b]indole-2,5-dicarboxylate (37 mg, 0.085 mmol) was dissolved in chloroform (3 mL) and ethyl alcohol (0.4 mL) at rt. A stream of dry hydrogen chloride gas was allowed to bubble through this solution for 3 min. The reaction was concentrated under reduced pressure to give the title compound as a white solid (26 mg, 90%). $^1$H NMR (CD$_3$OD, 300 MHz) δ 7.14 (s, 2H), 4.07–4.02 (m, 1H), 3.58–3.40 (m, 2H), 2.89–2.85 (m, 1H), 2.46 (s, 3H), 2.19–2.14 (m, 2H) ppm. MS (ESI): 236.3 (M+H).

Example 4

[cis-(4a,9b)-6-methylsulfanyl-2,3,4,4a,5,9b-hexahydro-1H-pyrido[4,3-b]indol-8-yl]-phenyl-amine

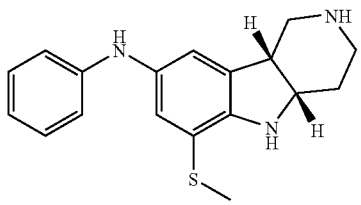

Step A. Triphenylbismuth (0.220 g, 0.50 mmol) was stirred with iodobenzene diacetate (0.18 g, 0.55 mmol) in CH$_2$Cl$_2$ (5 mL) for 15 h at rt. The solvent was evaporated and Et$_2$O (2 mL) with heptane (2 mL) was added and heated. The resulting solid was filtered hot affording bis(acetato)trisphenylbismuth (0.19 g, 70%) as a white flaky solid. $^1$H NMR (CDCl$_3$, 300 MHz) δ 8.15 (dd, 6H, J=1.1, 8.4 Hz), 7.62 (t, 6H, J=7.3 Hz), 7.50 (t, 3H, J=8.4 Hz), 1.81 (s, 6H) ppm.

Step B. Di(tert-butyl)cis-(4a,9b)-8-amino-6-methylsulfanyl-3,4,4a,9b-tetrahydro-1H-pyrido[4,3-b]indole-2,5-dicarboxylate (from example 6 step A 76 mg, 0.152 mmol) was combined with bis(acetato)trisphenylbismuth (93 mg, 0.167 mmol) and copper(II) acetate (2 mg, 0.015 mmol) in CH$_2$Cl$_2$ (2 mL) and stirred for 1.5 h. The solvent was evaporated and the black colored residue purified by silica gel column chromatography (20% EtOAc/Hex), affording a clear oil. This oil was then dissolved in EtOH (0.5 mL) and chloroform (2 ml) and HCl gas was allowed to bubble through for 10 min. The solvent was evaporated to give the title compound (50 mg, 78%). $^1$H NMR (CD$_3$OD, 300 MHz) δ 7.37–7.32 (m, 2H), 7.29–7.18 (m, 2H), 7.16–6.97 (m, 3H), 4.51–4.42 (m, 1H), 3.82–3.58 (m, 2H), 3.40–3.24 (m, 3H), 2.54 (s, 3H), 2.48–2.10 (m, 2H) ppm.

Example 5

(4-fluorophenyl)-[cis-(4a,9b)6-methylsulfanyl-2,3,4,4a,5,9b-hexahydro-1H-pyrido[4,3-b]indol-8-yl]-amine

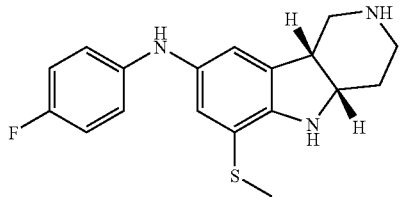

Step A. To a solution of p-fluorophenylmagnesium bromide (48.8 mL, 1.0 M THF) in dry diethyl ether (20 mL) was added bismuth(III)chloride (5.0 g, 15.8 mmol). The reaction was allowed to proceed at rt for 2 h. Ice was added and the aqueous layer extracted with ether (3×25 mL). The combined extracts were washed with brine (25 mL) and dried (MgSO$_4$) and evaporated. The residue was combined iodobenzene diacetate (3.4 g, 10.5 mmol) in CH$_2$Cl$_2$ (20 mL) for 15 h at rt. The solvent was evaporated affording bis(acetato)tris(4-fluorophenyl)bismuth (3.28 g, 34%). $^1$H NMR (CDCl$_3$, 300 MHz) δ 8.15–8.21 (m, 6H), 7.20–7.28 (m, 6H), 1.81 (s, 6H) ppm.

Step B. The title compound was prepared according to the procedure of Example 25, Step B (49 mg, 73%) using bis(acetato)tris(4-fluorophenyl)bismuth. $^1$H NMR (CD$_3$OD, 300 MHz) δ 7.20–6.93 (m, 6H), 4.53–4.40 (m, 1H), 3.82–3.56 (m, 2H), 3.40–3.31 (m, 3H), 2.53 (s, 3H), 2.50–2.01 (m, 2H) ppm.

Example 6

(4-methoxy-2-methyl-phenyl)-[cis-(4a,9b)-6-methylsulfanyl-2,3,4,4a,5,9b-hexahydro-1H-pyrido[4,3-b]indol-8-yl]-amine

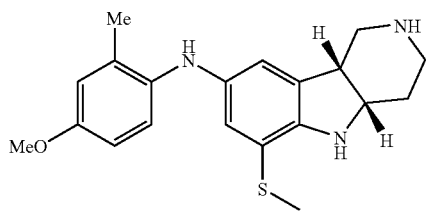

Step A. To a solution of 1-bromo-4-methoxy-2-methylbenzene (0.58 mg, 3.0 mmol) in dry THF (15 mL) was added magnesium turnings. The reaction was heated at 60° C. in an oil bath and the magnesium turnings were gently crushed with a glass rod. A small crystal of iodine was also added. Reaction was removed from the oil bath when bubbling was observed, and 1-bromo-4-methoxy-2-methylbenzene (5.18 g, 27.00 mmol) was added slowly in dry THF (25 mL). Reaction was stirred at rt for 15 min. Then the solution was transferred via syringe to a dry flask under nitrogen and cooled to 0° C. in an ice bath. Bismuth(III)chloride (2.84 g, 315 mmol) was added slowly and the resultant heterogeneous solution was allowed to warm to rt and stir for 4 h. The reaction was filtered through a bed of Celite and the filtrate collected. The filtrate was poured onto ice and the aqueous layer extracted with ethyl acetate (2×50 mL). The combined extracts were washed with brine (25 mL) and dried (MgSO$_4$) and evaporated. The residue was recrystallized from ethyl acetate to give a yellowish solid. This solid was combined with iodobenzene diacetate (1.33 g, 4.1 mmol) in CH$_2$Cl$_2$ (45 mL) for 15 h at rt. The solvent was evaporated affording bis(acetato)tris(2-methyl-4-methoxyphenyl)bismuth (805 mg, 4.3%). $^1$H NMR (CDCl$_3$, 300 MHz) δ 8.21(d, 3H, J=8.5 Hz), 6.95 (s, 6H), 3.83 (s, 9H), 2.57 (s, 9H), 1.73 (s, 6H) ppm.

Step B. The title compound was prepared according to the procedure of Example 7, Step B (49 mg, 73%) using bis(acetato)tris(2-methyl-4-methoxyphenyl)bismuth. $^1$H NMR (CD$_3$OD, 300 MHz): δ 7.10–7.05 (m, 1H), 6.84 (s, 1H), 6.80–6.72 (m, 1H), 6.64 (s, 1H), 6.51 (s, 1H), 4.52–4.41 (m, 1H), 3.76 (s, 3H), 3.66–3.56 (m, 1H), 3.40–3.19 (m, 3H), 2.48–2.39 (m, 4H), 2.17–2.04 (m, 4H) ppm.

Example 7 trans-(4a,9b)-8-bromo-2,5-dimethyl-6-[(4-methylphenyl)sulfanyl]-2,3,4,4a,5,9b-hexahydro-1H-pyrido[4,3-b]indole

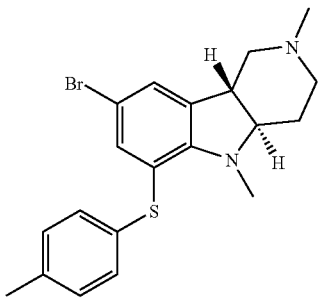

Step A. 2-Iodoaniline (16 g, 73 mmol) was suspended in concentrated hydrochloric acid (100 mL), and then cooled to 0° C. in an ice bath. Sodium nitrite (6 g, 87.6 mmol) in water (25 mL) was added slowly to reaction mixture and then reaction allowed to stir at 0° C. for 1.5 h. In a separate flask, tin(II) chloride (84.7 g, 182.5 mmol) was dissolved in concentrated hydrochloric acid (12 mL) and added slowly over 30 min to reaction mixture. The resulting suspension was allowed to warm to rt and stirred for 14 h. The solid was filtered off, and allowed to dry to afford 1-(2-iodophenyl)hydrazine hydrochloride (19 g, 96%). $^1$H NMR (CDCl$_3$, 300 MHz) δ 7.82 (dd, 1H, J=1.1, 7.7 Hz), 7.39 (dt, 1H, 1.2, 7.7 Hz), 6.96 (dd, 1H, J=1.1, 8.1 Hz), 6.82 (dt, 1H, J=1.1, 7.5) ppm. MS (ApCI) 275 (M$^+$+CH3CN+H).

Step B. 1-(2-Iodophenyl)hydrazine hydrochloride (1.67 g, 6.2 mmol) and 4-piperidone monohydrate hydrochloride (0.952 g, 6.2 mmol) were dissolved in trifluoroethanol (15 mL) and concentrated hydrochloric acid (5 mL) and heated at 87° C. and stirred for 3 h. The solid was filtered, washed with cold isopropyl alcohol (50 mL), and dried to give 6-iodo-2,3,4,5-tetrahydro-1H-pyrido[4,3-b]indole hydrochloride (1.76 g, 85%) as a tan solid. $^1$H NMR (CD$_3$OD, 300 MHz) δ 7.49 (d, 1H, J=7.7 Hz), 7.43 (d, 1H, J=8 Hz), 6.82 (t, 1H, J=7.7 Hz), 4.40 (s, 2H), 3.60 (t, 2H, J=6.25 Hz), 3.18 (t, 2H, J=5.85 Hz) ppm.

Step C. 6-Iodo-2,3,4,5-tetrahydro-1H-pyrido[4,3-b]indole hydrochloride (7 g, 21 mmol) was suspended in CH$_2$Cl$_2$ (150 mL) and to this suspension was added 4-dimethylamino-pyridine (0.1 g, 0.82 mmol) and saturated potassium carbonate solution (150 mL) with stirring. Then di-tert-butyl dicarbonate (5.5 g, 25.2 mmol) in dichloromethane (20 mL) was added in 5 portions over 5 min. The resulting two-phase mixture was stirred vigorously at rt for 1.5 h. Layers were separated and aqueous layer was back extracted with CH$_2$Cl$_2$ (2×100 mL). The organics were collected, dried over magnesium sulfate, filtered and then concentrated under reduced pressure to give tert-butyl 6-iodo-1,3,4,5-tetrahydro-2H-pyrido[4,3-b]indole-2-carboxylate (7.06 g, 84%). $^1$H NMR (CDCl$_3$ 300 MHz) δ 7.63 (d, 1H, J=7.7 Hz), 7.38 (d, 1H, J=7.7 Hz), 6.76 (t, 1H, J=7.5 Hz), 4.59 (br s, 2H), 3.82 (br s, 2H), 2.78 (t, 2H, J=5.3 Hz), 1.49 (s, 9H) ppm.

Step D. Tert-butyl 6-iodo-1,3,4,5-tetrahydro-2H-pyrido[4,3-b]indole-2-carboxylate (6.8 g, 17 mmol) was dissolved in DME (50 mL), and potassium hydroxide (4.8 g, 85.4 mmol) and iodomethane (15.7 g, 110.5 mmol) were added and heated at 80° C. in a pressure vessel for 3 h. The reaction was cooled to rt and diluted with ethyl acetate (50 mL). The solids were removed by vacuum filtration. The filtrate was concentrated under reduced pressure to give a brown oil (5.5 g, 79% crude yield). The oil was dissolved in CH$_2$Cl$_2$ (30 mL). Trifluoroacetic acid (30 mL) was added in ten portions over 5 min and stirred for 30 min. The reaction was basified with 50% sodium hydroxide to pH 12. This mixture was extracted with CH$_2$Cl$_2$ (3×150 mL). The organics were collected, dried over magnesium sulfate, filtered and then concentrated under reduced pressure to give 6-iodo-5-methyl-2,3,4,5-tetrahydro-1H-pyrido[4,3-b]indole (3.85 g, 73%). $^1$H NMR (CDCl$_3$ 300 MHz) δ 7.62 (d, 1H, J=7.6 Hz), 7.33 (d, 1H, J=7.7 Hz), 6.74 (t, 1H, J=7.5 Hz), 4.03 (s, 2H), 3.95 (s, 3H), 3.26 (t, 2H, J=5.6 Hz), 2.71 (t, 2H, J=5.6 Hz) ppm.

Step E. 6-Iodo-5-methyl-2,3,4,5-tetrahydro-1H-pyrido[4,3-b]indole (3.85 g, 12.3 mmol) was suspended in methanol (40 mL). Formaldehyde (14 mL of 37%) was added and heated at reflux for 2 h. The reaction was cooled to 0° C. in an ice bath and sodium borohydride (1.7 g, 46 mmol) was added slowly over 15 min and stirred for 2 h at 0–10° C. The reaction was diluted with water (200 mL) and extracted with CH$_2$Cl$_2$ (3×150 mL). The organics were collected, washed with brine (250 mL), dried over magnesium sulfate, filtered and concentrated under reduced pressure. The product was purified by silica gel column chromatography (3% MeOH/CH$_2$Cl$_2$) to give 6-iodo-2,5-dimethyl-2,3,4,5-tetrahydro-1H-pyrido[4,3-b]indole (0.6 g, 15%). $^1$H NMR (CDCl$_3$ 300 MHz) δ 7.59 (d, 1H, J=7.4 Hz), 7.33 (d, 1H, J=7.6 Hz), 6.73 (t, 1H, J=7.7 Hz), 3.98 (s, 3H), 3.62 (s, 2H), 2.83 (s, 4H), 2.55 (s, 3H) ppm.

Step F. 6-Iodo-2,5-dimethyl-2,3,4,5-tetrahydro-1H-pyrido[4,3-b]indole (1 g, 3 mmol) was dissolved in BH$_3$-THF complex (15 mL) and heated at 75° C. for 18 h in a pressure vessel. The reaction was cooled to rt and concentrated under reduced pressure to a residue. The residue was heated at reflux in 6N hydrochloric acid (15 mL) for 3.5 h. The reaction was basified with 50% sodium hydroxide to pH 12. The mixture was extracted with CH$_2$Cl$_2$ (3×100 mL). The organics were collected, dried over magnesium sulfate, filtered and concentrated under reduced pressure. The residue was purified by silica gel column chromatography (4% methanol, dichloromethane) to give trans-(4a,9b)-6-iodo-2,5-dimethyl-2,3,4,4a,5,9b-hexahydro-1H-pyrido[4,3-b]indole (0.12 g, 12%). $^1$H NMR (CDCl$_3$ 300 MHz) δ 7.56 (dt, 1H, J=2.2, 8.1 Hz), 7.33 (d, 1H, J=7.3 Hz), 6.50 (t, 1H, J=7.5 Hz), 3.48–3.41 (m, 1H), 3.04(s, 3H), 2.86–2.75 (m, 1H), 2.42 (s, 3H), 2.20–2.13 (m, 3H), 1.93–1.78 (m, 1H) ppm.

Step G. Trans-(4a,9b)-6-iodo-2,5-dimethyl-2,3,4,4a,5,9b-hexahydro-1H-pyrido[4,3-b]indole (910 mg, 2.7 mmol) was combined with p-tolylthiophenol (426 mg, 3.3 mmol), sodium hydride (132 mg, 3.3 mmol, 60% in oil dispersion), copper iodide (515 mg, 2.7 mmol) and 1,3-dimethyl-3,4,5,6-tetrahydro-2(1H)-pyrimidinone (5 mL) and stirred at 100° C. for 16 h. The reaction mixture was partitioned between water and CHCl$_3$. The aqueous layer was extracted with CHCl₃ (3×20 mL). The combined organics were washed with sat. NaCl (10 mL), water (10 mL), dried (MgSO₄) and evaporated. The residue was loaded onto a SCX resin. The resin was washed with 150 mL of MeOH followed by washing with 2.0 M methanolic ammonia. The collected residue was dissolved in CH₃CN and 1N HCl/Ether was added until no further precipitation was observed. The solid was filtered and washed with CH₃CN affording the trans-(4a,9b)-2,5-dimethyl-6-[(4-methylphenyl)sulfanyl]-2,3,4,4a,5,9b-hexahydro-1H-pyrido[4,3-b]indole (315 mg, 36%) as a white solid. ¹H NMR (CD₃OD, 300 MHz) δ 7.20 (d, 1H, J=7.7 Hz), 7.14 (d, 1H, J=7.3 Hz), 7.06 (d, 2H, J=8.1 Hz), 6.97 (d, 2H, J=8.4 Hz), 6.82–6.87 (m, 1H), 3.99–4.05 (m, 1H), 3.71–3.80 (m, 1H), 3.15–3.25 (m, 4H), 3.08 (s, 3H), 2.99 (s, 3H), 2.38–2.43 (m, 1H), 2.26 (s, 3H), 1.90–2.03 (m, 1H) ppm.

Step H. The title compound (140 mg, 45%) was prepared from trans-(4a,9b)-2,5-dimethyl-6-[(4-methylphenyl)sulfanyl]-2,3,4,4a,5,9b-hexahydro-1H-pyrido[4,3-b]indole (250 mg, 0.77 mmol) and NBS (164 mg, 0.92 mmol) using the same procedure described in Example 18, Step D. ¹H NMR (CD₃OD, 300 MHz) δ 7.32 (br s, 1H), 7.19 (d, 1H, J=1.5 Hz), 7.13 (q, 4H, J=8.4 Hz), 4.27–4.19 (m, 1H), 3.80–3.75 (m, 1H), 3.40–3.20 (m, 4H), 3.11 (s, 3H), 2.98 (s, 3H), 2.47–2.40 (m, 1H), 2.30 (s, 3H), 2.20–2.02 (m, 1H) ppm. MS (CI, NH3) 404 (M+H).

Example 8 cis-(4a,9b)-8-bromo-2,5-dimethyl-6-[(4-methylphenyl)sulfanyl]-2,3,4,4a,5,9b-hexahydro-1H-pyrido[4,3-b]indole

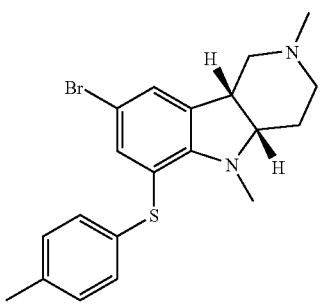

Trans-(4a,9b)-8-bromo-2,5-dimethyl-6-[(4-methylphenyl)sulfanyl]-2,3,4,4a,5,9b-hexahydro-1H-pyrido[4,3-b]indole (Example 28, 77 mg, 0.19 mmol) and NaOMe (5 mg, 0.10 mmol) were combined with MeOH (0.5 mL) and DMF (0.5 mL). This mixture was then heated at 100° C. and MeOH was allowed to distill out. Then CuI (3.6 mg, 0.019 mmol) was added in one portion. Reaction was maintained at 100° C. for 2 h. It was allowed to cool to rt. Ice water (10 mL) was added, solid was removed by filtration. The filtrate was extracted with chloroform (3×25 mL). Extracts were combined, dried, and concentrated. The residue was purified by silica gel column chromatography (CHCl₃, then 3% MeOH/CHCl₃) to give the title compound (25 mg, 32%) as a semi-solid. ¹H NMR (CDCl₃, 300 MHz) δ 7.26 (s, 1H), 7.11 (s, 1H), 7.07–7.04 (m, 2H), 6.99–6.96 (m, 2H), 3.33–3.19 (m, 2H), 3.02 (s, 3H), 2.67–2.60 (m, 1H), 2.44–2.37 (m, 1H), 2.29 (s, 3H), 2.26 (s, 3H), 2.23–2.19 (m, 1H), 2.17–1.86 (m, 3H) ppm.

Example 9 trans-(4a,9b)-2,5-dimethyl-6-[(4-methylphenyl)sulfanyl]-8-phenylsulfanyl-2,3,4,4a,5,9b-hexahydro-1H-pyrido[4,3-b]indole

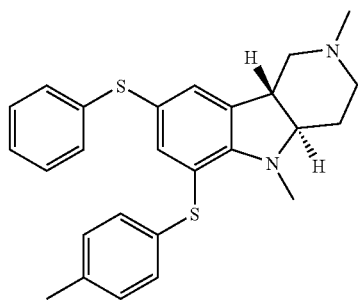

To an Et₂O solution (0.5 mL) of trans-(4a,9b)-8-bromo-2,5-dimethyl-6-[(4-methylphenyl)sulfanyl]-2,3,4,4a,5,9b-hexahydro-1H-pyrido[4,3-b]indole (Example 10, 100 mg, 0.25 mmol) and TMEDA (58 mg, 0.50 mmol) cooled in an acetone-dry ice bath was added dropwise t-BuLi (1.7 M pentane solution, 0.29 mL, 0.49 mmol). Resulted solution was allowed to maintain at −78° C. for 15 min at which time an Et₂O solution (0.5 mL) of S-phenylbenzosulfonate (124 mg, 0.49 mmol) was added dropwise over 2 min. Cooling bath was removed and reaction was allowed to warm to rt over 20 min. This reaction was then allowed to stir at rt for additional 20 min before it was poured onto ice-cooled 1 M H₂SO₄ aq solution (5 mL). This mixture was extracted with CHCl₃ (3×10 mL), organic phases were combined, dried (MgSO₄) and concentrated. Resulted residue was then purified by SGC (5% MeOH/CH₂Cl₂) to provide the title compound (35 mg, 28%) as a light brown colored oil. ¹H NMR (CDCl₃, 300 MHz) δ 7.32 (d, 1H, J=0.8 Hz), 7.24–7.01 (m, 10H), 3.37 (dd, 1H, J=10.3, 3.0 Hz), 3.09 9s, 3H), 2.83 (t, 1H, J=11.0 Hz), 2.60–2.51 (m, 1H), 2.40 (s, 3H), 2.29 (s, 3H), 2.20–2.01 (m, 2H), 1.89–1.77 (m, 1H) ppm.

Example 10 di(tert-butyl)cis-(4a,9b)-8-bromo-6-methyl-3,4,4a,9b-tetrahydro-1H-pyrido[4,3-b]indole-2,5-dicarboxylate

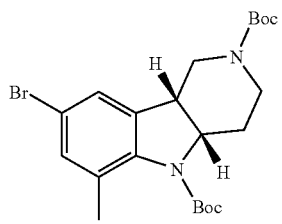

Step A. o-Tolylphenylhydrazine hydrogen chloride (25 g, 158.6 mmol) and 4-piperidone monohydrate hydrogen chloride (24.4 g, 158.6 mmol) were suspended in EtOH (310 mL). Concentrated aqueous HCl (26 g, 317 mmol) was then added. The mixture was refluxed for 3 h, and then the reaction was cooled to rt. The ppt was filtered and washed with cold EtOH. The white solid was air-dried for 18 h. 6-methyl-2,3,4,5-tetrahydro-1H-pyrido[4,3-b]indole hydrochloride (36.6 g, 141.2 mmol, 89%) was isolated and a white powder. $^1$H NMR (CD$_3$OD, 300 MHz) δ 7.22–7.25 (1H, m), 6.89–6.96 (2H, m), 4.40 (2H, m), 3.60 (2H, t, 6.2 Hz), 3.16 (2H, t, 6.2 Hz), 2.45 (3H, s) ppm.

Step B. 6-Methyl-2,3,4,5-tetrahydro-1H-pyrido[4,3-b]indole hydrochloride (36.6 g, 141.2 mmol) was suspended in TFA (200 mL). The mixture was cooled to 0° C. Et$_3$SiH (32.86 g, 282.6 mmol) was added slowly. The reaction was stirred at rt for 18 h. Add hexane (2×300 mL), separate the acid layer, then basified with 50% NaOH until pH=14. Extract reaction with CHCl$_3$ (3×300 mL). The combined organic layers were washed with brine, dried, and concentrated to afford a light brown amorphous solid cis-6-methyl-2,3,4,4a,5,9b-hexahydro-1H-pyrido[4,3-b]indole (20.7 g, 110.1 mmol, 78%). $^1$H NMR (CDCl$_3$, 300 MHz) δ 6.90 (1H, d, 7.3 Hz), 6.82 (1H, d, 7.4 Hz), 6.62 (1H, t, 7.3 Hz), 3.77–3.82 (1H, m), 2.65–3.08 (5H, m), 2.13 (3H, s), 1.72–1.92 (2H, m) ppm.

Step C. Cis-(4a,9b)-6-methyl-2,3,4,4a,5,9b-hexahydro-1H-pyrido[4,3-b]indole (20.7 g, 110.1 mmol) and BOC$_2$O (96.25 g, 440.4 mmol) is heated at 110° C. for 3 hrs. Cool to rt and quench with water (20 mL). Add brine (200 mL) and EtOAc (200 mL); stir 10 min. Separate layers and re-extract aqueous with EtOAc (2×100 mL). Wash combined organic layers with brine, dry, and conc. 43 g of a brown, amorphous solid was isolated. The residue was purified by column chromatography (20–40% EtOAc/Hexane). Di(tert-butyl)cis-(4a,9b)-6-methyl-3,4,4a,9b-tetrahydro-1H-pyrido[4,3-b]indole-2,5-dicarboxylate (42 g, 108.2 mmol, 98%) was isolated as a clear viscous oil. $^1$H NMR (DMSO, 400 MHz) δ 6.9–7.1 (3H, m), 4.5–4.7 (2H, m), 4.1–4.3 (1H, m), 3.55–3.65 (1H, m), 3.30–3.50 (2H, m), 2.8–3.0 (1H, m), 2.20 (3H, s), 1.50 (9H, s), 1.30 (9H, s) ppm.

Step D. Di(tert-butyl)cis-(4a,9b)-6-methyl-3,4,4a,9b-tetrahydro-1H-pyrido[4,3-b]indole-2,5-dicarboxylate (1,73 g, 4.46 mmol) was dissolved in DMF (8 mL); the solution was then cooled to 0° C. NBS (0.874 g, 4.90 mmol) was added as a solution in DMF(8 mL). The reaction was warmed to rt and stirred for 1 h. Add brine (10 mL) and EtOAc (10 mL). Stir 10 min and separate layers. Re-extract aqueous with EtOAc (2×20 mL). Wash combined organic with brine, dry, and concentrate. 1.88 g of an orange viscous oil was isolated. This crude residue was purified by column chromatography (10–30% acetone/hexane). Di(tert-butyl)cis-(4a,9b)-8-bromo-6-methyl-3,4,4a,9b-tetrahydro-1H-pyrido[4,3-b]indole-2,5-dicarboxylate (1.12 g, 2.41 mmol, 54%) was isolated as a pale-yellow, amorphous solid. $^1$H NMR (DMSO d$_6$, 400 MHz) δ 7.52 (1H, d, 7.5 Hz), 7.29–7.36 (2H, m), 4.55 (1H, ddd, 5.2 Hz, 6.4 Hz, 9.7 Hz), 3.66 (1H, dd, 3.7 Hz, 14.2 Hz), 3.64–3.66 (1H, m), 3.46 (1H, dd, 4.1 Hz, 13.9 Hz), 3.30–3.36 (1H, m), 2.00–3.09 (2H, m), 2.07–2.15 (1H, m), 1.65–1.76 (1H, m) ppm.

Example 11

Di(tert-butyl)(4aS,9bR)-8-bromo-6-methyl-3,4,4a,9b-tetrahydro-1H-pyrido[4,3-b]indole-2,5-dicarboxylate

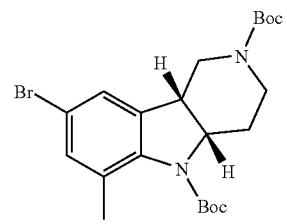

Step A. Di(tert-butyl)(4aS,9bR)-6-methyl-3,4,4a,9b-tetrahydro-1H-pyrido[4,3-b]indole-2,5-dicarboxylate was obtained from Di(tert-butyl)cis-(4a,9b)-6-methyl-3,4,4a,9b-tetrahydro-1H-pyrido[4,3-b]indole-2,5-dicarboxylate (Example 32 Step C) by using preparative HPLC on a ChiralPak® AD column (1% IPA in hexane).

Step B. Di(tert-butyl)(4aS,9bR)-6-methyl-3,4,4a,9b-tetrahydro-1H-pyrido[4,3-b]indole-2,5-dicarboxylate (20.2 g, 51.99 mmol) was brominated according to the procedure of Example 13, Step D to give the title compound (21.3 g, 45.7 mmol, 88%) as a pale-yellow, amorphous solid. $^1$H NMR (DMSO, 400 MHz) identical to Example 13.

Example 12 di(tert-butyl)(4aS,9bR)-8-amino-6-methyl-3,4,4a,9b-tetrahydro-1H-pyrido[4,3-b]indole-2,5-dicarboxylate

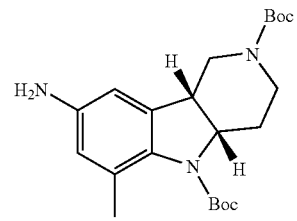

A solution of di(tert-butyl)(4aS,9bR)-8-bromo-6-methyl-3,4,4a,9b-tetrahydro-1H-pyrido[4,3-b]indole-2,5-dicarboxylate (Example 14) (9.35 g, 20.0 mmol), benzophenone imine (4.35 g, 24.0 mmol), (S)-(−)-2,2'-bis(diphenylphosphino)-1,1'-binaphthyl (BINAP) (934 mg, 1.5 mmol), Pd$_2$dba$_3$ (1.04 g, 1.0 mmol) and sodium tert-butoxide (2.7 g, 28.0 mmol) in degassed toluene (325 mL) was heated at reflux under Argon atmosphere for 18 h. The solution was cooled and filtered through a pad of silica gel and eluted with EtOAc. The volatiles were removed under reduced pressure. The residue was taken up in methanol (200 mL) and then there was added NaOAC (3.43 g, 41.76 mmol) and hydroxylamine hydrochloride (2.2 g, 31.32 mmol) and the mixture was stirred at rt for 1 h. The volatiles were removed under reduced pressure and the residue purified by column chromatography (20, 70% ethyl acetate/hexane) to afford the title compound (5.17 g, 12.8 mmol, 74%). MS (APCI): 404 (base, M+H).

General Method for Preparation of aryl-[(4aS,9bR)-6-methyl-2,3,4,4a,5,9b-hexahydro-1H-pyrido[4,3-b]indol-8-yl]-amine Step A. A solution of di(tert-butyl)(4aS,9bR)-8-amino-6-methyl-3,4,4a,9b-tetrahydro-1H-pyrido[4,3-b]indole-2,5-dicarboxylate (Example 18, 93.3 mg, 0.23 mmol), arylbromide (0.23 mmol), BINAP (4.6 mg, 0.0069 mmol), $Pd_2 dba_3$ (2.4 mg, 0.0023 mmol) and sodium tert-butoxide (44.5 mg, 0.46 mmol) in degassed toluene (2 mL) was heated at 80° C. for 18 h. The solution was cooled and filtered through a pad of silica gel and elute with EtOAc. The solvents were removed under reduced pressure and the residue purified by column chromatography (10, 20, 30% ethyl acetate/hexane) to afford di(tert-butyl)(4aS,9bR)-8-anilino-6-methyl-3,4,4a,9b-tetrahydro-1H-pyrido[4,3-b]indole-2,5-dicarboxylate.

Step B. A solution of di(tert-butyl)(4aS,9bR)-8-anilino-6-methyl-3,4,4a,9b-tetrahydro-1H-pyrido[4,3-b]indole-2,5-dicarboxylate in 20% $TFA/CH_2Cl_2$ (1 mL) was stirred at rt for 1 h. The reaction mixture was basified with $NH_4OH$ to pH=12, then extracted with $CHCl_3$ (3×3 mL). The combined organic layer was washed with brine, dried, and concentrated to afford the title compounds.

Example 13

(2,3-dichlorophenyl)-[(4aS,9bR)-6-methyl-2,3,4,4a,5,9b-hexahydro-1H-pyrido[4,3-b]indol-8-yl]-amine

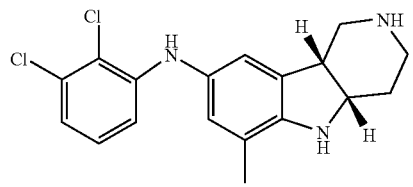

The title compound (40 mg, 50%) was prepared by the general method from di(tert-butyl)(4aS,9bR)-8-amino-6-methyl-3,4,4a,9b-tetrahydro-1H-pyrido [4,3-b]indole-2,5-dicarboxylate and 1-bromo-2,3-dichlorobenzene. $^1$H NMR ($CDCl_3$, 300 MHz) δ 6.95 (1H, t, 8.1 Hz), 6.75–6.80 (4H, m), 6.02 (1H, s), 3.90–3.96 (1H, m), 3.53 (1H,bs), 2.74–3.11 (5H, m), 2.15 (3H, s), 1.65–1.87 (3H, m) ppm. MS (APCI): 348 (base, M+H).

Example 14

(3,4-dichlorophenyl)-[(4aS,9bR)-6-methyl-2,3,4,4a,5,9b-hexahydro-1H-pyrido[4,3-b]indol-8-yl]-amine

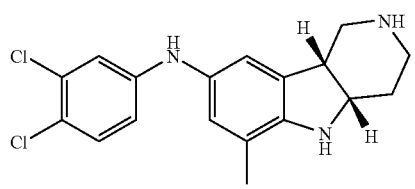

The title compound (27 mg, 34%) was prepared by the general method from di(tert-butyl)(4aS,9bR)-8-amino-6-methyl-3,4,4a,9b-tetrahydro-1H-pyrido[4,3-b]indole-2,5-dicarboxylate and 4-bromo-1,2-dichlorobenzene. $^1$H NMR ($CDCl_3$, 300 MHz) δ 7.17 (1H, d, 8.8 Hz), 6.85 (1H, d,2.6 Hz), 6.70–6.76 (2H, m), 6.61 (1H, dd, 8.8 Hz, 1.8 Hz), 5.44 (1H, s), 3.90–3.95 (1H, m), 3.53 (1H,bs), 2.73–3.09 (5H, m), 2.14 (3H, s), 1.67–1.98 (3H, m) ppm. MS (APCI): 348 (base, M+H).

Example 15

(3-chloro-4-methylphenyl)-[(4aS,9bR)-6-methyl-2,3,4,4a,5,9b-hexahydro-1H-pyrido[4,3-b]indol-8-yl]-amine

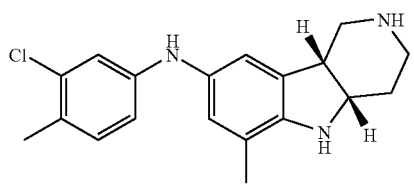

The title compound (30 mg, 40%) was prepared by the general method from di(tert-butyl)(4aS,9bR)-8-amino-6-methyl-3,4,4a,9b-tetrahydro-1H-pyrido[4,3-b]indole-2,5-dicarboxylate and 4-bromo-2-chloro-1-methylbenzene. $^1$H NMR ($CDCl_3$, 300 MHz) δ 7.01 (1H, d, 8.1 Hz), 6.83 (1H, d, 2.2 Hz), 6.75 (1H, s), 6.69 (1H, s), 6.64 (1H, dd, 8.4 Hz, 2.2 Hz), 5.34 (1H, s), 3.88–3.94 (1H, m), 3.53 (1H,bs), 2.73–3.12 (5H, m), 2.26 (3H, s), 2.13 (3H, s), 1.65–1.89 (3H, m) ppm. MS (APCI): 328 (base, M+H).

Example 16

(2,4-dichlorophenyl)-[(4aS,9bR)-6-methyl-2,3,4,4a,5,9b-hexahydro-1H-pyrido[4,3-b]indol-8-yl]-amine

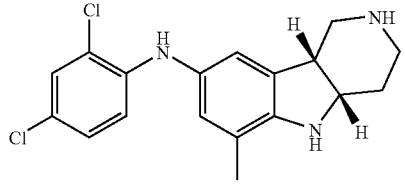

The title compound (40 mg, 50%) was prepared by the general method from di(tert-butyl)(4aS,9bR)-8-amino-6-methyl-3,4,4a,9b-tetrahydro-1H-pyrido[4,3-b]indole-2,5-dicarboxylate and 1-bromo-2,4-dichlorobenzene. $^1$H NMR ($CDCl_3$, 300 MHz) δ 7.27 (1H, d, 2.6 Hz), 6.99 (1H, dd, 8.8 Hz, 2.6 Hz), 6.81 (2H, d, 8.8 Hz), 6.75 (1H, s), 5.85 (1H, s), 3.90–3.95 (1H, m), 3.53 (1H,bs), 2.73–3.12 (5H, m), 2.14 (3H, s), 1.64–1.88 (3H, m) ppm. MS (APCI): 348 (base, M+H).

Example 17

(2,6-dichlorophenyl)-[(4aS,9bR)-6-methyl-2,3,4,4a,5,9b-hexahydro-1H-pyrido[4,3-b]indol-8-yl]-amine

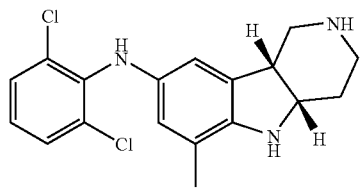

The title compound (15 mg, 19%) was prepared by the general method from di(tert-butyl)(4aS,9bR)-8-amino-6-methyl-3,4,4a,9b-tetrahydro-1H-pyrido[4,3-b]indole-2,5-dicarboxylate and 2-bromo-1,3-dichlorobenzene. $^1$H NMR (CDCl$_3$, 300 Hz) δ 7.31 (2H, d, 8.0 Hz), 6.90–6.96 (1H, m), 6.46 (1H, s), 6.41 (1H, s), 5.76 (1H, s), 3.85–3.89 (1H, m), 3.53 (1H,bs), 2.72–3.06 (5H, m), 2.11 (3H, s), 1.65–1.91 (3H, m) ppm. MS (APCI): 348 (base, M+H).

Example 18

(2,4-difluorophenyl)-[(4aS,9bR)-6-methyl-2,3,4,4a,5,9b-hexahydro-1H-pyrido[4,3-b]indol-8-yl]-amine

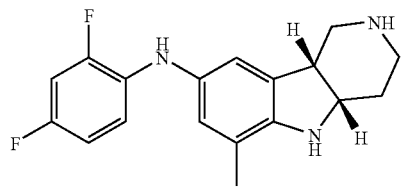

The title compound (11 mg, 15%) was prepared by the general method from di(tert-butyl)(4aS,9bR)-8-amino-6-methyl-3,4,4a,9b-tetrahydro-1H-pyrido[4,3-b]indole-2,5-dicarboxylate and 1-bromo-2,4-dichlorobenzene. $^1$H NMR (CDCl$_3$, 300 MHz) δ 6.78–6.97 (3H, m), 6.77 (1H, s), 6.70 (1H, s), 5.37 (1H, s), 3.90–3.93 (1H, m), 3.53 (1H,bs), 2.75–3.10 (5H, m), 2.14 (3H, s), 1.68–1.88 (3H, m) ppm. MS (APCI): 316 (base, M+H).

Example 19

(2-methoxy-5-methylphenyl)-[(4aS,9bR)-6-methyl-2,3,4,4a,5,9b-hexahydro-1H-pyrido[4,3-b]indol-8-yl]-amine

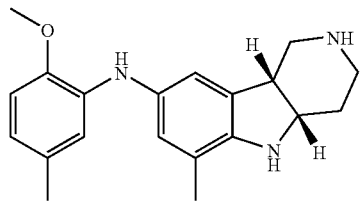

The title compound (29 mg, 39%) was prepared by the general method from di(tert-butyl)(4aS,9bR)-8-amino-6-methyl-3,4,4a,9b-tetrahydro-1H-pyrido[4,3-b]indole-2,5-dicarboxylate and 2-bromo-1-methoxy-4-methylbenzene. $^1$H NMR (CDCl$_3$, 300 MHz) δ 6.71–6.84 (4H, m), 6.54 (1H, d, 0.7 Hz), 5.85 (1H, s), 3.91–3.96 (1H, m), 3.85 (1H, s), 3.53 (1H,bs), 2.80–3.17 (5H, m), 2.20 (3H, s), 2.15 (3H, s), 1.70–1.95 (2H, m) ppm. MS (APCI): 324 (base, M+H).

Example 20

2-chloro-4-[(4aS,9bR)-6-methyl-2,3,4,4a,5,9b-hexahydro-1H-pyrido[4,3-b]indol-8-ylamino]-benzonitrile

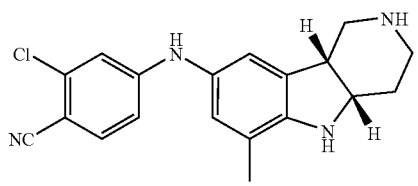

The title compound (50 mg, 64%) was prepared by the general method from di(tert-butyl)(4aS,9bR)-8-amino-6-methyl-3,4,4a,9b-tetrahydro-1H-pyrido[4,3-b]indole-2,5-dicarboxylate and 4-bromo-2-chloro-benzonitrile. $^1$H NMR (CDCl$_3$, 300 MHz) δ 7.48 (1H, d, 8.5 Hz), 6.58–6.76 (4H, m), 5.11 (1H, s), 3.93–3.97 (1H, m), 3.61 (1H, bs), 2.76–3.14 (5H, m), 3.61 (1H,bs), 2.14 (3H, s), 1.70–1.90 (2H, m) ppm. MS (APCI): 339 (base, M+H).

Example 21

(4-chloro-2-fluorophenyl)-[(4aS,9bR)-6-methyl-2,3,4,4a,5,9b-hexahydro-1H-pyrido[4,3-b]indol-8-yl]-amine

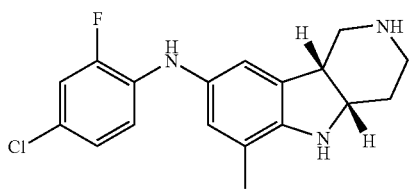

The title compound (26 mg, 34%) was prepared by the general method from di(tert-butyl)(4aS,9bR)-8-amino-6-methyl-3,4,4a,9b-tetrahydro-1H-pyrido[4,3-b]indole-2,5-dicarboxylate and 1-bromo-4-chloro-2-fluorobenzene. $^1$H NMR (CDCl$_3$, 300 MHz) δ 7.01–7.05 (1H, m), 6.84–6.92 (2H, m), 6.73–6.79 (2H, m), 5.53 (1H, s), 3.89–3.93 (1H, m), 3.53 (1H,bs), 2.75–3.11 (5H, m), 2.14 (3H, s), 1.68–1.89 (3H, m) ppm. MS (APCI): 332 (base, M+H).

Example 22

(2-fluoro-5-trifluoromethyl-phenyl)-[(4aS,9bR)-6-methyl-2,3,4,4a,5,9b-hexahydro-1H-pyrido[4,3-b]indol-8-yl]-amine

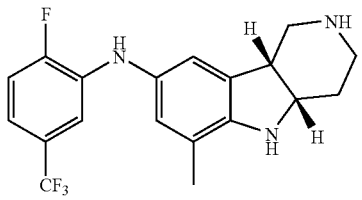

The title compound (37 mg, 44%) was prepared by the general method from di(tert-butyl)(4aS,9bR)-8-amino-6-methyl-3,4,4a,9b-tetrahydro-1H-pyrido[4,3-b]indole-2,5-dicarboxylate and 2-bromo-1-fluoro-4-trifluoromethyl-benzene. $^1$H NMR (CDCl$_3$, 300 MHz) δ 7.04–7.15 (2H, m), 6.89–6.94 (1H, m), 6.82 (1H, s), 6.77 (1H, s), 5.72 (1H, s), 3.92–3.97 (1H, m), 3.59 (1H,bs), 2.75–3.12 (5H, m), 2.16 (3H, s), 1.66–1.87 (3H, m) ppm. MS (APCI): 366 (base, M+H).

Example 23

(2-chloro-5-trifluoromethyl-phenyl)-[(4aS,9bR)-6-methyl-2,3,4,4a,5,9b-hexahydro-1H-pyrido[4,3-b]indol-8-yl]-amine

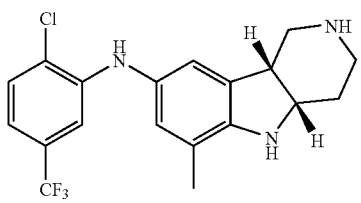

The title compound (37 mg, 42%) was prepared by the general method from di(tert-butyl)(4aS,9bR)-8-amino-6-methyl-3,4,4a,9b-tetrahydro-1H-pyrido[4,3-b]indole-2,5-dicarboxylate and 2-bromo-1-chloro-4-trifluoromethyl-benzene. $^1$H NMR (CDCl$_3$, 300 MHz) δ 7.35–7.38 (1H, m), 7.06 (1H, d, 1.9 Hz), 6.86–6.90 (1H, m), 6.74–6.83 (2H, m), 6.04 (1H, s), 3.95–3.97 (1H, m), 3.59 (1H,bs), 2.76–3.14 (5H, m), 2.16 (3H, s), 1.72–1.95 (3H, m) ppm. MS (APCI): 382 (base, M+H).

Example 24 cis-(4a,9b)-8-bromo-6-trifluoromethyl-1,3,4,4a,5,9b-hexahydro-pyrido[4,3-b]indole-2-carboxylic acid tert-butyl ester

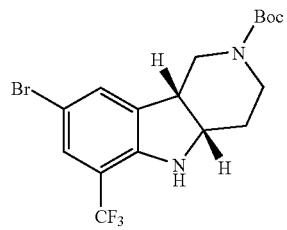

Step A. To a solution of (2-trifluoromethyl-phenyl)-hydrazine (12.0 g, 68.13 mmol) and 4-piperidone monohydrate (10.46 g, 68.09 mmol), in iso-propyl alcohol was bubbled HCl (g) for 15 minutes at rt. The reaction was sealed in a pressure vessel and heated to 95° C. for 5 h, then cooled to rt. The reaction mixture was filtered and washed with iso-propyl alcohol and dried in vacuo to yield 6-trifluoromethyl-2,3,4,5-tetrahydro-1H-pyrido[4,3-b]indole bis-hydrochloride as a white solid (13.3 g, 63% yield). $^1$H NMR (CD$_3$OD, 300 MHz) δ 3.203 (t, 2H, 12.4 Hz), 3.642 (t, 2H, 12.0 Hz), 4.472 (t, 2H, 2.6 Hz), 7.189 (t, 1H, 15.7 Hz), 7.435 (d, 1H, 7.7 Hz), 7.709 (d, 1H, 8.0 Hz) ppm.

Step B. A solution of 6-trifluoromethyl-2,3,4,5-tetrahydro-1H-pyrido[4,3-b]indole bis-hydrochloride (13.2 g, 42.15 mmol) in trifluoroacetic acid was stirred for 30 min at rt to dissolve the starting material. Triethyl-silane (9.88 g, 84.94 mmol) was added to form a biphasic mixture. The reaction was let stir at rt for 90 h. The reaction mixture was concentrated in vacuo. The reaction was then neutralized with base and extracted with chloroform. The organic layer was concentrated in vacuo to yield cis-(4a,9b)-6-trifluoromethyl-2,3,4,4a,5,9b-hexahydro-1H-pyrido[4,3-b]indole as an off white solid (11.3 g). $^1$H NMR (CDCl$_3$, 300 MHz) δ 1.609–1.707 (m, 1H), 1.739 (s, 1H), 1.806–1.912 (m, 1H), 2.713–2.789 (m, 1H), 2.859–2.985 (m, 2H), 3.026–3.131 (m, 2H), 3.970 (dd, 1H, 5.1, 10.3 Hz), 4.308 (s, 1H), 6.755 (t, 1H, 15.4 Hz), 7.190–7.243 (m, 2H) ppm.

Step C. To a solution of crude cis-(4a,9b)-6-trifluoromethyl-2,3,4,4a,5,9b-hexahydro-1H-pyrido[4,3-b]indole (11.3 g, <46.65 mmol) in 1,4-dioxane was added 1M NaOH in water (93.3 mL, 93.3 mmol) and let stir 5 min at rt. To the reaction mixture was added dropwise a solution of (BOc)$_2$O (12.2 g, 55.98 mmol) in 1,4-dioxane and let stir 18 h at rt. The reaction mixture was then quenched with water, washed with acid and extracted with ether. The organic layer was concentrated in vacuo and triturated with hexane and filtered to obtain cis-(4a,9b)-6-trifluoromethyl-1,3,4,4a,5,9b-hexahydro-pyrido[4,3-b]indole-2-carboxylic acid tert-butyl ester as an off white solid (10.6 g, 30.96 mmol). $^1$H NMR (CDCl$_3$, 300 MHz) δ 1.457 (s, 9H), 1,525 (s, 1H), 1.760–1.820 (m, 1H), 1.840–2.020 (m, 1H), 2.280–2.400 (m, 2H), 2.410–2.580 (m, 2H), 2.720–2.840 (m, 1H), 4.080–4.180 (m, 1H), 6.740–6.800 (t, 1H, 18.0 Hz), 7.238 (s, 1H), 7.262 (s, 1H) ppm.

Step D. To cis-(4a,9b)-6-trifluoromethyl-1,3,4,4a,5,9b-hexahydro-pyrido[4,3-b]indole-2-carboxylic acid tert-butyl ester (1.0 g, 2.92 mmol) in DMF at 0° C. was added dropwise solution of NBS (520 mg, 2.92 mmol) in DMF and let stir for 30 min at 0° C. The reaction mixture was then warmed to rt and let stir for 60 min. The reaction mixture was quenched with water and extracted with ether. The organic layer was concentrated in vacuo and triturated with hexane and filtered to obtain the title compound as a yellow solid (902 mg, 73% yield). $^1$H NMR (CDCl$_3$, 300 MHz) δ 1.471 (s, 9H), 1.650–1.800 (m, 1H), 1.880–2.000 (m, 1H), 3.300–3.400 (m, 2H), 3.420–3.580 (m, 2H), 3.620–3.780 (m, 2H), 4.080–4.180 (m, 1H), 7.340 (s, 1H), 7.357 (s, 1H) ppm.

Example 25

(4aS,9bR)-8-bromo-6-trifluoromethyl-1,3,4,4a,5,9b-hexahydro-pyrido[4,3-b]indole-2-carboxylic acid tert-butyl ester

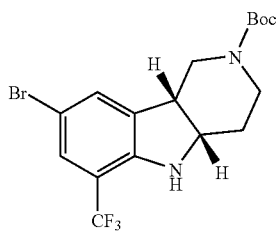

Step A. (4aS,9bR)-6-Trifluoromethyl-1,3,4,4a,5,9b-hexahydro-pyrido[4,3-b]indole-2-carboxylic acid tert-butyl ester was obtained from cis-(4a,9b)-6-trifluoromethyl-1,3,4,4a,5,9b-hexahydro-pyrido[4,3-b]indole-2-carboxylic acid tert-butyl ester (Example 30 step C) by using preparative HPLC on a ChiralPak® AD column (2% IPA in hexane).

Step B. The title compound was prepared by following the bromination method as exemplified by the step D of Example 30. $^1$H NMR (DMSO d$_6$, 400 MHz) identical to Example 30.

General method for preparation of alkyl(or benzyl)-[cis-(4a,9b)-6-trifluoromethyl-2,3,4,4a,5,9b-hexahydro-1H-pyrido[4,3-b]indol-8-yl]-amine Step A. To a solution of cis-(4a,9b)-8-bromo-6-trifluomethyl-1,3,4,4a,5,9b-hexahydro-pyrido[4,3-b]indole-2-carboxylic acid tert-butyl ester (1.0 mole equivalent) in toluene was added alkyl(or benzyl) amines (3.0 mole equivalent), NaOt-Bu (3.0 mole equivalent), (O-biPh)P(tBu)$_2$ (0.18 mole equivalent) and Pd$_2$(dba)$_3$ (0.06 mole equivalent). The reaction mixture was heated at 80° C. for 16–20 h, then cooled to rt. The reaction mixture was then quenched with water, washed with base and extracted with ethyl acetate. The organic layer was concentrated in vacuo and chromatographed on a silica gel column by elution with Hexane/Ethyl Acetate to give cis-(4a,9b)-8-alkyl(or benzyl)amino-6-trifluoromethyl-1-2,3,4,4a,5,9b-hexahydro-pyrido[4,3-b]indole-2-carboxylic acid tert-butyl ester.

Step B. A solution of cis-(4a,9b)-8-alkyl(or benzyl)amino-6-trifluoromethyl-1-2,3,4,4a,5,9b-hexahydro-pyrido[4,3-b]indole-2-carboxylic acid tert-butyl ester in 20% trifluoroacetic acid in dichloromethane was stirred for 1–2 h at rt. The reaction mixture was then concentrated in vacuo and then neutralized with base and extracted with chloroform. The organic layer was concentrated in vacuo to give the title compound (12–68% overall yield).

Example 26 cyclohexyl-[cis-(4a,9b)-6-trifluoromethyl-2,3,4,4a,5,9b-hexahydro-1H-pyrido[4,3-b]indol-8-yl]-amine

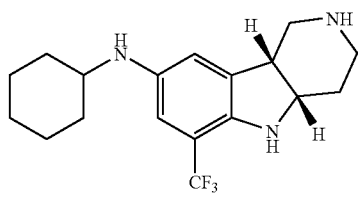

The title compound was prepared by following the general method as a yellow solid (15 mg, 44%) from cis-(4a,9b)-8-bromo-6-trifluomethyl-1,3,4,4a,5,9b-hexahydro-pyrido[4,3-b]indole-2-carboxylic acid tert-butyl ester (42 mg, 0.10 mmol) and cyclohexylamine (30 mg, 0.30 mmol). $^1$H NMR (CDCl$_3$, 300 MHz) δ 1.054–1.383 (m, 6H), 1.630–1.774 (m, 4H), 1.849–1.910 (m, 1H), 1.994–2.038 (m, 2H), 2.763–3.190 (m, 6H), 3.890–3.908 (m, 2H), 6.477 (s, 1H), 6.594 (s, 1H) ppm.

Example 27

(1,3-Dimethyl-butyl)-[cis-(4a,9b)-6-trifluoromethyl-2,3,4,4a,5,9b-hexahydro-1H-pyrido[4,3-b]indol-8-yl]-amine

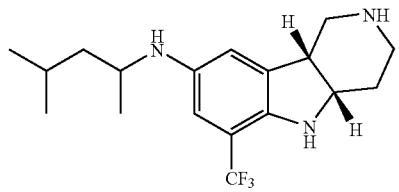

The title compound was prepared by following the general method as a yellow oil (4 mg, 12%) from cis-(4a,9b)-8-bromo-6-trifluomethyl-1,3,4,4a,5,9b-hexahydro-pyrido[4,3-b]indole-2-carboxylic acid tert-butyl ester (42 mg, 0.10 mmol) and 1,3-dimethyl-butylamine (30 mg, 0.30 mmol). $^1$H NMR (CDCl$_3$, 300 MHz) δ 0.835–0.900 (m, 9H), 1.060 (d, 3H, 6.2 Hz), 1.153–1.184 (m, 4H), 1.480–1.850 (m, 1H), 2.780–3.190 (m, 4H), 3.280–3.480 (m, 1H), 3.820–3.980 (m, 2H), 6.413 (s, 1H), 6.514 (s, 1H) ppm.

Example 28

Benzyl-[cis-(4a,9b)-6-trifluoromethyl-2,3,4,4a,5,9b-hexahydro-1H-pyrido[4,3-b]indol-8-yl]-amine

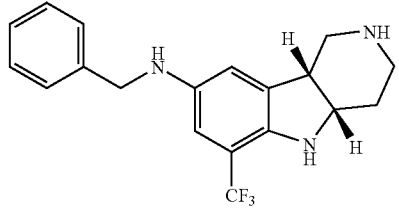

The title compound was prepared by following the general method as a yellow solid (24 mg, 68%) from cis-(4a,9b)-8-bromo-6-trifluomethyl-1,3,4,4a,5,9b-hexahydro-pyrido[4,3-b]indole-2-carboxylic acid tert-butyl ester (42 mg, 0.10 mmol) and benzylamine (32 mg, 0.30 mmol). $^1$H NMR (CDCl$_3$, 300 MHz) δ 1.697–1.708 (m, 1H), 1.855–1.900 (m, 1H), 2.192 (s, 2H), 2.772–2.819 (m, 1H), 2.896–3.108 (m, 4H), 3.911–3.963 (m, 2H), 4.276 (s, 2H), 6.559 (s, 1H), 6.661 (s, 1H), 7.300–7.384 (m, 5H) ppm.

Example 29

(1-phenyl-ethyl)-[cis-(4a,9b)-6-trifluoromethyl-2,3,4,4a,5,9b-hexahydro-1H-pyrido[4,3-b]indol-8-yl]-amine

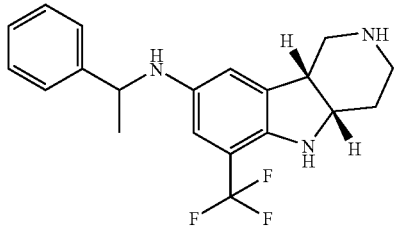

The title compound was prepared by following the general method as a yellow oil (8 mg, 22%) from cis-(4a,9b)-8-bromo-6-trifluomethyl-1,3,4,4a,5,9b-hexahydro-pyrido[4,3-b]indole-2-carboxylic acid tert-butyl ester (42 mg, 0.10 mmol) and 1-phenyl-ethylamine (36 mg, 0.30 mmol). $^1$H NMR (CDCl$_3$, 300 MHz) δ 1.253 (s, 1H), 1.481–1.508 (m, 3H), 1.618 (d, 1H, 6.9 Hz), 1.807–1.899 (m, 4H), 2.748–2.838 (m, 1H), 2.928–3.034 (m, 3H), 3.80–3.92 (m, 2H), 6.404 (d, 1H, 14.0 Hz), 6.512 (d, 1H, 9.5 Hz), 7.287–7.393 (m, 5H) ppm.

Example 30

(2-methyl-benzyl)-[cis-(4a,9b)-6-trifluoromethyl-2,3,4,4a,5,9b-hexahydro-1H-pyrido[4,3-b]indol-8-yl]-amine

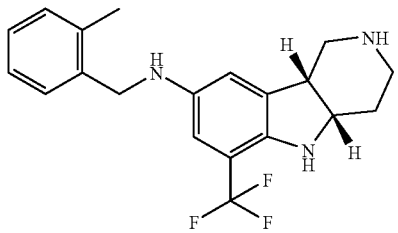

The title compound was prepared by following the general method as a yellow solid (20 mg, 55%) from cis-(4a,9b)-8-bromo-6-trifluomethyl-1,3,4,4a,5,9b-hexahydro-pyrido[4,3-b]indole-2-carboxylic acid tert-butyl ester (42 mg, 0.10 mmol) and 2-methyl-benzylamine (36 mg, 0.30 mmol). $^1$H NMR (CDCl$_3$, 300 MHz) δ 1.717–1.779 (m, 1H), 1.935–2.015 (m, 1H), 2.377 (s, 3H), 2.476–2.680 (m, 2H), 2.827–2.922 (m, 2H), 2.999–3.194 (m, 3H), 3.918–3.967 (m, 2H), 4.199 (s, 2H), 6.548 (s, 1H), 6.632 (s, 1H), 7.137–7.244 (m, 3H), 7.292–7.317 (m, 1H) ppm.

Example 31

(2-methoxybenzyl)-[cis-(4a,9b)-6-trifluoromethyl-2,3,4,4a,5,9b-hexahydro-1H-pyrido[4,3-b]indol-8-yl]-amine

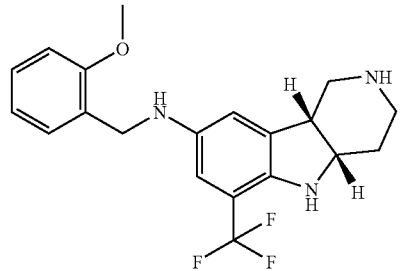

The title compound was prepared by following the general method as a yellow solid (20 mg, 53%) from cis-(4a,9b)-8-bromo-6-trifluomethyl-1,3,4,4a,5,9b-hexahydro-pyrido[4,3-b]indole-2-carboxylic acid tert-butyl ester (42 mg, 0.10 mmol) and 2-methoxy-benzylamine (41 mg, 0.30 mmol). $^1$H NMR (CDCl$_3$, 300 MHz) δ 1.708–1.719 (m, 1H), 1.911–1.927 (m, 1H), 2.400–2.600 (m, 2H), 2.808–2.903 (m, 2H), 2.960–3.122 (m, 3H), 3.864 (s, 3H), 3.879–3.933 (m, 2H), 4.255 (s, 2H), 6.579 (s, 1H), 6.657 (s, 1H), 6.879–6.941 (m, 3H), 7.278–7.290 (m, 1H) ppm.

Example 32

(2-chloro-6-fluoro-benzyl)-[cis-(4a,9b)-6-trifluoromethyl-2,3,4,4a,5,9b-hexahydro-1H-pyrido[4,3-b]indol-8-yl]-amine

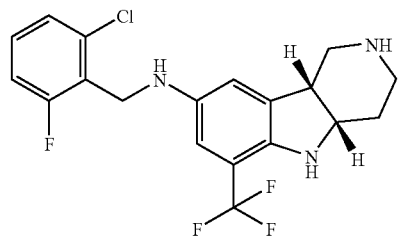

The title compound was prepared by following the general method as an orange solid (13 mg, 34%) from cis-(4a,9b)-8-bromo-6-trifluomethyl-1,3,4,4a,5,9b-hexahydro-pyrido[4,3-b]indole-2-carboxylic acid tert-butyl ester (42 mg, 0.10 mmol) and 2-chloro-6-fluoro-benzylamine (48 mg, 0.30 mmol). $^1$H NMR (CDCl$_3$, 300 MHz) δ 1.796–1.808 (m, 1H), 2.015–2.028 (m, 1H), 2.220–2.500 (m, 5H), 2.828–3.215 (m, 4H), 4.010 (d, 1H, 1.8 Hz), 4.445 (s, 1H), 6.679 (s, 1H), 6.758 (s, 1H), 6.974–7.180 (m, 1H), 7.190–7.233 (m, 2H) ppm.

Example 33

(4-tert-butyl-benzyl)-[cis-(4a,9b)-6-trifluoromethyl-2,3,4,4a,5,9b-hexahydro-1H-pyrido[4,3-b]indol-8-yl]-amine

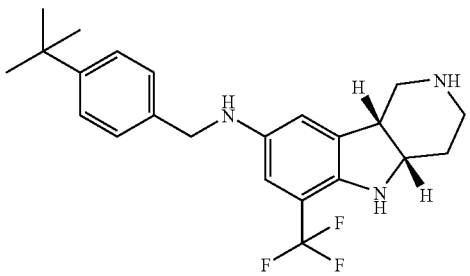

The title compound was prepared by following the general method as an orange solid (16 mg, 39%) from cis-(4a,9b)-8-bromo-6-trifluomethyl-1,3,4,4a,5,9b-hexahydro-pyrido[4,3-b]indole-2-carboxylic acid tert-butyl ester (42 mg, 0.10 mmol) and 4-tert-butyl-benzylamine (49 mg, 0.30 mmol). $^1$H NMR (CDCl$_3$, 300 MHz) δ 1.342 (s, 9H), 1.720–1.820 (m, 1H), 1.950–2.050 (m, 1H), 2.550–2.650 (m, 2H), 2.820–2.980 (m, 2H), 3.020–3.250 (m, 3H), 3.880–4.000 (m, 2H), 4.229 (s, 2H), 6.576 (s, 1H), 6.660 (s, 1H), 7.357 (dd, 4H, 8.5, 26.0 Hz) ppm.

Example 34

(3-methylbenzyl)-[cis-(4a,9b)-6-trifluoromethyl-2,3,4,4a,5,9b-hexahydro-1H-pyrido[4,3-b]indol-8-yl]-amine

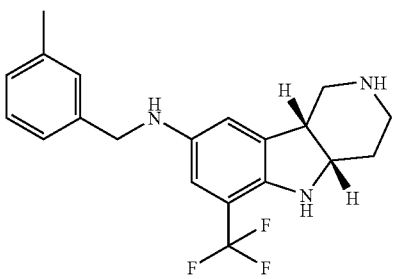

The title compound was prepared by following the general method as a yellow solid (14 mg, 38%) from cis-(4a,9b)-8-bromo-6-trifluomethyl-1,3,4,4a,5,9b-hexahydro-pyrido[4,3-b]indole-2-carboxylic acid tert-butyl ester (42 mg, 0.10 mmol) and 3-methyl-benzylamine (36 mg, 0.30 mmol). $^1$H NMR (CDCl$_3$, 300 MHz) δ 1.695–1.756 (m, 1H), 1.921–1.966 (m, 1H), 2.354 (s, 3H), 2.382–2.441 (m, 2H), 2.829–2.885 (m, 2H), 2.979–3.157 (m, 3H), 3.908–3.955 (m, 2H), 4.207 (s, 2H), 6.551 (s, 1H), 6.642 (s, 1H), 7.086–7.239 (m, 4H) ppm.

Example 35

(4-methylbenzyl)-[cis-(4a,9b)-6-trifluoromethyl-2,3,4,4a,5,9b-hexahydro-1H-pyrido[4,3-b]indol-8-yl]-amine

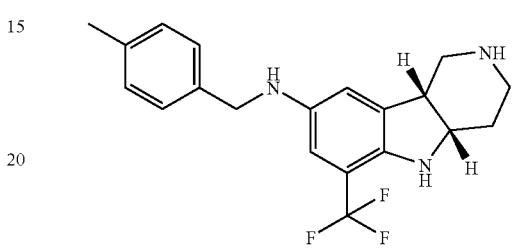

The title compound was prepared by following the general method as a yellow solid (16 mg, 45%) from cis-(4a,9b)-8-bromo-6-trifluomethyl-1,3,4,4a,5,9b-hexahydro-pyrido[4,3-b]indole-2-carboxylic acid tert-butyl ester (42 mg, 0.10 mmol) and 4-methyl-benzylamine (36 mg, 0.30 mmol). $^1$H NMR (CDCl$_3$, 300 MHz) δ 1.698–1.759 (m, 1H), 1.925–1.972 (m, 1H), 2.366 (s, 3H), 2.400–2.464 (m, 2H), 2.831–2.903 (m, 2H), 2.988–3.163 (m, 3H), 3.920–3.967 (m, 2H), 4.223 (s, 2H), 6.563 (s, 1H), 6.654 (s, 1H), 7.161–7.188 (d, 2H, 8.0 Hz), 7.225 (s, 2H) ppm.

Example 36

(2,5-Dimethylbenzyl)-[cis-(4a,9b)-6-trifluoromethyl-2,3,4,4a,5,9b-hexahydro-1H-pyrido[4,3-b]indol-8-yl]-amine

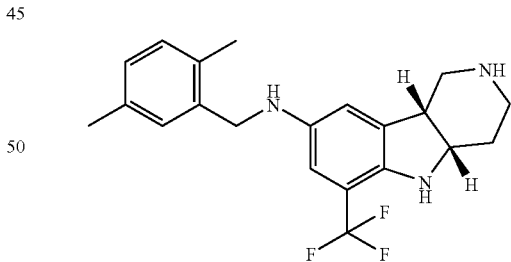

The title compound was prepared by following the general method as a yellow oil (17 mg, 46%) from cis-(4a,9b)-8-bromo-6-trifluomethyl-1,3,4,4a,5,9b-hexahydro-pyrido[4,3-b]indole-2-carboxylic acid tert-butyl ester (42 mg, 0.10 mmol) and 2,5-dimethyl-benzylamine (41 mg, 0.30 mmol). $^1$H NMR (CDCl$_3$, 300 MHz) δ 1.943–2.004 (m, 1H), 2.165–2.253 (m, 2H), 2.323 (s, 3H), 2.228 (s, 3H), 2.780 (dd, 1H, 10.2, 12.8 Hz), 3.155–3.360 (m, 4H), 3.990–4.033 (m, 3H), 4.162 (s, 2H), 6.595 (s, 1H), 6.650 (s, 1H), 7.034–7.175 (m, 3H) ppm.

Example 37

(3-fluoro-5-trifluoromethyl-benzyl)-[cis-(4a,9b)-6-trifluoromethyl-2,3,4,4a,5,9b-hexahydro-1H-pyrido[4,3-b]indol-8-yl]-amine

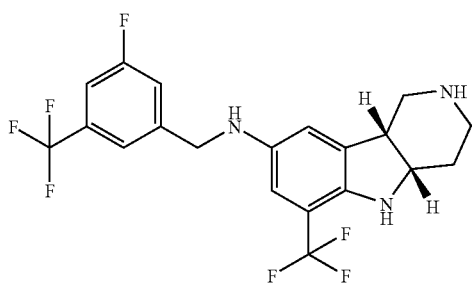

The title compound was prepared by following the general method as a yellow oil (25 mg, 58%) from cis-(4a,9b)-8-bromo-6-trifluomethyl-1,3,4,4a,5,9b-hexahydro-pyrido[4,3-b]indole-2-carboxylic acid tert-butyl ester (42 mg, 0.10 mmol) and 3-fluoro-5-trifluoromethyl-benzylamine (58 mg, 0.30 mmol). $^1$H NMR (CDCl$_3$, 300 MHz) δ 1.667–1.762 (m, 1H), 1.872–1.964 (m, 1H), 2.359–2.447 (m, 2H), 2.793–2.918 (m, 2H), 2.968–3.155 (m, 3H), 3.925–4.002 (m, 2H), 4.356 (s, 2H), 6.492 (s, 1H), 6.633 (s, 1H), 7.238–7.319 (m, 2H), 7.453 (s, 1H) ppm.

Example 38 cis-(4a,9b)-8-bromo-5-methyl-6-trifluoromethyl-1,3,4,4a,5,9b-hexahydro-pyrido[4,3-b]indole-2-carboxylic acid tert-butyl ester

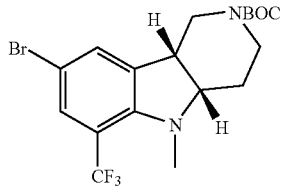

Step A. To a solution of cis-(4a,9b)-6-trifluoromethyl-1,3,4,4a,5,9b-hexahydro-pyrido[4,3-b]indole-2-carboxylic acid tert-butyl ester (Example 30 step C, 1.03 g, 3.0 mmol, 1.0 mole equivalent) in DMF (15 mL) was added NaH (0.24 g, 10 mmol, 3.3 mole equivalent). The reaction mixture was stirred at rt for 10 min before MeI (2 mL, 31 mmol, 10 mole equivalent) was added dropwise. The reaction mixture was stirred at rt for 0.5 h, quenched with water (100 mL) and extracted with ether (3×50 mL). The organic solution was dried (Na$_2$SO$_4$), concentrated in vacuo and the residue was chromatographed on a silica gel column by elution with EtOAc/Hexane (gradient) to give cis-(4a,9b)-5-methyl-6-trifluoromethyl-1,3,4,4a,5,9b-hexahydro-pyrido[4,3-b]indole-2-carboxylic acid tert-butyl ester as a white solid (0.71 g, 66%).

$^1$H NMR (CDCl$_3$, 300 MHz) δ (ppm) 1.41 (s, 9H), 1.78–2.12 (m, 2H), 2.94–3.00 (m, 3H), 3.22–3.58 (m, 4H), 3.60–3.82 (m, 2H), 6.67 (t, J=7.2 Hz, 1H), 7.16 (d, J=7.2 Hz, 1H), 7.32 (d, J=7.2 Hz, 1H).

Step B. To a solution cis-(4a,9b)-5-methyl-6-trifluoromethyl-1,3,4,4a,5,9b-hexahydro-pyrido[4,3-b]indole-2-carboxylic acid tert-butyl ester (0.39 g, 1.1 mmol, 1.0 mole equivalent) in DMF (4 mL) was added NBS (0.20 g, 1.1 mmol, 1.0 mole equivalent) dropwise at 0° C. The reaction mixture was stirred at 0° C. for 10 min, rt for 30 min, quenched with water (20 mL) and extracted with ether (3×10 mL). The ether solution was dried (Na$_2$SO$_4$), concentrated in vacuo and the residue was chromatographed on a silica gel column by elution with EtOAc/Hexane (gradient) to give the title compound as a yellow solid (0.40 g, 84%). $^1$H NMR (CDCl$_3$, 300 MHz) δ (ppm) 1.42 (s, 9H), 1.70–2.12 (m, 2H), 2.90–2.98 (m, 3H), 3.15–3.80 (m, 6H), 7.22 (d, J=1.7 Hz, 1H), 7.41(d, J=1.7 Hz, 1H).

Example 39

(4aS,9bR)-8-bromo-5-methyl-6-trifluoromethyl-1,3,4,4a,5,9b-hexahydro-pyrido[4,3-b]indole-2-carboxylic acid tert-butyl ester

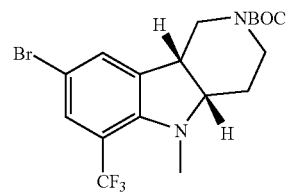

(4aS,9bR)-6-Trifluoromethyl-1,3,4,4a,5,9b-hexahydro-pyrido[4,3-b]indole-2-carboxylic acid tert-butyl ester (Example 31 Step A) was methylated and brominated according to the procedure of Example 44, Step A and B to give the title compound as a pale-yellow, amorphous solid. $^1$H NMR (DMSO d$_6$, 400 MHz) identical to example 86.

General method for preparation of alkyl(or benzyl)-(5-methyl-6-trifluoromethyl-2,3,4,4a,5,9b-hexahydro-1H-pyrido[4,3-b]indol-8-yl)-amine Step A. A solution of 8-bromo-5-methyl-6-trifluoromethyl-1,3,4,4a,5,9b-hexahydro-pyrido[4,3-b]indole-2-carboxylic acid tert-butyl ester (Example 44 or 45, 1.0 mole equivalent), alkyl (or benzyl)amine (2.0 mole equivalent), NaOt-Bu (3.0 mole equivalent) in toluene was degassed at 50° C. under Ar for 10 min and then cooled down to rt. A solution of Pd$_2$(dba)$_3$ (0.05 mole equivalent) and (o-biPh)P(t-Bu)$^2$ (0.15 mole equivalent) in toluene was degassed at rt under Ar for 10 min and added to the reaction mixture. The reaction mixture was then degassed at 50° C. under Ar for 10 min, heated at 80° C. for 16 h, cooled to rt and quenched with water. Hexane was added and the organic layer was loaded directly on a silica gel column. Gradient elution with EtOAc/Hexane gave the 8-alkyl(or benzyl)amino-5-methyl-6-trifluoromethyl-1-2,3,4,4a,5,9b-hexahydro-pyrido[4,3-b]indole-2-carboxylic acid tert-butyl ester.

Step B. To a solution of 8-alkyl(or benzyl)amino-5-methyl-6-trifluoromethyl-1-2,3,4,4a,5,9b-hexahydro-pyrido[4,3-b]indole-2-carboxylic acid tert-butyl ester (~0.1 mmol) in CH$_2$Cl$_2$ (4 mL) was added TFA (1 mL). The reaction mixture was stirred at rt for 2 h, concentrated in vacuo, basified with NH$_4$OH (10 mL) and extracted with CH$_2$Cl$_2$ (3×10 mL). The organic solution was dried (MgSO$_4$) and concentrated in vacuo to give the products in 35–75% overall yields.

Example 40 cyclohexyl-[cis-(4a,9b)-5-methyl-6-trifluoromethyl-2,3,4,4a,5,9b-hexahydro-1H-pyrido[4,3-b]indol-8-yl]-amine

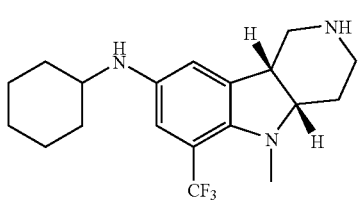

The title compound was prepared by following the general method as a yellow solid (19 mg, 55%) from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44, 44 mg, 0.10 mmol) and cyclohexylamine (20 mg, 0.20 mmol). $^1$H NMR (CDCl$_3$, 300 MHz) δ (ppm) 0.95–1.40 (m, 5H), 1.42–1.75 (m, 3H), 1.75–2.03 (m, 4H), 2.43 (dd, J=12.8, 9.5 Hz, 1H), 2.74 (d, J=1.5 Hz, 3H), 2.82–2.95 (m, 2H), 2.95–3.20 (m, 3H), 3.20–3.30 (m, 1H), 3.30–4.20 (m, 2H), 6.50 (s, 1H), 6.54 (d, J=2.2 Hz, 1H).

Example 41 benzyl-[cis-(4a,9b)-5-methyl-6-trifluoromethyl-2,3,4,4a,5,9b-hexahydro-1H-pyrido[4,3-b]indol-8-yl]-amine

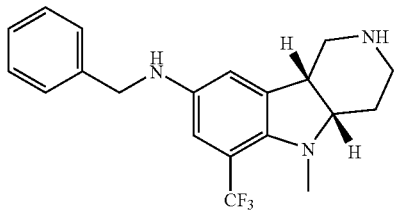

The title compound was prepared by following the general method as a yellow solid (23 mg, 64%) from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44, 44 mg, 0.10 mmol) and benzylamine (21 mg, 0.20 mmol). $^1$H NMR (CDCl$_3$, 300 MHz) δ (ppm) 1.87–2.03 (m, 2H), 2.64 (dd, J=9.5, 12.8 Hz, 1H), 2.75–2.88 (m, 3H), 2.88–3.10 (m, 1H), 3.08 (dd, J=6.2, 12.8 Hz, 1H), 3.23 (td, J=6.2, 9.2 Hz, 1H), 3.32–3.42 (m, 1H), 3.75–3.85 (br, 3H), 4.27 (s, 2H), 6.62 (d, J=2.2 Hz, 1H), 6.70 (d, J=2.2 Hz, 1H), 7.20–7.42 (m, 5H).

Example 42

[cis-(4a,9b)-5-methyl-6-trifluoromethyl-2,3,4,4a,5,9b-hexahydro-1H-pyrido[4,3-b]indol-8-yl]-(2-trifluoromethyl-benzyl)-amine

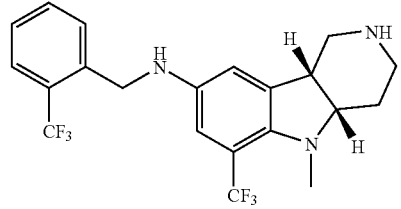

The title compound was prepared by following the general method as a yellow solid (33 mg, 75%) from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44, 44 mg, 0.10 mmol) and 2-trifluoromethyl-benzylamine (35 mg, 0.20 mmol). $^1$H NMR (CDCl$_3$, 300 MHz) δ (ppm) 1.78–2.00 (m, 2H), 2.64 (dd, J=9.5, 12.8 Hz, 1H), 2.75–2.95 (m, 4H), 3.02 (dd, J=6.2, 12.8 Hz, 1H), 3.08–3.30 (m, 3H), 3.37 (td, J=4.4, 8.6 Hz, 1H), 3.85–4.05 (br, 1H), 4.49 (s, 2H), 6.58 (d, J=2.2 Hz, 1H), 6.63 (d, J=2.2 Hz, 1H), 7.39 (t, J=7.5 Hz, 1H), 7.52 (t, J=7.5 Hz, 1H), 7.63 (d, J=7.7 Hz, 1H), 7.70 (d, J=7.7 Hz, 1H); $^{19}$F NMR (CDCl$_3$, 300 MHz) δ (ppm)-55.14, −60.45.

Example 43

[cis-(4a,9b)-5-methyl-6-trifluoromethyl-2,3,4,4a,5,9b-hexahydro-1H-pyrido[4,3-b]indol-8-yl]-(1-phenyl-ethyl)-amine

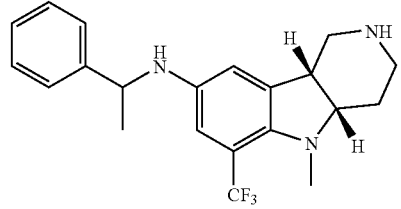

The title compound was prepared by following the general coupling procedure as a yellow solid (26 mg, 70%) from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44, 44 mg, 0.10 mmol) and α-methylbenzylamine (24 mg, 0.20 mmol). $^1$H NMR (CDCl$_3$, 300 MHz) δ (ppm) 1.51 (dd, J=1.8, 6.6 Hz, 3H), 1.75–1.92 (m, 2H), 2.20–2.55 (br, 2H), 2.55–2.66 (m, 1H), 2.72–3.12 (m, 6H), 3.23–3.40 (m, 1H), 3.60–4.10 (br, 1H), 4.41 (q, J=6.3 Hz, 1H), 6.48 (dd, J=2.2, 5.5 Hz, 1H), 6.56 (dd, J=2.6, 8.4 Hz, 1H), 7.18–7.42 (m, 5H).

Example 44

((S)-1-cyclohexyl-ethyl)-[cis-(4a,9b)-5-methyl-6-trifluoromethyl-2,3,4,4a,5,9b-hexahydro-1H-pyrido[4,3-b]indol-8-yl]-amine

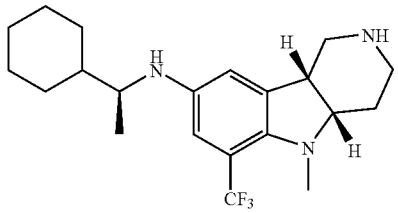

The title compound was prepared by following the general method as a yellow solid (16 mg, 42%) from cis-8-bromo-5-methyl-6-trifluoromethyl-1,3,4,4a,5,9b-hexahydro-pyrido[4,3-b]indole-2-carboxylic acid tert-butyl ester (Example 44, 44 mg, 0.10 mmol) and (S)-cyclohexyl-ethylamine (25 mg, 0.20 mmol). $^1$H NMR (CDCl$_3$, 300 MHz) δ (ppm) 0.95–1.49 (m, 10H), 1.55–1.95 (m, 7H), 2.00–2.42 (br, 2H), 2.60–2.78 (m, 1H), 2.78–2.95 (m, 4H), 3.02 (dd, J=6.2, 12.8 Hz, 1H), 3.08–3.30 (m, 2H), 3.30–4.20 (m, 1H), 6.55 (s, 1H), 6.58 (d, J=2.4 Hz, 1H).

Example 45

(exo-bicyclo[2.2.1]hept-2-yl)-[cis-(4a,9b)-5-methyl-6-trifluoromethyl-2,3,4,4a,5,9b-hexahydro-1H-pyrido[4,3-b]indol-8-yl]-amine

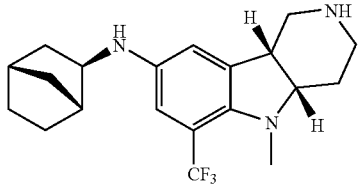

The title compound was prepared by following the general procedure as a yellow solid (23 mg, 64%) from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44, 44 mg, 0.10 mmol) and exo-2-aminonorborane (22 mg, 0.20 mmol).

$^1$H NMR (CDCl$_3$, 300 MHz) δ (ppm) 0.95–1.25 (m, 4H), 1.25–1.55 (m, 3H), 1.72 (dd, J=7.7, 12.4 Hz, 1H), 1.78–1.88 (m, 2H), 2.08–2.22 (m, 2H), 2.50–2.65 (m, 1H), 2.74 (d, J=1.8 Hz, 3H), 2.78–2.95 (m, 2H), 3.02 (dd, J=6.2, 12.8 Hz, 1H), 3.05–3.35 (m, 5H), 6.47 (d, J=2.4 Hz, 1H), 6.50 (d, J=2.4 Hz, 1H).

Example 46

[cis-(4a,9b)-5-methyl-6-trifluoromethyl-2,3,4,4a,5,9b-hexahydro-1H-pyrido[4,3-b]indol-8-yl]-((S)-2-phenyl-propyl)-amine

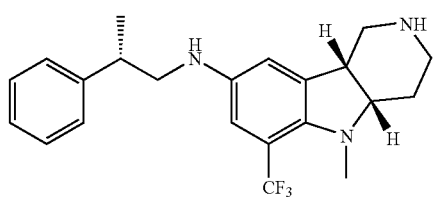

The title compound was prepared by following the general method as a yellow solid (13 mg, 34%) from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44, 44 mg, 0.10 mmol) and (S)-2-phenyl-propanylamine (27 mg, 0.20 mmol). $^1$H NMR (CDCl$_3$, 300 MHz) δ (ppm) 1.27 (d, J=6.9 Hz, 3H), 1.98–2.18 (m, 1H), 2.40–2.55 (m, 1H), 2.73 (d, J=1.5 Hz, 3H), 2.80–3.43 (m, 11H), 6.45 (s, 1H), 6.53 (d, J=1.5 Hz, 1H), 7.00–7.32 (m, 5H).

General Method for Preparation of aryl-[(4aS,9bR) 6-trifluoromethyl-2,3,4,4a,5,9b-hexahydro-1H-pyrido[4,3-b]indol-8-yl]-amine To a solution of (4aS,9bR)-8-bromo-5-methyl-6-trifluomethyl-1,3,4,4a,5,9b-hexahydro-pyrido[4,3-b]indole-2-carboxylic acid tert-butyl ester (Example 45, 1.0 mole equivalent) in toluene was added substituted anilines (3.0 mole equivalent), NaOt-Bu (3.0 mole equivalent), BINAP (0.18 mole equivalent) and Pd$_2$(dba)$_3$ (0.06 mole equivalent). The reaction mixture was heated at 80° C. for 16–20 h, then cooled to rt. The reaction mixture was then quenched with water, washed with base and extracted with ethyl acetate. The organic layer was concentrated in vacuo and chromatographed on a silica gel column by elution with Hexane/Ethyl Acetate to give 8-arylamino-5-methyl-6-trifluoromethyl-1-2,3,4,4a,5,9b-hexahydro-pyrido[4,3-b]indole-2-carboxylic acid tert-butyl ester. A solution of 8-arylamino-5-methyl-6-trifluoromethyl-1-2,3,4,4a,5,9b-hexahydro-pyrido[4,3-b]indole-2-carboxylic acid tert-butyl ester in 20% trifluoroacetic acid in dichloromethane was stirred for 1–2 h at rt. The reaction mixture was then concentrated in vacuo and then neutralized with base and extracted with chloroform. The organic layer was concentrated in vacuo to give aryl-(5-methyl-6-trifluoromethyl-2,3,4,4a,5,9b-hexahydro-1H-pyrido[4,3-b]indol-8-yl)-amine (12–68% yield).

Example 47

(2-methylthio-phenyl)-[(4aS,9bR)-5-methyl-6-trifloromethyl-2,3,4,4a,5,9b-hexahydro-1H-pyrido[4,3-b]indol-8-yl)]-amine

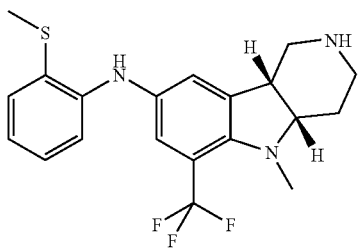

The title compound was prepared by following the general coupling procedure as a yellow solid (21 mg, 54%) from (4aS,9bR)-8-bromo-5-methyl-6-trifluomethyl-1,3,4,4a,5,9b-hexahydro-pyrido[4,3-b]indole-2-carboxylic acid tert-butyl ester (Example 45, 41 mg, 0.10 mmol) and 2-methylthio-phenylamine (42 mg, 0.30 mmol).

$^1$H NMR (CDCl$_3$, 300 MHz) δ 1.896–1.980 (m, 2H), 2.386 (s, 1H), 2.723–2.819 (m, 4H), 2.912–2.927 (m, 3H), 3.065–6.262 (m, 2H), 3.491–3.546 (m, 1H), 6.471 (s, 1H), 6.775 (dt, 1H, 1.1, 7.3 Hz), 6.908 (dd, 1H, 1.1, 8.4 Hz), 7.057 (d, 1H, 1.9 Hz), 7.121 (t, 1H, 6.7 Hz), 7.199 (d, 1H, 2.2 Hz), 7.429 (dd, 1H, 1.5, 7.7 Hz) ppm.

Example 48

(2-ethylphenyl)-[(4aS,9bR)-5-methyl-6-triflorom-ethyl-2,3,4,4a,5,9b-hexahydro-1H-pyrido[4,3-b]indol-8-yl)-amine

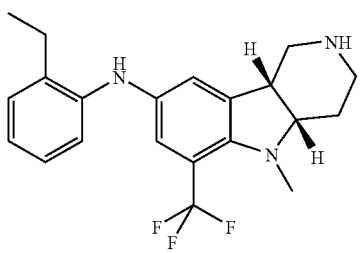

The title compound was prepared by following the general coupling procedure as a yellow solid (16 mg, 43%) from (4aS,9bR)-8-bromo-5-methyl-6-trifluomethyl-1,3,4,4a,5,9b-hexahydro-pyrido[4,3-b]indole-2-carboxylic acid tert-butyl ester (Example 45, 41 mg, 0.10 mmol) and 2-ethyl-phenylamine (36 mg, 0.30 mmol). $^1$H NMR (CDCl$_3$, 300 MHz) δ 1.274 (t, 3H, 7.4 Hz), 1.883–1.933 (m, 2H), 2.374 (s, 2H), 2.598 (dd, 2H, 7.7, 15.1 Hz), 2.678–2.747 (m, 1H), 2.820–2.979 (m, 4H), 3.041 (dd, 1H, 5.9, 12.8 Hz), 3.177 (dd, 1H, 6.6, 14.3 Hz), 3.457–3.509 (m, 1H), 5.261 (s, 1H), 6.883 (dt, 1H, 1.1, 7.3 Hz), 6.950–6.968 (m, 2H), 7.052–7.121 (m, 2H), 7.179 (d, 1H, 7.7 Hz) ppm.

Example 49

(2-methoxyl-5-methylphenyl)-[(4aS,9bR)-5-methyl-6-trifloromethyl-2,3,4,4a,5,9b-hexahydro-1H-pyrido[4,3-b]indol-8-yl)-amine

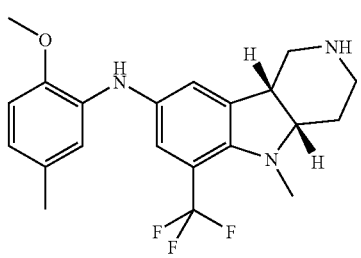

The title compound was prepared by following the general coupling procedure as a yellow solid (25 mg, 64%) from (4aS,9bR)-8-bromo-5-methyl-6-trifluomethyl-1,3,4,4a,5,9b-hexahydro-pyrido[4,3-b]indole-2-carboxylic acid tert-butyl ester (Example 45, 41 mg, 0.10 mmol) and 2-methoxy-5-methyl-phenylamine (41 mg, 0.30 mmol). $^1$H NMR (CDCl$_3$, 300 MHz) δ 1.879–1.938 (m, 2H), 2.221 (s, 3H), 2.507 (s, 2H), 2.670–2.741 (m, 1H), 2.829–2.963 (m, 4H), 3.032 (dd, 1H, 5.9, 12.9 Hz), 3.197 (dd, 1H, 6.6, 14.3 Hz), 3.474–3.527 (m, 1H), 5.889 (s, 1H), 6.580 (dd, 1H, 1.1, 8.1 Hz), 6.731–6.779 (m, 2H), 7.059 (d, 1H, 1.8 Hz), 7.184 (d, 1H, 2.2 Hz) ppm.

Example 50

[(4aS,9bR)-5-methyl-6-trifloromethyl-2,3,4,4a,5,9b-hexahydro-1H-pyrido[4,3-b]indol-8-yl]-phenyl-amine

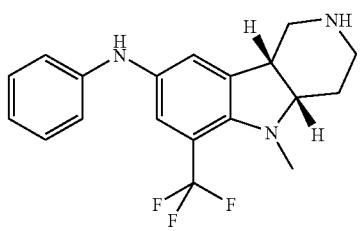

The title compound was prepared by following the general coupling procedure as a yellow solid (25 mg, 90%) from (4aS,9bR)-8-bromo-5-methyl-6-trifluomethyl-1,3,4,4a,5,9b-hexahydro-pyrido[4,3-b]indole-2-carboxylic acid tert-butyl ester (Example 45, 35 mg, 0.08 mmol) and phenylamine (22 mg, 0.24 mmol). $^1$H NMR (CDCl$_3$, 300 MHz) δ 1.945–2.068 (m, 2H), 2.693 (dd, 1H, 9.2, 12.9 Hz), 2.915 (d, 2H, 2.2 Hz), 2.950–3.022 (m, 2H), 3.135 (dd, 1H, 6.3, 12.9 Hz), 3.281–3.354 (m, 1H), 3.471–3.572 (m, 3H), 5.539 (s, 1H), 6.852–6.987 (m, 3H), 7.043 (d, 1H, 1.8 Hz), 7.172 (d, 1H, 2.2 Hz), 7.218–7.271 (m, 2H) ppm.

Example 51

(2-fluorophenyl)-[(4aS,9bR)-5-methyl-6-triflorom-ethyl-2,3,4,4a,5,9b-hexahydro-1H-pyrido[4,3-b]in-dol-8-yl]-amine

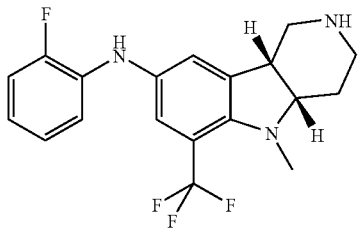

The title compound was prepared by following the general coupling procedure as a yellow solid (29 mg, 99%) from (4aS,9bR)-8-bromo-5-methyl-6-trifluomethyl-1,3,4,4a,5,9b-hexahydro-pyrido[4,3-b]indole-2-carboxylic acid tert-butyl ester (Example 45, 35 mg, 0.08 mmol) and 2-fluoro-phenylamine (27 mg, 0.24 mmol). $^1$H NMR (CDCl$_3$, 300 MHz) δ 2.006–2.049 (m, 2H), 2.712 (dd, 1H, 9.2, 12.9 Hz), 2.927 (t, 2H, 2.2 Hz), 2.984–3.027 (m, 2H), 3.141 (dd, 1H, 5.8, 12.8 Hz), 3.306–3.337 (m, 1H), 3.499–3.630 (m, 3H), 5.646 (d, 1H, 2.5 Hz), 6.764–6.821 (m, 1H), 6.986–7.101 (m, 4H), 7.211 (d, 1H, 2.2 Hz) ppm.

Example 52

(3-fluorophenyl)-[(4aS,9bR)-5-methyl-6-triflorom-ethyl-2,3,4,4a,5,9b-hexahydro-1H-pyrido[4,3-b]in-dol-8-yl)-amine

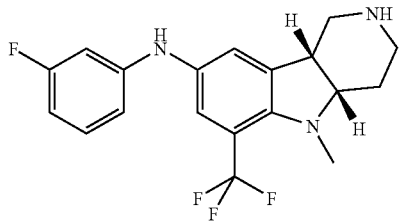

The title compound was prepared by following the general coupling procedure as a yellow solid (27 mg, 92%) from (4aS,9bR)-8-bromo-5-methyl-6-trifluomethyl-1,3,4,4a,5,9b-hexahydro-pyrido[4,3-b]indole-2-carboxylic acid tert-butyl ester (Example 45, 35 mg, 0.08 mmol) and 3-fluoro-phenylamine (27 mg, 0.24 mmol). $^1$H NMR (CDCl$_3$, 300 MHz) δ 1.967–2.085 (m, 2H), 2.713 (dd, 1H, 9.1, 12.8 Hz), 2.922–2.935 (m, 2H), 2.974–3.032 (m, 2H), 3.152 (dd, 1H, 6.2, 13.2 Hz), 3.305–3.378 (m, 3H), 3.487–3.558 (m, 1H), 5.611 (s, 1H), 6.493–6.617 (m, 3H), 7.055 (d, 1H, 1.8 Hz), 7.117–7.191 (m, 2H) ppm.

Example 53

(4-fluorophenyl)-[(4aS,9bR)5-methyl-6-triflorom-ethyl-2,3,4,4a,5,9b-hexahydro-1H-pyrido[4,3-b]in-dol-8-yl]-amine

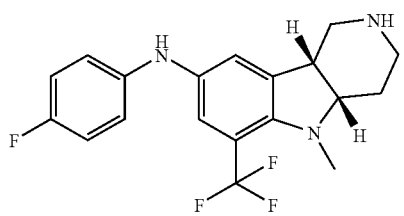

The title compound was prepared by following the general coupling procedure as a yellow solid (25 mg, 86%) from (4aS,9bR)-8-bromo-5-methyl-6-trifluomethyl-1,3,4,4a,5,9b-hexahydro-pyrido[4,3-b]indole-2-carboxylic acid tert-butyl ester (Example 45, 35 mg, 0.08 mmol) and 4-Fluoro-phenylamine (27 mg, 0.24 mmol). $^1$H NMR (CDCl$_3$, 300 MHz) δ 1.874–1.961 (m, 2H), 2.659–2.995 (m, 7H), 3.056 (dd, 1H, 5.9, 12.5 Hz), 3.207 (dd, 1H, 6.2, 14.6 Hz), 3.452–3.504 (m, 1H), 5.386 (s, 1H), 6.801–6.868 (m, 2H), 6.884–6.964 (m, 3H), 7.065 (d, 1H, 2.2 Hz) ppm.

Example 54

(2-ethoxyphenyl)-[(4aS,9bR)-5-methyl-6-triflorom-ethyl-2,3,4,4a,5,9b-hexahydro-1H-pyrido[4,3-b]in-dol-8-yl)-amine

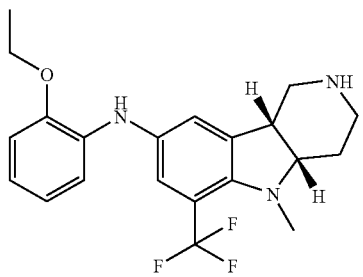

The title compound was prepared by following the general coupling procedure as a yellow solid (30 mg, 96%) from (4aS,9bR)-8-bromo-5-methyl-6-trifluomethyl-1,3,4,4a,5,9b-hexahydro-pyrido[4,3-b]indole-2-carboxylic acid tert-butyl ester (Example 45, 35 mg, 0.08 mmol) and 2-ethoxy-phenylamine (33 mg, 0.24 mmol). $^1$H NMR (CDCl$_3$, 300 MHz) δ 1.460 (t, 3H, 7.0 Hz), 1.891–1.943 (m, 2H), 2.679–2.954 (m, 7H), 3.064 (dd, 1H, 6.3, 12.9 Hz), 3.199–3.226 (m, 1H), 3.483–3.505 (m, 1H), 4.106 (dd, 2H, 6.9, 13.9 Hz), 5.970 (s, 1H), 6.757–6.861 (m, 3H), 6.963 (dd, 1H, 1.8, 8.1 Hz), 7.084 (d, 1H, 2.2 Hz), 7.209 (d, 1H, 2.2 Hz) ppm.

Example 55

[(4aS,9bR)-5-methyl-6-trifloromethyl-2,3,4,4a,5,9b-hexahydro-1H-pyrido[4,3-b]indol-8-yl]-o-tolyl-amine

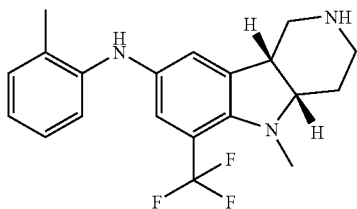

The title compound was prepared by following the general coupling procedure as a yellow solid (16 mg, 57%) from (4aS,9bR)-8-bromo-5-methyl-6-trifluomethyl-1,3,4,4a,5,9b-hexahydro-pyrido[4,3-b]indole-2-carboxylic acid tert-butyl ester (Example 45, 35 mg, 0.08 mmol) and o-tolylamine (26 mg, 0.24 mmol). $^1$H NMR (CDCl$_3$, 300 MHz) δ 2.115–2.162 (m, 2H), 2.255 (s, 3H), 2.664 (dd, 1H, 9.9, 12.8 Hz), 2.908 (d, 3H, 1.9 Hz), 3.068–3.223 (m, 3H), 3.361–3.505 (m, 2H), 5.255 (s, 1H), 6.840–6.931 (m, 1H), 6.964–6.986 (m, 2H), 7.055–7.217 (m, 3H) ppm.

Example 56

(3-fluoro-4-methylphenyl)-[(4aS,9bR)-5-methyl-6-trifloromethyl-2,3,4,4a,5,9b-hexahydro-1H-pyrido[4,3-b]indol-8-yl]-amine

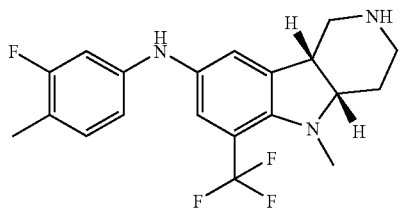

The title compound was prepared by following the general coupling procedure as a yellow solid (21 mg, 69%) from (4aS,9bR)-8-bromo-5-methyl-6-trifluomethyl-1,3,4,4a,5,9b-hexahydro-pyrido[4,3-b]indole-2-carboxylic acid tert-butyl ester (Example 45, 35 mg, 0.08 mmol) and 3-fluoro-4-methyl-phenylamine (30 mg, 0.24 mmol). $^1$H NMR (CDCl$_3$, 300 MHz) δ 1.886–2.032 (m, 2H), 2.196 (d, 3H, 1.5 Hz), 2.682–3.017 (m, 7H), 3.089 (dd, 1H, 6.2, 12.8 Hz), 3.249 (dd, 1H, 6.2, 14.6 Hz), 3.489–3.543 (m, 1H), 5.480 (s, 1H), 6.525–6.567 (m, 2H), 6.962–7.039 (m, 2H), 7.315 (d, 1H, 2.2 Hz) ppm.

Example 57

(3-chloro-4-fluorophenyl)-[(4aS,9bR)-5-methyl-6-trifloromethyl-2,3,4,4a,5,9b-hexahydro-1H-pyrido[4,3-b]indol-8-yl]-amine

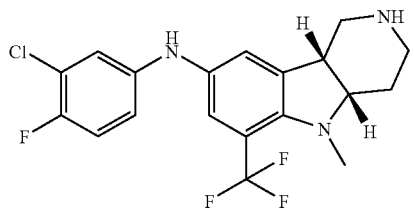

The title compound was prepared by following the general coupling procedure as a yellow solid (22 mg, 63%) from (4aS,9bR)-8-bromo-5-methyl-6-trifluomethyl-1,3,4,4a,5,9b-hexahydro-pyrido[4,3-b]indole-2-carboxylic acid tert-butyl ester (Example 45, 35 mg, 0.08 mmol) and 3-chloro-4-fluoro-phenylamine (35 mg, 0.24 mmol). $^1$H NMR (CDCl$_3$, 300 MHz) δ 1.978–1.990 (m, 2H), 2.184–2.221 (m, 3H), 2.663 (dd, 1H, 9.2, 12.4 Hz), 2.887 (d, 2H, 1.8 Hz), 2.952–2.995 (m, 1H), 3.093 (dd, 1H, 5.8, 12.8 Hz), 3.236–3.488 (m, 2H), 5.336 (s, 1H), 6.649–6.757 (m, 2H), 6.847–6.933 (m, 2H), 7.059 (d, 1H, 2.2 Hz) ppm.

Example 58

(4-fluoro-3-methylphenyl)-[(4aS,9bR)-5-methyl-6-trifloromethyl-2,3,4,4a,5,9b-hexahydro-1H-pyrido[4,3-b]indol-8-yl]-amine

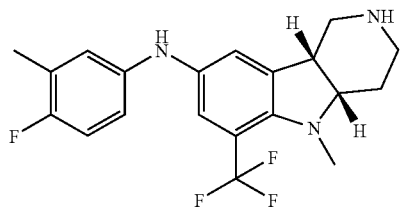

The title compound was prepared by following the general coupling procedure as a yellow solid (20 mg, 67%) from (4aS,9bR)-8-bromo-5-methyl-6-trifluomethyl-1,3,4,4a,5,9b-hexahydro-pyrido[4,3-b]indole-2-carboxylic acid tert-butyl ester (Example 45, 35 mg, 0.08 mmol) and 4-fluoro-3-methyl-phenylamine (30 mg, 0.24 mmol). $^1$H NMR (CDCl$_3$, 300 MHz) δ 1.845–1.990 (m, 2H), 2.399–3.605 (m, 4H), 2.717 (dd, 1H, 8.4, 12.8 Hz), 2.816–2.984 (m, 5H), 3.056 (dd, 1H, 5.9, 12.8 Hz), 3.176–3.247 (m, 1H), 3.492–3.546 (m, 1H), 5.394 (s, 1H), 6.647–6.699 (m, 1H), 6.822–6.914 (m, 1H), 6.951–7.008 (m, 2H), 7.088 (d, 1H, 2.2 Hz) ppm.

Example 59

(4-Chloro-3-methylphenyl)-[(4aS,9bR)-5-methyl-6-trifloromethyl-2,3,4,4a,5,9b-hexahydro-1H-pyrido[4,3-b]indol-8-yl]-amine

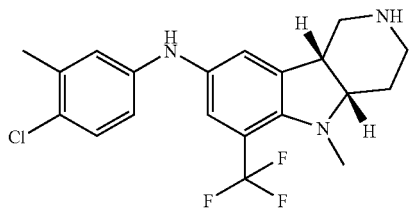

The title compound was prepared by following the general coupling procedure as a yellow solid (19 mg, 58%) from (4aS,9bR)-8-bromo-5-methyl-6-trifluomethyl-1,3,4,4a,5,9b-hexahydro-pyrido[4,3-b]indole-2-carboxylic acid tert-butyl ester (Example 45, 35 mg, 0.08 mmol) and 4-chloro-3-methyl-phenylamine (34 mg, 0.24 mmol). $^1$H NMR (CDCl$_3$, 300 MHz) δ 1.886–2.027 (m, 2H), 2.294 (s, 3H), 2.657–2.967 (m, 7H), 3.074 (dd, 1H, 6.3, 12.9 Hz), 3.245 (dd, 1H, 6.6, 15.0 Hz), 3.471–3.524 (m, 1H), 5.417 (s, 1H), 6.635 (dd, 1H, 2.6, 8.4 Hz), 6.712 (d, 1H, 2.5 Hz), 6.976 (d, 1H, 1.8 Hz), 7.110–7.162 (m, 2H) ppm.

Example 60

(4aS,9bR)-(2-methoxylphenyl)-(5-methyl-6-trifluoromethyl-2,3,4,4a,5,9b-hexahydro-1H-pyrido[4,3-b]indol-8-yl)-amine

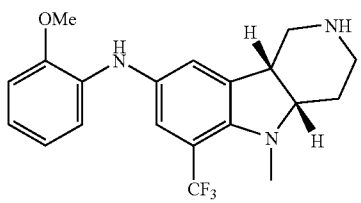

The title compound was prepared by following the general coupling procedure as a yellow solid (22 mg, 61%) from (4aS,9bR)-8-bromo-5-methyl-6-trifluoromethyl-1,3,4,4a,5,9b-hexahydro-pyrido[4,3-b]indole-2-carboxylic acid tert-butyl ester (Example 45, 41 mg, 0.095 mmol) and 2-methoxyaniline (37 mg, 0.30 mmol). $^1$H NMR (CDCl$_3$, 300 MHz) δ (ppm) 1.82–2.00 (m, 2H), 2.58–2.80 (m, 3H), 2.80–3.00 (m, 5H), 3.07 (dd, J=12.9, 5.9 Hz, 1H), 3.15–3.25 (m, 1H), 3.45–3.55 (m, 1H), 3.91 (s, 3H), 5.97 (s, 1H), 6.75–6.90 (m, 3H), 6.99 (dd, J=1.6, 7.5 Hz, 1H), 7.09 (d, J=1.8 Hz, 1H).

Example 61

(4aS,9bR)-(2,6-dimethylphenyl)-(5-methyl-6-trifluoromethyl-2,3,4,4a,5,9b-hexahydro-1H-pyrido[4,3-b]indol-8-yl)-amine

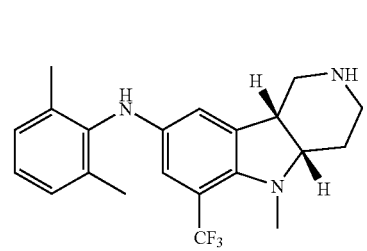

The title compound was prepared by following the general coupling procedure as a yellow solid (18 mg, 50%) from (4aS,9bR)-bromo-5-methyl-6-trifluoromethyl-1,3,4,4a,5,9b-hexahydro-pyrido[4,3-b]indole-2-carboxylic acid tert-butyl ester (Example 45, 41 mg, 0.095 mmol) and 2,6-dimethylaniline (39 mg, 0.30 mmol). $^1$H NMR (CDCl$_3$, 300 MHz) δ (ppm) 1.87–1.98 (m, 2H), 2.20 (s, 6H), 2.30–2.70 (m, 3H), 2.78–3.20 (m, 6H), 3.33–3.45 (m, 1H), 5.07 (s, 1H), 6.46 (d, J=2.2 Hz, 1H), 6.59 (d, J=2.2 Hz, 1H), 7.00–7.18 (m, 3H).

Example 62

(4aS,9bR)-(2,4-Difluoro-phenyl)-(5-methyl-6-trifluoromethyl-2,3,4,4a,5,9b-hexahydro-1H-pyrido[4,3-b]indol-8-yl)-amine

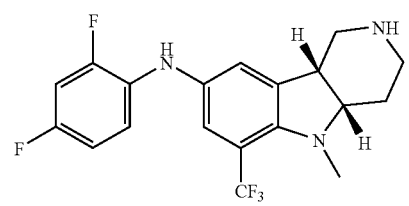

The title compound was prepared by following the general coupling procedure as a yellow solid (21 mg, 55%) from (4aS,9bR)-bromo-5-methyl-6-trifluoromethyl-1,3,4,4a,5,9b-hexahydro-pyrido[4,3-b]indole-2-carboxylic acid tert-butyl ester (Example 45, 41 mg, 0.095 mmol) and 2,4-difluoroaniline (39 mg, 0.30 mmol). MS (APCI): 384 (base, M+H).

Example 63

(4aS,9bR)-(2,6-Difluoro-phenyl)-(5-methyl-6-trifluoromethyl-2,3,4,4a,5,9b-hexahydro-1H-pyrido[4,3-b]indol-8-yl)-amine

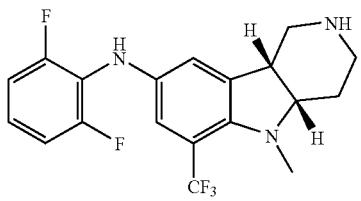

The title compound was prepared by following the general coupling procedure as a yellow solid (12 mg, 31%) from (4aS,9bR)-bromo-5-methyl-6-trifluoromethyl-1,3,4,4a,5,9b-hexahydro-pyrido[4,3-b]indole-2-carboxylic acid tert-butyl ester (Example 45, 41 mg, 0.095 mmol) and 2,6-difluoroaniline (39 mg, 0.30 mmol). MS (APCI): 384 (base, M+H).

Example 64 cis-(4a,9b)-8-hydroxy-5-methyl-6-trifluoromethyl-1,3,4,4a,5,9b-hexahydro-pyrido[4,3-b]indole-2-carboxylic acid tert-butyl ester

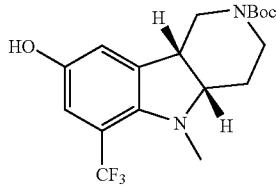

To a solution of 8-bromo-5-methyl-6-trifluoromethyl-1,3,4,4a,5,9b-hexahydro-pyrido[4,3-b]indole-2-carboxylic acid tert-butyl ester (Example 44, 12.6 g, 29 mmol) in anhydrous THF (120 mL) at −78° C. was added n-BuLi (2.5 M in hexanes, 17.6 mL, 44 mmol). The reaction was warmed to −60° C. for 45 min. The mixture was cooled to −78° C. and triisopropyl borate (13.5 mL, 58 mmol) was added dropwise. The reaction was stirred at −78° C. for 30 min and then at 0° C. for an additional 20 min. Acetic acid (7.4 mL, 129 mmol) was added followed by the addition of hydrogen peroxide (35 wt % in water, 4.5 mL, 47 mmol). The reaction was stirred at room temperature for 20 min. The mixture was partitioned between 1:1 ether/water (1000 mL). The ether layer was then washed successively with 10% aq sodium thiosulfate (100 mL), water (100 mL), and brine (100 mL), dried over sodium sulfate, and concentrated in vacuo. Purification of the residue by column chromatography (silica gel, 2:1 hexanes/EtOAc) followed by trituration in ether provided the title compound (7.2 g, 67%) as a white solid: MS (ESI): 373 (base, M+H).

Example 65

(4aS,9bR)-8-hydroxy-5-methyl-6-trifluoromethyl-1,3,4,4a,5,9b-hexahydro-pyrido[4,3-b]indole-2-carboxylic acid tert-butyl ester

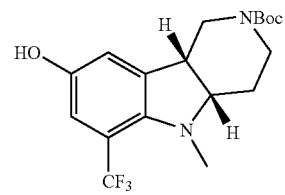

The title compound was prepared by following the above procedure for Example 70 as a white solid from (4aS,9bR)-bromo-5-methyl-6-trifluoromethyl-1,3,4,4a,5,9b-hexahydro-pyrido[4,3-b]indole-2-carboxylic acid tert-butyl ester (Example 45). MS (ESI): 373 (base, M+H).

Example 66 cis-(4a,9b)-5-methyl-6-trifluoromethyl-2,3,4,4a,5,9b-hexahydro-1H-pyrido[4,3-b]indol-8-ol

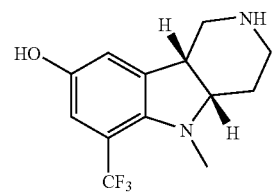

A solution of cis-(4a,9b)-8-hydroxy-5-methyl-6-trifluoromethyl-1,3,4,4a,5,9b-hexahydro-pyrido[4,3-b]indole-2-carboxylic acid tert-butyl ester (Example 70, 150 mg, 0.4 mmol) in 20% trifluoroacetic acid in dichloromethane (2.5 mL) was stirred for 1 h at rt. The reaction mixture was then concentrated in vacuo. The residue was dissolved in CHCl$_3$ and washed with 1 M NaOH. The organic layer was dried over MgSO$_4$, filtered, and concentrated in vacuo to give the title compound as a pale yellow solid (103 mg, 95%) MS (ESI): 273 (base, M+H).

Example 67

(4aS,9bR)-5-methyl-6-trifluoromethyl-2,3,4,4a,5,9b-hexahydro-1H-pyrido[4,3-b]indol-8-ol

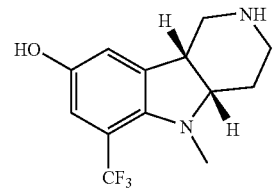

The title compound was prepared by following the above procedure for Example 72 as a pale yellow solid from (4aS,9bR)-8-hydroxy-5-methyl-6-trifluoromethyl-1,3,4,4a,5,9b-hexahydro-pyrido[4,3-b]indole-2-carboxylic acid tert-butyl ester (Example 71). MS (ESI): 273 (base, M+H).

Example 68 cis-(4a,9b)-8-cyclopropylmethoxy-5-methyl-6-trifluoromethyl-2,3,4,4a,5,9b-hexahydro-1H-pyrido[4,3-b]indole

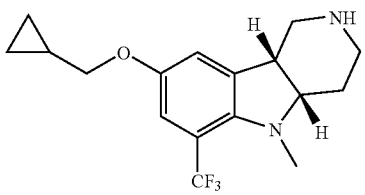

Step A. To a suspension of NaH (60% in mineral oil, 30 mg, 0.75 mmol) in DMF (0.5 mL) at 0° C. was added dropwise a solution of cis-(4a,9b)-8-hydroxy-5-methyl-6-trifluoromethyl-1,3,4,4a,5,9b-hexahydro-pyrido[4,3-b]indole-2-carboxylic acid tert-butyl ester (Example 70, 162 mg, 0.44 mmol) in DMF (0.5 mL). The reaction mixture was stirred for 30 min at 0° C. then cyclopropylmethyl bromide (60 µL, 0.60 mmol) was added. The ice bath was removed and the reaction mixture was stirred for 1 h. The reaction was quenched with the careful addition of crushed ice, then water (2 mL). The mixture was extracted with EtOAc (25 mL) and the organic layer was washed with water (10 mL) and brine (10 mL), dried over anhydrous $Na_2SO_4$, filtered, and evaporated. Purification of the residue by column chromatography (silica gel, 2:1 hexanes/$Et_2O$) provided cis-(4a,9b)-8-cyclopropylmethoxy-5-methyl-6-trifluoromethyl-1,3,4,4a,5,9b-hexahydro-pyrido[4,3-b]indole-2-carboxylic acid tert-butyl ester (125 mg, 67%) as an oil: $^1$H NMR (300 MHz, $CDCl_3$) δ 6.89–6.82 (m, 2H), 3.89–3.73 (m, 1H), 3.72 (d, J=6.9 Hz, 2H), 3.61–3.23 (m, 3H), 2.91–2.83 (m, 3H), 1.96–1.68 (m, 2H), 1.44 (s, 9H), 0.6–0.57 (m, 2H), 0.36–0.27 (m, 2H); MS (ESI): 427 (Base, M+H).

Step B. To a stirred solution of cis-(4a,9b)-8-cyclopropylmethoxy-5-methyl-6-trifluoromethyl-1,3,4,4a,5,9b-hexahydro-pyrido[4,3-b]indole-2-carboxylic acid tert-butyl ester (109 mg, 0.25 mmol) in $CH_2Cl_2$ (5 mL) was added TFA (0.50 mL). The reaction was stirred at room temperature for 3 h and the solvent was evaporated under vacuum. The residue was dissolved in $CH_2Cl_2$ and the solution was washed with sat. $NaHCO_3$, dried over $Na_2SO_4$, filtered, and concentrated in vacuo. Purification of the residue by CombiFlash chromatography [silica gel, 0–20% ($CHCl_3$/MeOH/$NH_4OH$)/EtOAc] provided the title compound (48 mg, 58%) as a light yellow oil: $^1$H NMR (300 MHz, $CD_3OD$) δ 6.94 (d, J=2.3 Hz, 1H), 6.83 (d, J=2.5 Hz, 1H), 3.75 (d, J=6.8 Hz, 1H), 3.43–3.34 (m, 1H), 3.18–3.07 (m, 1H), 2.95 (dd J=6.2, 12.9 Hz, 1H), 2.89–2.71 (m, 5H), 2.48 (dd, J=9.2, 12.9 Hz, 1H), 1.98–1.75 (m, 2H), 1.28–1.12 (m, 1H), 0.63–0.54 (m, 2H), 0.36–0.27 (m, 2H); MS (ESI): 327 (Base M+H).

Example 69 cis-(4a,9b)-8-cyclopentylmethoxy-5-methyl-6-trifluoromethyl-2,3,4,4a,5,9b-hexahydro-1H-pyrido[4,3-b]indole

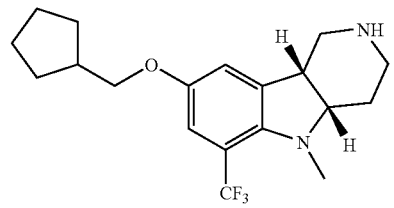

Following the procedure described for Example 74 Step A, and B, the title compound was prepared as a yellow oil in 57% yield: $^1$H NMR (300 MHz, $CD_3OD$) δ 6.93 (d, J=2.3 Hz, 1H), 6.82 (d, J=2.5 Hz, 1H), 3.78 (d, J=6.9 Hz, 2H), 3.42–3.37 (m, 1H), 3.19–3.08 (m, 1H), 2.96 (dd, J=12.9, 6.1 Hz, 1H), 2.89–2.74 (m, 5H), 2.48 (dd, J=12.9, 9.1 Hz, 1H), 2.39–2.24 (m, 1H), 1.99–1.74 (m, 4H), 1.74–1.5 (m, 4H), 1.47–1.28 (m, 2H); ESI MS m/z 355 $[C_{19}H_{25}F_3N_2O+H]^+$.

Example 70 cis-(4a,9b)-5-methyl-8-(3-methyl-butoxy)-6-trifluoromethyl-2,3,4,4a,5,9b-hexahydro-1H-pyrido[4,3-b]indole

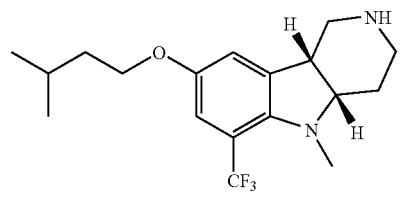

Following the procedure described for Example 74 Step A, cis-(4a,9b)-5-methyl-8-(3-methyl-butoxy)-6-trifluoromethyl-1,3,4,4a,5,9b-hexahydro-pyrido[4,3-b]indole-2-carboxylic acid tert-butyl ester was prepared using Example 70 (124 mg, 0.33 mmol), 3-methylbromobutane (60 µL, 0.48 mmol), and NaH (60% in mineral oil, 27 mg, 0.68 mmol) in 76% yield (111 mg) as an oil: $^1$H NMR (300 MHz, $CD_3OD$) δ 6.95 (d, J=2.4 Hz, 1H), 6.80 (d, J=2.4 Hz, 1H), 3.96–3.91 (m, 2H), 3.79–3.12 (m, 6H), 2.89–2.83 (m, 3H), 2.04–1.73 (m, 3H), 1.68–1.57 (m, 2H), 1.36 (s, 9H), 0.95 (d, J=6.8 Hz, 6H); ESI MS m/z 443 $[C_{23}H_{33}F_3N_2O_3+H]^+$.

The title compound was prepared by following the deprotection procedure of Example 74 Step B as a as a yellow oil: $^1$H NMR (300 MHz, $CD_3OD$) δ 6.94 (d, J=2.3 Hz, 1H), 6.83 (d, J=2.5 Hz, 1H), 3.94 (t, J=6.5 Hz, 1H), 3.44–3.35 (m, 1H), 3.19–3.09 (m, 1H), 2.95 (dd, J=12.9, 6.1 Hz, 1H), 2.86–2.73 (m, 5H), 2.48 (dd, J=12.9, 9.1 Hz, 1H), 1.98–1.77 (m, 3H), 1.62 (q, J=6.6 Hz, 2H), 0.96 (d, J=6.7 Hz, 6H); ESI MS m/z 343 $[C_{17}H_{25}F_3N_2O+H]^+$.

Example 71 cis-(4a,9b)-5-methyl-8-propoxy-6-trifluoromethyl-2,3,4,4a,5,9b-hexahydro-1H-pyrido[4,3-b]indole

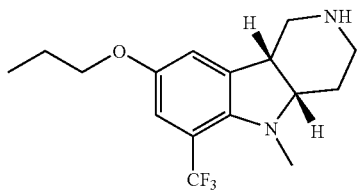

Following the procedure described for Example 74 Step A, cis-(4a,9b)-5-methyl-8-propoxy-6-trifluoromethyl-1,3,4,4a,5,9b-hexahydro-pyrido[4,3-b]indole-2-carboxylic acid tert-butyl ester was prepared using Example 70 (130 mg, 0.35 mmol), bromopropane (40 μL, 0.44 mmol), and NaH (60% in mineral oil, 30 mg, 0.75 mmol) in 83% yield (120 mg) as an oil: $^1$H NMR (300 MHz, CD$_3$OD) δ 6.95 (d, J=2.4 Hz, 1H), 6.80 (d, J=2.4 Hz, 1H), 3.92–3.80 (m, 2H), 3.75–3.14 (m, 6H), 2.91–2.85 (m, 3H), 2.02–1.68 (m, 4H), 1.37 (s, 9H), 1.03 (t, J=7.4 Hz, 3H); ESI MS m/z 415 [C$_{21}$H$_{29}$F$_3$N$_2$O$_3$+H]$^+$.

The title compound was prepared by following the deprotection procedure of Example 74 Step B as a as a light yellow oil in 52% yield: $^1$H NMR (300 MHz, CD$_3$OD) δ 6.94 (d, J=2.4 Hz, 1H), 6.84 (d, J=2.5 Hz, 1H), 3.89 (t, J=6.4 Hz, 1H), 3.47–3.27 (m, 1H), 3.21–3.09 (m, 1H), 2.96 (dd, J=12.9, 6.1 Hz, 1H), 2.86–2.70 (m, 5H), 2.48 (dd, J=12.9, 9.2 Hz, 1H), 2.00–1.68 (m, 4H), 1.02 (t, J=7.4 Hz, 3H); ESI MS m/z 315 [C$_{16}$H$_{21}$F$_3$N$_2$O+H]$^+$.

Example 72 cis-(4a,9b)-8-butoxy-5-methyl-6-trifluoromethyl-2,3,4,4a,5,9b-hexahydro-1H-pyrido[4,3-b]indole

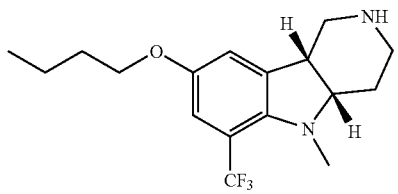

Following the procedure described for Example 74 Step A, cis-(4a,9b)-5-methyl-8-butoxy-6-trifluoromethyl-1,3,4,4a,5,9b-hexahydro-pyrido[4,3-b]indole-2-carboxylic acid tert-butyl ester was prepared using Example 70 (122 mg, 0.33 mmol), bromobutane (50 μL, 0.46 mmol), and NaH (60% in mineral oil, 37 mg, 0.92 mmol) in 84% yield (119 mg) as an oil: $^1$H NMR (300 MHz, CD$_3$OD) δ 6.95 (d, J=2.4 Hz, 1H), 6.80 (d, J=2.4 Hz, 1H), 3.98–3.87 (m, 2H), 3.76–3.16 (m, 6H), 2.91–2.85 (m, 3H), 2.05–1.65 (m, 4H), 1.56–1.42 (m, 2H), 1.36 (s, 9H), 0.98 (t, J=7.4 Hz, 3H); ESI MS m/z 429 [C$_{22}$H$_{31}$F$_3$N$_2$O$_3$+H]$^+$.

The title compound was prepared by following the deprotection procedure of Example 74 Step B as a as a light yellow oil in 44% yield: $^1$H NMR (300 MHz, CD$_3$OD) δ 6.94 (d, J=2.4 Hz, 1H), 6.83 (d, J=2.5 Hz, 1H), 3.91 (t, J=6.3 Hz, 1H), 3.44–3.36 (m, 1H), 3.19–3.10 (m, 1H), 2.96 (dd, J=12.9, 6.2 Hz, 1H), 2.89–2.74 (m, 5H), 2.49 (dd, J=12.8, 9.2 Hz, 1H), 1.99–1.80 (m, 2H), 1.58–1.42 (m, 2H), 0.98 (t, J=7.3 Hz, 3H); ESI MS m/z 329 [C$_{17}$H$_{23}$F$_3$N$_2$O+H]$^+$.

Example 73 cis-(4a,9b)-8-(3,3-dimethyl-butoxy)-5-methyl-6-trifluoromethyl-2,3,4,4a,5,9b-hexahydro-1H-pyrido[4,3-b]indole

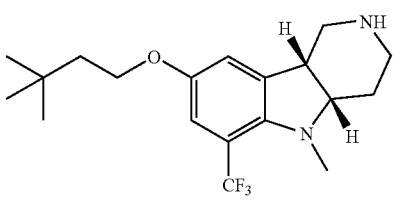

Following the procedure described for Example 74 Step A, and B, the title compound was prepared as a light yellow oil in 53% yield: $^1$H NMR (300 MHz, CD$_3$OD) δ 6.93 (d, J=2.4 Hz, 1H), 6.82 (d, J=2.6 Hz, 1H), 3.98 (t, J=6.9 Hz, 1H), 3.43–3.37 (m, 1H), 3.19–3.09 (m, 1H), 2.96 (dd, J=12.8, 6.1 Hz, 1H), 2.88–2.73 (m, 5H), 2.49 (dd, J=12.8, 9.2 Hz, 1H), 1.98–1.77 (m, 2H), 1.68 (t, J=7.0 Hz, 2H), 0.99 (s, 9H); ESI MS m/z 357 [C$_{19}$H$_{27}$F$_3$N$_2$O+H]$^+$.

Example 74 cis-(4a,9b)-8-cyclobutylmethoxy-5-methyl-6-trifluoromethyl-2,3,4,4a,5,9b-hexahydro-1H-pyrido[4,3-b]indole

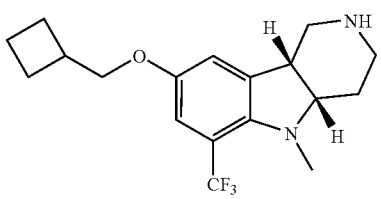

Following the procedure described for Example 74 Step A, cis-(4a,9b)-5-methyl-8-cyclobutylmethoxy-6-trifluoromethyl-1,3,4,4a,5,9b-hexahydro-pyrido[4,3-b]indole-2-carboxylic acid tert-butyl ester was prepared using Example 70 (122 mg, 0.33 mmol), cyclobutylmethyl bromide (44 μL, 0.40 mmol), and NaH (60% in mineral oil, 16 mg, 0.40 mmol) in 36% yield (52 mg) as an oil: $^1$H NMR (300 MHz, CD$_3$OD) δ 6.96 (d, J=2.5 Hz, 1H), 6.80 (d, J=2.5 Hz, 1H), 3.92–3.81 (m, 2H), 3.78–3.32 (m 7H), 3.28–3.13 (m 1H), 2.91–2.84 (m, 3H), 2.79–2.65 (m, 1H), 2.20–1.76 (m, 6H), 1.37 (s, 9H); ESI MS m/z 441 [C$_{23}$H$_{31}$F$_3$N$_2$O$_3$+H]$^+$.

The title compound was prepared by following the deprotection procedure of Example 74 Step B as a as a light yellow oil in 33% yield: $^1$H NMR (300 MHz, CD$_3$OD δ 6.94 (d, J=2.4 Hz, 1H), 6.83 (d, J=2.5 Hz, 1H), 3.87 (d, J=6.4 Hz, 1H), 3.43–3.35 (m, 1H), 3.29–3.19 (m, 1H), 2.96 (dd, J=12.9, 6.2 Hz, 1H), 2.89–2.64 (m, 6H), 2.49 (dd, J=12.9, 9.2 Hz, 1H), 2.18–2.04 (m, 2H), 2.04–1.78 (m, 6H); ESI MS m/z 341 [C$_{18}$H$_{23}$F$_3$N$_2$O+H]$^+$.

General Method for Preparation of 5-methyl-8-(pyridin-yl-methoxy)-6-trifluoromethyl-2,3,4,4a,5,9b-hexahydro-1H-pyrido[4,3-b]indole 8-Hydroxy-5-methyl-6-trifluoromethyl-1,3,4,4a,5,9b-hexahydro-pyrido[4,3-b]indole-2-carboxylic acid tert-butyl ester (1.0 eq.), bromomethylpyridine (2.0 eq.), and $K_2CO_3$ (4.0 eq.) were dissolved in anhydrous DMF(0.3 M). The mixture was stirred under Ar at rt for 24 h. Same work up and deprotection procedure were followed as described in Example 74 Method A and B to obtain the title compound.

Example 75

(4aS,9bR)-5-methyl-8-(pyridin-2-ylmethoxy)-6-trifluoromethyl-2,3,4,4a,5,9b-hexahydro-1H-pyrido[4,3-b]indole

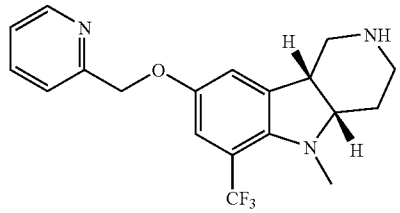

The title compound was prepared by following the general method as a yellow solid (60 mg, 61%) from (4aS,9bR)-8-hydroxy-5-methyl-6-trifluoromethyl-1,3,4,4a,5,9b-hexahydro-pyrido[4,3-b]indole-2-carboxylic acid tert-butyl ester (Example 71, 100 mg, 0.27 mmol), 2-bromomethyl-pyridine (141 mg, 0.56 mmol) and $K_2CO_3$ (156 mg, 1.12 mmol). MS (ESI): 364 (base, M+H).

Example 76

(4aS,9bR)-5-methyl-8-(pyridin-3-ylmethoxy)-6-trifluoromethyl-2,3,4,4a,5,9b-hexahydro-1H-pyrido[4,3-b]indole

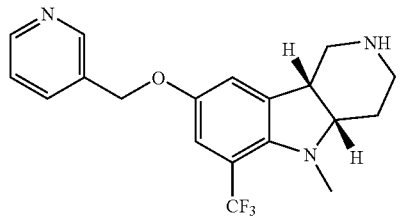

The title compound was prepared by following the general method as a white solid (48 mg, 49%) from (4aS,9bR)-8-hydroxy-5-methyl-6-trifluoromethyl-1,3,4,4a,5,9b-hexahydro-pyrido[4,3-b]indole-2-carboxylic acid tert-butyl ester (Example 71, 100 mg, 0.27 mmol), 3-bromomethyl-pyridine (141 mg, 0.56 mmol) and $K_2CO_3$ (156 mg, 1.12 mmol). MS (ESI): 364 (base, M+H).

Example 77

(4aS,9bR)-5-methyl-8-(pyridin-4-ylmethoxy)-6-trifluoromethyl-2,3,4,4a,5,9b-hexahydro-1H-pyrido[4,3-b]indole

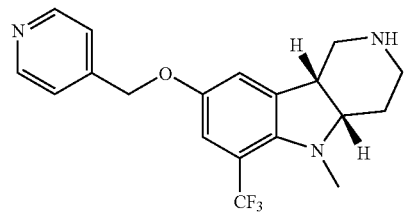

The title compound was prepared by following the general Method C as a light yellow solid (56 mg, 57%) from (4aS,9bR)-8-hydroxy-5-methyl-6-trifluoromethyl-1,3,4,4a,5,9b-hexahydro-pyrido[4,3-b]indole-2-carboxylic acid tert-butyl ester (Example 71, 100 mg, 0.27 mmol), 4-bromomethyl-pyridine (141 mg, 0.56 mmol) and K2CO3 (156 mg, 1.12 mmol). MS (ESI): 364 (base, M+H).

Example 78 cis-(4a,9b)-5-methyl-8-o-tolyloxy-6-trifluoromethyl-2,3,4,4a,5,9b-hexahydro-1H-pyrido[4,3-b]indole

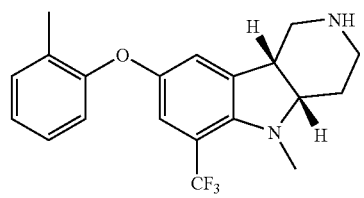

To a solution of cis-(4a,9b)-8-hydroxy-5-methyl-6-trifluoromethyl-1,3,4,4a,5,9b-hexahydro-pyrido[4,3-b]indole-2-carboxylic acid tert-butyl ester (Example 70, 50 mg, 0.13 mmol) in triethylamine (38 µL, 0.27 mmol) and $CH_2Cl_2$ was added 2-methylphenyl boronic acid (37 mg, 0.27 mmol) and $Cu(OAc)_2$ (36 mg, 0.2 mg). The reaction mixture was stirred open to the air at rt for 15 h. The reaction mixture was filtered and concentrated in vacuo. The residue was chromatographed (silica gel, Hex/EtoAc 0–30%) to give 5-methyl-8-o-tolyloxy-6-trifluoromethyl-1,3,4,4a,5,9b-hexahydro-pyrido[4,3-b]indole-2-carboxylic acid tert-butyl ester. Deprotection of Boc group was followed as described in Example 74 to obtain the title compound as a yellow oil (13 mg, 28%). MS (ESI): 364 (Base M+H).

Example 79 cis-(4a,9b)-8-(2,5-dimethyl-phenoxy)-5-methyl-6-trifluoromethyl-2,3,4,4a,5,9b-hexahydro-1H-pyrido[4,3-b]indole

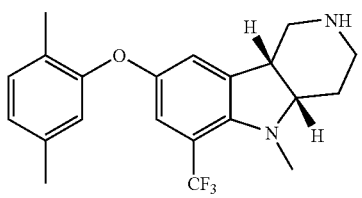

Following the procedure described for Example 84 Step A, the title compound was prepared using cis-(4a,9b)-8-hydroxy-5-methyl-6-trifluoromethyl-1,3,4,4a,5,9b-hexahydro-pyrido[4,3-b]indole-2-carboxylic acid tert-butyl ester (Example 70, 50 mg, 0.13 mmol), triethylamine (38 µL, 0.27 mmol), 2,5-dimethylphenyl boronic acid (41 mg, 0.27 mmol) and Cu(OAc)$_2$ (36 mg, 0.2 mg) as a yellow oil (10 mg, 20%). MS (ESI): 377 (Base M+H).

Example 80 cis-(4a,9b)-2-(5-methyl-6-trifluoromethyl-2,3,4,4a,5,9b-hexahydro-1H-pyrido[4,3-b]indol-8-yloxy)-benzonitrile

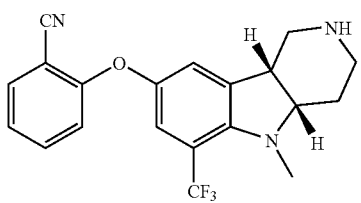

A mixture of cis-(4a,9b)-8-hydroxy-5-methyl-6-trifluoromethyl-1,3,4,4a,5,9b-hexahydro-pyrido[4,3-b]indole-2-carboxylic acid tert-butyl ester (Example 70, 50 mg, 0.13 mmol), 2-fluoro-benzylcarbonitrile (22 µL, 0.2 mmol), K$_2$CO$_3$ (29 mg, 0.21 mmol) in DMF (1 ml) was irradiated in microwave for 900 sec. at 160° C. The reaction mixture was partitioned between H$_2$O and EtOAc. The organic layer was washed with H$_2$O, dried over MgSO$_4$, filtered and concentrated in vacuo. The residue was chromatographed (silica gel, Hex/EtoAc 0–50%) to give 8-(2-cyano-phenoxy)-5-methyl-6-trifluoromethyl-1,3,4,4a,5,9b-hexahydro-pyrido[4,3-b]indole-2-carboxylic acid tert-butyl ester. Deprotection of Boc group was followed as described in Example 74 to obtain the title compound as a yellow oil (21 mg, 43%). MS (ESI): 374 (Base M+H).

Example 81 cis-(4a,9b)-4-(5-methyl-6-trifluoromethyl-2,3,4,4a,5,9b-hexahydro-1H-pyrido[4,3-b]indol-8-yloxy)-benzonitrile

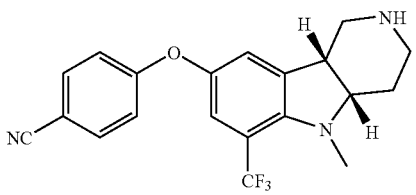

Following the procedure described for Example 84 Step A, the title compound was prepared using cis-(4a,9b)-8-hydroxy-5-methyl-6-trifluoromethyl-1,3,4,4a,5,9b-hexahydro-pyrido[4,3-b]indole-2-carboxylic acid tert-butyl ester (Example 70, 50 mg, 0.13 mmol), triethylamine (38 µL, 0.27 mmol), 4-cyano-phenyl boronic acid (39 mg, 0.27 mmol) and CuF$_6$(MeCN)$_4$ (36 mg, 0.2 mg) as a yellow oil (12 mg, 25%). MS (ESI): 374 (Base M+H).

Example 82 cis-(4a,9b)-8-(2-methoxy-phenoxy)-5-methyl-6-trifluoromethyl-2,3,4,4a,5,9b-hexahydro-1H-pyrido[4,3-b]indole

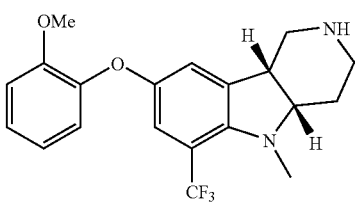

Following the procedure described for Example 84 Step A, the title compound was prepared using cis-(4a,9b)-8-hydroxy-5-methyl-6-trifluoromethyl-1,3,4,4a,5,9b-hexahydro-pyrido[4,3-b]indole-2-carboxylic acid tert-butyl ester (Example 70, 50 mg, 0.13 mmol), triethylamine (38 µL, 0.27 mmol), 2-methoxy-phenyl boronic acid (41 mg, 0.27 mmol) and CuF$_6$(MeCN)$_4$ (36 mg, 0.2 mg) as a yellow oil (11 mg, 22%). MS (ESI): 388 (Base M+H).

Example 83 cis-(4a,9b)-8-amino-5-methyl-6-trifluoromethyl-1,3,4,4a,5,9b-hexahydro-pyrido[4,3-b]indole-2-carboxylic acid tert-butyl ester

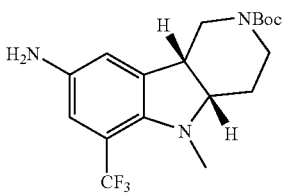

A solution of cis-(4a,9b)-8-bromo-5-methyl-6-trifluoromethyl-1,3,4,4a,5,9b-hexahydro-pyrido[4,3-b]indole-2-carboxylic acid tert-butyl ester. (Example 44) (434 mg, 1.0 mmol), benzophenone imine (218 mg, 1.2 mmol), (S)-(−)-2,2'-bis(diphenylphosphino)-1,1'-binaphthyl (BINAP) (46.7 mg, 0.075 mmol), Pd$_2$dba$_3$ (46 mg, 0.05 mmol) and sodium tert-butoxide (135 mg, 1.4 mmol) in degassed toluene (5 mL) was heated at reflux under Argon atmosphere for 15 h. The solution was cooled, and H$_2$O was added to the reaction mixture. The mixture extracted with CH$_2$Cl$_2$. The organic layer was dried over MgSO$_4$, filtered and concentrated in vacuo. The residue was taken up in methanol (15 mL) and then there was added NaOAC (197 mg) and hydroxylamine hydrochloride (127 mg) and the mixture was stirred at rt for 3 h. To the reaction mixture was diluted with CH$_2$Cl$_2$ then washed with H$_2$O. The organic solution was dried over MgSO$_4$, filtered and concentrated in vacuo. The residue was purified by column chromatography (EtOAc/hexane 2/8) to afford the title compound (269 mg, 73%) as a yellow solid. MS (APCI): 372 (base, M+H).

Example 84

(4aS,9bR)-8-amino-5-methyl-6-trifluoromethyl-1,3,4,4a,5,9b-hexahydro-pyrido[4,3-b]indole-2-carboxylic acid tert-butyl ester

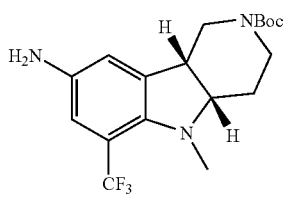

The title compound was prepared by following the procedure described for Example 89 using (4aS,9bR)-8-bromo-5-methyl-6-trifluoromethyl-1,3,4,4a,5,9b-hexahydro-pyrido[4,3-b]indole-2-carboxylic acid tert-butyl ester (Example 45). MS (APCI): 372 (base, M+H).

Example 85 cis-(4a,9b)-5-methyl-6-trifluoromethyl-2,3,4,4a,5,9b-hexahydro-1H-pyrido[4,3-b]indol-8-ylamine

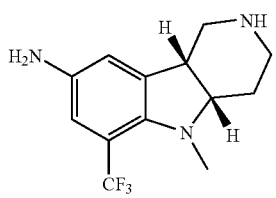

To a solution of cis-(4a,9b)-8-amino-5-methyl-6-trifluoromethyl-1,3,4,4a,5,9b-hexahydro-pyrido[4,3-b]indole-2-carboxylic acid tert-butyl ester (Example 89, 100 mg, 0.27 mmol) in CH$_2$Cl$_2$ (5 mL) was added TFA (1 mL) at rt. The reaction mixture was stirred for 1 h at rt then concentrated in vacuo. The residue was dissolved in CHCl$_3$ (20 mL) and washed with 1 M NaOH (5 mL). The organic solution was dried over MgSO$_4$, filtered and concentrated in vacuo. to yield the title compound (70 mg, 95%) as a yellow solid: MS (ESI): 272 (base, M+H).

Example 86

(4aS,9bR)-5-methyl-6-trifluoromethyl-2,3,4,4a,5,9b-hexahydro-1H-pyrido[4,3-b]indol-8-ylamine

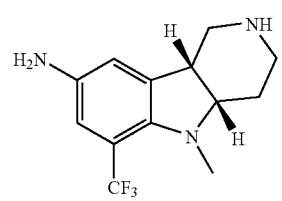

The title compound was prepared by following the procedure described for Example 91 using (4aS,9bR)-8-amino-5-methyl-6-trifluoromethyl-1,3,4,4a,5,9b-hexahydro-pyrido[4,3-b]indole-2-carboxylic acid tert-butyl ester (Example 90). MS (APCI): 272 (base, M+H).

General Coupling Method for Preparation of (5-methyl-6-trifluoromethyl-2,3,4,4a,5,9b-hexahydro-1H-pyrido[4,3-b]indol-8-yl)-pyridin-3-yl-amine Method A. 8-bromo-5-methyl-6-trifluoromethyl-1,3,4,4a,5,9b-hexahydro-pyrido[4,3-b]indole-2-carboxylic acid tert-butyl ester (Example 44 or 45, 1.0 eq.), aminopyridine (3.0 eq.), and NaOt-Bu (3.0 eq.) were dissolved in anhydrous toluene (0.17 M). The mixture was degassed with argon for 30 min. Pd$_2$(dba)$_3$ (0.06 eq.) and 2,2'-bis(diphenylphosphino)-1,1'-binaphthyl (0.18 eq.) were added; the reaction was heated at 80° C. for 16 h. The reaction was cooled to room temperature, diluted with EtOAc, filtered through a bilayer pad of diatomaceous earth and silica gel, and concentrated. Purification of the residue by flash column chromatography (silica gel, 2–30% EtOAc/hexanes) provided 5-methyl-8-(pyridinylamino)-6-trifluoromethyl-1,3,4,4a,5,9b-hexahydro-pyrido[4,3-b]indole-2-carboxylic acid tert-butyl ester derivatives. The intermediate was dissolved in CH$_2$Cl$_2$/TFA (5/1) at rt stirred for 1 h. Upon concentration in vacuo, the residue was partitioned between CH$_2$Cl$_2$/1 M NaOH. The aqueous phase was extracted with CH$_2$Cl$_2$. The combined organic phases were dried over MgSO$_4$, filtered, and concentrated in vacuo. The residue was purified by flash column chromatography to give the title compound.

Method B. 8-amino-5-methyl-6-trifluoromethyl-1,3,4,4a,5,9b-hexahydro-pyrido[4,3-b]indole-2-carboxylic acid tert-butyl ester (Example 91 or 92, 1.0 eq.), bromopyridine (1.0 eq.), and CsCO$_3$ (2.0 eq.) were dissolved in anhydrous toluene (0.1 M). The mixture was degassed with argon for 30 min. Pd$_2$(dba)$_3$ (0.01 eq.) and 2,2'-bis(diphenylphosphino)-1,1'-binaphthyl (0.13 eq.) were added; the reaction was heated at 80° C. for 16 h. Same work up and deprotection procedure were followed as described in Method A to obtain the title compound.

Example 87 cis-(4a,9b)-(5-Methyl-6-trifluoromethyl-2,3,4,4a,5,9b-hexahydro-1H-pyrido[4,3-b]indol-8-yl)-pyridin-3-yl-amine

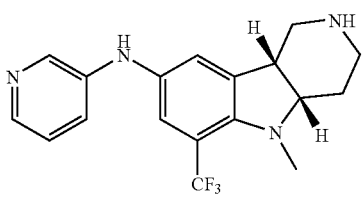

The title compound was prepared by following the general Method A as a yellow solid (24 mg, 14%) from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44, 217 mg, 0.5 mmol), 3-amino-pyridine (141 mg, 1.5 mmol) and NaOt-Bu (144 mg, 1.5 mmol). MS (ESI): 349 (base, M+H).

Example 88 cis-(4a,9b)-(2-chloro-pyridin-3-yl)-(5-methyl-6-trifluoromethyl-2,3,4,4a,5,9b-hexahydro-1H-pyrido[4,3-b]indol-8-yl)-amine

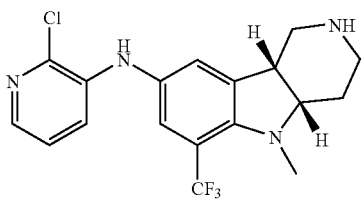

The title compound was prepared by following the general Method A as a yellow solid (68 mg, 36%) from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44, 217 mg, 0.5 mmol), 3-amino-2-chloro-pyridine (192 mg, 1.5 mmol) and NaOt-Bu (144 mg, 1.5 mmol). MS (ESI): 383 (base, M+H).

Example 89 cis-(4a,9b)-3-(5-methyl-6-trifluoromethyl-2,3,4,4a,5,9b-hexahydro-1H-pyrido[4,3-b]indol-8-ylamino)-pyridine-2-carbonitrile

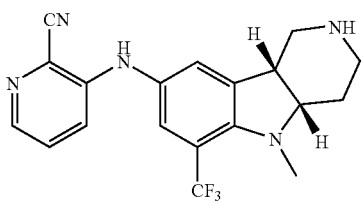

The title compound was prepared by following the general Method B as a yellow solid (67 mg, 60%) from cis-(4a,9b)-8-amino-5-methyl-6-trifluoromethyl-1,3,4,4a,5,9b-hexahydro-pyrido[4,3-b]indole-2-carboxylic acid tert-butyl ester (Example 89, 111 mg, 0.3 mmol), 3-bromo-2-cyano-pyridine (55 mg, 0.3 mmol) and CsCO₃ (196 mg, 0.6 mmol). MS (ESI): 374 (base, M+H).

Example 90

(4aS,9bR)-3-(5-methyl-6-trifluoromethyl-2,3,4,4a,5,9b-hexahydro-1H-pyrido[4,3-b]indol-8-ylamino)-pyridine-2-carbonitrile

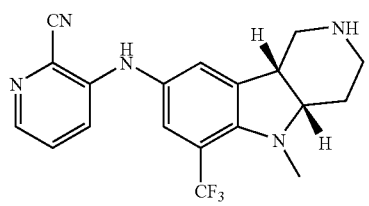

The title compound was prepared by following the general Method B as a yellow solid from (4aS,9bR)-8-amino-5-methyl-6-trifluoromethyl-1,3,4,4a,5,9b-hexahydro-pyrido[4,3-b]indole-2-carboxylic acid tert-butyl ester (Example 90). MS (ESI): 374 (base, M+H).

Example 91 cis-(4a,9b)-(6-methoxy-pyridin-3-yl)-(5-methyl-6-trifluoromethyl-2,3,4,4a,5,9b-hexahydro-1H-pyrido[4,3-b]indol-8-yl)-amine

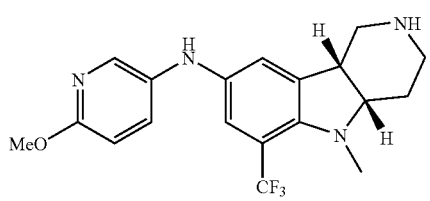

The title compound was prepared by following the general Method A as a yellow solid (52 mg, 28%) from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44, 217 mg, 0.5 mmol), 5-amino-2-methoxy-pyridine (186 mg, 1.5 mmol) and NaOt-Bu (144 mg, 1.5 mmol). MS (ESI): 379 (base, M+H).

Example 92

(4aS,9bR)-(6-methoxy-pyridin-3-yl)-(5-methyl-6-trifluoromethyl-2,3,4,4a,5,9b-hexahydro-1H-pyrido[4,3-b]indol-8-yl)-amine

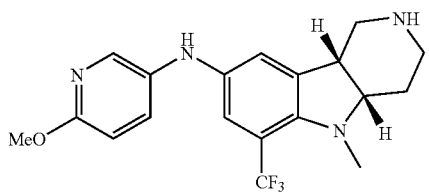

The title compound was prepared by following the general Method A as a yellow solid (85 mg, 45%) from (4aS,9bR)-8-bromo-5-methyl-6-trifluoromethyl-1,3,4,4a,5,9b-hexahydro-pyrido[4,3-b]indole-2-carboxylic acid tert-butyl ester (Example 45, 217 mg, 0.5 mmol), 5-amino-2-methoxy-pyridine (186 mg, 1.5 mmol) and NaOt-Bu (144 mg, 1.5 mmol). MS (ESI): 379 (base, M+H).

Example 93 cis-(4a,9b)-(6-fluoro-pyridin-3-yl)-(5-methyl-6-trifluoromethyl-2,3,4,4a,5,9b-hexahydro-1H-pyrido[4,3-b]indol-8-yl)-amine

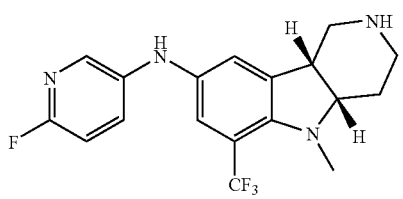

The title compound was prepared by following the general Method A as a yellow solid (14 mg, 8%) from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44, 217 mg, 0.5 mmol), 5-amino-2-fluoro-pyridine (168 mg, 1.5 mmol) and NaOt-Bu (144 mg, 1.5 mmol). MS (ESI): 367 (base, M+H).

Example 94

(4aS,9bR)-(6-fluoro-pyridin-3-yl)-(5-methyl-6-trifluoromethyl-2,3,4,4a,5,9b-hexahydro-1H-pyrido[4,3-b]indol-8-yl)-amine

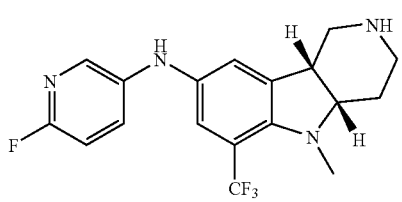

The title compound was prepared by following the general Method A as a yellow solid from (4aS,9bR)-8-bromo-5-methyl-6-trifluoromethyl-1,3,4,4a,5,9b-hexahydro-pyrido[4,3-b]indole-2-carboxylic acid tert-butyl ester (Example 45). MS (ESI): 367 (base, M+H).

Example 95 cis-(4a,9b)-5-(5-methyl-6-trifluoromethyl-2,3,4,4a,5,9b-hexahydro-1H-pyrido[4,3-b]indol-8-ylamino)-pyridine-2-carbonitrile

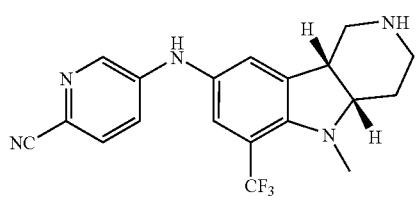

The title compound was prepared by following the general Method A as a yellow solid (10 mg, 6%) from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44, 217 mg, 0.5 mmol), 5-amino-2-cyano-pyridine (179 mg, 1.5 mmol) and NaOt-Bu (144 mg, 1.5 mmol). MS (ESI): 374 (base, M+H).

Example 96 cis-(4a,9b)-5-(5-Methyl-6-trifluoromethyl-2,3,4,4a,5,9b-hexahydro-1H-pyrido[4,3-b]indol-8-ylamino)-nicotinonitrile

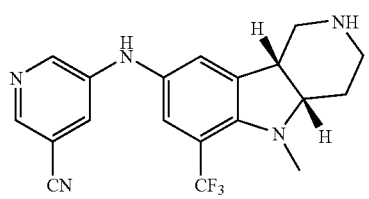

The title compound was prepared by following the general Method B as a yellow solid (33 mg, 18%) from cis-(4a,9b)-8-amino-5-methyl-6-trifluoromethyl-1,3,4,4a,5,9b-hexahydro-pyrido[4,3-b]indole-2-carboxylic acid tert-butyl ester (Example 89, 186 mg, 0.5 mmol), 5-bromo-3-cyano-pyridine (92 mg, 0.5 mmol) and CsCO₃ (326 mg, 1.0 mmol). MS (ESI): 374 (base, M+H).

Example 97 cis-(4a,9b)-5-(5-methyl-6-trifluoromethyl-2,3,4,4a,5,9b-hexahydro-1H-pyrido[4,3-b]indol-8-ylamino)-nicotinic acid methyl ester

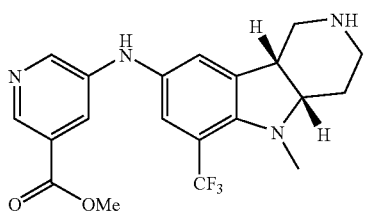

The title compound was prepared by following the general Method B as a yellow solid (29 mg, 14%) from cis-(4a,9b)-8-amino-5-methyl-6-trifluoromethyl-1,3,4,4a,5,9b-hexahydro-pyrido[4,3-b]indole-2-carboxylic acid tert-butyl ester (Example 89, 186 mg, 0.5 mmol), 5-bromo-nicotinic acid methyl ester (108 mg, 0.5 mmol) and CsCO$_3$ (326 mg, 1.0 mmol). MS (ESI): 407 (base, M+H).

Example 98 cis-(4a,9b)-5-(5-methyl-6-trifluoromethyl-2,3,4,4a,5,9b-hexahydro-1H-pyrido[4,3-b]indol-8-ylamino)-nicotinic acid ethyl ester

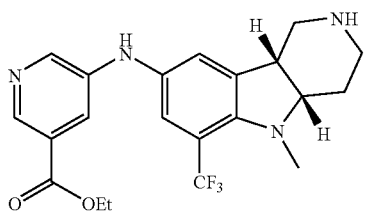

The title compound was prepared by following the general Method B as a yellow oil (52 mg, 25%) from cis-(4a,9b)-8-amino-5-methyl-6-trifluoromethyl-1,3,4,4a,5,9b-hexahydro-pyrido[4,3-b]indole-2-carboxylic acid tert-butyl ester (Example 89, 186 mg, 0.5 mmol), 5-Bromo-nicotinic acid ethyl ester (115 mg, 0.5 mmol) and CsCO$_3$ (326 mg, 1.0 mmol). MS (ESI): 421 (base, M+H).

Example 99

(4aS,9bR)-(2-methoxy-pyridin-3-yl)-(5-methyl-6-trifluoromethyl-2,3,4,4a,5,9b-hexahydro-1H-pyrido[4,3-b]indol-8-yl)-amine

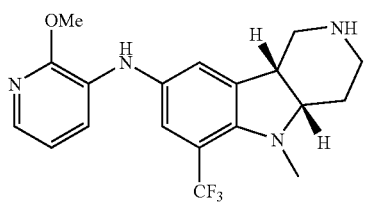

The title compound was prepared by following the general Method A as a yellow solid (25 mg, 13%) from (4aS,9bR)-8-bromo-5-methyl-6-trifluoromethyl-1,3,4,4a,5,9b-hexahydro-pyrido[4,3-b]indole-2-carboxylic acid tert-butyl ester (Example 45, 217 mg, 0.5 mmol), 3-amino-2-methoxy-pyridine (186 mg, 1.5 mmol) and NaOt-Bu (144 mg, 1.5 mmol). MS (ESI): 379 (base, M+H).

Example 100 cis-(4a,9b)-(6-Chloro-pyridin-3-yl)-(5-methyl-6-trifluoromethyl-2,3,4,4a,5,9b-hexahydro-1H-pyrido[4,3-b]indol-8-yl)-amine

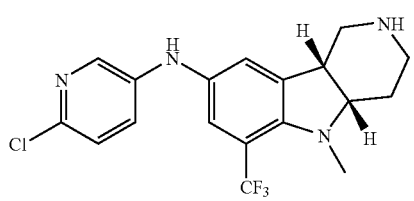

The title compound was prepared by following the general Method A as a yellow solid (48 mg, 25%) from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44, 217 mg, 0.5 mmol), 5-amino-2-chloro-pyridine (193 mg, 1.5 mmol) and NaOt-Bu (144 mg, 1.5 mmol). MS (ESI): 383 (base, M+H).

Example 101

(4aS,9bR)-(6-Chloro-pyridin-3-yl)-(5-methyl-6-trifluoromethyl-2,3,4,4a,5,9b-hexahydro-1H-pyrido[4,3-b]indol-8-yl)-amine

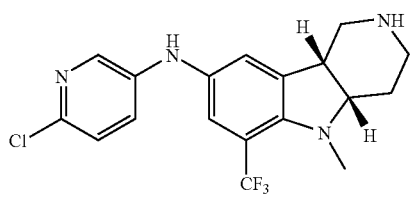

The title compound was prepared by following the general Method A as a yellow solid (56 mg, 29%) from (4aS,9bR)-8-bromo-5-methyl-6-trifluoromethyl-1,3,4,4a,5,9b-hexahydro-pyrido[4,3-b]indole-2-carboxylic acid tert-butyl ester (Example 45, 217 mg, 0.5 mmol), 5-amino-2-chloro-pyridine (193 mg, 1.5 mmol) and NaOt-Bu (144 mg, 1.5 mmol). MS (ESI): 383 (base, M+H).

Example 102 cis-(4a,9b)-(2-ethoxy-pyridin-3-yl)-(5-methyl-6-trifluoromethyl-2,3,4,4a,5,9b-hexahydro-1H-pyrido[4,3-b]indol-8-yl)-amine

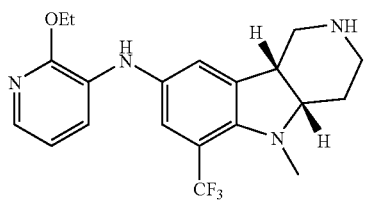

The title compound was prepared by following the general Method B as a yellow solid (12 mg, 7%) from cis-(4a,9b)-8-amino-5-methyl-6-trifluoromethyl-1,3,4,4a,5,9b-hexahydro-pyrido[4,3-b]indole-2-carboxylic acid tert-butyl ester (Example 89, 160 mg, 0.43 mmol), 3-bromo-2-ethoxy-pyridine (101 mg, 0.5 mmol) and $CsCO_3$ (326 mg, 1.0 mmol). MS (ESI): 393 (base, M+H).

Example 103 cis-(4a,9b)-(2,6-dimethoxy-pyridin-3-yl)-(5-methyl-6-trifluoromethyl-2,3,4,4a,5,9b-hexahydro-1H-pyrido[4,3-b]indol-8-yl)-amine

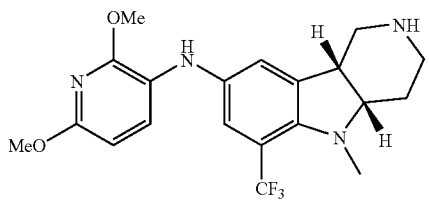

The title compound was prepared by following the general Method A as a yellow solid (22 mg, 11%) from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44, 217 mg, 0.5 mmol), 3-amino-2,6-dimethoxy-pyridine hydrochloride (286 mg, 1.5 mmol) and NaOt-Bu (144 mg, 1.5 mmol). MS (ESI): 409 (base, M+H).

Example 104

(4aS,9bR)-(2,6-dimethoxy-pyridin-3-yl)-(5-methyl-6-trifluoromethyl-2,3,4,4a,5,9b-hexahydro-1H-pyrido[4,3-b]indol-8-yl)-amine

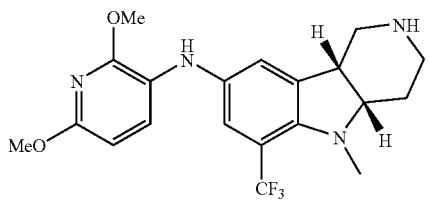

The title compound was prepared by following the general Method A as a yellow solid (4aS,9bR)-8-bromo-5-methyl-6-trifluoromethyl-1,3,4,4a,5,9b-hexahydro-pyrido[4,3-b]indole-2-carboxylic acid tert-butyl ester (Example 45). MS (ESI): 409 (base, M+H).

Example 105 cis-(4a,9b)-(2,6-dichloro-pyridin-3-yl)-(5-methyl-6-trifluoromethyl-2,3,4,4a,5,9b-hexahydro-1H-pyrido[4,3-b]indol-8-yl)-amine

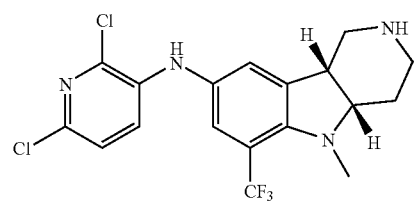

The title compound was prepared by following the general Method A as a yellow solid (21 mg, 10%) from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44, 217 mg, 0.5 mmol), 3-amino-2,6-dichloropyridine (244 mg, 1.5 mmol) and NaOt-Bu (144 mg, 1.5 mmol). MS (ESI): 417 (base, M+H).

Example 106 cis-(4a,9b)-4-methyl-3-(5-methyl-6-trifluoromethyl-2,3,4,4a,5,9b-hexahydro-1H-pyrido[4,3-b]indol-8-ylamino)-pyridine-2-carbonitrile

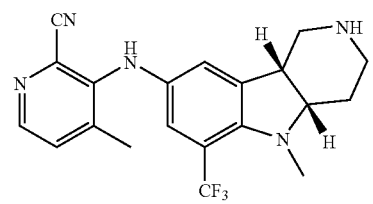

The title compound was prepared by following the general Method B as a yellow solid (20 mg, 10%) from cis-(4a,9b)-8-amino-5-methyl-6-trifluoromethyl-1,3,4,4a,5,9b-hexahydro-pyrido[4,3-b]indole-2-carboxylic acid tert-butyl ester (Example 89, 186 mg, 0.5 mmol), 3-bromo-4-methyl-pyridine-2-carbonitrile (99 mg, 0.5 mmol) and $CsCO_3$ (326 mg, 1.0 mmol). MS (ESI): 388 (base, M+H).

Example 107 cis-(4a,9b)-(6-fluoro-5-methyl-pyridin-3-yl)-(5-methyl-6-trifluoromethyl-2,3,4,4a,5,9b-hexahydro-1H-pyrido[4,3-b]indol-8-yl)-amine

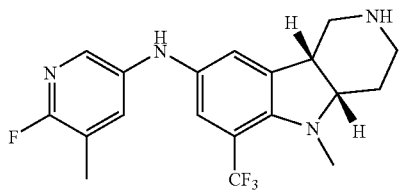

The title compound was prepared by following the general Method A as a yellow solid (18 mg, 10%) from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44, 217 mg, 0.5 mmol), 5-amino-2-fluoro-3-methylpyridine (189 mg, 1.5 mmol) and NaOt-Bu (144 mg, 1.5 mmol). MS (ESI): 381 (base, M+H).

Example 108

(4aS,9bR)-(6-fluoro-5-methyl-pyridin-3-yl)-(5-methyl-6-trifluoromethyl-2,3,4,4a,5,9b-hexahydro-1H-pyrido[4,3-b]indol-8-yl)-amine

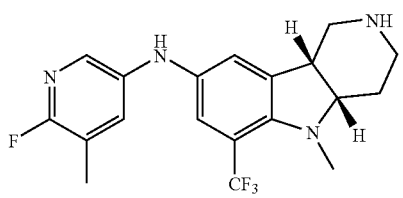

The title compound was prepared by following the general Method A as a yellow solid from (4aS,9bR)-8-bromo-5-methyl-6-trifluoromethyl-1,3,4,4a,5,9b-hexahydro-pyrido[4,3-b]indole-2-carboxylic acid tert-butyl ester (Example 45). MS (ESI): 381 (base, M+H).

Example 109 cis-(4a,9b)-(2,5-dichloro-pyridin-3-yl)-(5-methyl-6-trifluoromethyl-2,3,4,4a,5,9b-hexahydro-1H-pyrido[4,3-b]indol-8-yl)-amine

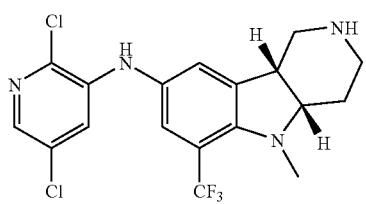

The title compound was prepared by following the general Method A as a yellow solid (22 mg, 11%) from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44, 217 mg, 0.5 mmol), 3-amino-2,5-dichloropyridine (245 mg, 1.5 mmol) and NaOt-Bu (144 mg, 1.5 mmol). MS (ESI): 417 (base, M+H).

Example 110 cis-(4a,9b)-5-methoxy-3-(5-methyl-6-trifluoromethyl-2,3,4,4a,5,9b-hexahydro-1H-pyrido[4,3-b]indol-8-ylamino)-pyridine-2-carbonitrile

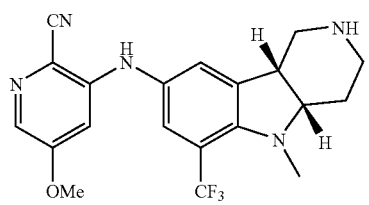

The title compound was prepared by following the general Method B as a yellow solid (142 mg, 70%) from cis-(4a,9b)-8-amino-5-methyl-6-trifluoromethyl-1,3,4,4a,5,9b-hexahydro-pyrido[4,3-b]indole-2-carboxylic acid tert-butyl ester (Example 89, 186 mg, 0.5 mmol), 3-bromo-2-cyano-5-methoxy-pyridine (107 mg, 0.5 mmol) and CsCO$_3$ (326 mg, 1.0 mmol). MS (ESI): 404 (base, M+H).

Example 111 cis-(4a,9b)-(2-methoxy-6-methyl-pyridin-3-yl)-(5-methyl-6-trifluoromethyl-2,3,4,4a,5,9b-hexahydro-1H-pyrido[4,3-b]indol-8-yl)-amine

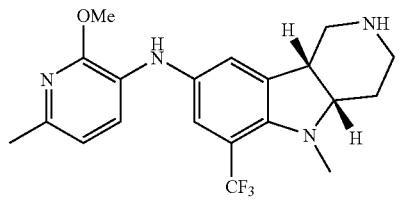

The title compound was prepared by following the general Method B as a yellow solid (42 mg, 25%) from cis-(4a,9b)-8-amino-5-methyl-6-trifluoromethyl-1,3,4,4a,5,9b-hexahydro-pyrido[4,3-b]indole-2-carboxylic acid tert-butyl ester (Example 89, 160 mg, 0.43 mmol), 3-bromo-2-methoxy-6-methylpyridine (101 mg, 0.5 mmol) and CsCO$_3$ (326 mg, 1.0 mmol). MS (ESI): 393 (base, M+H).

Example 112 cis-(4a,9b)-(6-chloro-2-methyl-pyridin-3-yl)-(5-methyl-6-trifluoromethyl-2,3,4,4a,5,9b-hexahydro-1H-pyrido[4,3-b]indol-8-yl)-amine

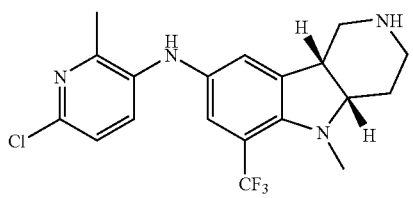

The title compound was prepared by following the general Method B as a yellow solid (47 mg, 28%) from cis-(4a,9b)-8-amino-5-methyl-6-trifluoromethyl-1,3,4,4a,5,9b-hexahydro-pyrido[4,3-b]indole-2-carboxylic acid tert-butyl ester (Example 89, 160 mg, 0.43 mmol), 3-bromo-6-chloro-2-methylpyridine (101 mg, 0.5 mmol) and CsCO$_3$ (326 mg, 1.0 mmol) as a major product. MS (ESI): 397 (base, M+H).

Example 113 cis-(4a,9b)-6-methyl-3-(5-methyl-6-trifluoromethyl-2,3,4,4a,5,9b-hexahydro-1H-pyrido[4,3-b]indol-8-ylamino)-pyridine-2-carbonitrile

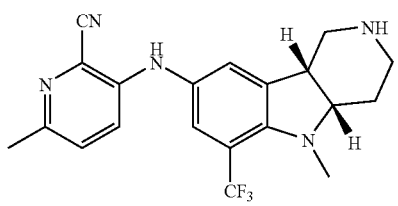

The title compound was prepared by following the general Method B as a yellow solid (109 mg, 66%) from cis-(4a,9b)-8-amino-5-methyl-6-trifluoromethyl-1,3,4,4a,5,9b-hexahydro-pyrido[4,3-b]indole-2-carboxylic acid tert-butyl ester (Example 89, 160 mg, 0.43 mmol), 3-bromo-2-cyano-6-methylpyridine (99 mg, 0.5 mmol) and CsCO$_3$ (326 mg, 1.0 mmol) as a major product. MS (ESI): 388 (base, M+H).

Example 114 cis-(4a,9b)-(2,6-dimethyl-pyridin-3-yl)-(5-methyl-6-trifluoromethyl-2,3,4,4a,5,9b-hexahydro-1H-pyrido[4,3-b]indol-8-yl)-amine

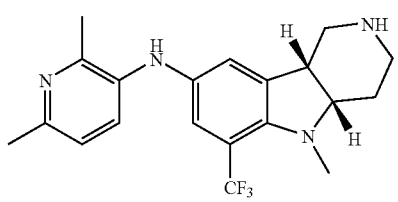

The title compound was prepared by following the general Method B as a yellow solid (28 mg, 17%) from cis-(4a,9b)-8-amino-5-methyl-6-trifluoromethyl-1,3,4,4a,5,9b-hexahydro-pyrido[4,3-b]indole-2-carboxylic acid tert-butyl ester (Example 89, 160 mg, 0.43 mmol), 3-bromo-2,6-dimethylpyridine (93 mg, 0.5 mmol) and CsCO$_3$ (326 mg, 1.0 mmol) as a major product. MS (ESI): 377 (base, M+H).

Example 115 cis-(4a,9b)-(2-isopropoxy-6-methyl-pyridin-3-yl)-(5-methyl-6-trifluoromethyl-2,3,4,4a,5,9b-hexahydro-1H-pyrido[4,3-b]indol-8-yl)-amine

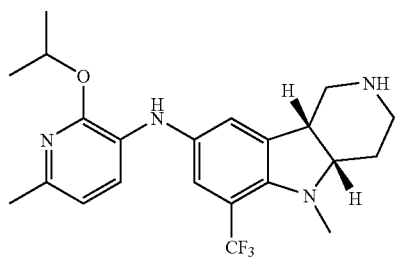

The title compound was prepared by following the general Method B as a yellow solid (58 mg, 32%) from cis-(4a,9b)-8-amino-5-methyl-6-trifluoromethyl-1,3,4,4a,5,9b-hexahydro-pyrido[4,3-b]indole-2-carboxylic acid tert-butyl ester (Example 89, 160 mg, 0.43 mmol), 3-bromo-2-isopropoxy-6-methylpyridine (115 mg, 0.5 mmol) and CsCO$_3$ (326 mg, 1.0 mmol). MS (ESI): 421 (base, M+H).

Example 116 cis-(4a,9b)-(2-ethoxy-6-methyl-pyridin-3-yl)-(5-methyl-6-trifluoromethyl-2,3,4,4a,5,9b-hexahydro-1H-pyrido[4,3-b]indol-8-yl)-amine

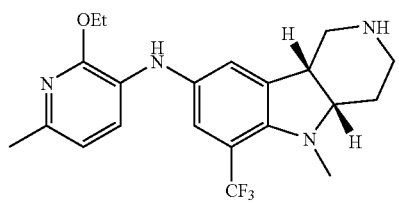

The title compound was prepared by following the general Method B as a yellow solid (10 mg, 6%) from cis-(4a,9b)-8-amino-5-methyl-6-trifluoromethyl-1,3,4,4a,5,9b-hexahydro-pyrido[4,3-b]indole-2-carboxylic acid tert-butyl ester (Example 89, 160 mg, 0.43 mmol), 3-bromo-2-ethoxy-6-methylpyridine (108 mg, 0.5 mmol) and CsCO$_3$ (326 mg, 1.0 mmol). MS (ESI): 407 (base, M+H).

Example 117 cis-(4a,9b)-(2-methoxy-4-methyl-pyridin-3-yl)-(5-methyl-6-trifluoromethyl-2,3,4,4a,5,9b-hexahydro-1H-pyrido[4,3-b]indol-8-yl)-amine

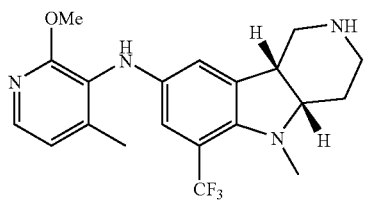

The title compound was prepared by following the general Method B as a yellow solid (15 mg, 9%) from cis-(4a,9b)-8-amino-5-methyl-6-trifluoromethyl-1,3,4,4a,5,9b-hexahydro-pyrido[4,3-b]indole-2-carboxylic acid tert-butyl ester (Example 89, 160 mg, 0.43 mmol), 3-bromo-2-methoxy-4-methylpyridine (101 mg, 0.5 mmol) and CsCO₃ (326 mg, 1.0 mmol). MS (ESI): 393 (base, M+H).

Example 118 cis-(4a,9b)-isoquinolin-4-yl-(5-methyl-6-trifluoromethyl-2,3,4,4a,5,9b-hexahydro-1H-pyrido[4,3-b]indol-8-yl)-amine

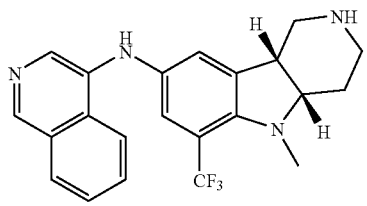

The title compound was prepared by following the general Method B as a yellow solid (51 mg, 43%) from cis-(4a,9b)-8-amino-5-methyl-6-trifluoromethyl-1,3,4,4a,5,9b-hexahydro-pyrido[4,3-b]indole-2-carboxylic acid tert-butyl ester (Example 89, 111 mg, 0.3 mmol), 4-bromo-isoquinoline (62 mg, 0.3 mmol) and CsCO₃ (196 mg, 0.6 mmol). MS (ESI): 399 (base, M+H).

Example 119 cis-(4a,9b)-(5-methyl-pyridin-2-yl)-(5-methyl-6-trifluoromethyl-2,3,4,4a,5,9b-hexahydro-1H-pyrido[4,3-b]indol-8-yl)-amine

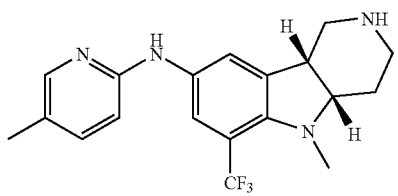

The title compound was prepared by following the general Method A as a yellow solid (10 mg, 6%) from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44, 217 mg, 0.5 mmol), 2-amino-5-methylpyridine (162 mg, 1.5 mmol) and NaOt-Bu (144 mg, 1.5 mmol). MS (ESI): 363 (base, M+H).

Example 120 cis-(4a,9b)-(5-bromo-6-methyl-pyridin-2-yl)-(5-methyl-6-trifluoromethyl-2,3,4,4a,5,9b-hexahydro-1H-pyrido[4,3-b]indol-8-yl)-amine

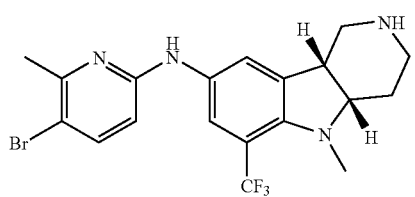

The title compound was prepared by following the general Method B as a yellow solid (31 mg, 16%) from cis-(4a,9b)-8-amino-5-methyl-6-trifluoromethyl-1,3,4,4a,5,9b-hexahydro-pyrido[4,3-b]indole-2-carboxylic acid tert-butyl ester (Example 89, 160 mg, 0.43 mmol), 3-bromo-6-chloro-2-methylpyridine (101 mg, 0.5 mmol) and CsCO₃ (326 mg, 1.0 mmol) as a minor product. MS (ESI): 441 (base, M+H).

General Method for Preparation of 8-alkyl-5-methyl-6-trifluoromethyl-2,3,4,4a,5,9b-hexahydro-1H-pyrido[4,3-b]indole Step A. To a degassed solution of 8-bromo-5-methyl-6-trifluomethyl-1,3,4,4a,5,9b-hexahydro-pyrido[4,3-b]indole-2-carboxylic acid tert-butyl ester (Example 44 or 45, 1.0 mole equivalent) in DMF (0.067 M) was added alkyl zinc bromide (0.5 M in THF, 2.5 mole equivalent) and Pd(PPh₃)₄ (0.06 mole equivalent). The reaction mixture was heated at 90° C. for 2–5 h, then cooled to rt. The reaction mixture was then quenched with water and extracted with ethyl acetate. The organic layer was dried over MgSO₄, filtered and concentrated in vacuo. The crude product was chromatographed on a silica gel column by elution with Hexane/Ethyl Acetate to give 8-alkyl-5-methyl-6-trifluoromethyl-1-2,3,4,4a,5,9b-hexahydro-pyrido[4,3-b]indole-2-carboxylic acid tert-butyl ester in 20–80% yield.

Step B. A solution of 8-alkyl-5-methyl-6-trifluoromethyl-1-2,3,4,4a,5,9b-hexahydro-pyrido[4,3-b]indole-2-carboxylic acid tert-butyl ester in 20% trifluoroacetic acid in CH₂Cl₂ was stirred for 1 h at rt. The reaction mixture was then concentrated in vacuo and then neutralized with base and extracted with chloroform. The organic layer was concentrated in vacuo to give 8-alkyl-5-methyl-6-trifluoromethyl-2,3,4,4a,5,9b-hexahydro-1H-pyrido[4,3-b]indole (90–100% yield).

Example 121 cis-(4a,9b)-8-(2-ethyl-butyl)-5-methyl-6-trifluoromethyl-2,3,4,4a,5,9b-hexahydro-1H-pyrido[4,3-b]indole

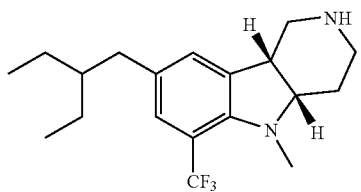

The title compound was prepared by following the general coupling procedure as a colorless oil from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44) and 2-ethylbutyl zinc bromide. MS (ES+): 341 (base, M+H).

Example 122 cis-(4a,9b)-8-benzyl-5-methyl-6-trifluoromethyl-2,3,4,4a,5,9b-hexahydro-1H-pyrido[4,3-b]indole

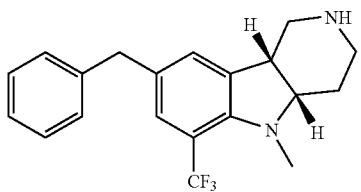

The title compound was prepared by following the general coupling procedure as a colorless oil from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44) and benzyl zinc bromide. MS (ES+): 347 (base, M+H).

Example 123

(4aS,9bR)-8-benzyl-5-methyl-6-trifluoromethyl-2,3,4,4a,5,9b-hexahydro-1H-pyrido[4,3-b]indole

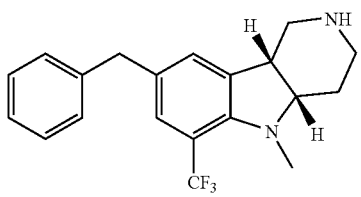

The title compound was prepared by following the general coupling procedure as a colorless oil from (4aS,9bR)-8-bromo-5-methyl-6-trifluoromethyl-1,3,4,4a,5,9b-hexahydro-pyrido[4,3-b]indole-2-carboxylic acid tert-butyl ester (Example 45) and benzyl zinc bromide. MS (ES+): 347 (base, M+H).

Example 124 cis-(4a,9b)-8-cyclohexyl-5-methyl-6-trifluoromethyl-2,3,4,4a,5,9b-hexahydro-1H-pyrido[4,3-b]indole

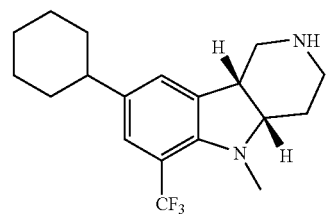

The title compound was prepared by following the general coupling procedure as a colorless oil from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44) and cyclohexyl zinc bromide. MS (ES+): 339 (base, M+H).

Example 125 cis-(4a,9b)-2-(5-methyl-6-trifluoromethyl-2,3,4,4a,5,9b-hexahydro-1H-pyrido[4,3-b]indol-8-ylmethyl)-benzonitrile

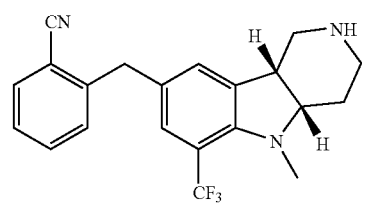

The title compound was prepared by following the general coupling procedure as a colorless oil from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44) and 2-cyanobenzyl zinc bromide. MS (ES+): 372 (base, M+H).

Example 126 cis-(4a,9b)-5-methyl-8-(3-methyl-butyl)-6-trifluoromethyl-2,3,4,4a,5,9b-hexahydro-1H-pyrido[4,3-b]indole

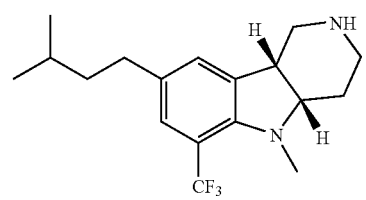

The title compound was prepared by following the general coupling procedure as a colorless oil from cis-(4a,9b)-

8-bromo-5-methyl-6-trifluoromethyl-1,3,4,4a,5,9b-hexahydro-pyrido[4,3-b]indole-2-carboxylic acid tert-butyl ester (Example 44) and 3-methylbutyl zinc bromide. MS (ES+): 327 (base, M+H).

Example 127 cis-(4a,9b)-4-(5-methyl-6-trifluoromethyl-2,3,4,4a,5,9b-hexahydro-1H-pyrido[4,3-b]indol-8-yl)-butyronitrile

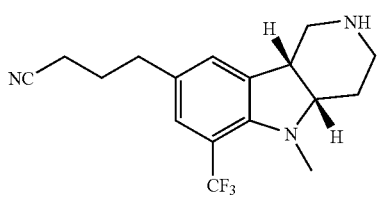

The title compound was prepared by following the general coupling procedure as a colorless oil from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44) and 3-cyanopropyl zinc bromide. MS (ES+): 324 (base, M+H).

Example 128 cis-(4a,9b)-8-isobutyl-5-methyl-6-trifluoromethyl-2,3,4,4a,5,9b-hexahydro-1H-pyrido[4,3-b]indole

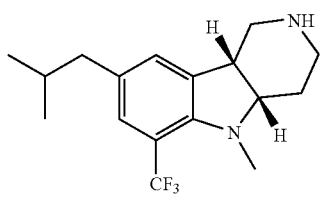

The title compound was prepared by following the general coupling procedure as a colorless oil from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44) and isobutyl zinc bromide. MS (ES+): 313 (base, M+H).

Example 129

(4aS,9bR)-8-isobutyl-5-methyl-6-trifluoromethyl-2,3,4,4a,5,9b-hexahydro-1H-pyrido[4,3-b]indole

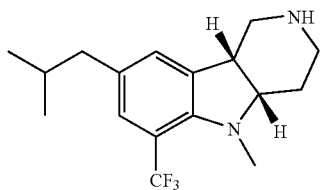

The title compound was prepared by following the general coupling procedure as a colorless oil from (4aS,9bR)-8-bromo-5-methyl-6-trifluoromethyl-1,3,4,4a,5,9b-hexahydro-pyrido[4,3-b]indole-2-carboxylic acid tert-butyl ester (Example 45) and iso-butyl zinc bromide. MS (ES+): 313 (base, M+H).

Example 130 cis-(4a,9b)-8-tert-butyl-5-methyl-6-trifluoromethyl-2,3,4,4a,5,9b-hexahydro-1H-pyrido[4,3-b]indole

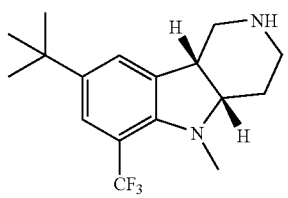

The title compound was prepared by following the general coupling procedure as a colorless oil from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44) and tert-butyl zinc bromide. MS (ES+): 313 (base, M+H).

Example 131 cis-(4a,9b)-8-(1-ethyl-propyl)-5-methyl-6-trifluoromethyl-2,3,4,4a,5,9b-hexahydro-1H-pyrido[4,3-b]indole

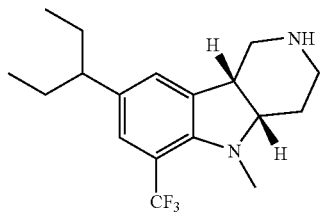

The title compound was prepared by following the general coupling procedure as a colorless oil from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44) and 1-ethylpropyl zinc bromide. MS (ES+): 327 (base, M+H).

Example 132 cis-(4a,9b)-5-methyl-8-propyl-6-trifluoromethyl-2,3,4,4a,5,9b-hexahydro-1H-pyrido[4,3-b]indole

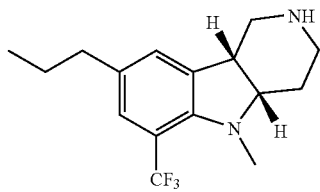

The title compound was prepared by following the general coupling procedure as a colorless oil from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44) and propyl zinc bromide. MS (ES+): 299 (base, M+H).

Example 133 cis-(4a,9b)-8-butyl-5-methyl-6-trifluoromethyl-2,3,4,4a,5,9b-hexahydro-1H-pyrido[4,3-b]indole

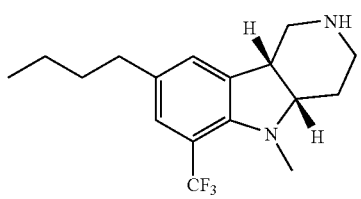

The title compound was prepared by following the general coupling procedure as a colorless oil from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44) and n-butyl zinc bromide. MS (ES+): 313 (base, M+H).

Example 134

(4aS,9bR)-8-butyl-5-methyl-6-trifluoromethyl-2,3,4,4a,5,9b-hexahydro-1H-pyrido[4,3-b]indole

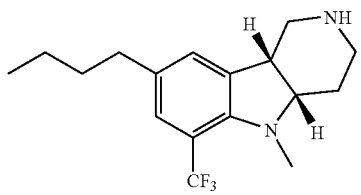

The title compound was prepared by following the general coupling procedure as a colorless oil from (4aS,9bR)-8-bromo-5-methyl-6-trifluoromethyl-1,3,4,4a,5,9b-hexahydro-pyrido[4,3-b]indole-2-carboxylic acid tert-butyl ester (Example 45) and n-butyl zinc bromide. MS (ES+): 313 (base, M+H).

Example 135 cis-(4a,9b)-5-methyl-8-pentyl-6-trifluoromethyl-2,3,4,4a,5,9b-hexahydro-1H-pyrido[4,3-b]indole

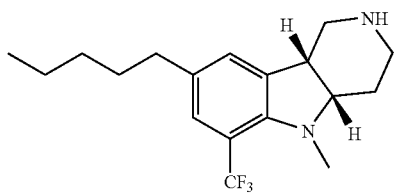

The title compound was prepared by following the general coupling procedure as a colorless oil from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44) and n-pentyl zinc bromide. MS (ES+): 327 (base, M+H).

Example 136 cis-(4a,9b)-3-(5-methyl-6-trifluoromethyl-2,3,4,4a,5,9b-hexahydro-1H-pyrido[4,3-b]indol-8-ylmethyl)-benzonitrile

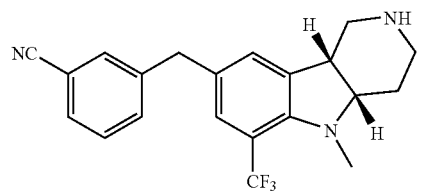

The title compound was prepared by following the general coupling procedure as a colorless oil from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44) and 3-cyanobenzyl zinc bromide. MS (ES+): 372 (base, M+H).

Example 137 cis-(4a,9b)-5-methyl-8-phenethyl-6-trifluoromethyl-2,3,4,4a,5,9b-hexahydro-1H-pyrido[4,3-b]indole

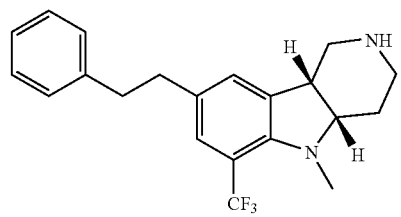

The title compound was prepared by following the general coupling procedure as a colorless oil from cis-(4a,9b)-8-bromo-5-methyl-6-trifluoromethyl-1,3,4,4a,5,9b-hexahydro-pyrido[4,3-b]indole-2-carboxylic acid tert-butyl ester (Example 44) and phenethyl zinc bromide. MS (ES+): 361 (base, M+H).

Example 138 cis-(4a,9b)-8-(2-ethyl-butyl)-6-trifluoromethyl-2,3,4,4a,5,9b-hexahydro-1H-pyrido[4,3-b]indole

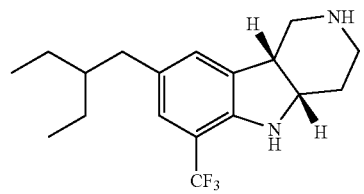

The title compound was prepared by following the general coupling procedure as a colorless oil from cis-(4a,9b)-8-bromo-6-trifluoromethyl-1,3,4,4a,5,9b-hexahydro-pyrido

[4,3-b]indole-2-carboxylic acid tert-butyl ester (Example 30) and 2-ethylbutyl zinc bromide. MS (ES+): 327 (base, M+H).

Example 139 cis-(4a,9b)-8-(3-methyl-butyl)-6-trifluoromethyl-2,3,4,4a,5,9b-hexahydro-1H-pyrido[4,3-b]indole

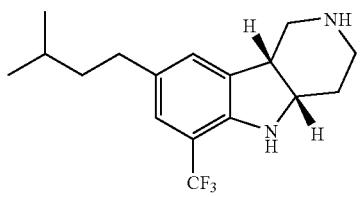

The title compound was prepared by following the general coupling procedure as a colorless oil from cis-(4a,9b)-8-bromo-6-trifluoromethyl-1,3,4,4a,5,9b-hexahydro-pyrido[4,3-b]indole-2-carboxylic acid tert-butyl ester (Example 30) and 3-methylbutyl zinc bromide. MS (ES+): 313 (base, M+H).

Example 140 cis-(4a,9b)-8-benzyl-6-trifluoromethyl-2,3,4,4a,5,9b-hexahydro-1H-pyrido[4,3-b]indole

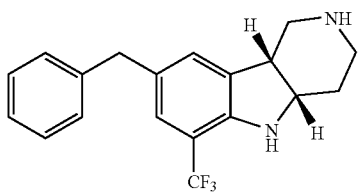

The title compound was prepared by following the general coupling procedure as a colorless oil from cis-(4a,9b)-8-bromo-6-trifluoromethyl-1,3,4,4a,5,9b-hexahydro-pyrido[4,3-b]indole-2-carboxylic acid tert-butyl ester (Example 30) and benzyl zinc bromide. MS (ES+): 333 (base, M+H).

Example 141 cis-(4a,9b)-8-fluoro-6-trifluoromethyl-2,3,4,4a,5,9b-hexahydro-1H-pyrido[4,3-b]indole

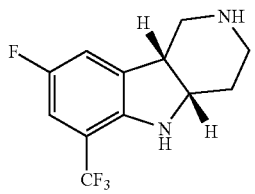

Step A. In a microwave-compatible tube, a solution of (4-fluoro-2-trifluoromethyl-phenyl)-hydrazine monohydrogen chloride (100 mg, 0.43 mmol) and 4-piperidone (67 mg, 0.44 mmol) in 2-PrOH (1.5 mL) was saturated with HCl gas and then sealed. The reaction mixture was irradiated in a microwave at 140° C. for 10 min. The reaction was cooled to 0° C. and filtered. The solid was washed with ether to provide the indole HCl salt (75 mg, 55%) as an off-white solid. A solution of the indole HCl salt (75 mg) in water (10 mL) and $CH_2Cl_2$ (10 mL) was made basic (pH 10) using $K_2CO_3$. The basic solution was extracted with $CH_2Cl_2$ (10 mL) and the organic layer was dried over $Na_2SO_4$, filtered, and evaporated. The residue was triturated with hexanes to provide 8-fluoro-6-trifluoromethyl-2,3,4,5-tetrahydro-1H-pyrido[4,3-b]indole (67 mg, 99%) as a white solid: $^1$H NMR (300 MHz, $CD_3OD$) δ 7.29 (d, J=10.2 Hz, 1H), 7.11–7.07 (m, 1H), 3.99–3.96 (m, 2H), 3.18–3.14 (m, 2H), 2.87–2.83 (m, 2H); $^{19}$F NMR (282 MHz, $CD_3OD$) δ −61.1, −125.4; MS (APCI) 259 (base, M+H)

Step B. Trifluoroacetic acid (5 mL) was added slowly to 8-fluoro-6-trifluoromethyl-2,3,4,5-tetrahydro-1H-pyrido[4,3-b]indole (95 mg, 0.43 mmol) under nitrogen at −10° C. After 20 min, $NaBH_3CN$ (82 mg, 1.32 mmol) was added over 5 min and the reaction was warmed to room temperature. The reaction was quenched with water (5 mL) and 2 N HCl (5 mL). The reaction mixture was cooled to 0° C. and was made basic (pH 10) using $K_2CO_3$. The mixture was extracted with $CH_2Cl_2$ and the combined organic extracts were dried over $Na_2SO_4$, filtered, and concentrated to provide the crude indoline. The crude indoline was purified by preparative HPLC (Varian Dynamax C18 column, 50–100%, $CH_3CN/H_2O$ with 0.05% TFA) and the residue (34 mg) was dissolved in ether and treated with 1 N HCl to give the title compound (26 mg, 20%) as a white foam: $^1$H NMR (300 MHz, $CD_3OD$) δ 7.30–7.28 (m, 1H), 7.10–7.15 (m, 1H), 4.10–4.05 (m, 1H), 3.53–3.30 (m, 4H), 2.97–2.88 (m, 1H), 2.23–2.18 (m, 2H); $^{19}$F NMR (282 MHz, $CD_3OD$ δ −61.9, −125.2; MS (APCI) 261 (base, M+H).

Example 142 cis-(4a,9b)-8-methyl-6-trifluoromethyl-2,3,4,4a,5,9b-hexahydro-1H-pyrido[4,3-b]indole

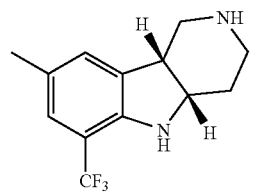

Step A. A microwave-compatible sealable tube was charged with (4-methyl-2-trifluoromethyl-phenyl)-hydrazine hydrochloride (434 mg, 1.6 mmol), 4-piperidone monohydrate hydrochloride (300 mg, 1.6 mmol), and 2-PrOH (3 mL). The reaction was saturated with HCl gas and the tube was sealed. The reaction mixture was subjected to microwave irradiation at 120° C. for 12 min. The solids were filtered and washed with ether to provide crude 8-methyl-6-trifluoromethyl-2,3,4,5-tetrahydro-1H-pyrido[4,3-b]indole hydrochloride. The resulting crude product was dissolved in THF (12 mL) and $H_2O$ (3 mL), then $Na_2CO_3$ (184 mg, 1.7 mmol) and Boc$_2$O (374 mg, 1.7 mmol) were added consecutively. After 2 h, EtOAc (25 mL) and water (10 mL) were added. The aqueous layer was extracted with EtOAc (25 mL) and the combined organic extracts were washed with brine, dried over Na$_2$SO$_4$, filtered, and concentrated in vacuo. The residue was purified by column chromatography (silica gel, 1–2.5% MeOH/CH$_2$Cl$_2$) to provide 8-methyl-6-trifluoromethyl-1,3,4,5-tetrahydro-pyrido[4,3-b]indole-2-carboxylic acid tert-butyl ester (200 mg, 29%).

Step B. 8-Methyl-6-trifluoromethyl-1,3,4,5-tetrahydro-pyrido[4,3-b]indole-2-carboxylic acid tert-butyl ester (110 mg, 0.31 mmol) was dissolved in TFA (5 mL) at 0° C., then NaBH$_3$CN (49 mg, 0.78 mmol) was added. The reaction mixture was stirred for 1 h at room temperature then quenched with 2 N HCl (2.5 mL). The mixture was made basic (pH=9) with 6 N NaOH and extracted with EtOAc (2×25 mL). The combined organic layers were washed with H$_2$O (25 mL) and brine (25 mL), dried over Na$_2$SO$_4$, filtered, and concentrated in vacuo. Purification of the residue by column chromatography [silica gel, 5–50% (80:18:2 CHCl$_3$/MeOH/concd NH$_4$OH)/CH$_2$Cl$_2$] provided the title compound (44 mg, 37%) as a light yellow oil: $^1$H NMR (300 MHz, CDCl$_3$) δ 7.15–7.18 (m, 2H), 4.04–3.92 (m, 1H), 3.80–3.74 (m, 1H), 3.20–3.05 (m, 2H), 3.01–2.75 (m, 3H), 2.17 (s, 3H), 1.98–1.82 (m, 2H), 1.76–1.63 (m, 1H); ESI MS m/z 257 [C$_{13}$H$_{15}$F$_3$N$_2$+H]$^+$.

Example 143 cis-(4a,9b)-8-methoxy-6-trifluoromethyl-2,3,4,4a,5,9b-hexahydro-1H-pyrido[4,3-b]indole

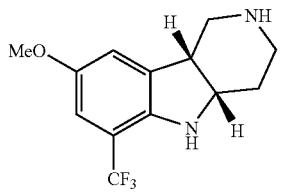

Step A. A microwave-compatible seal tube was charged with (4-methoxy-2-trifluoromethyl-phenyl)-hydrazine hydrochloride (406 mg, 1.7 mmol), 4-piperidone monohydrate hydrochloride (268 mg, 1.7 mmol), and 2-PrOH (4 mL). The reaction mixture was saturated with HCl gas and the tube was sealed. The reaction mixture was subjected to microwave irradiation at 120° C. for 12 min. The solids were filtered, washed with ether and treated with sat. NaHCO$_3$ (10 mL). The basic solution was extracted with EtOAc (2×25 mL) and the combined organic extracts were dried over Na$_2$SO$_4$, filtered, and concentrated in vacuo. Purification of the residue by column chromatography [silica gel, 5–75% (80:18:2 CHCl$_3$/MeOH/concd NH$_4$OH)/CH$_2$Cl$_2$] provided 8-methoxy-6-trifluoromethyl-2,3,4,5-tetrahydro-1H-pyrido[4,3-b]indole (192 mg, in 42%) as an off-white solid: mp 140–144° C.; $^1$H NMR (300 MHz, CD$_3$OD) δ 7.10 (d, J=2.0 Hz, 1H), 6.93 (d, J=2.1 Hz, 1H), 3.97 (s, 2H), 3.83 (s, 3H), 3.16 (t, J=5.8 Hz, 2H), 2.87 (t, J=5.7 Hz, 2H); $^{19}$F NMR (282 MHz, CD$_3$OD) δ −61.0; ESI MS 271 [C$_{13}$H$_{13}$F$_3$N$_2$O+H]$^+$.

Step B. To a solution of 8-methoxy-6-trifluoromethyl-2,3,4,5-tetrahydro-1H-pyrido[4,3-b]indole (77 mg, 0.28 mmol) in TFA (4 mL) at 0° C. was added NaBH$_3$CN (43 mg, 0.68 mmol), and the reaction was stirred for 2 h. The reaction was quenched with 2 N HCl (2 mL) at rt then made basic (pH=9) with 6 N NaOH. The aqueous layer was extracted with EtOAc (2×15 mL) and the combined organic layers were washed with brine (15 mL), dried over Na$_2$SO$_4$, filtered, and concentrated in vacuo. Purification of the residue by column chromatography [silica gel, 5–50% (80:18:2 CHCl$_3$/MeOH/concd NH$_4$OH)/CH$_2$Cl$_2$] provided the title compound (49 mg, 63%) as an off-white semisolid: $^1$H NMR (300 MHz, CD$_3$OD) δ 6.96 (d, J=2.3 Hz, 1H), 6.73 (d, 1H, J=2.5 Hz, 1H), 3.94–3.87 (m, 1H), 3.74 (s, 3H), 3.12–2.86 (m, 3H), 2.80–2.61 (m, 2H), 1.93–1.69 (m, 2H); $^{19}$F NMR (282 MHz, CD$_3$OD) δ −61.3; ESI MS 273 [C$_{13}$H$_{15}$F$_3$N$_2$O+H]$^+$.

Example 144 cis-(4a,9b)-8-bromo-6-cyano-1,3,4,4a,5,9b-hexahydro-pyrido[4,3-b]indole-2-carboxylic acid tert-butyl ester

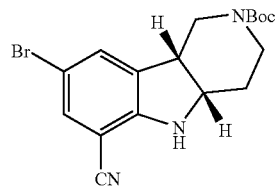

Step A. To a solution of 2-iodophenyl hydrazine hydrochloride (1.0 eq.) and 4-piperidone (1.0 eq.) in 2,2,2-trifluoroethanol was added 12 N HCl (2.0 eq.). The reaction mixture was heated at 60–65° C. for 3 h and cooled to rt. then filtered. The residue was purified by column chromatography to provide 6-iodo-2,3,4,5-tetrahydro-1H-pyrido[4,3-b]indole in 69% yield.

Step B. To a solution of 6-iodo-2,3,4,5-tetrahydro-1H-pyrido[4,3-b]indole in THF and H$_2$O (3 mL) was added Na$_2$CO$_3$ (1.1 eq.) and Boc$_2$O (1.1 eq.), consecutively. After 2 h, EtOAc and water were added. The aqueous layer was extracted with EtOAc (25 mL) and the combined organic extracts were washed with brine, dried over Na$_2$SO$_4$, filtered, and concentrated in vacuo. The residue was purified by column chromatography to give 6-iodo-1,3,4,5-tetrahydro-pyrido[4,3-b]indole-2-carboxylic acid tert-butyl ester in 88% yield.

Step C. 6-Iodo-2,3,4,5-tetrahydro-1H-pyrido[4,3-b]indole (7.70 g, 25 mmol), tris(dibenzylideneacetone)dipalladium(0) (482 mg, 0.52 mmol), zinc (202 mg, 3.0 mmol), Zn(CN)$_2$ (1.819 g, 15 mmol), and 1,1'-(diphenylphosphino)ferrocene (572 mg, 1.03 mmol) were dissolved in N,N-dimethylacetamide (40 mL). The reaction was heated at 120° C. for 1 h then cooled to room temperature. The reaction mixture was diluted with CH$_2$Cl$_2$, filtered through diatomaceous earth, and concentrated. The crude material was dissolved in THF (15 mL) and water (3 mL) and treated with K$_2$CO$_3$ (3.74 g, 27 mmol) and (Boc)$_2$O (5.91 g, 27 mmol). After 2 h, the reaction was diluted with water and extracted with CH$_2$Cl$_2$ (4×20 mL). The combined CH$_2$Cl$_2$ layers were dried over Na$_2$SO$_4$, filtered, and concentrated.

The crude material was purified by flash column chromatography (silica gel, 5–25% EtOAc/hexanes) to afford 6-cyano-1,3,4,5-tetrahydro-pyrido[4,3-b]indole-2-carboxylic acid tert-butyl ester (5.24 g, 91%) as an oil.

Step D. A solution of 6-cyano-1,3,4,5-tetrahydro-pyrido[4,3-b]indole-2-carboxylic acid tert-butyl ester (1.00 g) in $CH_2Cl_2$ (10 mL) was treated with TFA (2 mL). The reaction mixture was stirred for 7 h then converted to the free base with $K_2CO_3$ to provide 2,3,4,5-tetrahydro-1H-pyrido[4,3-b]indole-6-carbonitrile (0.66 g, 99%) as a white solid: mp 230–235° C.; $^1$H NMR (300 MHz, $CD_3OD$) δ 7.71–7.69 (m, 1H), 7.50–7.46 (m, 1H), 7.16–7.11 (m, 1H), 4.05–4.04 (m, 2H), 3.26–3.21 (m, 2H), 2.91–2.87 (m, 2H); ESI MS m/z 198 $[C_{12}H, N_3+H]^+$.

Step E. Trifluoroacetic acid (15 mL) was added slowly to 2,3,4,5-tetrahydro-1H-pyrido[4,3-b]indole-6-carbonitrile (900 mg, 4.56 mmol) under nitrogen at −10° C. After 20 min, sodium cyanoborohydride (860 mg, 13.68 mmol) was added over 20 min and the reaction was stirred for 2 h at −10° C. The reaction was quenched with water and the solution was made basic (pH 9) using $K_2CO_3$. The mixture was extracted with $CH_2Cl_2$ (2×4 L), dried over $Na_2SO_4$, filtered, and concentrated to provide the crude indoline. To a stirred solution of indoline in THF (15 mL) and $H_2O$ (1 mL) was added $K_2CO_3$ (662 mg, 4.79 mmol) and $Boc_2O$ (1.05 g, 4.79 mmol) at room temperature. After 1 h, the reaction mixture was diluted with EtOAc (1 L) and the layers were separated. The organic phase was dried over $Na_2SO_4$, filtered, and evaporated. The residue was purified by flash column chromatography (silica gel, 5–50% EtOAc/hexanes) to afford cis-(4a,9b)-6-cyano-1,3,4,4a,5,9b-hexahydro-pyrido[4,3-b]indole-2-carboxylic acid tert-butyl ester (250 mg, 20%) as white solid: $^1$H NMR (300 MHz, $CDCl_3$) δ 7.22–7.18 (m, 2H), 6.68 (d, J=7.8 Hz, 1H), 4.46–4.44 (m, 1H), 4.19–4.12 (m, 1H), 3.90–3.50 (m, 4H), 2.08–1.96 (m, 1H), 1.86–1.72 (m, 1H), 1.44 (s, 9H); ESI MS m/z 244 $[C_{17}H_{21}N_3O_2—C_4H_8+H]^+$.

Step F. To a solution of cis-(4a,9b)-6-cyano-1,3,4,4a,5,9b-hexahydro-pyrido[4,3-b]indole-2-carboxylic acid tert-butyl ester (693 mg, 2.3 mmol) in DMF (20 mL) at 0° C. was added NBS (436 mg, 2.4 mmol). The reaction mixture was stirred at 0° C. for 1 h then quenched by adding crushed ice and then water. The mixture was extracted with $Et_2O$ (2×75 mL) and the combined organic extracts were washed with brine (50 mL), dried over $Na_2SO_4$, and evaporated in vacuo. Purification of the residue by column chromatography (silica gel, 5–30% $Et_2O$/hexanes) provided the title compound as a yellow solid (782 mg, 90%). MS (ESI): 378 (Base M+H).

Example 145 cis-(4a,9b)-8-bromo-6-cyano-3,4,4a,9b-tetrahydro-1H-pyrido[4,3-b]indole-2,5-dicarboxylic acid di-tert-butyl ester

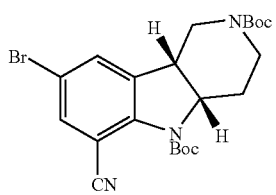

A solution of cis-(4a,9b)-8-bromo-6-cyano-1,3,4,4a,5,9b-hexahydro-pyrido[4,3-b]indole-2-carboxylic acid tert-butyl ester (770 mg, 2.0 mmol). It was dissolved in DMF (25 mL), cooled to 0° C. and NaH (254 mg, 6.3 mmol) was carefully added. After 30 min at 0° C., $Boc_2O$ (1.01 g, 4.6 mmol) was added. The reaction mixture was warmed to room temperature and stirred for 45 min. The reaction mixture was quenched by adding ice and water (20 mL) and extracted with $Et_2O$ (2×50 mL). The combined organic layers were washed with water (50 mL) and brine (50 mL), dried over $Na_2SO_4$, filtered, and concentrated in vacuo. Purification of the residue by column chromatography (silica gel, 5–30% $Et_2O$/hexanes) provided cis-(4a,9b)-8-bromo-6-cyano-3,4,4a,9b-tetrahydro-1H-pyrido[4,3-b]indole-2,5-dicarboxylic acid di-tert-butyl ester (880 mg, 92%) as a yellow solid: mp 74–78° C.; $^1$H NMR (300 MHz, $CDCl_3$) δ 6.58 (br s, 1H), 7.51 (br s, 1H), 4.74–4.60 (m, 1H), 4.38–4.10 (m, 1H), 3.82–3.32 (m, 3H), 3.17–2.78 (m, 1H), 2.16–2.06 (m, 2H), 1.59 (s, 9H), 1.50–1.37 (m, 9H); ESI MS m/z 478 $[C_{22}H_{28}BrN_3O_4+H]^+$.

Example 146 cis-(4a,9b)-8-bromo-2,3,4,4a,5,9b-hexahydro-1H-pyrido[4,3-b]indole-6-carbonitrile

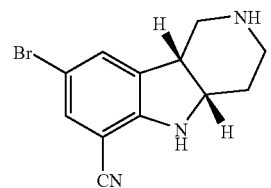

The title compound was prepared from Example 150 by following the procedure for Example 72 as a yellow solid. MS (ESI): 278 (Base, M+H).

Example 147

(4aS,9bR)-8-bromo-6-cyano-1,3,4,4a,5,9b-hexahydro-pyrido[4,3-b]indole-2-carboxylic acid tert-butyl ester

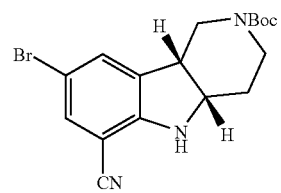

(4aS,9bR)-6-cyano-1,3,4,4a,5,9b-hexahydro-pyrido[4,3-b]indole-2-carboxylic acid tert-butyl ester were obtained by Prep. HPLC chiral separation (Chiralpak AD column; 80:20 heptane/2-PrOH) from the racemate Example 150 Step E ($1^{st}$ peak eluted) in >99% ee.

The title compound was prepared by following procedures as described in Step F for Example 150. MS (ESI): 378 (Base M+H).

Example 148

(4aS,9bR)-8-bromo-6-cyano-3,4,4a,9b-tetrahydro-1H-pyrido[4,3-b]indole-2,5-dicarboxylic acid di-tert-butyl ester

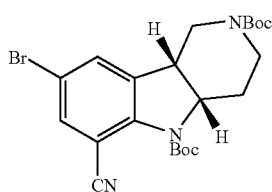

The title compound was prepared by following procedures as described for Example 151 from (4aS,9bR)-8-bromo-6-cyano-1,3,4,4a,5,9b-hexahydro-pyrido[4,3-b]indole-2-carboxylic acid tert-butyl ester. MS (ESI): 478 (Base M+H).

Example 149 cis-(4a,9b)-8-bromo-2,3,4,4a,5,9b-hexahydro-1H-pyrido[4,3-b]indole-6-carbonitrile

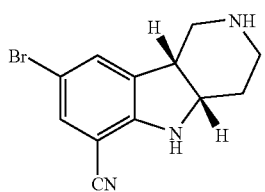

The title compound was prepared from Example 153 by following the procedure for Example 72 as a yellow solid. MS (ESI): 278 (Base, M+H).

Example 150 cis-(4a,9b)-8-bromo-6-cyano-5-methyl-1,3,4,4a,5,9b-hexahydro-pyrido[4,3-b]indole-2-carboxylic acid tert-butyl ester

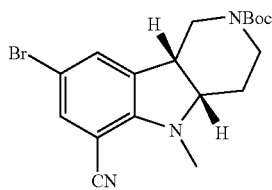

Step A. To a solution of cis-(4a,9b)-6-cyano-1,3,4,4a,5,9b-hexahydro-pyrido[4,3-b]indole-2-carboxylic acid tert-butyl ester (Example 150 step E, 900 mg, 3.0 mmol, 1.0 mole equivalent) in DMF (15 mL) was added NaH (0.24 g, 10 mmol, 3.3 mole equivalent). The reaction mixture was stirred at 0° C. for 10 min before MeI (2 mL, 31 mmol, 10 mole equivalent) was added dropwise. The reaction mixture was warmed to rt and stirred for 0.5 h, quenched with water (100 mL) and extracted with EtOAc (3×50 mL). The organic solution was dried (Na$_2$SO$_4$), concentrated in vacuo and the residue was chromatographed on a silica gel column by elution with EtOAc/Hexane (gradient) to give cis-(4a,9b)-5-methyl-6-cyamo-1,3,4,4a,5,9b-hexahydro-pyrido[4,3-b]indole-2-carboxylic acid tert-butyl ester as a white solid (865 mg, 92%).

Step B. To a solution of cis-(4a,9b)-5-methyl-6-cyano-1,3,4,4a,5,9b-hexahydro-pyrido[4,3-b]indole-2-carboxylic acid tert-butyl ester (722 mg, 2.3 mmol) in DMF (20 mL) at 0° C. was added NBS (436 mg, 2.4 mmol). The reaction mixture was stirred at 0° C. for 1 h then quenched by adding crushed ice and then water. The mixture was extracted with EtOAc (2×75 mL) and the combined organic extracts were washed with brine (50 mL), dried over Na$_2$SO$_4$, filtered, and evaporated in vacuo. The crude product was chromatographed to provide cis-(4a,9b)-8-bromo-5-methyl-6-cyano-1,3,4,4a,5,9b-hexahydro-pyrido[4,3-b]indole-2-carboxylic acid tert-butyl ester (731 mg, 81%). MS (ESI): 392 (Base, M+H).

Example 151 cis-(4a,9b)-8-bromo-5-methyl-2,3,4,4a,5,9b-hexahydro-1H-pyrido[4,3-b]indole-6-carbonitrile

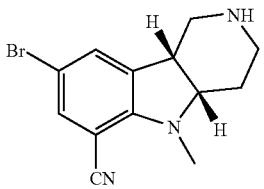

The title compound was prepared from Example 156 by following the procedure for Example 72 as a yellow solid. MS (ESI): 292 (Base, M+H).

Example 152

(4aS,9bR)-8-bromo-6-cyano-5-methyl-1,3,4,4a,5,9b-hexahydro-pyrido[4,3-b]indole-2-carboxylic acid tert-butyl ester

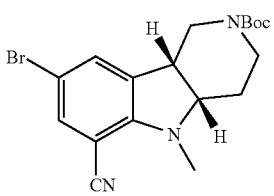

The title compound was prepared by following procedures as described in Step A B and for Example 156 from (4aS,9bR)-6-cyano-1,3,4,4a,5,9b-hexahydro-pyrido[4,3-b]indole-2-carboxylic acid tert-butyl ester. MS (ESI): 392 (Base, M+H).

Example 153

(4aS,9bR)-8-bromo-5-methyl-2,3,4,4a,5,9b-hexahydro-1H-pyrido[4,3-b]indole-6-carbonitrile

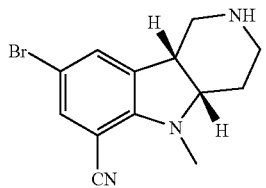

The title compound was prepared from Example 158 by following the procedure for Example 72 as a yellow solid. MS (ESI): 292 (Base, M+H).

Example 154 cis-(4a,9b)-8-amino-6-cyano-5-methyl-1,3,4,4a,5,9b-hexahydro-pyrido[4,3-b]indole-2-carboxylic acid tert-butyl ester

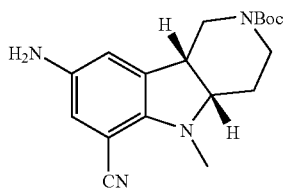

The title compound was prepared from Example 156 by following the procedure for Example 89 as a yellow solid. MS (ESI): 329 (Base, M+H).

Example 155 cis-(4a,9b)-8-amino-5-methyl-2,3,4,4a,5,9b-hexahydro-1H-pyrido[4,3-b]indole-6-carbonitrile

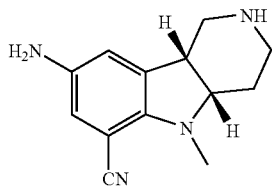

cis-(4a,9b)-6-Cyano-5-methyl-1,3,4,4a,5,9b-hexahydro-pyrido[4,3-b]indole-2-carboxylic acid tert-butyl ester was dissolved in CH$_2$Cl$_2$/TFA (5/1) at rt stirred for 1 h. Upon concentration in vacuo, the residue was partitioned between CH$_2$Cl$_2$/1 M NaOH. The aqueous phase was extracted with CH$_2$Cl$_2$. The combined organic phases were dried over MgSO$_4$, filtered, and concentrated in vacuo to obtain the title compound MS (ESI): 229 (base, M+H).

Example 156

(4aS,9bR)-8-amino-6-cyano-5-methyl-1,3,4,4a,5,9b-hexahydro-pyrido[4,3-b]indole-2-carboxylic acid tert-butyl ester

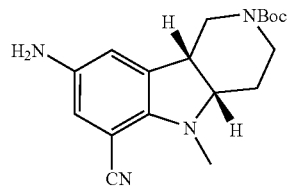

The title compound was prepared from Example 158 by following the procedure for Example 89 as a yellow solid. MS (ESI): 329 (Base, M+H).

Example 157

(4aS,9bR)-8-amino-5-methyl-2,3,4,4a,5,9b-hexahydro-1H-pyrido[4,3-b]indole-6-carbonitrile

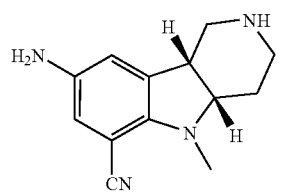

The title compound was prepared from Example 162 by following the procedure for Example 161 as a yellow solid. MS (ESI): 229 (Base, M+H).

Example 158 cis-(4a,9b)-8-(2-methoxy-pyridin-3-ylamino)-5-methyl-2,3,4,4a,5,9b-hexahydro-1H-pyrido[4,3-b]indole-6-carbonitrile

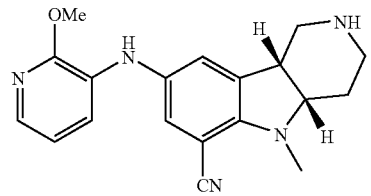

The title compound was prepared by following the general method for preparation of (5-Methyl-6-trifluoromethyl-2,3,4,4a,5,9b-hexahydro-1H-pyrido[4,3-b]indol-8-yl)-pyridin-3-yl-amine (Method A) as an oil (70 mg, 42%) from cis-(4a,9b)-8-bromo-6-cyano-5-methyl-1,3,4,4a,5,9b-hexahydro-pyrido[4,3-b]indole-2-carboxylic acid tert-butyl ester (Example 156, 196 mg, 0.5 mmol), 2-methoxy-pyridin-3-ylamine(186 mg, 1.5 mmol) and NaOt-Bu (144 mg, 1.5 mmol). MS (ESI): 336 (base, M+H).

Example 159

(4aS,9bR)-8-(2-methoxy-pyridin-3-ylamino)-5-methyl-2,3,4,4a,5,9b-hexahydro-1H-pyrido[4,3-b]indole-6-carbonitrile

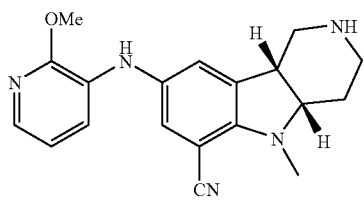

The title compound was prepared by following the general method for preparation of (5-Methyl-6-trifluoromethyl-2,3,4,4a,5,9b-hexahydro-1H-pyrido[4,3-b]indol-8-yl)-pyridin-3-yl-amine (Method A) from (4aS,9bR)-8-bromo-6-cyano-5-methyl-1,3,4,4a,5,9b-hexahydro-pyrido[4,3-b]indole-2-carboxylic acid tert-butyl ester (Example 158, 196 mg, 0.5 mmol). MS (ESI): 336 (base, M+H).

Example 160

(4aS,9bR)-5-methyl-8-(pyridin-3-ylamino)-2,3,4,4a,5,9b-hexahydro-1H-pyrido[4,3-b]indole-6-carbonitrile

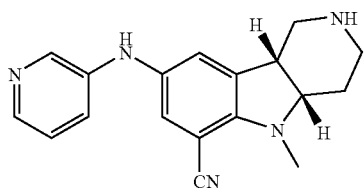

The title compound was prepared by following the general method for (5-Methyl-6-trifluoromethyl-2,3,4,4a,5,9b-hexahydro-1H-pyrido[4,3-b]indol-8-yl)-pyridin-3-yl-amine (Method A) as an oil (40 mg, 26%) from (4aS,9bR)-8-bromo-6-cyano-5-methyl-1,3,4,4a,5,9b-hexahydro-pyrido[4,3-b]indole-2-carboxylic acid tert-butyl ester (Example 158, 196 mg, 0.5 mmol), 3-amino-pyridine (141 mg, 1.5 mmol) and NaOt-Bu (144 mg, 1.5 mmol). MS (ESI): 306 (base, M+H).

Example 161

(4aS,9bR)-8-(2-cyano-pyridin-3-ylamino)-5-methyl-2,3,4,4a,5,9b-hexahydro-1H-pyrido[4,3-b]indole-6-carbonitrile

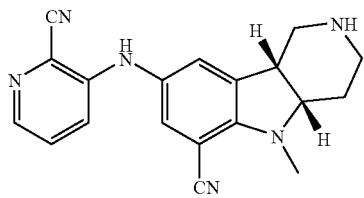

The title compound was prepared by following the general method for (5-methyl-6-trifluoromethyl-2,3,4,4a,5,9b-hexahydro-1H-pyrido[4,3-b]indol-8-yl)-pyridin-3-yl-amine (Method B) as a yellow solid (35 mg, 35%) from (4aS,9bR)-8-amino-6-cyano-3,4,4a,9b-tetrahydro-1H-pyrido[4,3-b]indole-2,5-dicarboxylic acid tert-butyl ester (Example 162, 100 mg, 0.31 mmol), 3-bromo-pyridine-2-carbonitrile (56 mg, 0.31 mmol) and Cs$_2$CO$_3$ (199 mg, 0.6 mmol). MS (ESI): 331 (base, M+H).

Example 162

(4aS,9bR)-5-methyl-8-(4-trifluoromethyl-pyridin-3-ylamino)-2,3,4,4a,5,9b-hexahydro-1H-pyrido[4,3-b]indole-6-carbonitrile

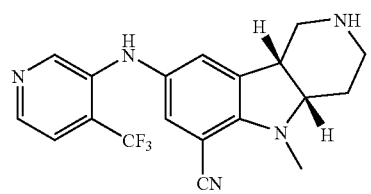

The title compound was prepared by following the general method for (5-methyl-6-trifluoromethyl-2,3,4,4a,5,9b-hexahydro-1H-pyrido[4,3-b]indol-8-yl)-pyridin-3-yl-amine (Method A) as a yellow solid (50 mg, 26%) from (4aS,9bR)-8-bromo-6-cyano-5-methyl-1,3,4,4a,5,9b-hexahydro-pyrido[4,3-b]indole-2-carboxylic acid tert-butyl ester (Example 158, 196 mg, 0.5 mmol), 4-trifluoromethyl-pyridin-3-ylamine (141 mg, 1.5 mmol) and NaOt-Bu (144 mg, 1.5 mmol). MS (ESI): 374 (base, M+H).

Example 163

(4aS,9bR)-5-methyl-8-(6-trifluoromethyl-pyridin-3-ylamino)-2,3,4,4a,5,9b-hexahydro-1H-pyrido[4,3-b]indole-6-carbonitrile

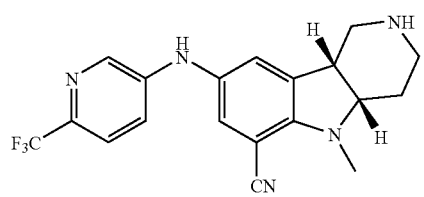

The title compound was prepared by following the general method for (5-methyl-6-trifluoromethyl-2,3,4,4a,5,9b-hexahydro-1H-pyrido[4,3-b]indol-8-yl)-pyridin-3-yl-amine (Method A) as an oil (25 mg, 13%) from (4aS,9bR)-8-bromo-6-cyano-5-methyl-1,3,4,4a,5,9b-hexahydro-pyrido[4,3-b]indole-2-carboxylic acid tert-butyl ester (Example 158, 196 mg, 0.5 mmol), 6-trifluoromethyl-pyridin-3-ylamine (141 mg, 1.5 mmol) and NaOt-Bu (144 mg, 1.5 mmol). MS (ESI): 374 (base, M+H).

Example 164

(4aS,9bR)-8-(2-ethoxy-pyridin-3-ylamino)-5-methyl-2,3,4,4a,5,9b-hexahydro-1H-pyrido[4,3-b]indole-6-carbonitrile

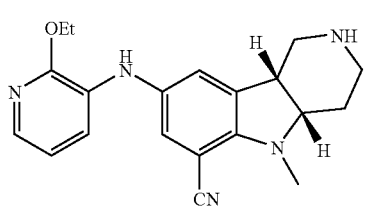

The title compound was prepared by following the general method for (5-methyl-6-trifluoromethyl-2,3,4,4a,5,9b-hexahydro-1H-pyrido[4,3-b]indol-8-yl)-pyridin-3-yl-amine (Method B) as a yellow solid (30 mg, 28%) from (4aS,9bR)-8-amino-6-cyano-3,4,4a,9b-tetrahydro-1H-pyrido[4,3-b]indole-2,5-dicarboxylic acid tert-butyl ester (Example 162, 100 mg, 0.31 mmol), 3-bromo-2-ethoxypyridine (63 mg, 0.31 mmol) and $Cs_2CO_3$ (199 mg, 0.6 mmol). MS (ESI): 350 (base, M+H).

Example 165

(4aS,9bR)-8-(2-isopropoxy-pyridin-3-ylamino)-5-methyl-2,3,4,4a,5,9b-hexahydro-1H-pyrido[4,3-b]indole-6-carbonitrile

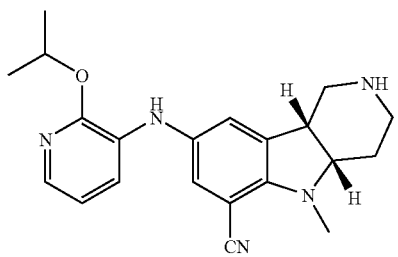

The title compound was prepared by following the general method for (5-methyl-6-trifluoromethyl-2,3,4,4a,5,9b-hexahydro-1H-pyrido[4,3-b]indol-8-yl)-pyridin-3-yl-amine (Method B) as a tan solid (32 mg, 21%) from (4aS,9bR)-8-amino-6-cyano-3,4,4a,9b-tetrahydro-1H-pyrido[4,3-b]indole-2,5-dicarboxylic acid tert-butyl ester (Example 162, 150 mg, 0.46 mmol), 3-bromo-2-iso-propoxypyridine (91 mg, 0.42 mmol) and NaOt-Bu (66 mg, 0.69 mmol). $^1$H NMR (300 MHz, $CDCl_3$) δ 7.58 (dd, J=5.0, 1.4 Hz, 1H), 7.18–6.97 (m, 3H), 6.71 (dd, J=7.6, 5.0 Hz, 1H), 5.83 (br s, 1H), 5.41 (sept, J=6.2 Hz, 1H), 3.53–3.48 (m, 1H), 3.33–3.01 (m, 4H), 2.99–2.80 (m, 2H), 2.79–2.61 (m, 1H), 2.59–2.01 (m, 1H), 2.00–1.80 (m, 2H), 1.39 (d, J=6.2 Hz, 6H); APCI MS m/z 364 $[C_{21}H_{25}N_5O+H]^+$.

Example 166

(4aS,9bR)-8-(6-chloro-pyridin-3-ylamino)-5-methyl-2,3,4,4a,5,9b-hexahydro-1H-pyrido[4,3-b]indole-6-carbonitrile

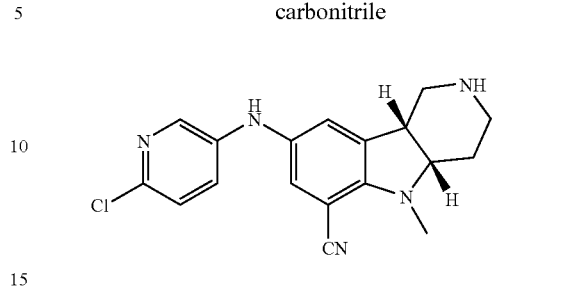

The title compound was prepared by following the general method for (5-methyl-6-trifluoromethyl-2,3,4,4a,5,9b-hexahydro-1H-pyrido[4,3-b]indol-8-yl)-pyridin-3-yl-amine (Method A) as an oil (20 mg, 12%) from (4aS,9bR)-8-bromo-6-cyano-5-methyl-1,3,4,4a,5,9b-hexahydro-pyrido[4,3-b]indole-2-carboxylic acid tert-butyl ester (Example 158, 196 mg, 0.5 mmol), 6-chloro-pyridin-3-ylamine (186 mg, 1.5 mmol) and NaOt-Bu (144 mg, 1.5 mmol). MS (ESI): 340 (base, M+H).

Example 167

(4aS,9bR)-8-(2,5-dichloro-pyridin-3-ylamino)-5-methyl-2,3,4,4a,5,9b-hexahydro-1H-pyrido[4,3-b]indole-6-carbonitrile

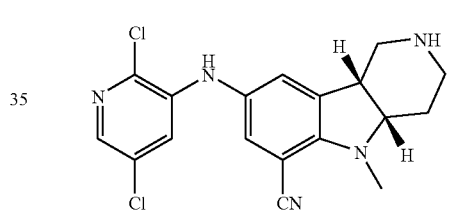

The title compound was prepared by following the general method for (5-methyl-6-trifluoromethyl-2,3,4,4a,5,9b-hexahydro-1H-pyrido[4,3-b]indol-8-yl)-pyridin-3-yl-amine (Method A) as a yellow solid (60 mg, 32%) from (4aS,9bR)-8-bromo-6-cyano-5-methyl-1,3,4,4a,5,9b-hexahydro-pyrido[4,3-b]indole-2-carboxylic acid tert-butyl ester (Example 158, 196 mg, 0.5 mmol), 2,5-dichloro-pyridin-3-ylamine (186 mg, 1.5 mmol) and NaOt-Bu (144 mg, 1.5 mmol). MS (ESI): 375 (base, M+H).

Example 168

(4aS,9bR)-8-(6-fluoro-5-methyl-pyridin-3-ylamino)-5-methyl-2,3,4,4a,5,9b-hexahydro-1H-pyrido[4,3-b]indole-6-carbonitrile

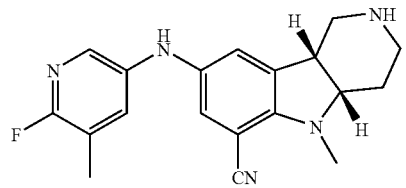

The title compound was prepared by following the general method for (5-methyl-6-trifluoromethyl-2,3,4,4a,5,9b- hexahydro-1H-pyrido[4,3-b]indol-8-yl)-pyridin-3-yl-amine (Method A) as an oil (50 mg, 30%) from (4aS,9bR)-8-bromo-6-cyano-5-methyl-1,3,4,4a,5,9b-hexahydro-pyrido[4,3-b]indole-2-carboxylic acid tert-butyl ester (Example 158, 196 mg, 0.5 mmol), 6-fluror-5-methyl-pyridin-3-ylamine(186 mg, 1.5 mmol) and NaOt-Bu (144 mg, 1.5 mmol). MS (ESI): 338 (base, M+H).

Example 169

(4aS,9bR)-8-(2-methoxy-5-methyl-pyridin-3-ylamino)-5-methyl-2,3,4,4a,5,9b-hexahydro-1H-pyrido[4,3-b]indole-6-carbonitrile

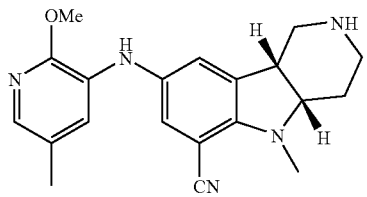

The title compound was prepared by following the general method for (5-methyl-6-trifluoromethyl-2,3,4,4a,5,9b-hexahydro-1H-pyrido[4,3-b]indol-8-yl)-pyridin-3-yl-amine (Method B) as a tan solid (57 mg, 39%) from (4aS,9bR)-8-amino-6-cyano-3,4,4a,9b-tetrahydro-1H-pyrido[4,3-b]indole-2,5-dicarboxylic acid tert-butyl ester (Example 162, 150 mg, 0.46 mmol), 3-bromo-2-methoxy-5-methylpyridine (84 mg, 0.42 mmol) and NaOt-Bu (66 mg, 0.69 mmol): mp 76–80° C.; $^1$H NMR (300 MHz, CDCl$_3$) δ 7.38 (m, 1H), 7.07 (d, J=2.2 Hz, 1H), 7.00 (d, J=1.8 Hz, 1H), 6.91 (d, J=1.8 Hz, 1H), 5.79 (br s, 1H), 3.99 (s, 3H), 3.63–3.51 (m, 1H), 3.23–3.00 (m, 4H), 2.98–2.79 (m, 2H), 2.73–2.26 (m, 2H), 2.18 (s, 3H), 1.99–1.81 (m, 2H); ESI MS m/z 350 [C$_{20}$H$_{23}$N$_5$O+H]$^+$.

Example 170

(4aS,9bR)-8-(2-chloro-6-trifluoromethyl-pyridin-3-ylamino)-5-methyl-2,3,4,4a,5,9b-hexahydro-1H-pyrido[4,3-b]indole-6-carbonitrile

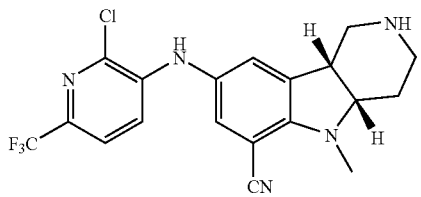

The title compound was prepared by following the general method for (5-methyl-6-trifluoromethyl-2,3,4,4a,5,9b-hexahydro-1H-pyrido[4,3-b]indol-8-yl)-pyridin-3-yl-amine (Method A) as an oil (40 mg, 20%) from (4aS,9bR)-8-bromo-6-cyano-5-methyl-1,3,4,4a,5,9b-hexahydro-pyrido[4,3-b]indole-2-carboxylic acid tert-butyl ester (Example 158, 196 mg, 0.5 mmol), 2-chloro-6-trifluoromethyl-pyridin-3-ylamine(186 mg, 1.5 mmol) and NaOt-Bu (144 mg, 1.5 mmol). MS (ESI): 408 (base, M+H).

Example 171

(4aS,9bR)-8-(2,6-dichloro-4-trifluoromethyl-pyridin-3-ylamino)-5-methyl-2,3,4,4a,5,9b-hexahydro-1H-pyrido[4,3-b]indole-6-carbonitrile

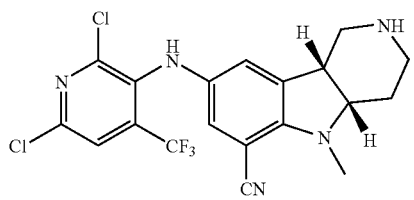

The title compound was prepared by following the general method for (5-methyl-6-trifluoromethyl-2,3,4,4a,5,9b-hexahydro-1H-pyrido[4,3-b]indol-8-yl)-pyridin-3-yl-amine (Method A) as an oil (35 mg, 16%) from (4aS,9bR)-8-bromo-6-cyano-5-methyl-1,3,4,4a,5,9b-hexahydro-pyrido[4,3-b]indole-2-carboxylic acid tert-butyl ester (Example 158, 196 mg, 0.5 mmol), 2,6-dichloro-4-trifluoromethyl-pyridin-3-ylamine(186 mg, 1.5 mmol) and NaOt-Bu (144 mg, 1.5 mmol). MS (ESI): 443 (base, M+H).

General Method for Preparation of 8-arylamino-5-methyl-6-cyano-2,3,4,4a,5,9b-hexahydro-1H-pyrido[4,3-b]indole 8-Bromo-5-methyl-6-cyano-1,3,4,4a,5,9b-hexahydro-pyrido[4,3-b]indole-2-carboxylic acid tert-butyl ester (1.0 eq.), 2,4-dimethoxyaniline (1.33 eq.), and NaOt-Bu (2.4 eq.) were dissolved in anhydrous toluene (0.06 M) while stirring under an argon atmosphere in a sealable test tube. The mixture was degassed with argon for 30 min. Tris(dibenzylideneacetone)dipalladium(0) (0.01 eq.) and 2,2'-bis(diphenylphosphino)-1,1'-binaphthyl (0.03 eq.) were added; the reaction was sealed and heated at 85° C. for 16 h. The reaction was cooled to room temperature, diluted with EtOAc, filtered through a bilayer pad of diatomaceous earth and silica gel, and concentrated in vacuo. Purification of the residue by flash column chromatography (silica gel, 10–50% EtOAc/hexanes) provided 6-cyano-8-arylamino-5-methyl-1,3,4,4a,5,9b-hexahydro-pyrido[4,3-b]indole-2-carboxylic acid tert-butyl ester. The intermediate was dissolved in CH$_2$Cl$_2$/TFA (4/1) at 0° C. The reaction mixture was stirred for 3 h then basified with K$_2$CO$_3$. The solution was extracted with CH$_2$Cl$_2$ then the organic layer was dried over Na$_2$SO$_4$, filtered, and concentrated in vacuo. The crude material was purified by reverse phase prep. HPLC to afford 8-arylamino-5-methyl-6-cyano-2,3,4,4a,5,9b-hexahydro-1H-pyrido[4,3-b]indole TFA salt.

Example 172

(4aS,9bR)-8-(2-methoxy-phenylamino)-5-methyl-2,3,4,4a,5,9b-hexahydro-1H-pyrido[4,3-b]indole-6-carbonitrile

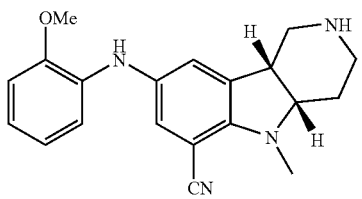

Following the general procedure described above, the title compound was prepared (67 mg, 62%) as a yellow solid using (4aS,9bR)-8-bromo-6-cyano-5-methyl-1,3,4,4a,5,9b-hexahydro-pyrido[4,3-b]indole-2-carboxylic acid tert-butyl ester (Example 158, 100 mg, 0.25 mmol), 2-methoxy-aniline (40 mg, 0.33 mmol), and NaOt-Bu (56 mg, 0.59 mmol): $^1$H NMR (300 MHz, DMSO-$d_6$) δ 8.58 (br s, 1H), 7.30–7.22 (m, 2H), 7.00–6.95 (m, 3H), 6.83–6.80 (m, 2H), 3.80 (s, 3H), 3.70–3.28 (m, 4H), 3.18–3.09 (m, 1H), 3.00 (m, 3H), 2.78–2.69 (m, 1H), 2.10–1.97 (m, 2H); APCI MS m/z 335 $[C_{20}H_{22}N_4O+H]^+$.

Example 173

(4aS,9bR)-5-methyl-8-(2-trifluoromethoxy-phenylamino)-2,3,4,4a,5,9b-hexahydro-1H-pyrido[4,3-b]indole-6-carbonitrile

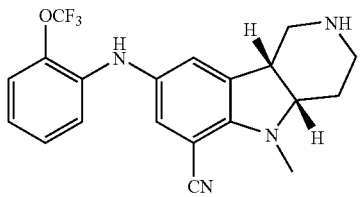

Following the general procedure described above, the title compound was prepared (15 mg, 12%) as a tan solid using (4aS,9bR)-8-bromo-6-cyano-5-methyl-1,3,4,4a,5,9b-hexahydro-pyrido[4,3-b]indole-2-carboxylic acid tert-butyl ester (Example 158, 100 mg, 0.25 mmol), 2-trifluoromethoxyaniline (58 mg, 0.33 mmol), and NaOt-Bu (56 mg, 0.59 mmol): $^1$H NMR (300 MHz, DMSO-$d_6$) δ 8.59 (br s, 1H), 7.80 (s, 1H), 7.29–7.26 (m, 2H), 7.18–7.16 (m, 1H), 7.07–7.03 (m, 2H), 6.88–6.85 (m, 1H), 3.91–3.29 (m, 4H), 3.18–2.98 (m, 4H), 2.88–2.72 (m, 1H), 2.10–2.01 (m, 2H); APCI MS m/z 389 $[C_{20}H_{19}F_3N_4O+H]^+$.

Example 174

(4aS,9bR)-8-(2-ethoxy-phenylamino)-5-methyl-2,3,4,4a,5,9b-hexahydro-1H-pyrido[4,3-b]indole-6-carbonitrile

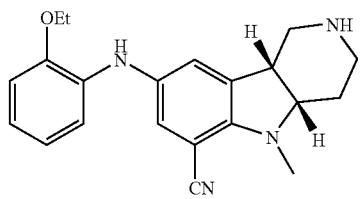

Following the general procedure described above, the title compound was prepared (15 mg, 13%) as a yellow-orange solid using (4aS,9bR)-8-bromo-6-cyano-5-methyl-1,3,4,4a,5,9b-hexahydro-pyrido[4,3-b]indole-2-carboxylic acid tert-butyl ester (Example 158, 100 mg, 0.25 mmol), 2-ethoxy-aniline (45 mg, 0.33 mmol), and NaOt-Bu (56 mg, 0.59 mmol): $^1$H NMR (300 MHz, DMSO-$d_6$) δ 8.58 (br s, 1H), 7.26 (s, 1H), 6.98–6.92 (m, 3H), 6.81–6.78 (m, 2H), 4.03 (q, J=6.8 Hz, 2H), 3.85–3.28 (m, 5H), 3.18–2.98 (m, 4H), 2.80–2.70 (m, 1H), 2.13–2.00 (m, 2H), 1.31 (t, J=6.9 Hz, 3H); APCI MS m/z 349 $[C_{21}H_{24}N_4O+H]^+$.

Example 175

(4aS,9bR)-8-(2-fluoro-phenylamino)-5-methyl-2,3,4,4a,5,9b-hexahydro-1H-pyrido[4,3-b]indole-6-carbonitrile

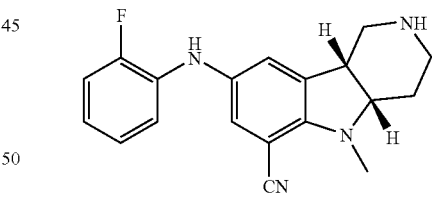

Following the general procedure described above, the title compound was prepared (45 mg, 43%) as a light green solid as a yellow solid using (4aS,9bR)-8-bromo-6-cyano-5-methyl-1,3,4,4a,5,9b-hexahydro-pyrido[4,3-b]indole-2-carboxylic acid tert-butyl ester (Example 158, 100 mg, 0.25 mmol), 2-fluoroaniline (36 mg, 0.33 mmol), and NaOt-Bu (56 mg, 0.59 mmol): $^1$H NMR (300 MHz, DMSO-$d_6$) δ 8.60 (br s, 1H), 7.80 (br s, 1H), 7.24–7.23 (m, 1H), 7.20–6.98 (m, 3H), 6.91–6.90 (m 1H), 6.88–6.80 (m, 1H), 3.61–3.28 (m, 4H), 3.14–2.97 (m, 4H), 2.80–2.70 (m, 1H), 2.10–1.98 (m, 2H); ESI MS m/z 323 $[C_{19}H_{19}FN_4+H]^+$.

Example 176

(4aS,9bR)-5-methyl-8-o-tolylamino-2,3,4,4a,5,9b-hexahydro-1H-pyrido[4,3-b]indole-6-carbonitrile

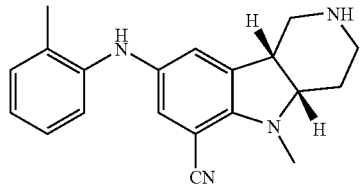

Following the general procedure described above, the title compound was prepared (67 mg, 62%) as a yellow solid using (4aS,9bR)-8-bromo-6-cyano-5-methyl-1,3,4,4a,5,9b-hexahydro-pyrido[4,3-b]indole-2-carboxylic acid tert-butyl ester (Example 158, 100 mg, 0.25 mmol), 2-methylaniline (35 mg, 0.33 mmol), and NaOt-Bu (56 mg, 0.59 mmol): $^1$H NMR (300 MHz, DMSO-$d_6$) δ 9.60 (br s, 1H), 7.23–7.12 (m, 3H), 7.10–7.03 (m, 1H), 6.98–6.93 (m, 1H), 6.84–6.80 (m, 2H), 3.61–3.33 (m, 4H), 3.18–3.09 (m, 1H), 3.01 (s, 3H), 2.78–2.70 (m, 1H), 2.20–1.93 (m, 5H); APCI MS m/z 319 $[C_{20}H_{22}N_4+H]^+$.

Example 177

(4aS,9bR)-8-(2-ethyl-phenylamino)-5-methyl-2,3,4,4a,5,9b-hexahydro-1H-pyrido[4,3-b]indole-6-carbonitrile

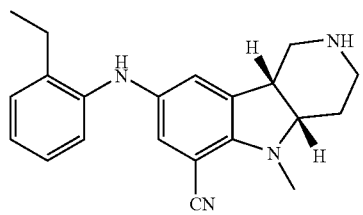

Following the general procedure described above, the title compound was prepared (70 mg, 63%) as a light green solid using (4aS,9bR)-8-bromo-6-cyano-5-methyl-1,3,4,4a,5,9b-hexahydro-pyrido[4,3-b]indole-2-carboxylic acid tert-butyl ester (Example 158, 100 mg, 0.25 mmol), 2-ethylaniline (40 mg, 0.33 mmol), and NaOt-Bu (56 mg, 0.59 mmol): $^1$H NMR (300 MHz, DMSO-$d_6$) δ 8.63 (br s, 1H), 7.34–7.17 (m, 3H), 7.11–7.05 (m, 1H), 6.99–6.96 (m, 1H), 6.92–6.87 (m, 1H). 6.81–6.80 (m, 1H), 4.20–3.91 (m, 1H), 3.55–3.49 (m, 1H), 3.39–3.28 (m, 2H), 3.13–3.09 (m, 1H), 3.02–3.00 (m, 3H), 2.75–2.49 (m, 3H), 2.14–1.93 (m, 2H), 1.14 (t, J=7.5 Hz, 3H); APCI MS m/z 333 $[C_{21}H_{24}N_4+H]^+$.

Example 178

(4aS,9bR)-8-(4-fluoro-phenylamino)-5-methyl-2,3,4,4a,5,9b-hexahydro-1H-pyrido[4,3-b]indole-6-carbonitrile

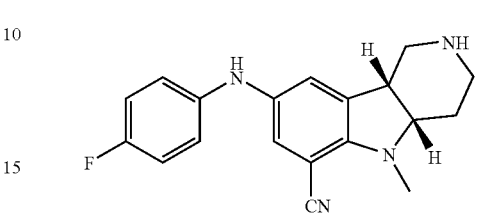

Following the general procedure described above, the title compound was prepared (49 mg, 47%) as a light green solid using (4aS,9bR)-8-bromo-6-cyano-5-methyl-1,3,4,4a,5,9b-hexahydro-pyrido[4,3-b]indole-2-carboxylic acid tert-butyl ester (Example 158, 100 mg, 0.25 mmol), 4-fluoroaniline (36 mg, 0.33 mmol), and NaOt-Bu (56 mg, 0.59 mmol): $^1$H NMR (300 MHz, DMSO-$d_6$) δ 8.59 (br s, 1H), 7.90 (br s, 1H), 7.25–7.24 (m, 1H), 7.08–7.01 (m, 2H), 6.95–6.91 (m, 3H), 3.68–3.30 (m,4H), 3.18–2.99 (m, 4H), 2.80–2.72 (m, 1H), 2.11–1.99 (m, 2H); APCI MS m/z 323 $[C_{19}H_{19}FN_4+H]^+$.

Example 179

(4aS,9bR)-5-methyl-8-m-tolylamino-2,3,4,4a,5,9b-hexahydro-1H-pyrido[4,3-b]indole-6-carbonitrile

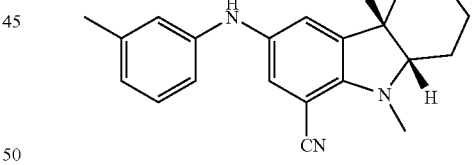

Following the general procedure described above, the title compound was prepared (61 mg, 58%) as a yellow solid using (4aS,9bR)-8-bromo-6-cyano-5-methyl-1,3,4,4a,5,9b-hexahydro-pyrido[4,3-b]indole-2-carboxylic acid tert-butyl ester (Example 158, 100 mg, 0.25 mmol), 3-methylaniline (35 mg, 0.33 mmol), and NaOt-Bu (56 mg, 0.59 mmol): $^1$H NMR (300 MHz, DMSO-$d_6$) δ 8.55 (br s, 1H), 7.90 (br s, 1H), 7.30–7.29 (m, 1H), 7.07 (t, J=7.5 Hz, 1H), 6.97–6.96 (m, 1H), 6.72–6.70 (m, 2H), 6.60 (d, J=7.5 Hz, 1H), 3.60–3.29 (m, 4H), 3.20–3.11 (m, 1H), 3.04 (s, 3H), 2.81–2.73 (m, 1H), 2.21 (s, 3H), 2.12–1.97 (m, 2H); APCI MS m/z 319 $[C_{20}H_{22}N_4+H]^+$.

Example 180

(4aS,9bR)-8-(2-cyano-phenylamino)-5-methyl-2,3,4,4a,5,9b-hexahydro-1H-pyrido[4,3-b]indole-6-carbonitrile

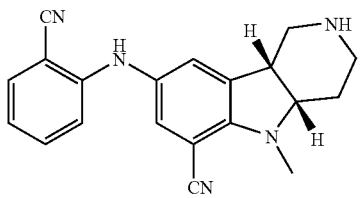

Following the general procedure described above, the title compound was prepared (7 mg, 10%) as a yellow solid using (4aS,9bR)-8-bromo-6-cyano-5-methyl-1,3,4,4a,5,9b-hexahydro-pyrido[4,3-b]indole-2-carboxylic acid tert-butyl ester (Example 158, 62 mg, 0.116 mmol), 2-cyanoaniline (24 mg, 0.21 mmol), and $Cs_2CO_3$ (118 mg, 0.36 mmol): $^1$H NMR (300 MHz, DMSO-$d_6$) δ 8.59 (br s, 1H), 8.31 (s, 1H), 7.60–7.58 (m, 1H), 7.48–7.40 (m, 1H), 7.33–7.32 (m, 1H), 7.10–7.09 (m, 1H), 7.00–6.98 (m, 1H), 6.90–6.84 (m, 1H), 3.72–3.29 (m, 4H), 3.12–3.00 (m, 4H), 2.88–2.80 (m, 1H), 2.04–2.00 (m, 2H); ESI MS m/z 330 $[C_{20}H_{19}N_5+H]^+$.

Example 181

(4aS,9bR)-8-(2,4-dimethoxy-phenylamino)-5-methyl-2,3,4,4a,5,9b-hexahydro-1H-pyrido[4,3-b]indole-6-carbonitrile

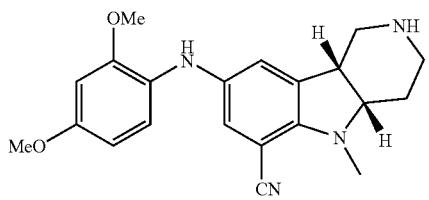

Following the general procedure described above, the title compound was prepared (25 mg, 21%) as a yellow solid using (4aS,9bR)-8-bromo-6-cyano-5-methyl-1,3,4,4a,5,9b-hexahydro-pyrido[4,3-b]indole-2-carboxylic acid tert-butyl ester (Example 158, 100 mg, 0.25 mmol), 2,4-dimethoxyaniline (51 mg, 0.33 mmol), and NaOt-Bu (56 mg, 0.59 mmol): $^1$H NMR (300 MHz, DMSO-$d_6$) δ 6.96–6.90 (m, 3H), 6.62–6.51 (m, 1H), 6.43–6.39 (m, 1H), 5.51 (br s, 1H), 3.84 (s, 3H), 3.79 (s, 3H), 3.48–3.45 (m, 1H), 3.13–3.02 (m, 5H), 2.89–2.86 (m, 2H), 2.67–2.61 (m, 1H), 1.90–1.87 (m, 2H); APCI MS m/z 365 $[C_{21}H_{24}N_4O_2+H]^+$.

Example 182

(4aS,9bR)-8-(2,3-difluoro-phenylamino)-5-methyl-2,3,4,4a,5,9b-hexahydro-1H-pyrido[4,3-b]indole-6-carbonitrile

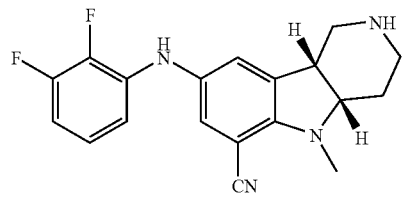

Following the general procedure described above, the title compound was prepared (12 mg, 11%) as a yellow solid using (4aS,9bR)-8-bromo-6-cyano-5-methyl-1,3,4,4a,5,9b-hexahydro-pyrido[4,3-b]indole-2-carboxylic acid tert-butyl ester (Example 158, 100 mg, 0.25 mmol), 2,3-difluoroaniline (42 mg, 0.33 mmol), and NaOt-Bu (56 mg, 0.59 mmol): $^1$H NMR (300 MHz, DMSO-$d_6$) δ 7.09–7.08 (m, 1H), 7.04–7.03 (m 1H), 6.92–6.89 (m, 1H), 6.70–6.59 (m, 2H), 5.62 (br, 1H), 3.61–3.59 (m, 1H), 3.34–3.29 (m, 1H), 3.18–3.11 (m, 4H), 3.03–2.90 (m, 2H), 2.71–2.63 (m, 1H), 2.11–1.82 (m, 2H); APCI MS m/z 341 $[C_{19}H_{18}F_2N_4+H]^+$.

Example 183

(4aS,9bR)-8-(5-fluoro-2-methyl-phenylamino)-5-methyl-2,3,4,4a,5,9b-hexahydro-1H-pyrido[4,3-b]indole-6-carbonitrile

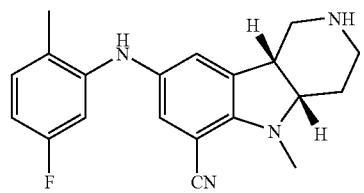

Following the general procedure described above, the title compound was prepared (28 mg, 25%) as a yellow solid using (4aS,9bR)-8-bromo-6-cyano-5-methyl-1,3,4,4a,5,9b-hexahydro-pyrido[4,3-b]indole-2-carboxylic acid tert-butyl ester (Example 158, 100 mg, 0.25 mmol), 5-fluoro-2-methylaniline (41 mg, 0.33 mmol), and NaOt-Bu (56 mg, 0.59 mmol): $^1$H NMR (300 MHz, CDCl$_3$) δ 7.07–6.98 (m, 3H), 6.55–6.45 (m, 2H), 5.20 (br s, 1H), 3.57–3.55 (m, 1H), 3.18–3.08 (m, 5H), 2.92–2.88 (m, 2H), 2.72–2.68 (m, 1H), 2.18–1.92 (m, 5H); APCI MS m/z 337 $[C_{20}H_{21}FN_4+H]^+$.

Example 184

(4aS,9bR)-8-(4-fluoro-3-methyl-phenylamino)-5-methyl-2,3,4,4a,5,9b-hexahydro-1H-pyrido[4,3-b]indole-6-carbonitrile

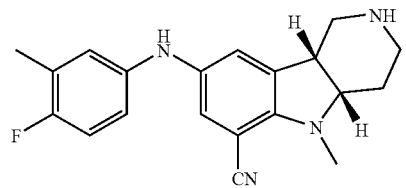

Following the general procedure described above, the title compound was prepared (25 mg, 23%) as a yellow solid using (4aS,9bR)-8-bromo-6-cyano-5-methyl-1,3,4,4a,5,9b-hexahydro-pyrido[4,3-b]indole-2-carboxylic acid tert-butyl ester (Example 158, 100 mg, 0.25 mmol), 4-fluoro-3-methylaniline (41 mg, 0.33 mmol), and NaOt-Bu (56 mg, 0.59 mmol): $^1$H NMR (300 MHz, CDCl$_3$, DMSO-d$_6$) δ 9.46 (br s, 1H), 7.09–7.08 (m, 1H), 7.05–7.04 (m, 1H), 6.97–6.73 (m, 3H), 3.61–3.29 (m, 4H), 3.18–2.91 (m, 3H), 2.69–2.58 (m, 2H), 2.37–2.16 (m, 5H); APCI MS m/z 337 [C$_{20}$H$_{21}$FN$_4$+H]$^+$.

Example 185

(4aS,9bR)-8-(4-chloro-3-methyl-phenylamino)-5-methyl-2,3,4,4a,5,9b-hexahydro-1H-pyrido[4,3-b]indole-6-carbonitrile

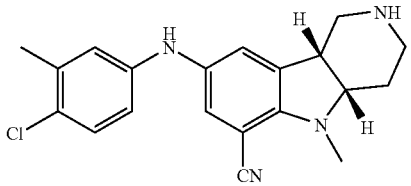

Following the general procedure described above, the title compound was prepared (15 mg, 13%) as a light green solid using (4aS,9bR)-8-bromo-6-cyano-5-methyl-1,3,4,4a,5,9b-hexahydro-pyrido[4,3-b]indole-2-carboxylic acid tert-butyl ester (Example 158, 100 mg, 0.25 mmol), 4-chloro-3-methylaniline (46 mg, 0.33 mmol), and NaOt-Bu (56 mg, 0.59 mmol): $^1$H NMR (300 MHz, DMSO-d$_6$) δ 8.58 (br s, 1H), 8.04 (s, 1H), 7.29–7.28 (m, 1H), 7.20–7.17 (m, 1H), 6.98–6.97 (m, 1H), 6.8–6.84 (m, 1H), 6.76–6.73 (m, 1H), 3.62–3.30 (m, 4H), 3.19–3.01 (m, 4H), 2.80–2.71 (m, 1H), 2.24 (s, 3H), 2.11–2.00 (m, 2H); APCI MS m/z 353 [C$_{20}$H$_{21}$ClN$_4$+H]$^+$.

Example 186

(4aS,9bR)-8-(4-fluoro-2-methyl-phenylamino)-5-methyl-2,3,4,4a,5,9b-hexahydro-1H-pyrido[4,3-b]indole-6-carbonitrile

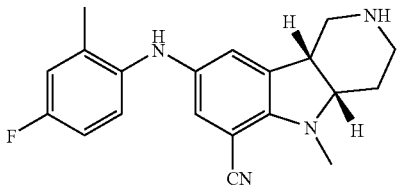

Following the general procedure described above, the title compound was prepared (8 mg, 7%) as a tan solid using (4aS,9bR)-8-bromo-6-cyano-5-methyl-1,3,4,4a,5,9b-hexahydro-pyrido[4,3-b]indole-2-carboxylic acid tert-butyl ester (Example 158, 100 mg, 0.25 mmol), 4-fluoro-2-methylaniline (41 mg, 0.33 mmol), and NaOt-Bu (56 mg, 0.59 mmol):): $^1$H NMR (300 MHz, DMSO-d$_6$) δ 8.65 (br s, 1H), 7.24 (s, 1H), 7.10–6.91 (m, 3H), 6.71–6.70 (m, 1H), 6.59 (br s, 1H), 3.55–3.30 (m, 4H), 3.20–2.98 (m, 4H), 2.77–2.68 (m, 1H), 2.21–1.92 (m, 5H); APCI MS m/z 337 [C$_{20}$H$_{21}$FN$_4$+H]$^+$.

Example 187

(4aS,9bR)-8-(4-chloro-2-methyl-phenylamino)-5-methyl-2,3,4,4a,5,9b-hexahydro-1H-pyrido[4,3-b]indole-6-carbonitrile

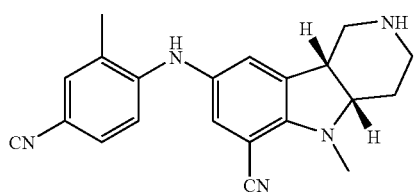

Following the general procedure described above, the title compound was prepared (75 mg, 65%) as a light green solid using (4aS,9bR)-8-bromo-6-cyano-5-methyl-1,3,4,4a,5,9b-hexahydro-pyrido[4,3-b]indole-2-carboxylic acid tert-butyl ester (Example 158, 100 mg, 0.25 mmol), 4-chloro-2-methylaniline (46 mg, 0.33 mmol), and NaOt-Bu (56 mg, 0.59 mmol): ): $^1$H NMR (300 MHz, DMSO-d$_6$) δ 8.58 (br s, 1H), 7.28 (s, 1H), 7.19–7.18 (m, 2H), 7.10–7.07 (m, 1H), 6.92–6.90 (m, 2H), 3.80–3.52 (m, 2H), 3.42–3.31 (m, 2H), 3.20–3.09 (m, 1H), 3.02 (s, 3H), 2.79–2.70 (m, 1H), 2.20–1.97 (m, 5H); APCI MS m/z 353 [C$_{20}$H$_{21}$ClN$_4$+H]$^+$.

Example 188

(4aS,9bR)-8-(2,4-difluoro-phenylamino)-S-methyl-2,3,4,4a,5,9b-hexahydro-1H-pyrido[4,3-b]indole-6-carbonitrile

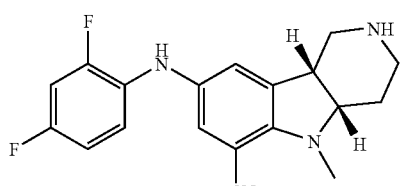

Following the general procedure described above, the title compound was prepared (52 mg, 47%) as a light green solid using (4aS,9bR)-8-bromo-6-cyano-5-methyl-1,3,4,4a,5,9b-hexahydro-pyrido[4,3-b]indole-2-carboxylic acid tert-butyl ester (Example 158, 100 mg, 0.25 mmol), 2,4-difluoro-aniline (42 mg, 0.33 mmol), and NaOt-Bu (56 mg, 0.59 mmol): ): $^1$H NMR (300 MHz, DMSO-d$_6$) δ 8.57 (br s, 1H), 7.78 (s, 1H), 7.29–7.06 (m, 3H), 6.92–6.89 (m, 1H), 6.84 (s, 1H), 3.89–3.48 (m, 2H), 3.38–3.29 (m, 2H), 3.19–3.07 (m, 1H), 3.01 (s, 3H), 2.73–2.69 (m, 1H), 2.10–1.98 (m, 2H); APCI MS m/z 341 [C$_{19}$H$_{18}$F$_2$N$_4$+H]$^+$.

Example 189

(4aS,9bR)-8-(3,4-difluoro-phenylamino)-5-methyl-2,3,4,4a,5,9b-hexahydro-1H-pyrido[4,3-b]indole-6-carbonitrile

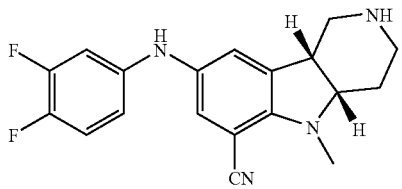

Following the general procedure described above, the title compound was prepared (52 mg, 47%) as a light green solid using (4aS,9bR)-8-bromo-6-cyano-5-methyl-1,3,4,4a,5,9b-hexahydro-pyrido[4,3-b]indole-2-carboxylic acid tert-butyl ester (Example 158, 100 mg, 0.25 mmol), 3,4-difluoro-aniline (42 mg, 0.33 mmol), and NaOt-Bu (56 mg, 0.59 mmol): ): $^1$H NMR (300 MHz, DMSO-$d_6$) δ 8.60 (br s, 1H), 8.10 (s, 1H), 7.31–7.18 (m, 2H), 7.00–6.98 (m, 1H), 6.89–6.80 (m, 1H), 6.70–6.63 (m, 1H), 4.03–3.58 (m, 2H), 3.49–3.32 (m, 2H), 3.20–3.00 (m, 4H), 2.89–2.78 (m, 1H), 2.10–2.01 (m, 2H); APCI MS m/z 341 $[C_{19}H_{18}F_2N_4+H]^+$.

Example 190

(4aS,9bR)-8-(3-chloro-4-fluoro-phenylamino)-5-methyl-2,3,4,4a,5,9b-hexahydro-1H-pyrido[4,3-b]indole-6-carbonitrile

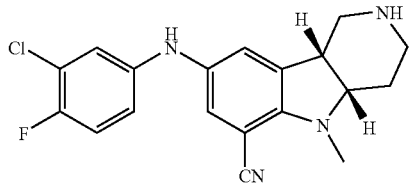

Following the general procedure described above, the title compound was prepared (53 mg, 44%) as a light green solid using (4aS,9bR)-8-bromo-6-cyano-5-methyl-1,3,4,4a,5,9b-hexahydro-pyrido[4,3-b]indole-2-carboxylic acid tert-butyl ester (Example 158, 100 mg, 0.25 mmol), 3-chloro-4-fluoroaniline (48 mg, 0.33 mmol), and NaOt-Bu (56 mg, 0.59 mmol): ): $^1$H NMR (300 MHz, DMSO-$d_6$) δ 8.59 (br s, 1H), 8.10–8.06 (m, 1H), 7.33–7.19 (m, 2H), 7.03–6.94 (m, 2H), 6.87–6.84 (m, 1H), 3.78–3.30 (m, 4H), 3.19–3.00 (m, 4H), 2.85–2.77 (m, 1H), 2.09–1.99 (m, 2H); APCI MS m/z 357 $[C_{19}H_{18}ClFN_4+H]^+$.

Example 191

(4aS,9bR)-8-(2,4-dimethyl-phenylamino)-5-methyl-2,3,4,4a,5,9b-hexahydro-1H-pyrido[4,3-b]indole-6-carbonitrile

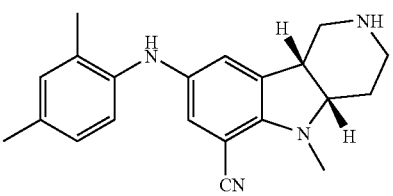

Following the general procedure described above, the title compound was prepared (60 mg, 54%) as a yellow solid using (4aS,9bR)-8-bromo-6-cyano-5-methyl-1,3,4,4a,5,9b-hexahydro-pyrido[4,3-b]indole-2-carboxylic acid tert-butyl ester (Example 158, 100 mg, 0.25 mmol), 2,4-dimethyl-aniline (44 mg, 0.33 mmol), and NaOt-Bu (56 mg, 0.59 mmol): ): $^1$H NMR (300 MHz, DMSO-$d_6$) δ 8.64 (br s, 1H), 7.18 (br s, 1H), 7.10–7.09 (m, 1H), 7.01–7.00 (m, 1H), 6.91–6.90 (m, 2H), 6.60–6.59 (m, 1H), 4.02–3.82 (m, 1H), 3.53–3.48 (m, 1H), 2.39–3.31 (m, 2H), 3.19–3.11 (m, 1H), 3.00 (s, 3H), 2.74–2.62 (m, 1H), 2.23 (s, 3H), 2.13–1.95 (m, 5H); APCI MS m/z 333 $[C_{21}H_{24}N_4+H]^+$.

Example 192

(4aS,9bR)-8-(4-methoxy-2-methyl-phenylamino)-5-methyl-2,3,4,4a,5,9b-hexahydro-1H-pyrido[4,3-b]indole-6-carbonitrile

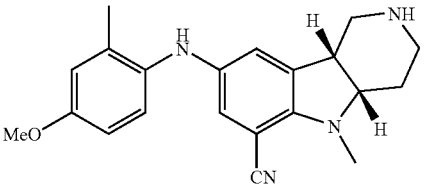

Following the general procedure described above, the title compound was prepared (82 mg, 72%) as a light green solid using (4aS,9bR)-8-bromo-6-cyano-5-methyl-1,3,4,4a,5,9b-hexahydro-pyrido[4,3-b]indole-2-carboxylic acid tert-butyl ester (Example 158, 100 mg, 0.25 mmol), 4-methoxy-2-methylaniline (45 mg, 0.33 mmol), and NaOt-Bu (56 mg, 0.59 mmol): ): $^1$H NMR (300 MHz, DMSO-$d_6$) δ 8.59 (br s, 1H), 7.11 (br s, 1H), 6.97–6.90 (m, 2H), 6.80–6.79 (m, 1H), 6.71–6.70 (m, 1H), 6.51–6.50 (m, 1H), 3.79–3.41 (m, 3H), 3.34–3.25 (m, 2H), 3.19–3.08 (m, 1H), 3.02–2.97 (m, 3H), 2.70–2.62 (m, 1H), 2.12–1.96 (m, 5H); APCI MS m/z 349 $[C_{21}H_{24}N_4O+H]^+$.

Example 193

(4aS,9bR)-8-(5-chloro-2-methoxy-phenylamino)-5-methyl-2,3,4,4a,5,9b-hexahydro-1H-pyrido[4,3-b]indole-6-carbonitrile

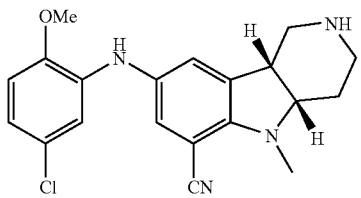

Following the general procedure described above, the title compound was prepared (74 mg, 60%) as a light green solid using (4aS,9bR)-8-bromo-6-cyano-5-methyl-1,3,4,4a,5,9b-hexahydro-pyrido[4,3-b]indole-2-carboxylic acid tert-butyl ester (Example 158, 100 mg, 0.25 mmol), 5-chloro-2-methoxyaniline (52 mg, 0.33 mmol), and NaOt-Bu (56 mg, 0.59 mmol): ): $^1$H NMR (300 MHz, DMSO-$d_6$) δ 8.59 (br s, 1H), 7.43 (s, 1H), 7.35–7.34 (s, 1H), 7.08–7.07 (s, 1H), 6.96–6.93 (m, 1H), 6.80–6.74 (m, 2H), 3.83–3.52 (m, 5H), 3.48–3.28 (m, 2H), 3.19–2.98 (m, 4H), 2.82–2.71 (m, 1H), 2.18–1.98 (m, 2H); APCI MS m/z 369 $[C_{20}H_{21}ClN_4O+H]^+$.

Example 194

(4aS,9bR)-8-(2,4-dichloro-phenylamino)-5-methyl-2,3,4,4a,5,9b-hexahydro-1H-pyrido[4,3-b]indole-6-carbonitrile

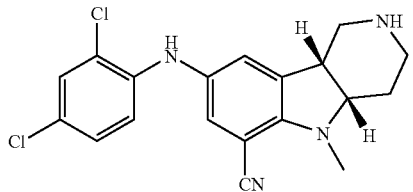

Following the general procedure described above, the title compound was prepared (45 mg, 37%) as a yellow solid using (4aS,9bR)-8-bromo-6-cyano-5-methyl-1,3,4,4a,5,9b-hexahydro-pyrido[4,3-b]indole-2-carboxylic acid tert-butyl ester (Example 158, 100 mg, 0.25 mmol), 2,4-dichloroaniline (53 mg, 0.33 mmol), and NaOt-Bu (56 mg, 0.59 mmol): ): $^1$H NMR (300 MHz, DMSO-$d_6$) δ 8.58 (br s, 1H), 7.63–7.62 (m, 1H), 7.51–7.52 (m, 1H), 7.31–7.30 (m, 1H), 7.20–7.18 (m, 1H), 7.10–7.08 (m, 1H), 6.98–6.97 (m, 1H), 3.80–3.62 (m, 1H), 3.49–3.30 (m, 3H), 3.18–3.01 (m, 4H), 2.88–2.79 (m, 1H), 2.07–1.99 (m, 2H); ESI MS m/z 373 $[C_{19}H_{18}Cl_2N_4+H]^+$.

Example 195

(4aS,9bR)-8-(2,5-dimethyl-phenylamino)-5-methyl-2,3,4,4a,5,9b-hexahydro-1H-pyrido[4,3-b]indole-6-carbonitrile

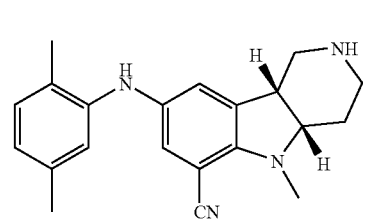

Following the general procedure described above, the title compound was prepared (70 mg, 64%) as a yellow solid using (4aS,9bR)-8-bromo-6-cyano-5-methyl-1,3,4,4a,5,9b-hexahydro-pyrido[4,3-b]indole-2-carboxylic acid tert-butyl ester (Example 158, 100 mg, 0.25 mmol), 2,5-dimethylaniline (53 mg, 0.33 mmol), and NaOt-Bu (56 mg, 0.59 mmol):): $^1$H NMR (300 MHz, DMSO-$d_6$) δ 8.54 (br s, 1H), 7.15–7.13 (m, 2H), 7.02–7.00 (m, 1H), 6.80–6.75 (m, 2H), 6.66–6.63 (m, 1H), 3.54–3.52 (m, 1H), 3.40–3.30 (m, 3H), 3.19–3.13 (m, 1H), 3.01 (s, 3H), 2.79 (m, 1H), 2.18 (s, 3H), 2.11 (s, 3H), 2.08–1.93 (m, 2H); ESI MS m/z 333 $[C_{21}H_{24}N_4+H]^+$.

Example 196

(4aS,9bR)-8-(2,5-difluoro-phenylamino)-5-methyl-2,3,4,4a,5,9b-hexahydro-1H-pyrido[4,3-b]indole-6-carbonitrile

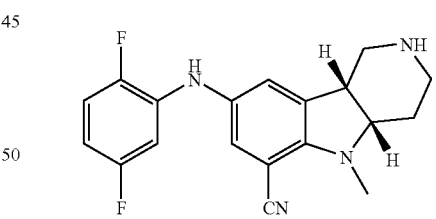

Following the general procedure described above, the title compound was prepared (27 mg, 24%) as a light green solid using (4aS,9bR)-8-bromo-6-cyano-5-methyl-1,3,4,4a,5,9b-hexahydro-pyrido[4,3-b]indole-2-carboxylic acid tert-butyl ester (Example 158, 100 mg, 0.25 mmol), 2,5-difluoroaniline (53 mg, 0.33 mmol), and NaOt-Bu (56 mg, 0.59 mmol): ): $^1$H NMR (300 MHz, DMSO-$d_6$) δ 8.59 (br s, 1H), 8.01 (br s, 1H), 7.38–7.37 (m, 1H), 7.21–7.12 (m, 1H), 7.05–7.04 (m, 1H), 6.69–6.62 (m, 1H), 6.60–6.54 (m, 1H), 3.69–3.31 (m, 4H), 3.19–3.00 (m, 4H), 2.89–2.81 (m, 1H), 2.11–2.05 (m, 2H); ESI MS m/z 341 $[C_{19}H_{18}F_2N_4+H]^+$.

Example 197

(4aS,9bR)-8-(2,6-difluoro-phenylamino)-5-methyl-2,3,4,4a,5,9b-hexahydro-1H-pyrido[4,3-b]indole-6-carbonitrile

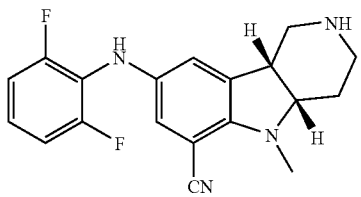

Following the general procedure described above, the title compound was prepared (10 mg, 9%) as a yellow solid using (4aS,9bR)-8-bromo-6-cyano-5-methyl-1,3,4,4a,5,9b-hexahydro-pyrido[4,3-b]indole-2-carboxylic acid tert-butyl ester (Example 158, 100 mg, 0.25 mmol), 2,6-difluoro-aniline (53 mg, 0.33 mmol), and NaOt-Bu (56 mg, 0.59 mmol): ): $^1$H NMR (300 MHz, DMSO-d$_6$) δ 8.59 (br s, 1H), 7.81 (s, 1H), 7.12–7.08 (m, 3H), 6.92–6.90 (m, 1H), 6.58–6.57 (m, 1H), 3.5–3.29 (m, 4H), 3.20–3.11 (m, 1H), 2.98 (s, 3H), 2.70–2.62 (m, 1H), 2.18–1.92 (m, 2H); ESI MS m/z 341 [C$_{19}$H$_{18}$F$_2$N$_4$+H]$^+$.

Example 198

(4aS,9bR)-8-iso-butyl-5-methyl-2,3,4,4a,5,9b-hexahydro-1H-pyrido[4,3-b]indole-6-carbonitrile

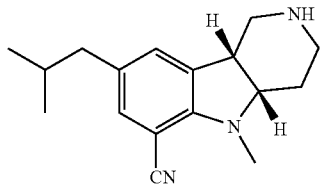

Following the general procedure for Example 127–146, the title compound was prepared (13 mg, 48%) as a light yellow oil using (4aS,9bR)-8-bromo-6-cyano-5-methyl-1,3,4,4a,5,9b-hexahydro-pyrido[4,3-b]indole-2-carboxylic acid tert-butyl ester (Example 158, 40 mg, 0.10 mmol), iso-butylzinc bromide (0.5 M in THF, 2.5 mole equivalent) and Pd(PPh$_3$)$_4$ (0.06 mole equivalent).: MS (ESI): 270 (base, M+H).

Example 199

(4aS,9bR)-5-methyl-8-(3-methyl-butyl)-2,3,4,4a,5,9b-hexahydro-1H-pyrido[4,3-b]indole-6-carbonitrile

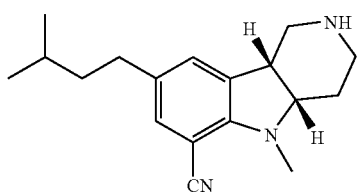

Following the general procedure for Example 127–146, the title compound was prepared (11 mg, 39%) as a light yellow oil using (4aS,9bR)-8-bromo-6-cyano-5-methyl-1,3,4,4a,5,9b-hexahydro-pyrido[4,3-b]indole-2-carboxylic acid tert-butyl ester (Example 158, 40 mg, 0.10 mmol), 3-methyl-butylzinc bromide (0.5 M in THF, 2.5 mole equivalent) and Pd(PPh$_3$)$_4$ (0.06 mole equivalent).: MS (ESI): 284 (base, M+H).

Example 200

(4aS,9bR)-8-butyl-5-methyl-2,3,4,4a,5,9b-hexahydro-1H-pyrido[4,3-b]indole-6-carbonitrile

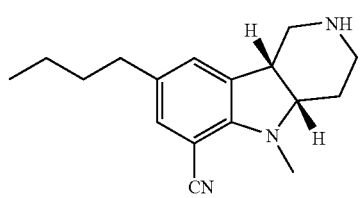

Following the general procedure for Example 127–146, the title compound was prepared (8 mg, 30%) as a light yellow oil using (4aS,9bR)-8-bromo-6-cyano-5-methyl-1,3,4,4a,5,9b-hexahydro-pyrido[4,3-b]indole-2-carboxylic acid tert-butyl ester (Example 158, 40 mg, 0.10 mmol), n-butylzinc bromide (0.5 M in THF, 2.5 mole equivalent) and Pd(PPh$_3$)$_4$ (0.06 mole equivalent).: MS (ESI): 270 (base, M+H).

Example 201

(4aS,9bR)-8-benzyl-5-methyl-2,3,4,4a,5,9b-hexahydro-1H-pyrido[4,3-b]indole-6-carbonitrile

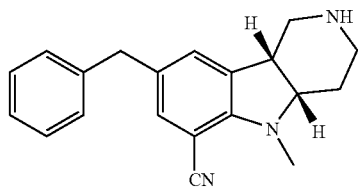

Following the general procedure for Example 127–146, the title compound was prepared (25 mg, 83%) as a light yellow oil using (4aS,9bR)-8-bromo-6-cyano-5-methyl-1,3,4,4a,5,9b-hexahydro-pyrido[4,3-b]indole-2-carboxylic acid tert-butyl ester (Example 158, 40 mg, 0.10 mmol), benzylzinc bromide (0.5 M in THF, 2.5 mole equivalent) and Pd(PPh$_3$)$_4$ (0.06 mole equivalent).: MS (ESI): 304 (base, M+H).

Example 202

(4aS,9bR)-8-(2,4-difluoro-benzyl)-5-methyl-2,3,4,4a,5,9b-hexahydro-1H-pyrido[4,3-b]indole-6-carbonitrile

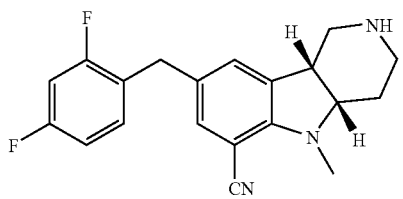

Following the general procedure for Example 127–146, the title compound was prepared (20 mg, 59%) as a light yellow oil using (4aS,9bR)-8-bromo-6-cyano-5-methyl-1,3,4,4a,5,9b-hexahydro-pyrido[4,3-b]indole-2-carboxylic acid tert-butyl ester (Example 158, 40 mg, 0.10 mmol), 2,4-difluoro-benzylzinc bromide (0.5 M in THF, 2.5 mole equivalent) and Pd(PPh$_3$)$_4$ (0.06 mole equivalent).: MS (ESI): 340 (base, M+H).

Example 203

(4aS,9bR)-8-(2,5-difluoro-benzyl)-5-methyl-2,3,4,4a,5,9b-hexahydro-1H-pyrido[4,3-b]indole-6-carbonitrile

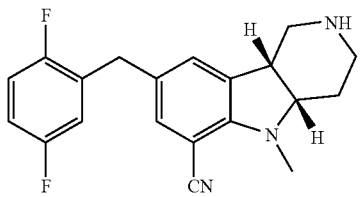

Following the general procedure for Examples 127–146, the title compound was prepared (18 mg, 53%) as a light yellow oil using (4aS,9bR)-8-bromo-6-cyano-5-methyl-1,3,4,4a,5,9b-hexahydro-pyrido[4,3-b]indole-2-carboxylic acid tert-butyl ester (Example 158, 40 mg, 0.10 mmol), 2,5-difluoro-benzylzinc bromide (0.5 M in THF, 2.5 mole equivalent) and Pd(PPh$_3$)$_4$ (0.06 mole equivalent).: MS (ESI): 340 (base, M+H).

Example 204

(4aS,9bR)-5-methyl-8-phenethyl-2,3,4,4a,5,9b-hexahydro-1H-pyrido[4,3-b]indole-6-carbonitrile

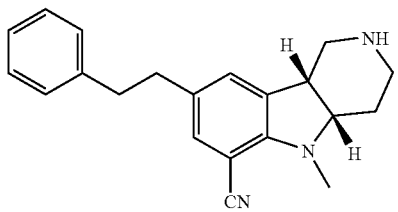

Following the general procedure for Examples 127–146, the title compound was prepared (8 mg, 25%) as a light yellow oil using (4aS,9bR)-8-bromo-6-cyano-5-methyl-1,3,4,4a,5,9b-hexahydro-pyrido[4,3-b]indole-2-carboxylic acid tert-butyl ester (Example 158, 40 mg, 0.10 mmol), phenethylzinc bromide (0.5 M in THF, 2.5 mole equivalent) and Pd(PPh$_3$)$_4$ (0.06 mole equivalent).: MS (ESI): 318 (base, M+H).

Example 205 cis-(4a,9b)-8-(2-methoxy-phenylamino)-2,3,4,4a,5,9b-hexahydro-1H-pyrido[4,3-b]indole-6-carbonitrile

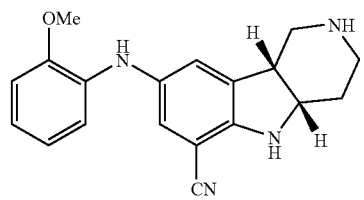

The title compound was prepared by following the general method for cis-(4a,9b)-(5-methyl-6-trifluoromethyl-2,3,4,4a,5,9b-hexahydro-1H-pyrido[4,3-b]indol-8-yl)-pyridin-3-yl-amine (Method B) as a yellow solid (35 mg, 24%) from cis-(4a,9b)-8-amino-6-cyano-3,4,4a,9b-tetrahydro-1H-pyrido[4,3-b]indole-2,5-dicarboxylic acid tert-butyl ester (Example 151, 187 mg, 0.45 mmol), 1-bromo-2-methoxy-benzene (84 mg, 0.45 mmol) and NaOtBu (87 mg, 0.9 mmol). MS (ESI): 321 (base, M+H).

Example 206

(4aS,9bR)-8-(2,6-dimethyl-pyridin-3-ylamino)-2,3,4,4a,5,9b-hexahydro-1H-pyrido[4,3-b]indole-6-carbonitrile

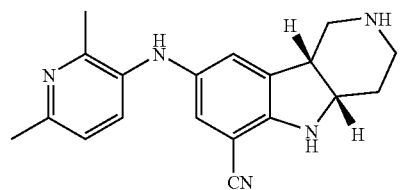

The title compound was prepared by following the general method for cis-(4a,9b)-(5-methyl-6-trifluoromethyl-2,3,4,4a,5,9b-hexahydro-1H-pyrido[4,3-b]indol-8-yl)-pyridin-3-yl-amine (Method B) as a yellow solid (35 mg, 24%) from cis-(4a,9b)-8-amino-6-cyano-3,4,4a,9b-tetrahydro-1H-pyrido[4,3-b]indole-2,5-dicarboxylic acid tert-butyl ester (Example 151, 187 mg, 0.45 mmol), 3-bromo-2,6-dimethyl-pyridine (84 mg, 0.45 mmol) and Cs2CO$_3$ (293 mg, 0.9 mmol). MS (ESI): 320 (base, M+H).

TABLE 1

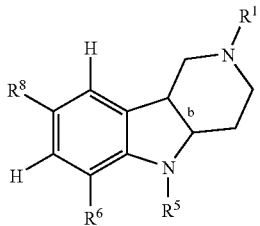

| Ex# | R5 | R6 | R8 | b | R1 |
|---|---|---|---|---|---|
| 1 | H | MeS— | Br | cis | H |
| 2 | Me | MeS— | Br | cis | H |
| 7 | Me | 4-Me—Ph—S— | Br | trans | Me |
| 8 | Me | 4-Me—Ph—S— | Br | Cis | Me |
| 9 | Me | 4-Me—Ph—S— | Ph—S— | trans | Me |
| 10 | Boc | Me— | Br | Cis | Boc |
| 11 | Boc | Me— | Br | 4aS,9bR | Boc |
| 12 | Boc | Me— | H$_2$N— | 4aS,9bR | Boc |
| 24 | H | F$_3$C— | Br | Cis | Boc |
| 25 | H | F$_3$C— | Br | 4aS,9bR | Boc |
| 38 | Me | F$_3$C— | Br | Cis | Boc |
| 39 | Me | F$_3$C— | Br | 4aS,9bR | Boc |
| 64 | Me | F$_3$C— | OH | Cis | Boc |
| 65 | Me | F$_3$C— | OH | 4aS,9bR | Boc |
| 66 | Me | F$_3$C— | OH | Cis | H |
| 67 | Me | F$_3$C— | OH | 4aS,9bR | H |
| 83 | Me | F$_3$C— | H2N | Cis | Boc |
| 84 | Me | F$_3$C— | H2N | 4aS,9bR | Boc |
| 85 | Me | F$_3$C— | H2N | Cis | H |
| 86 | Me | F$_3$C— | H2N | 4aS,9bR | H |
| 141 | H | F$_3$C— | F— | Cis | H |
| 142 | H | F$_3$C— | Me— | Cis | H |
| 143 | H | F$_3$C— | OMe— | Cis | H |
| 144 | H | NC— | Br | Cis | Boc |
| 145 | Boc | NC— | Br | Cis | Boc |
| 146 | H | NC— | Br | Cis | H |
| 147 | H | NC— | Br | 4aS,9bR | Boc |
| 148 | Boc | NC— | Br | 4aS,9bR | Boc |
| 149 | H | NC— | Br | 4aS,9bR | H |
| 150 | Me | NC— | Br | Cis | Boc |
| 151 | Me | NC— | Br | Cis | H |
| 152 | Me | NC— | Br | 4aS,9bR | Boc |
| 153 | Me | NC— | Br | 4aS,9bR | H |
| 154 | Me | NC— | H2N— | Cis | Boc |
| 155 | Me | NC— | H2N— | Cis | H |
| 156 | Me | NC— | H2N— | 4aS,9bR | Boc |
| 157 | Me | NC— | H2N— | 4aS,9bR | H |

TABLE 2

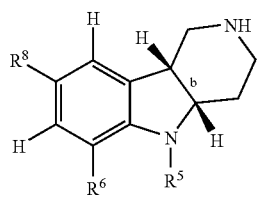

| Ex# | R5 | R6 | b | R8 |
|---|---|---|---|---|
| 3 | H | MeS— | cis | —NH$_2$ |
| 4 | H | MeS— | cis | Ph—NH— |
| 5 | H | MeS— | cis | 4-F—Ph—NH— |
| 6 | H | MeS— | cis | 2-Me-4-MeO—Ph—NH— |
| 13 | H | Me— | 4aS,9bR | 2,3-diCl—Ph—NH— |
| 14 | H | Me— | 4aS,9bR | 3,4-diCl—Ph—NH— |
| 15 | H | Me— | 4aS,9bR | 3-Cl-4-Me—Ph—NH— |
| 16 | H | Me— | 4aS,9bR | 2,4-diCl—Ph—NH— |
| 17 | H | Me— | 4aS,9bR | 2,6-diCl—Ph—NH— |
| 18 | H | Me— | 4aS,9bR | 2,4-diF—Ph—NH— |

TABLE 2-continued

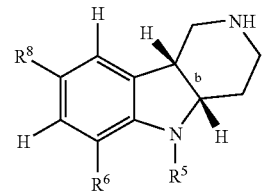

| Ex# | R5 | R6 | b | R8 |
|---|---|---|---|---|
| 19 | H | Me— | 4aS,9bR | 2-MeO-5-Me—Ph—NH— |
| 20 | H | Me— | 4aS,9bR | 3-Cl-4-CN—Ph—NH— |
| 21 | H | Me— | 4aS,9bR | 2-F-4-Cl—Ph—NH— |
| 22 | H | Me— | 4aS,9bR | 2-F-5-CF$_3$—Ph—NH— |
| 23 | H | Me— | 4aS,9bR | 2-Cl-5-CF$_3$—Ph—NH— |
| 26 | H | F$_3$C— | Cis | Cyclohexyl-NH— |
| 27 | H | F$_3$C— | Cis | Me$_2$CH$_2$CH(CH$_3$)—NH— |
| 28 | H | F$_3$C— | Cis | Benzyl-NH— |
| 29 | H | F$_3$C— | Cis | 1-Phenyl-ethyl-NH— |
| 30 | H | F$_3$C— | Cis | 2-Me-Benzyl-NH— |
| 31 | H | F$_3$C— | Cis | 2-OMe-Benzyl-NH— |
| 32 | H | F$_3$C— | Cis | 2-Cl-6-F-Benzyl-NH— |
| 33 | H | F$_3$C— | Cis | 4-t-Bu-Benzyl-NH— |
| 34 | H | F$_3$C— | Cis | 3-Me-Benzyl-NH— |
| 35 | H | F$_3$C— | Cis | 4-Me-Benzyl-NH— |
| 36 | H | F$_3$C— | Cis | 2,5-diMe-Benzyl-NH— |
| 37 | H | F$_3$C— | Cis | 2-F-4-CF$_3$-Benzyl-NH— |
| 40 | Me | F$_3$C— | Cis | Cyclohexyl-NH— |
| 41 | Me | F$_3$C— | Cis | Benzyl-NH— |
| 42 | Me | F$_3$C— | Cis | 2-CF$_3$-Benzyl-NH— |
| 43 | Me | F$_3$C— | Cis | 1-Phenyl-ethyl-NH— |
| 44 | Me | F$_3$C— | Cis | (s)1-cyclohexyl-ethyl-NH— |
| 45 | Me | F$_3$C— | Cis | Exo-bicyclo[2,2,1]hept-2-yl-NH— |
| 46 | Me | F$_3$C— | Cis | (S)-2-Phenyl-propyl-NH— |
| 47 | Me | F$_3$C— | 4aS,9bR | 2-SMe—Ph—NH— |
| 48 | Me | F$_3$C— | 4aS,9bR | 2-Et—Ph—NH— |
| 49 | Me | F$_3$C— | 4aS,9bR | 2-OMe-5-Me—Ph—NH— |
| 50 | Me | F$_3$C— | 4aS,9bR | Ph—NH— |
| 51 | Me | F$_3$C— | 4aS,9bR | 2-F—Ph—NH— |
| 52 | Me | F$_3$C— | 4aS,9bR | 3-F—Ph—NH— |
| 53 | Me | F$_3$C— | 4aS,9bR | 4-F—Ph—NH— |
| 54 | Me | F$_3$C— | 4aS,9bR | 2-OEt—Ph—NH— |
| 55 | Me | F$_3$C— | 4aS,9bR | 2-Me—Ph—NH— |
| 56 | Me | F$_3$C— | 4aS,9bR | 3-F-4-Me—Ph—NH— |
| 57 | Me | F$_3$C— | 4aS,9bR | 3-Cl-4-F—Ph—NH— |
| 58 | Me | F$_3$C— | 4aS,9bR | 4-F-3-Me—Ph—NH— |
| 59 | Me | F$_3$C— | 4aS,9bR | 4-Cl-3-Me—Ph—NH— |
| 60 | Me | F$_3$C— | 4aS,9bR | 2-OMe—Ph—NH— |
| 61 | Me | F$_3$C— | 4aS,9bR | 2,6-diMe—Ph—NH— |
| 62 | Me | F$_3$C— | 4aS,9bR | 2,4-diF—Ph—NH— |
| 63 | Me | F$_3$C— | 4aS,9bR | 2,6-diF—Ph—NH— |
| 68 | Me | F$_3$C— | Cis | Cyclopropylmethoxy- |
| 69 | Me | F$_3$C— | Cis | Cyclopentylmethoxy- |
| 70 | Me | F$_3$C— | Cis | 3-me-butoxy- |
| 71 | Me | F$_3$C— | Cis | n-propoxy- |
| 72 | Me | F$_3$C— | Cis | n-butoxy- |
| 73 | Me | F$_3$C— | Cis | 3,3-diMe-butoxy- |
| 74 | Me | F$_3$C— | Cis | Cyclobutylmethoxy- |
| 75 | Me | F$_3$C— | 4aS,9bR | 2-Py-methoxy- |
| 76 | Me | F$_3$C— | 4aS,9bR | 3-Py-methoxy- |
| 77 | Me | F$_3$C— | 4aS,9bR | 4-Py-methoxy- |
| 78 | Me | F$_3$C— | Cis | 2-Me—Ph—O— |
| 79 | Me | F$_3$C— | Cis | 2,5-diMe—Ph—O— |
| 80 | Me | F$_3$C— | Cis | 2-CN—Ph—O— |
| 81 | Me | F$_3$C— | Cis | 4-CN—Ph—O— |
| 82 | Me | F$_3$C— | Cis | 2-OMe—Ph—O— |
| 87 | Me | F$_3$C— | Cis | 3-Py—NH— |
| 88 | Me | F$_3$C— | Cis | 3-(2-Cl-Py)—NH— |
| 89 | Me | F$_3$C— | Cis | 3-(2-CN-Py)—NH— |
| 90 | Me | F$_3$C— | 4aS,9bR | 3-(2-CN-Py)—NH— |
| 91 | Me | F$_3$C— | Cis | 3-(4-OMe-Py)—NH— |
| 92 | Me | F$_3$C— | 4aS,9bR | 3-(4-OMe-Py)—NH— |
| 93 | Me | F$_3$C— | Cis | 3-(4-F-Py)—NH— |
| 94 | Me | F$_3$C— | 4aS,9bR | 3-(4-OMe-Py)—NH— |
| 95 | Me | F$_3$C— | Cis | 3-(4-CN-Py)—NH— |
| 96 | Me | F$_3$C— | Cis | 3-(5-CN-Py)—NH— |

TABLE 2-continued

| Ex# | R⁵ | R⁶ | b | R⁸ |
|---|---|---|---|---|
| 97 | Me | F₃C— | Cis | 3-(5-COOMe—Py)—NH— |
| 98 | Me | F₃C— | Cis | 3-(5-COOEt—Py)—NH— |
| 99 | Me | F₃C— | 4aS,9bR | 3-(2-OMe—Py)—NH— |
| 100 | Me | F₃C— | Cis | 3-(4-Cl—Py)—NH— |
| 101 | Me | F₃C— | 4aS,9bR | 3-(4-Cl—Py)—NH— |
| 102 | Me | F₃C— | Cis | 3-(2-OEt—Py)—NH— |
| 103 | Me | F₃C— | Cis | 3-(2,4-diOMe—Py)—NH— |
| 104 | Me | F₃C— | 4aS,9bR | 3-(2,4-diOMe—Py)—NH— |
| 105 | Me | F₃C— | Cis | 3-(2,5-diCl—Py)—NH— |
| 106 | Me | F₃C— | Cis | 3-(2-CN-6-Me—Py)—NH— |
| 107 | Me | F₃C— | Cis | 3-(4-F-5-Me—Py)—NH— |
| 108 | Me | F₃C— | 4aS,9bR | 3-(4-F-5-Me—Py)—NH— |
| 109 | Me | F₃C— | Cis | 3-(2,5-diCl—Py)—NH— |
| 110 | Me | F₃C— | Cis | 3-(2-CN-5-OMe—Py)—NH— |
| 111 | Me | F₃C— | Cis | 3-(2-OMe-4-Me—Py)—NH— |
| 112 | Me | F₃C— | Cis | 3-(2-Me-4-Cl—Py)—NH— |
| 113 | Me | F₃C— | Cis | 3-(2-CN-4-Me—Py)—NH— |
| 114 | Me | F₃C— | Cis | 3-(2,4-diMe—Py)—NH— |
| 115 | Me | F₃C— | Cis | 3-(2-I—PrO-4-Me—Py)—NH— |
| 116 | Me | F₃C— | Cis | 3-(2-EtO-4-Me—Py)—NH— |
| 117 | Me | F₃C— | Cis | 3-(2-EtO-6-Me—Py)—NH— |
| 118 | Me | F₃C— | Cis | 3-(2-EtO-4-Me—Py)—NH— |
| 119 | Me | F₃C— | Cis | 2-(4-Me—Py)—NH— |
| 120 | Me | F₃C— | Cis | 2-(3-Me-4-Br—Py)—NH— |
| 121 | Me | F₃C— | Cis | 2-Et-butyl- |
| 122 | Me | F₃C— | Cis | benzyl- |
| 123 | Me | F₃C— | 4aS,9bR | benzyl- |
| 124 | Me | F₃C— | Cis | Cyclohex- |
| 125 | Me | F₃C— | Cis | 2-CN-benzyl- |
| 126 | Me | F₃C— | Cis | 2-Et-butyl- |
| 127 | Me | F₃C— | Cis | 3-CN-propyl- |
| 128 | Me | F₃C— | Cis | isobutyl- |
| 129 | Me | F₃C— | 4aS,9bR | isobutyl- |
| 130 | Me | F₃C— | Cis | tert-butyl- |
| 131 | Me | F₃C— | Cis | 1-Et-propyl- |
| 132 | Me | F₃C— | Cis | n-propyl- |
| 133 | Me | F₃C— | Cis | n-butyl- |
| 134 | Me | F₃C— | 4aS,9bR | n-butyl- |
| 135 | Me | F₃C— | Cis | n-pentyl- |
| 136 | Me | F₃C— | Cis | 3-CN-benzyl- |
| 137 | Me | F₃C— | Cis | phenethyl- |
| 138 | H | F₃C— | Cis | 2-Et-butyl- |
| 139 | H | F₃C— | Cis | 3-Me-butyl- |
| 140 | H | F₃C— | Cis | benzyl- |
| 158 | Me | NC— | Cis | 3-(2-OMe—Py)—NH— |
| 159 | Me | NC— | 4aS,9bR | 3-(2-OMe—Py)—NH— |
| 160 | Me | NC— | 4aS,9bR | 3-Py—NH— |
| 161 | Me | NC— | 4aS,9bR | 3-(2-CN—Py)—NH— |
| 162 | Me | NC— | 4aS,9bR | 3-(6-CF3—Py)—NH— |
| 163 | Me | NC— | 4aS,9bR | 3-(4-CF3—Py)—NH— |
| 164 | Me | NC— | 4aS,9bR | 3-(2-OEt—Py)—NH— |
| 165 | Me | NC— | 4aS,9bR | 3-(2-iOPr—Py)—NH— |
| 166 | Me | NC— | 4aS,9bR | 3-(4-Cl—Py)—NH— |
| 167 | Me | NC— | 4aS,9bR | 3-(2,5-diCl—Py)—NH— |
| 168 | Me | NC— | 4aS,9bR | 3-(4-F-5-Me—Py)—NH— |
| 169 | Me | NC— | 4aS,9bR | 3-(2-OMe-5-Me—Py)—NH— |
| 170 | Me | NC— | 4aS,9bR | 3-(2-Cl-4-CF3—Py)—NH— |
| 171 | Me | NC— | 4aS,9bR | 3-(2,4-diCl-6-CF3—Py)—NH— |
| 172 | Me | NC— | 4aS,9bR | 2-OMe—Ph—NH— |
| 173 | Me | NC— | 4aS,9bR | 2-OCF3—Ph—NH— |
| 174 | Me | NC— | 4aS,9bR | 2-OEt—Ph—NH— |
| 175 | Me | NC— | 4aS,9bR | 2-F—Ph—NH— |
| 176 | Me | NC— | 4aS,9bR | 2-Me—Ph—NH— |
| 177 | Me | NC— | 4aS,9bR | 2-Et—Ph—NH— |
| 178 | Me | NC— | 4aS,9bR | 4-F—Ph—NH— |
| 179 | Me | NC— | 4aS,9bR | 3-Me—Ph—NH— |
| 180 | Me | NC— | 4aS,9bR | 2-CN—Ph—NH— |
| 181 | Me | NC— | 4aS,9bR | 2,4-diOMe—Ph—NH— |
| 182 | Me | NC— | 4aS,9bR | 2,3-diF—Ph—NH— |
| 183 | Me | NC— | 4aS,9bR | 2-Me-5-F—Ph—NH— |
| 184 | Me | NC— | 4aS,9bR | 3-Me-4-F—Ph—NH— |
| 185 | Me | NC— | 4aS,9bR | 3-Me-4-Cl—Ph—NH— |
| 186 | Me | NC— | 4aS,9bR | 2-Me-4-F—Ph—NH— |
| 187 | Me | NC— | 4aS,9bR | 2-Me-4-Cl—Ph—NH— |
| 188 | Me | NC— | 4aS,9bR | 2,4-diF—Ph—NH— |
| 189 | Me | NC— | 4aS,9bR | 2,4-diF—Ph—NH— |
| 190 | Me | NC— | 4aS,9bR | 3-Cl-4-F—Ph—NH— |
| 191 | Me | NC— | 4aS,9bR | 2,4-diMe—Ph—NH— |
| 192 | Me | NC— | 4aS,9bR | 2-Me-4-OMe—Ph—NH— |
| 193 | Me | NC— | 4aS,9bR | 2-OMe-5-Cl—Ph—NH— |
| 194 | Me | NC— | 4aS,9bR | 2,4-diCl—Ph—NH— |
| 195 | Me | NC— | 4aS,9bR | 2,5-diMe—Ph—NH— |
| 196 | Me | NC— | 4aS,9bR | 2,5-diF—Ph—NH— |
| 197 | Me | NC— | 4aS,9bR | 2,6-diF—Ph—NH— |
| 198 | Me | NC— | 4aS,9bR | Isobutyl- |
| 199 | Me | NC— | 4aS,9bR | 3-Me-butyl- |
| 200 | Me | NC— | 4aS,9bR | n-butyl- |
| 201 | Me | NC— | 4aS,9bR | benzyl- |
| 202 | Me | NC— | 4aS,9bR | 2,4-diF-benzyl- |
| 203 | Me | NC— | 4aS,9bR | 2,5-diF-benzyl- |
| 204 | Me | NC— | 4aS,9bR | Phenethyl- |
| 205 | H | NC— | Cis | 2-OMe—Ph—NH— |
| 206 | H | NC— | Cis | 3-(2,4-diMe—Py)—NH— |

Utilities and Combinations

Utilities

The compounds of the present invention are 5HT$_{2C}$ modulators, and include compounds which are, for example, selective agonists, partial agonists, antagonists or partial antagonists of the 5HT$_{2C}$ receptor. Accordingly, the compounds of the present invention may be useful for the treatment or prevention of diseases and disorders associated with 5HT$_{2C}$ receptor activity. Preferably, compounds of the present invention possess activity as agonists of the 5HT$_{2C}$ receptor, and may be used in the treatment of diseases or disorders associated with the activity of the 5HT$_{2C}$ receptor.

Accordingly, the compounds of the present invention can be administered to mammals, preferably humans, for the treatment of a variety of conditions and disorders, including, but not limited to metabolic and eating disorders as well as conditions associated with metabolic disorders, (e.g., obesity, diabetes, arteriosclerosis, hypertension, polycystic ovary disease, cardiovascular disease, osteoarthritis, dermatological disorders, impaired glucose hemostatsis, insulin resistance, hypercholesterolemia, hypertriglyceridemia, cholelithiasis and sleep disorders, dislipidemic conditions, bulimia nervosa and compulsive eating disorders); pain; sleep disorders and psychiatric disorders, such as substance abuse, depression, anxiety, psychosis, mania and schizophrenia.

These compounds could also be used for the improvement of cognitive function (e.g., the treatment of dementia, including Alzheimer's disease, short term memory loss and attention deficit disorders); neurodegenerative disorders (e.g., Parkinson's Disease, cerebral apoplexy and craniocerebral trauma) and hypotension (e.g., hemorrhagic and endotoxin-induced hypotension). These compounds could also be used for treatment of cardiac dysfunction (e.g., associated with valvular disease, myocardial infarction, cardiac hypertrophy or congestive heart failure); and improvement of the overall pulmonary function; transplant rejection; rheumatoid arthritis; osteoarthritis; fibromyalgia; multiple sclerosis; inflammatory bowel disease; lupus; graft vs. host disease; T-cell mediated hypersensitivity disease; psoriasis; asthma; Hashimoto's thyroiditis; Guillain-Barre syndrome; cancer; contact dermatitis; allergic rhinitis; and ischemic or reperfusion injury. These compounds could also be used for treatment of sexual dysfunction and erectogenesis.

Compounds useful in the treatment of appetite or motivational disorders regulate desires to consume sugars, carbohydrates, alcohol or drugs and more generally to regulate the consumption of ingredients with hedonic value. In the present description and in the claims, appetite disorders are understood as meaning: disorders associated with a substance and especially abuse of a substance and/or dependency on a substance, disorders of eating behaviors, especially those liable to cause excess weight, irrespective of its origin, for example: bulimia nervosa, craving for sugars. The present invention therefore further relates to the use of a $5HT_{2C}$ receptor agonist for the treatment of bulimia and obesity, including obesity associated with type II diabetes (non-insulin-dependent diabetes), or more generally any disease resulting in the patient becoming overweight. Overweight and obesity, as described herein, is defined by a body mass index ($kg/m^2$) for example, at least 26. It may be due to any cause, whether genetic or environmental, including overeating and bulemia, polycycstic ovary disease, craniopharyngeoma, Prader-Willi Syndrome, Frohlich's Syndrome, Type II diabetes, growth hormone deficiency, Turner's Syndrome and other pathological states characterized by reduced metabolic activity or reduced energy expenditure. As used with reference to the utilities described herein, the term "treating" or "treatment" encompasses prevention, partial alleviation, or cure of the disease or disorder. Further, treatment of obesity is expected to prevent progression of medical covariants of obesity, such as arteriosclerosis, Type II diabetes, polycystic ovary disease, cardiovascular disease, osteoarthritis, dermatological disorders, hypertension, insulin resistance, hypercholesterolemia, hypertriglyceridemia, cholelithiasis and sleep disorders.

Compounds in the present invention may also be useful in treating substance abuse disorders, including substance dependence or abuse without physiological dependence. Substances of abuse include alcohol, amphetamines (or amphetamine-like substances), caffeine, cannabis, cocaine, hallucinogens, inhalents, nicotine, opioids, phencyclidine (or phencyclidine-like compounds), sedative-hypnotics or benzodiazepines, and other (or unknown) substances and combinations of the above. The terms "substance abuse disorders" also includes drug, nicotine or alcohol withdrawal syndromes and substance-induced anxiety or mood disorder with onset during withdrawal.

Compounds in the present invention may be useful in treating memory impairment and cognitive disorders. The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, attention deficit-hyperactivity disorder, HIV, cardiovascular disease such as ischemia or stroke, and head trauma as well as age-related cognitive decline. Dementias are diseases that include memory loss and additional intellectual impairment separate from memory. $5HT_{2C}$ modulators may also be useful in treating cognitive impairments related to attentional deficits, such as attention deficit-hyperactivity disorders.

Compounds in the present invention may also be useful in treating diseases associated with dysfunction of brain dopaminergic systems, such as Parkinson's Disease and substance abuse disorders. Parkinsons's Disease is a neurodenerative movement disorder characterized by bradykinesia and tremor.

Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other suitable therapeutic agents useful in the treatment of the aforementioned disorders including: anti-obesity agents; anti-diabetic agents, appetite suppressants; cholesterol/lipid-lowering agents, cognition enhancing agents, agents used to treat neurodegeneration, agents used to treat respiratory conditions, agents used to treat bowel disorders, anti-inflammatory agents; anti-anxiety agents; anti-depressants; anti-psychotic agents; sedatives; hypnotics; anti-hypertensive agents; anti-tumor agents and analgesics.

Such other therapeutic agent(s) may be administered prior to, simultaneously with, or following the administration of the $5HT_{2C}$ modulators in accordance with the invention.

Examples of suitable anti-obesity agents for use in combination with the compounds of the present invention include leptin and leptin-sensitizing agents, melanocortin receptor (MC4R) agonists, agouti-related peptide (AGRP) antagonists, melanin-concentrating hormone receptor (MCHR) antagonists, growth hormone secretagogue receptor (GHSR) antagonists, orexin antagonists, CCK agonists, GLP-1 agonists, NPY1 or NPY5 antagonsits, NPY2 modulators, corticotropin releasing factor agonists, histamine receptor-3 (H3) modulators, aP2 inhibitors, PPAR gamma modulators, PPAR delta modulators, beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a thyroid receptor beta modulator, such as a thyroid receptor ligand as disclosed in WO 97/21993 (U. Cal SF), WO 99/00353 (KaroBio) and GB98/284425 (KaroBio), a lipase inhibitor, such as orlistat or ATL-962 (Alizyme), leptinergics, adiponectin modulating agents, cannabinoid-1 receptor antagonists, such as SR-141716 (Sanofi) or SLV-319 (Solvay) and monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), axokine (Regeneron).

Examples of suitable anti-diabetic agents for use in combination with the compounds of the present invention include: insulin, which may include short- and long-lasting forms as well as oral and inhaled forms, insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists such as the compounds described in Bristol-Myers Squibb U.S. Pat. No. 6,414,002, dipeptidyl peptidase IV (DP4) inhibitors such as the compounds described in Bristol-Myers Squibb U.S. Pat. Nos. 6,395,767 and 6,573,287, SGLT2 inhibitors such as the compounds described in Bristol-Myers Squibb U.S. Pat. Nos. 6,414,126 and 6,515,117, glycogen phosphorylase inhibitors, and/or meglitinides, as well as insulin, and/or glucagon-like peptide-1 (GLP-1), and/or a PTP-1B inhibitor (protein tyrosine phosphatase-1B inhibitor).

The antidiabetic agent may be glucokinase inhibitors, 11 β HSD inhibitors or oral antihyperglycemic agents, which is preferably a biguanide such as metformin or phenformin or salts thereof, preferably metformin HCl. Where the antidiabetic agent is a biguanide, the compounds of the present invention will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present invention may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's REZULIN, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-1 19702 (Sankyo/WL), NN-2344 (Dr. Reddy/NN), or YM-440 (Yamanouchi), preferably rosiglitazone and pioglitazone.

The compounds of the present invention may be employed in combination with anti-hyperlipidemia agents, or agents used to treat arteriosclerosis. An example of an hypolipidemic agent would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869–1871, including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1–40 (1996).

In addition, other squalene synthetase inhibitors suitable for use herein include the terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 109, 5544, cyclopropanes reported by Capson, T. L., PhD dissertation, June, 1987, Dept. Med. Chem. U of Utah, Abstract, Table of Contents, pp 16, 17, 40–43, 48–51, Summary, pyrrolidine derivatives as disclosed by Sasyou, et al, WO 02/083636 and N-aryl-substituted cyclic amine derivatives disclosed by Okada et al, WO 02/076973.

Other hypolipidemic agents suitable for use herein include, but are not limited to, fibric acid derivatives, a PPAR agonists, such as fenofibrate, gemfibrozil, clofibrate, bezafibrate, ciprofibrate, clinofibrate and the like, probucol, and related compounds as disclosed in U.S. Pat. No. 3,674,836, probucol, phenylfibrate and gemfibrozil being preferred, bile acid sequestrants such as cholestyramine, colestipol and DEAE-Sephadex (SECHOLEX, POLICEXIDE) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, Drugs of the Future 24, 9–15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137 (1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62, or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's $SCH_{48461}$ (ezetimibe) as well as those disclosed in Atherosclerosis 115, 45–63 (1995) and J. Med. Chem. 41, 973 (1998).

The other lipid agent or lipid-modulating agent may be a cholesteryl transfer protein inhibitor (CETP) such as Pfizer's Torcetrapib® as well as those disclosed in WO/0038722 and in EP 818448 (Bayer) and EP 992496, and Pharmacia's SC-744 and SC-795, as well as CETi-1 and JTT-705.

The hypolipidemic agent may be an ileal $Na^+$/bile acid cotransporter inhibitor such as disclosed in Drugs of the Future, 24, 425–430 (1999). The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 2000/050574, for example, a sphingolipid, such as ceramide, or neutral sphingomyelenase (N-SMase) or fragment thereof, and inhibitors or lipid synthesis enzymes such as, for example, ACC, FAS, DGAT, MGAT, GPAT, AMP kinase, CPT1 and SCD1. Preferred dislipidemic agents are pravastatin, lovastatin, simvastatin, atorvastatin, fluvastatin, pitavastatin, rosuvastatin, phenylfibrate and Pfizer's Torcetrapib® as well as niacin and/or cholestagel.

The compounds of the present invention may be employed in combination with anti-hypertensive agents. Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan, candasartan and talmisartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

$5HT_{2C}$ modulators could be useful in treating other diseases associated with obesity, including sleep disorders. Therefore, the compounds described in the present invention could be used in combination with therapeutics for treating sleep disorders. Examples of suitable therapies for treatment of sleeping disorders for use in combination with the compounds of the present invention include melatonin analogs, melatonin receptor agonists, ML 1 B agonists. GABA A receptor agonists such as barbiturates (e.g., amobarbital, aprobarbital, butabarbital, mephobarbital, pentobarbital, phenobarbital, secobarbital and talbutal), benzodiazepines (e.g., diazepam, lorazepam, oxazepam, alprazolam, chlordiazepoxide, clonazepam, chlorazepate, halazepam and prazepam), also specifically including triazolam (Halcion). Other agents for treating sleep disorders include zolpidem (Ambien) and Neurocrine's indiplon.

$5HT_{2C}$ modulators may reduce or ameliorate substance abuse or addictive disorders. Therefore, combination of $5HT_{2C}$ modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion and opiate antagonists.

$5HT_{2C}$ modulators may reduce anxiety or depression; therefore, the compounds described in this application may be used in combination with anti-anxiety agents or antidepressants. Examples of suitable anti-anxiety agents for use in combination with the compounds of the present invention include benzodiazepines (e.g., diazepam, lorazepam, oxazepam, alprazolam, chlordiazepoxide, clonazepam, chlorazepate, halazepam and prazepam), $5HT_{1A}$ receptor agonists (e.g., buspirone, flesinoxan, gepirone, ipsapirone and serzone), corticotropin releasing factor (CRF) antagonists and SSRI's.

Examples of suitable classes of anti-depressants for use in combination with the compounds of the present invention include norepinephrine reuptake inhibitors (tertiary and secondary amine tricyclics), selective serotonin reuptake inhibitors (SSRIs) (fluoxetine, fluvoxamine, paroxetine, citalopram and sertraline), monoamine oxidase inhibitors (MAOIs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists (Britsol-Myers Squibb U.S. Pat. Nos. 6,642,230; 6,630,476; 6,589,952; 6,579,876; 6,525,056; 6,521,636; 6,518,271; 6,515,005; 6,448,261; 6,399,609; 6,362,180; and 6,358,950), alpha-adrenoreceptor antagonists, and a typical antidepressants (bupropion, lithium, nefazodone, trazodone and viloxazine).

The combination of a conventional antipsychotic drug with a $5HT_{2C}$ modulator could also enhance symptom reduction in the treatment of psychosis or mania. Further, such a combination could enable rapid symptom reduction, reducing the need for chronic treatment with antipsychotic agents. Such a combination could also reduce the effective antipsychotic dose requirement, resulting in reduced probability of developing the motor dysfunction typical of chronic antipsychotic treatment.

Examples of suitable antipsychotic agents for use in combination with the compounds of the present invention include the phenothiazine (chlorpromazine, mesoridazine, thioridazine, acetophenazine, fluphenazine, perphenazine and trifluoperazine), thioxanthine (chlorprothixene, thiothixene), heterocyclic dibenzazepine (clozapine, olanzepine and aripiprazole), butyrophenone (haloperidol), diphenylbutylpiperidine (pimozide) and indolone (molindolone) classes of antipsychotic agents. Other antipsychotic agents with potential therapeutic value in combination with the compounds in the present invention include loxapine, sulpiride and risperidone.

Combination of the compounds in the present invention with conventional antipsychotic drugs could also provide an enhanced therapeutic effect for the treatment of schizophrenic disorders, as described above for manic disorders. As used here, schizophrenic disorders include paranoid, disorganized, catatonic, undifferentiated and residual schizophrenia, schizophreniform disorder, schizoaffective disorder, delusional disorder, brief psychotic disorder and psychotic disorder not specified. Examples of suitable antipsychotic drugs for combination with the compounds in the present invention include the antipsychotics mentioned above, as well as dopamine receptor antagonists, muscarinic receptor agonists, $5HT_{2A}$ receptor antagonists and $5HT_{2A}$/dopamine receptor antagonists or partial agonists (e.g., olanzepine, aripiprazole, risperidone, ziprasidone).

The compounds described in the present invention could be used to enhance the effects of cognition-enhancing agents, such as acetylcholinesterase inhibitors (e.g., tacrine the active agent in Cognex®), ADHD agents (e.g. methylphenidate, atomoxetine the active agent in Strattera® and histamine 3 antagonists), muscarinic receptor-1 agonists (e.g., milameline), nicotinic agonists, glutamic acid receptor (AMPA and NMDA) modulators such as memantine, and nootropic agents (e.g., piracetam, levetiracetam). Examples of suitable therapies for treatment of Alzheimer's disease and cognitive disorders for use in combination with the compounds of the present invention include donepezil, tacrine, revastigraine, 5HT6 receptor antagonists, gamma secretase inhibitors, beta secretase inhibitors, SK channel blockers, Maxi-K blockers, and KCNQs blockers.

The compounds described in the present invention could be used to enhance the effects of agents used in the treatment of Parkinson's Disease. Examples of agents used to treat Parkinson's Disease include: levadopa with or without a COMT inhibitor, antiglutamatergic drugs (amantadine, riluzole), alpha-2 adrenergic antagonists such as idazoxan, opiate antagonists, such as naltrexone, other dopamine agonists or transportor modulators, such as ropinirole, or pramipexole or neurotrophic factors such as glial derived neurotrophic factor (GDNF).

The compounds described in the present invention could be used in combination with agents used to treat erectile dysfunction. Examples of suitable treatment for erectile dysfunction include sildenafil (Viagra), vardenafil (Levitra) and tadalafil (Cialis). Other compounds that could be used in combination for erectile dysfunction include yohimbine, phentolamine and papaverine.

The compounds described in the present invention could be used in combination with suitable anti-inflammatory agents. Examples of suitable anti-inflammatory agents for use in combination with the compounds of the present invention include prednisone, dexamethasone, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®, Arcoxia®, and Bextra®), CTLA4-Ig agonists/antagonists, CD40 ligand antagonists, IMPDH inhibitors, such as mycophenolate (CellCept®), integrin antagonists, alpha-4 beta-7 integrin antagonists, cell adhesion inhibitors, interferon gamma antagonists, ICAM-1 inhibitor, tumor necrosis factor (TNF) antagonists (e.g., infliximab, OR1384, including TNF-alpha inhibitors, such as tenidap, anti-TNF antibodies or soluble TNF receptor such as etanercept (Enbrel®), Remicade®, rapamycin (sirolimus or Rapamune) and leflunomide (Arava)), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelnorm® and Maxi-K® openers such as those disclosed in U.S. Pat. No. 6,184,231 B1).

Exemplary of such other therapeutic agents which may be used in combination with $5HT_{2C}$ modulators include the following: cyclosporins (e.g., cyclosporin A), anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), gold compounds, antiproliferative agents such as methotrexate, FK506 (tacrolimus, Prograf), mycophenolate mofetil, cytotoxic drugs such as azathiprine and cyclophosphamide, anticytokines such as antiIL-4 or IL-4 receptor fusion proteins and PDE 4 inhibitors such as Ariflo, and the PTK inhibitors disclosed in the following U.S. patent applications, incorporated herein by reference in their entirety: Ser. No. 09/097,338, filed Jun. 15, 1998; Ser. No. 09/094,797, filed Jun. 15, 1998; Ser. No. 09/173,413, filed Oct. 15, 1998; and Ser. No. 09/262,525, filed Mar. 4, 1999. See also the following documents and references cited therein and incorporated herein by reference: Hollenbaugh, D., Et Al, "Cleavable CD40Ig Fusion Proteins and the Binding to Sgp39", J. Immunol. Methods (Netherlands), 188(1), pp. 1–7 (Dec. 15, 1995); Hollenbaugh, D., et al, "The Human T Cell Antigen Gp39, A Member of the TNF Gene Family, Is a Ligand for the CD40 Receptor: Expression of a Soluble Form of Gp39 with B Cell Co-Stimulatory Activity", EMBO J (England), 11(12), pp. 4313–4321 (December 1992); and Moreland, L. W. et al., "Treatment of Rheumatoid Arthritis with a Recombinant Human Tumor Necrosis Factor Receptor (P75)-Fc Fusion Protein," New England J. of Medicine, 337(3), pp. 141–147 (1997).

The above other therapeutic agents, when employed in combination with the compounds of the present invention, may be used, for example, in those amounts indicated in the Physicians' Desk Reference (PDR) or as otherwise determined by one of ordinary skill in the art.

The compounds of formula I of the invention can be administered orally or parenterally, such as subcutaneously or intravenously, as well as by nasal application, transdermally, rectally or sublingually to various mammalian species known to be subject to such maladies, e.g., humans, in an effective amount within the dosage range of about 0.2 to 1000 mg, preferably from about 1 to 100 mg in a regimen of single, two or four divided daily doses.

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intracisternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

Pharmacological Analysis

The pharmacological analysis of each compound for either antogonism or agonism of at $5\text{-HT}_{2A}$, $5\text{-HT}_{2B}$ and $5\text{-HT}_{2C}$ receptors consisted of in vitro and in vivo studies. In vitro analyses included $K_i$ determinations at $5\text{-HT}_{2A}$, $5\text{-HT}_{2B}$ and $5\text{-HT}_{2C}$ receptors and an assessment of functional (i.e., agonism or antagonism) activity at each receptor class by IP3 hydrolysis assays. Additional receptor assays were conducted to evaluate receptor specificity of $5\text{-HT}_{2C}$ receptors over monoamine and nuisance receptors (e.g. histamine, dopamine, and muscarinic). A compound is considered active as a $5\text{-HT}_{2C}$ agonist if it has an $IC_{50}$ value or a $K_i$ value of less than about 50 micromolar; preferably less than about 1.0 micromolar; more preferably less than about 0.1 micromolar. Using the assays disclosed herein, compounds of the present invention have been shown to have an $IC_{50}$ value of less than about 50 micromolar for $5\text{-HT}_{2C}$ agonism.

In vivo assays assessed compound activity in a variety of behavioral paradigms including acute and chronic feeding models, anxiety and depression models (learned-helplessness, elevated plus maze, Geller-Siefter, conditioned taste aversion, taste reactivity, satiety sequence). In aggregate, these models reflect activity as a $5\text{-HT}_{2C}$ agonist (feeding models, anxiety models, depression models) and provide some indication as to bioavailability, metabolism and pharmacokinetics.

Radioligand binding experiments were conducted on recombinant human $5\text{-HT}_{2A}$, $5\text{-HT}_{2B}$, and $5\text{-HT}_{2C}$ receptors expressed in HEK293E cells. The affinities of compounds of the present invention to bind at these receptors is determined by their capacity to compete for [$^{125}$I]-1-(2,5-dimethoxy-4-iodophenyl)-2-amino-propane (DOI) binding at the 5-HT$_{2A}$, 5-HT$_{2B}$, or 5-HT$_2$C. General references for binding assays include 1) Lucaites V L, Nelson D L, Wainscott D B, Baez M (1996) Receptor subtype and density determine the coupling repertoire of the 5-HT$_2$ receptor subfamily. Life Sci., 59(13):1081–95. J Med Chem 1988 January; 31(1):5–7; 2) Glennon R A, Seggel M R, Soine W H, Herrick-Davis K, Lyon R A, Titeler M (1988) [125I]-1-(2,5-dimethoxy-4-iodophenyl)-2-amino-propane: an iodinated radioligand that specifically labels the agonist high-affinity state of 5-HT2 serotonin receptors. J Med. Chem. 31(1):5–7 and 3) Leonhardt S, Gorospe E, Hoffman B J, Teitler M (1992) Molecular pharmacological differences in the interaction of serotonin with 5-hydroxytryptamine1C and 5-hydroxytryptamine2 receptors. Mol Pharmacol., 42(2):328–35.

The functional properties of compounds (efficacy and potency) were determined in whole cells expressing 5-HT$_{2A}$, 5-HT$_{2B}$, or 5-HT$_{2C}$ receptors by assessing their ability to stimulate or inhibit receptor-mediated phosphoinositol hydrolysis. The procedures used are described below.

In Vitro Binding Assays

Stable Expression of 5-HT$_{2A}$, 5-HT$_{2B}$ and 5-HT$_{2C}$ Receptors in HEK293E Cells Stable cell lines were generated by transfecting 293EBNA cells with plasmids containing human 5-HT$_{2A}$, 5-HT$_{2B}$, or 5-HT$_{2C}$ receptor (INI, INV, VNV or VGV RNA-edited isoforms) cDNA using calcium phosphate. These plasmids also contained the cytomegalovirus (CMV) immediate early promoter to drive receptor expression and EBV oriP for their maintenance as an extrachromosomal element, and the hph gene from E. Coli to yield hygromycin B resistance (Horlick et al., 1997). Transfected cells were maintained in Dulbecco's Modified Eagle medium (DMEM) containing dialyzed 10% fetal bovine serum at 37° C. in a humid environment (5% CO$_2$) for 10 days. The 5-HT$_{2A}$ cells were adapted to spinner culture for bulk processing whereas it was necessary to maintain the other lines as adherent cultures. On the day of harvest, cells were washed in phosphate-buffered saline (PBS), counted, and stored at −80° C.

Membrane Preparation

On the day of assay, pellets of whole cells (containing approximately 1×10$^8$ cells) expressing the 5-HT$_{2A}$, 5-HT$_{2B}$ or 5-HT$_{2C}$ receptor were thawed on ice and homogenized in 50 mM Tris HCl (pH 7.7) containing 1.0 mM EDTA using a Brinkman Polytron (PT-10, setting 6 for 10 sec). The homogenate was centrifuged at 48,000×g for 10 min and the resulting pellet washed twice by repeated homogenization and centrifugation steps. The final pellet was resuspended in tissue buffer and protein determinations were made by the bichichoninic acid (BCA) assay (Pierce Co., IL) using bovine serum albumin as the standard.

Radioligand Binding Assays for the 5-HT$_{2A}$, 5-HT$_{2B}$ and 5-HT$_{2C}$ Receptors Radioligand binding studies were conducted to determine the binding affinities (Ki values) of compounds for the human recombinant 5-HT$_{2A}$, 5-HT$_{2B}$, and 5-HT$_{2C}$ receptors (Fitzgerald et al., 1999). Assays were conducted in disposable polypropylene 96-well plates (Costar Corp., Cambridge, Mass.) and were initiated by the addition of 5-HT$_{2A}$, 5-HT$_{2B}$, or 5-HT$_{2C}$ membrane homogenate in tissue buffer (10–30 (g/well) to assay buffer (50 mM Tris HCl, 0.5 mM EDTA, 10 mM pargyline, 10 mM MgSO$_4$, 0.05% ascorbic acid, pH 7.5) containing [$^{125}$I]DOI for the 5-HT$_{2A}$ and 5-HT$_{2C}$ receptors (0.3–0.5 nM, final) or [$^3$H]LSD (1–2.0 nM, final) for the 5-HT$_{2B}$ receptor, with or without competing drug (i.e, newly synthesized chemical entity). For a typical competition experiment, a fixed concentration of radioligand was competed with duplicate concentrations of ligand (12 concentrations ranging from 10 picomolar to 10 micromolar). The reaction mixtures were incubated to equilibrium for 45 min at 37° C. and terminated by rapid filtration (Packard cell harvester; Perkin-Elmer) over GFF glass-fiber filters that had been pre-soaked in 0.3% polyethyleneimine. Filters were washed in ice-cold 50 mM Tris HCl buffer (pH 7.5) and then counted on a Top Count (Packard).

Phosphoinositide Hydrolysis Studies

The ability of newly synthesized compounds to stimulate phosphoinositide (PI) hydrolysis was monitored in whole cells using a variant (Egan et al., 1998) of a protocol described previously (Berridge et al., 1982). HEK293E cells expressing the human 5-HT$_{2A}$, 5-HT$_{2B}$, or 5-HT$_{2C}$ receptor were lifted with 0.5 mM EDTA and plated at a density of 100,000/well onto poly-D-lysine-coated 24-well plates (Biocoat; Becton Dickinson, Bedford, Mass.) in Dulbecco's modified Eagle's serum (DMEM; Gibco B RL) containing high glucose, 2 mM glutamine, 10% dialyzed fetal calf serum, 250 (g/ml hygromycin B, and 250(g/ml G418. Following a 24–48 hr period, the growth media was removed and replaced with DMEM without fetal calf serum and inositol (Gibco BRL). The cells were then incubated with DMEM (without serum and inositol) containing a final concentration of 0.5 uCi/well myo-[$^3$H]inositol for 16–18 hr. Following this incubation, the cells were washed with DMEM (without serum or inositol) containing 10 mM LiCl and 10 (M pargyline and then incubated for 30 min with the same media but now containing one of several test compounds. Reactions were terminated by aspirating the media and lysing the cells by freeze-thaw. [$^3$H]phosphoinositides were extracted with chloroform/methanol (1:2 v/v), separated by anion exchange chromatography (Bio-Rad AGI-X8 resin), and counted by liquid scintillation spectroscopy as described previously (Egan et al., 1998).

Calcium Fluorescence Studies

The ability of newly synthesized compounds to stimulate calcium fluorescence was monitored in whole cells using a protocol described previously (Fitzgerlad et al., 1999). HEK293E cells expressing the human 5-HT$_{2C}$, or 5-HT$_{2B}$ receptor were lifted with 0.5 mM EDTA and plated at a density of 50,000/well onto poly-D-lysine-coated 96-well plates (Biocoat; Becton Dickinson, Bedford, Mass.) in Dulbecco's modified Eagle's serum (DMEM; Gibco BRL) containing high glucose, 2 mM glutamine, 10% dialyzed fetal calf serum, 250 µg/ml hygromycin B, and 250 µg/ml G418. Following a 24 hr period, the cell plates are removed from the incubator and an equal volume of Loading Buffer (Hanks BSS with 200 mM HEPES, pH 5.98) containing the calcium dye reagent (Fluo-3) is added to each well (100 µL per well for 96-well plates and then incubated for 1 hour at 37° C. Following the dye loading of the cells he plates are transferred to the FLIPR. Test compounds are added to the plate as a concentration response curve and the changes in fluorescence units due to calcium influx are monitored for a period of three seconds.

Data Analyses

The equilibrium apparent dissociation constants (Ki's) from the competition experiments were calculated using an iterative nonlinear regression curve-fitting program (Excelfit and TA Activity Base). For the PI hydrolysis and FLIPR experiments, EC50's were calculated using a one-site 'pseudo' Hill model: y=((Rmax−Rmin)/(1+R/EC50)nH))+ Rmax where R=response (GraphPad Prism; San Diego, Calif.). Emax (maximal response) was derived from the fitted curve maxima (net IP stimulation) for each compound. Intrinsic activity (IA) was determined by expressing the Emax of a compound as a percentage of the Emax of 5-HT (IA=1.0).

Efficacy Models to Evaluate Food Consumption and Weight Loss

Acute overnight feeding assay. Compounds are assessed to for their ability to reduce food consumption during the dark cycle, which is the most active period of feeding in the rat. Fischer 344 rats are trained on a fixed ratio three (FR3) response paradigm which requires them to press a bar 3 consecutive times in order to obtain a food pellet. The number of bar presses occurring throughout the dark cycle can be monitored electronically as a measure of food intake by the animal. Rats are dosed orally or intraperitoneally with test compound 30 minutes prior to the onset of the dark cycle. The treated animals are then placed in individual operant boxes for 15 hours (12 hrs of dark cycle and the first three hours of the light cycle). Food intake in compound treated animals is compared to that of vehicle treated animals in order to determine percent reductions in food intake. Simultaneous measurements of water intake and locomotor activity are also measured during the period to assess for potential adverse effects.

Chronic Feeding Assay

Compounds are assessed for their long term impact on food intake and body weight in a three to fourteen week chronic treatment paradigm in Sprague-Dawley rats (starting weight ~450 g). Male Sprague-Dawley rats are pre-handled for one week prior to the onset of dosing during which time they are also assessed for food intake behavior. Rats are then assigned to treatment groups. Rats are dosed with vehicle or compound by oral gavage. The food intake and body weights are cumulatively assessed at the end of each treatment week and compared to vehicle treated animals. In some studies food intake is measured daily in order to assess the impact of reduced food consumption on pair-fed animals. At the end of the study period the animals are assessed for changes in body composition utilizing DEXA and are then sacrificed in order to examine changes in various blood plasma parameters.

REFERENCES

Arnt, J. Acta Pharmacol. et Toxicol. 1982: 51, 321–329.

Berridge M. J., Downes P. C., Hanley M. R. (1982) Lithium amplifies agonist-dependent phosphotidyinositol response in brain and salivary glands. Biochem. J., 206, 587–595.

Costall, B and Naylor, R J. Psychopharmacology. 1975: 43, 69–74.

Egan C. T., Herrick-Davis K., Miller K., Glennon R. A., and Teitler M. (1998) Agonist activity of LSD and lisuride at cloned $5\text{-}HT_{2A}$ and $5\text{-}HT_{2C}$ receptors. Psychopharmacology, 136, 409–414.

Fitzgerald L W, Conklin D S, Krause C M, Marshall A P, Patterson J P, Tran D P, Iyer G, Kostich W A, Largent B L, Hartig P R (1999) High-affinity agonist binding correlates with efficacy (intrinsic activity) at the human serotonin $5\text{-}HT_{2A}$ and $5\text{-}HT_{2C}$ receptors: evidence favoring the ternary complex and two-state models of agonist action. J. Neurochem., 72, 2127–2134.

Horlick, R. A., Sperle, K., Breth, L. A., Reid, C. C., Shen, E. S., Robbinds, A. K., Cooke, G. M., Largent, B. L. (1997) Rapid Generation of stable cell lines expressing corticotrophin-releasing hormone receptor for drug discovery. Protein Expr. Purif. 9, 301–308.

Dosage and Formulations

The serotonin agonist and serotonin antagonist compounds of this invention can be administered as treatment for the control or prevention of central nervous system disorders including obesity, anxiety, depression, psychosis, schizophrenia, sleep and sexual disorders, migraine and other conditions associated with cephalic pain, social phobias, and gastrointestinal disorders such as dysfunction of the gastrointestinal tract motility by any means that produces contact of the active agent with the agent's site of action, i.e., 5-HT2 receptors, in the body of a mammal. It can be administered by any conventional means available for use in conjunction with pharmaceuticals, either as an individual therapeutic agent or in a combination of therapeutic agents. It can be administered alone, but preferably is administered with a pharmaceutical carrier selected on the basis of the chosen route of administration and standard pharmaceutical practice.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. By way of general guidance, a daily dosage of active ingredient can be expected to be about 0.001 to about 1000 milligrams per kilogram of body weight, with the preferred dose being about 0.01 to about 100 mg/kg; with the more preferred dose being about 0.01 to about 30 mg/kg. Advantageously, compounds of the present invention may be administered in a single daily dose, or the total daily dosage may be administered in divided doses of two, three, or four times daily.

Dosage forms of compositions suitable for administration contain from about 0.5 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences*, supra, a standard reference text in this field.

Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

While it is apparent that the embodiments of the invention herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present invention.

A number of references have been cited and the entire disclosures of which are incorporated herein by reference.

What is claimed is:

1. A compound of Formula (I):

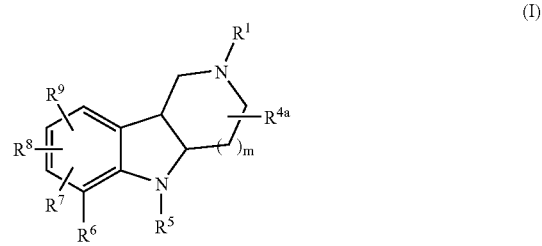

(I)

or a stereoisomer or a pharmaceutically acceptable salt form thereof, wherein:

$R^1$ is selected from
H, $C(=O)R^{2a}$, $C(=O)OR^{2a}$, $S(=O)R^{2a}$, $S(=O)_2R^{2a}$,
$C_{3-7}$ cycloalkyl,
$C_{1-4}$ alkyl substituted with 0–3 $R^2$,
$C_{2-4}$ alkenyl substituted with 0–2 $R^2$,
$C_{2-4}$ alkynyl substituted with 0–2 $R^2$,
aryl substituted with 0–5 $R^{42}$,
$C_{3-10}$ carbocyclic residue substituted with 0–3 $R^{41}$, and
5–6 membered heterocyclic ring system containing from 1–4 heteroatoms selected from the group consisting of N, O, and S substituted with 0–3 $R^{41}$;

$R^2$, at each occurrence, is independently selected from
halo, $C_{1-3}$ haloalkyl, $C_{1-4}$ alkoxy, $C_{1-4}$ alkyl,
$C_{2-4}$ alkenyl, $C_{2-4}$ alkynyl, $C_{3-6}$ cycloalkyl,
aryl substituted with 0–5 $R^{42}$;

$R^8$ is selected from —$OCF_3$, —$CF_2CF_3$, —$C(O)NR^{12}R^{13}$, —$NR^{14}C(O)R^{12}$, —$OC(O)R^{12}$, —$OC(O)OR^{12}$, —$S(O)R^{12}$, —$S(O)_2R^{12}$, —$S(O)NR^{12}R^{13}$, —$S(O)_2NR^{12}R^{13}$, —$NR^{14}S(O)R^{12}$, —$NR^{14}S(O)_2R^{12}$, —$NR^{12}C(O)R^{15}$, —$NR^{12}C(O)OR^{15}$, —$NR^{12}S(O)_2R^{15}$, —$NR^{12}C(O)NHR^{15}$;
$C_{2-6}$ alkenyl substituted with 0–2 $R^{8a}$,
$C_{2-6}$ alkynyl substituted with 0–2 $R^{8a}$,
$C_{3-6}$ cycloalkyl substituted with 0–2 $R^{8a}$,
$C_{3-10}$ carbocyclic residue substituted with 0–3 $R^{33}$;

$R^{8a}$, at each occurrence, is independently selected from
halo, —$CF_3$, —$OCF_3$, —OH, —CN, —$NO_2$, —$CF_2CF_3$,
methyl, ethyl, n-propyl, i-propyl, n-butyl, i-butyl, s-butyl, t-butyl,
—$OR^{12}$, —$SR^{12}$, —$NR^{12}R^{13}$, —$C(O)H$, —$C(O)R^{12}$, —$C(O)NR^{12}R^{13}$, —$NR^{14}C(O)R^{12}$, —$C(O)OR^{12}$, —$OC(O)R^{12}$, —$OC(O)OR^{12}$, —$S(O)R^{12}$, —$S(O)_2R^{12}$, —$S(O)NR^{12}R^{13}$, —$S(O)_2NR^{12}R^{13}$, —$NR^{14}S(O)R^{12}$, —$NR^{14}S(O)_2R^{12}$, —$NR^{12}C(O)R^{15}$, —$NR^{12}C(O)OR^{15}$, —$NR^{12}S(O)_2R^{15}$, —$NR^{12}C(O)NHR^{15}$;
phenyl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{33}$;

$R^{10}$ is H or $C_{1-4}$ alkyl;
$R^{11}$ is selected from
$C_{1-6}$ alkyl substituted with 0–2 $R^{20}$,
$C_{2-6}$ alkenyl substituted with 0–2 $R^{20}$,
$C_{2-6}$ alkynyl substituted with 0–1 $R^{20}$,
$C_{3-10}$ carbocyclic residue substituted with 0–3 $R^{21}$, aryl substituted with 0–5 $R^{23}$, and
5–10 membered heterocyclic ring system containing from 1–4 heteroatoms selected from the group consisting of N, O, and S substituted with 0–3 $R^{21}$;
alternatively, $R^{10}$ and $R^{11}$ join to form a 5- or 6-membered ring optionally substituted with —O— or —N($R^{14}$)—;
alternatively, $R^{10}$ and $R^{11}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;
$R^{12}$ is selected from H,
   $C_{1-6}$ alkyl substituted with 0–2 $R^{12a}$,
   $C_{2-6}$ alkenyl substituted with 0–2 $R^{12a}$,
   $C_{2-6}$ alkynyl substituted with 0–2 $R^{12a}$,
   $C_{3-6}$ cycloalkyl substituted with 0–3 $R^{33}$,
   aryl substituted with 0–5 $R^{33}$;
   $C_{3-10}$ carbocyclic residue substituted with 0–3 $R^{33}$, and
   5–10 membered heterocyclic ring system containing from 1–4 heteroatoms selected from the group consisting of N, O, and S substituted with 0–3 $R^{33}$;
$R^{12a}$, at each occurrence, is independently selected from
   H, halo, —OH, —CN, —NO$_2$, —CO$_2$H, —SO$_2R^{45}$, —SOR$^{45}$, —SR$^{45}$, —NR$^{46}$SO$_2R^{45}$, —NR$^{46}$COR$^{45}$, —NR$^{46}R^{47}$, —SO$_2$NR$^{46}R^{47}$, —CONR$^{46}R^{47}$, —OR$^{45}$, =O,
   $C_{1-4}$ alkyl, $C_{2-6}$ alkenyl, $C_{2-6}$ alkynyl,
   phenyl substituted with 0–5 $R^{33}$;
   $C_{3-10}$ carbocyclic residue substituted with 0–3 $R^{33}$, and
   5–10 membered heterocyclic ring system containing from 1–4 heteroatoms selected from the group consisting of N, O, and S substituted with 0–3 $R^{33}$;
$R^{13}$, at each occurrence, is independently selected from H, $C_{1-4}$ alkyl, $C_{2-4}$ alkenyl, and $C_{2-4}$ alkynyl;
alternatively, $R^{12}$ and $R^{13}$ join to form a 5- or 6-membered ring optionally substituted with —O— or —N($R^{14}$)—;
alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;
$R^{14}$, at each occurrence, is independently selected from H and $C_{1-4}$ alkyl;
$R^{15}$, at each occurrence, is independently selected from H, $C_{1-4}$ alkyl, $C_{2-4}$ alkenyl, and $C_{2-4}$ alkynyl;
$R^{16}$, at each occurrence, is independently selected from
   H, OH, halo, CN, NO$_2$, CF$_3$, SO$_2R^{45}$, NR$^{46}R^{47}$, —C(=O)H,
   $C_{1-4}$ alkyl, $C_{2-4}$ alkenyl, $C_{2-4}$ alkynyl, $C_{1-1}$ haloalkyl,
   $C_{1-3}$ haloalkyl-oxy-, and $C_{1-3}$ alkyloxy-;
$R^{20}$ is selected from
   H, halo, —OH, —CF$_3$, —CN, —NO$_2$, —CO$_2$H, —SO$_2R^{45}$, —SOR$^{45}$, —SR$^{45}$, —NR$^{46}$SO$_2R^{45}$, —NR$^{46}$COR$^{45}$, —NR$^{46}R^{47}$,
   $C_{1-14}$ alkyl, $C_{2-6}$ alkenyl, $C_{2-6}$ alkynyl, $C_{1-4}$ alkoxy, $C_{1-4}$ haloalkyl;
   $C_{3-10}$ carbocyclic residue substituted with 0–3 $R^{21}$;
   aryl substituted with 0–5 $R^{23}$; and
   5–10 membered heterocyclic ring system containing from 1–4 heteroatoms selected from the group consisting of N, O, and S substituted with 0–3 $R^{21}$;
$R^{21}$, at each occurrence, is independently selected from
   H, OH, halo, CF$_3$, SO$_2R^{45}$, NR$^{46}R^{47}$, CN, NO$_2$, =O,
   $C_{1-4}$ alkyl, $C_{1-4}$ alkoxy, and ($C_{1-4}$ haloalkyl)oxy;
$R^{23}$, at each occurrence, is independently selected from
   H, OH, halo, CF$_3$, SO$_2R^{45}$, NR$^{46}R^{47}$, CN, NO$_2$, $C_{1-4}$ alkyl, $C_{1-4}$ alkoxy, and ($C_{1-4}$ haloalkyl)oxy;
$R^{33}$, at each occurrence, is independently selected from
   H, OH, halo, —CN, —NO$_2$, —CF$_3$, —OCF$_3$, —SO$_2R^{35}$, —S(=O)R$^{35}$, —SR$^{35}$, —NR$^{36}R^{37}$, —NHC(=O)R$^{35}$, —C(=O)NR$^{36}R^{37}$, —C(=O)H, —C(=O)R$^{35}$, —C(=O)OR$^{35}$, —OC(=O)R$^{35}$, —OR$^{35}$,
   $C_{1-6}$ alkyl, $C_{2-6}$ alkenyl, $C_{2-6}$ alkynyl, $C_{1-4}$ haloalkyl, $C_{1-4}$ alkoxy, ($C_{1-4}$ haloalkyl)oxy,
   $C_{3-6}$ cycloalkyl, phenyl, aryl substituted with 0–2 $R^{34}$,
   $C_{1-6}$ alkyl substituted with $R^{34}$, and
   $C_{2-6}$ alkenyl substituted with $R^{34}$;
$R^{34}$, at each occurrence, is independently selected from
   OH, $C_{1-4}$ alkoxy, —SO$_2R^{35}$, —NR$^{36}R^{37}$, NR$^{36}R^{37}$C(=O)—, and
   ($C_{1-4}$ alkyl)CO$_2$—;
$R^{35}$, at each occurrence, is independently selected from
   $C_{1-4}$ alkyl, $C_{1-4}$ haloalkyl, $C_{3-6}$ cycloalkyl, ($C_{3-6}$ cycloalkyl)methyl-, and ($C_{3-6}$ cycloalkyl)ethyl-;
$R^{36}$, at each occurrence, is independently selected from H and $C_{1-4}$ alkyl;
$R^{37}$, at each occurrence, is independently selected from H, $C_{1-4}$ alkyl,
   —C(=O)NH($C_{1-4}$ alkyl), —SO$_2$($C_{1-4}$ alkyl), —C(=O)O($C_{1-4}$ alkyl), —C(=O)($C_{1-4}$ alkyl), and —C(=O)H;
$R^{41}$, at each occurrence, is independently selected from
   H, CF$_3$, halo, OH, CO$_2$H, SO$_2R^{45}$, NR$^{46}R^{47}$, NO$_2$, CN, =O,
   $C_{1-4}$ alkyl, $C_{2-8}$ alkenyl, $C_{2-8}$ alkynyl, $C_{1-4}$ alkoxy, and $C_{1-4}$ haloalkyl;
$R^{42}$, at each occurrence, is independently selected from
   H, CF$_3$, halo, OH, CO$_2$H, SO$_2R^{45}$, SOR$^{45}$, SR$^{45}$, NR$^{46}$SO$_2R^{45}$, NR$^{46}$COR$^{45}$, NR$^{46}R^{47}$, NO$_2$, CN,
   $C_{1-4}$ alkyl, $C_{2-6}$ alkenyl, $C_{2-6}$ alkynyl, $C_{1-4}$ alkoxy, and $C_{1-4}$ haloalkyl;
$R^{45}$ is $C_{1-4}$ alkyl;
$R^{46}$, at each occurrence, is independently selected from H and $C_{1-4}$ alkyl;
$R^{47}$, at each occurrence, is independently selected from H, $C_{1-4}$ alkyl,
   —C(=O)NH($C_{1-4}$ alkyl), —SO$_2$($C_{1-4}$ alkyl), —C(=O)O($C_{1-4}$ alkyl), —C(=O)($C_{1-4}$ alkyl), and —C(=O)H;
m is 1 or 2;
provided that when $R^{11}$ is $C_{1-6}$ alkyl, then $R^1$ is not a $C_{1-4}$ alkyl substituted by a) an unsubstituted 3H-pyrimidine-4-one moiety, b) a substituted 3H-pyrimidine-4-one moiety, c) an unsubstituted bicyclic derivative of 3H-pyrimidine-4-one, or d) a substituted bicyclic derivative of 3H-pyrimidine-4-one;
provided that when $R^6$ is —O—$R^{11}$ or $R^6$ is $C_{1-6}$ alkyl; then $R^{8a}$ is not a substituted or unsubstituted indole moiety.

2. A compound of claim 1 of Formula (Ia):

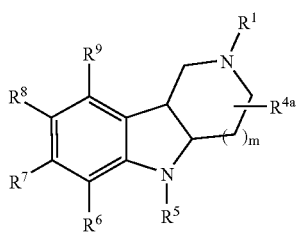

(Ia)

or a stereoisomer or a pharmaceutically acceptable salt form thereof, wherein:
$R^1$ is selected from
  H, $C_{1-3}$ haloalkyl, $C_{3-6}$ cycloalkyl,
  $C_{1-14}$ alkyl substituted with 0–2 $R^2$,
  $C_{2-4}$ alkenyl substituted with 0–2 $R^2$, and
  $C_{2-4}$ alkynyl substituted with 0–2 $R^2$;
$R^2$, at each occurrence, is independently selected from
  halo, $C_{1-3}$ haloalkyl, $C_{1-4}$ alkoxy, $C_{1-4}$ alkyl, $C_{3-6}$ cycloalkyl, and phenyl substituted with 0–5 $R^{42}$;
$R^{4a}$ is H or $C_{1-4}$ alkyl;
$R^5$ is H, $C_{1-4}$ alkyl substituted with 0–1 $R^{20}$, or $C_{1-4}$ haloalkyl;
$R^6$ is selected from
  —OCF$_3$, —SCH$_3$, —CF$_2$CF$_3$, —O—R$^{11}$, —OCF$_2$CF$_3$, —OCF$_2$H, —OCF$_2$CH$_3$,
  —S(=O)—R$^{11}$, —S(=O)$_2$—R$^{11}$, —CH$_2$O—R$^{11}$, —CH$_2$S—R$^{11}$, CH$_2$S(=O)—R$^{11}$, CH$_2$S(=O)$_2$—R$^{11}$, —CH$_2$NR$^{10}$—R$^{11}$,
  $C_{1-4}$ haloalkyl, ($C_{1-4}$ haloalkyl)oxy;
  $C_{2-4}$ alkenyl substituted with 0–2 $R^{20}$,
  $C_{2-4}$ alkynyl substituted with 0–1 $R^{20}$, and
  $C_{3-6}$ carbocyclic residue substituted with 0–3 $R^{21}$,
$R^7$ and $R^9$ are independently selected from
  —OCF$_3$, CF$_2$CF$_3$,
  $C_{2-4}$ alkenyl, $C_{2-4}$ alkynyl, $C_{1-4}$ haloalkyl, and ($C_{1-4}$ haloalkyl)oxy;
$R^8$ is selected from
  —OCF$_3$, —CF$_2$CF$_3$, —C(O)NR$^{12}$R$^{13}$, —NR$^{14}$C(O)R$^{12}$, —OC(O)R$^{12}$, —OC(O)OR$^{12}$, —S(O)R$^{12}$, —S(O)$_2$R$^{12}$, —S(O)NR$^{12}$R$^{13}$, —S(O)$_2$NR$^{12}$R$^{13}$, —NR$^{14}$S(O)R$^{12}$, —NR$^{14}$S(O)$_2$R$^{12}$, —NR$^{12}$C(O)R$^{15}$, —NR$^{12}$C(O)OR$^{15}$, —NR$^{12}$S(O)$_2$R$^{15}$, —NR$^{12}$C(O)NHR$^{15}$;
  $C_{2-6}$ alkenyl substituted with 0–2 $R^{8a}$,
  $C_{2-6}$ alkynyl substituted with 0–2 $R^{8a}$,
  $C_{3-6}$ cycloalkyl substituted with 0–2 $R^{8a}$, and
  $C_{3-10}$ carbocyclic residue substituted with 0–3 $R^{33}$;
$R^{8a}$, at each occurrence, is independently selected from
  halo, —CF$_3$, —OCF$_3$, —OH, —CN, —NO$_2$, —CF$_2$CF$_3$,
  methyl, ethyl, n-propyl, i-propyl, n-butyl, i-butyl, s-butyl, t-butyl,
  —OR$^{12}$, —SR$^{12}$, —NR$^{12}$R$^{13}$, —C(O)H, —C(O)R$^{12}$, —C(O)NR$^{12}$R$^{13}$, —NR$^{14}$C(O)R$^{12}$, —C(O)OR$^{12}$, —OC(O)R$^{12}$, —OC(O)OR$^{12}$—S(O)R$^{12}$, —S(O)$_2$R$^{12}$, —S(O)NR$^{12}$R$^{13}$, —S(O)$_2$NR$^{12}$R$^{13}$, —NR$^{14}$S(O)R$^{12}$, —NR$^{14}$S(O)$_2$R$^{12}$, —NR$^{12}$C(O)R$^{15}$, —NR$^{12}$C(O)OR$^{15}$, —NR$^{12}$S(O)$_2$R$^{15}$, —NR$^{12}$C(O)NHR$^{15}$;
  phenyl substituted with 0–5 $R^{33}$;
  $C_{3-10}$ carbocyclic residue substituted with 0–3 $R^{33}$, and
  5–6 membered heterocyclic ring system containing from 1–4 heteroatoms selected from the group consisting of N, O, and S substituted with 0–3 $R^{33}$;
$R^{10}$ is H or $C_{1-4}$ alkyl;
$R^{11}$ is selected from
  $C_{1-6}$ alkyl substituted with 0–2 $R^{20}$,
  $C_{2-6}$ alkenyl substituted with 0–2 $R^{20}$,
  $C_{2-6}$ alkynyl substituted with 0–1 $R^{20}$,
  $C_{3-10}$ carbocyclic residue substituted with 0–3 $R^{21}$,
  aryl substituted with 0–5 $R^{23}$, and
  5–10 membered heterocyclic ring system containing from 1–4 heteroatoms selected from the group consisting of N, O, and S substituted with 0–3 $R^{21}$;
alternatively, $R^{10}$ and $R^{11}$ join to form a 5- or 6-membered ring optionally substituted with —O— or —N(R$^{14}$)—;
alternatively, $R^{10}$ and $R^{11}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;
$R^{12}$ is selected from H,
  $C_{1-6}$ alkyl substituted with 0–2 $R^{12a}$,
  $C_{2-6}$ alkenyl substituted with 0–2 $R^{12a}$,
  $C_{2-6}$ alkynyl substituted with 0–2 $R^{12a}$,
  $C_{3-6}$ cycloalkyl substituted with 0–3 $R^{33}$,
  aryl substituted with 0–5 $R^{33}$;
  $C_{3-10}$ carbocyclic residue substituted with 0–3 $R^{33}$, and
  5–10 membered heterocyclic ring system containing from 1–4 heteroatoms selected from the group consisting of N, O, and S substituted with 0–3 $R^{33}$;
$R^{12a}$, at each occurrence, is independently selected from
  H, halo, —OH, —CN, —NO$_2$, —CO$_2$H, —SO$_2$R$^{45}$, —SOR$^{45}$, —SR$^{45}$, —NR$^{46}$SO$_2$R$^{45}$, —NR$^{46}$COR$^{45}$, —NR$^{46}$R$^{47}$, —SO$_2$NR$^{46}$R$^{47}$, —CONR$^{46}$R$^{47}$, —OR$^{45}$, =O,
  $C_{1-4}$ alkyl, $C_{2-6}$ alkenyl, $C_{2-6}$ alkynyl,
  phenyl substituted with 0–5 $R^{33}$;
  $C_{3-10}$ carbocyclic residue substituted with 0–3 $R^{33}$, and
  5–10 membered heterocyclic ring system containing from 1–4 heteroatoms selected from the group consisting of N, O, and S substituted with 0–3 $R^{33}$;
$R^{13}$, at each occurrence, is independently selected from
  H, $C_{1-4}$ alkyl, $C_{2-4}$ alkenyl, and $C_{2-4}$ alkynyl;
alternatively, $R^{12}$ and $R^{13}$ join to form a 5- or 6-membered ring optionally substituted with —O— or —N(R$^{14}$)—;
alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;
$R^{14}$, at each occurrence, is independently selected from H and $C_{1-4}$ alkyl;
$R^{15}$, at each occurrence, is independently selected from H, $C_{1-4}$ alkyl, $C_{2-4}$ alkenyl, and $C_{2-4}$ alkynyl;
$R^{16}$, at each occurrence, is independently selected from
  H, OH, halo, CN, NO$_2$, CF$_3$, SO$_2$R$^{45}$, NR$^{46}$R$^{47}$, —C(=O)H,
  $C_{1-4}$ alkyl, $C_{2-4}$ alkenyl, $C_{2-4}$ alkynyl, $C_{1-4}$ haloalkyl, $C_{1-3}$ haloalkyl-oxy-, and $C_{1-3}$ alkyloxy-;
$R^{20}$ is selected from H, halo, —OH, —CF$_3$, —CN, —NO$_2$, —CO$_2$H, —SO$_2$R$^{45}$, —SOR$^{45}$, —SR$^{45}$, —NR$^{46}$SO$_2$R$^{45}$, —NR$^{46}$COR$^{45}$, —NR$^{46}$R$^{47}$, C$_{1-4}$ alkyl, C$_{2-6}$ alkenyl, C$_{2-6}$ alkynyl, C$_{1-4}$ alkoxy, C$_{1-4}$ haloalkyl;

C$_{3-10}$ carbocyclic residue substituted with 0–3 R$^{21}$;

aryl substituted with 0–5 R$^{23}$; and

5–10 membered heterocyclic ring system containing from 1–4 heteroatoms selected from the group consisting of N, O, and S substituted with 0–3 R$^{21}$;

R$^{21}$, at each occurrence, is independently selected from H, OH, halo, CF$_3$, SO$_2$R$^{45}$, NR$^{46}$R$^{47}$, CN, NO$_2$, =O, C$_{1-4}$ alkyl;

C$_{1-4}$ alkoxy, and (C$_{1-4}$ haloalkyl)oxy;

R$^{23}$, at each occurrence, is independently selected from H, OH, halo, CF$_3$, SO$_2$R$^{45}$, NR$^{46}$R$^{47}$, CN, NO$_2$, C$_{1-4}$ alkyl;

C$_{1-4}$ alkoxy, and (C$_{1-4}$ haloalkyl)oxy;

R$^{33}$, at each occurrence, is independently selected from H, OH, halo, —CN, —NO$_2$, —CF$_3$, —OCF$_3$, —SO$_2$R$^{35}$, —S(=O)R$^{35}$, —SR$^{35}$, —NR$^{36}$R$^{37}$, —NHC(=O)R$^{35}$, —C(=O)NR$^{36}$R$^{37}$, —C(=O)H, —C(=O)R$^{35}$, —C(=O)OR$^{35}$, —OC(=O)R$^{35}$, —OR$^{35}$, C$_{1-6}$ alkyl, C$_{2-6}$ alkenyl, C$_{2-6}$ alkynyl, C$_{1-4}$ haloalkyl, C$_{1-4}$ alkoxy, (C$_{1-4}$ haloalkyl)oxy, C$_{3-6}$ cycloalkyl, phenyl, aryl substituted with 0–2 R$^{34}$, C$_{1-6}$ alkyl substituted with R$^{34}$, and C$_{2-6}$ alkenyl substituted with R$^{34}$;

R$^{34}$, at each occurrence, is independently selected from OH, C$_{1-4}$ alkoxy, —SO$_2$R$^{35}$, —NR$^{36}$R$^{37}$, NR$^{36}$R$^{37}$C(=O)—, and (C$_{1-4}$ alkyl)CO$_2$—;

R$^{35}$, at each occurrence, is independently selected from C$_{1-4}$ alkyl, C$_{1-4}$ haloalkyl, C$_{3-6}$ cycloalkyl, (C$_{3-6}$ cycloalkyl)methyl-, and (C$_{3-6}$ cycloalkyl)ethyl-;

R$^{36}$, at each occurrence, is independently selected from H and C$_{1-4}$ alkyl;

R$^{37}$, at each occurrence, is independently selected from H, C$_{1-4}$ alkyl, —C(=O)NH(C$_{1-4}$ alkyl), —SO$_2$(C$_{1-4}$ alkyl), —C(=O)O(C$_{1-4}$ alkyl), —C(=O)(C$_{1-4}$ alkyl), and —C(=O)H;

R$^{41}$, at each occurrence, is independently selected from H, CF$_3$, halo, OH, CO$_2$H, SO$_2$R$^{45}$, NR$^{46}$R$^{47}$, NO$_2$, CN, =O, C$_{1-4}$ alkyl, C$_{2-8}$ alkenyl, C$_{2-8}$ alkynyl, C$_{1-4}$ alkoxy, and C$_{1-4}$ haloalkyl;

R$^{42}$, at each occurrence, is independently selected from H, CF$_3$, halo, OH, CO$_2$H, SO$_2$R$^{45}$, SOR$^{45}$, SR$^{45}$, NR$^{46}$SO$_2$R$^{45}$, NR$^{46}$COR$^{45}$, NR$^{46}$R$^{47}$, NO$_2$, CN, C$_{1-4}$ alkyl, C$_{2-6}$ alkenyl, C$_{2-6}$ alkynyl, C$_{1-4}$ alkoxy, and C$_{1-4}$ haloalkyl;

R$^{45}$ is C$_{1-4}$ alkyl;

R$^{46}$, at each occurrence, is independently selected from H and C$_{1-4}$ alkyl;

R$^{47}$, at each occurrence, is independently selected from H, C$_{1-4}$ alkyl, —C(=O)NH(C$_{1-4}$ alkyl), —SO$_2$(C$_{1-4}$ alkyl), —C(=O)O(C$_{1-4}$ alkyl), —C(=O)(C$_{1-4}$ alkyl), and —C(=O)H;

m is 1 or 2.

3. A compound of claim 2 of Formula (Ia):

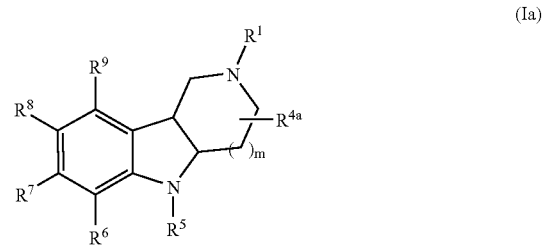

(Ia)

or a stereoisomer or a pharmaceutically acceptable salt form thereof, wherein:

R$^1$ is selected from
H, CF$_3$, methyl, ethyl, cyclopropyl, cyclobutyl, cyclopentyl, cyclohexyl, C$_{1-4}$ alkyl substituted with 0–1 R$^2$,
C$_{2-4}$ alkenyl substituted with 0–1 R$^2$, and
C$_{2-4}$ alkynyl substituted with 0–1 R$^2$;

R$^2$ is selected from
F, Cl, CH$_2$F, CHF$_2$, CF$_3$, methyl, ethyl, cyclopropyl, cyclobutyl, cyclopentyl, cyclohexyl, and phenyl;

R$^4$a is H or methyl;

R$^5$ is H, methyl, or ethyl;

R$^6$ is selected from
—OCF$_3$, —CF$_2$CF$_3$, —OCF$_2$CF$_3$, —OCF$_2$H, —OCF$_2$CH$_3$, —S(=O)—R$^{11}$, —S(=O)$_2$—R$^{11}$, —CH$_2$O—R$^{11}$, —CH$_2$S—R$^{11}$, CH$_2$S(=O)—R$^{11}$, and CH$_2$S(=O)$_2$—R$^{11}$;

R$^7$ and R$^9$ are independently selected from
—OCF$_3$;

R$^8$ is selected from
—S(O)R$^{12}$, —S(O)$_2$R$^{12}$,
C$_{2-6}$ alkenyl substituted with 0–2 R$^{8a}$,
C$_{2-6}$ alkynyl substituted with 0–2 R$^{8a}$,
C$_{3-6}$ cycloalkyl substituted with 0–2 R$^{8a}$, and
C$_{3-10}$ carbocyclic residue substituted with 0–3 R$^{33}$;

R$^{8a}$, at each occurrence, is independently selected from
halo, —CF$_3$, —OCF$_3$, —OH, —CN, —NO$_2$, —CF$_2$CF$_3$, methyl, ethyl, n-propyl, i-propyl, n-butyl, i-butyl, s-butyl, t-butyl,
—OR$^{12}$, —SR$^{12}$, —NR$^{12}$R$^{13}$, —C(O)H, —C(O)R$^{12}$, —C(O)NR$^{12}$R$^{13}$, —NR$^{14}$C(O)R$^{12}$, —C(O)OR$^{12}$, —OC(O)R$^{12}$, —OC(O)OR$^{12}$, —S(O)R$^{12}$, —S(O)$_2$R$^{12}$, —S(O)NR$^{12}$R$^{13}$, —S(O)$_2$NR$^{12}$R$^{13}$, —NR$^{14}$S(O)R$^{12}$, —NR$^{14}$S(O)$_2$R$^{12}$, —NR$^{12}$C(O)R$^{15}$, —NR$^{12}$C(O)OR$^{15}$, —NR$^{12}$S(O)$_2$R$^{15}$, —NR$^{12}$C(O)NHR$^{15}$;

phenyl substituted with 0–5 R$^{33}$;

C$_{3-10}$ carbocyclic residue substituted with 0–3 R$^{33}$, and

5–6 membered heterocyclic ring system containing from 1–4 heteroatoms selected from the group consisting of N, O, and S substituted with 0–3 R$^{33}$;

R$^{11}$ is selected from
methyl, ethyl, propyl, and phenyl substituted with 0–5 R$^{23}$, R$^{12}$ is selected from
C$_{1-6}$ alkyl substituted with 0–2 R$^{12a}$,
C$_{2-6}$ alkenyl substituted with 0–2 R$^{12a}$,
C$_{2-6}$ alkynyl substituted with 0–2 R$^{12a}$,
C$_{3-6}$ cycloalkyl substituted with 0–3 R$^{33}$,
aryl substituted with 0–5 R$^{33}$;

C$_{3-10}$ carbocyclic residue substituted with 0–3 R$^{33}$, and

5–10 membered heterocyclic ring system containing from 1–4 heteroatoms selected from the group consisting of N, O, and S substituted with 0–3 $R^{33}$;

$R^{12a}$, at each occurrence, is independently selected from H, halo, —OH, —CN, —$NO_2$, —$CO_2H$, —$SO_2R^{45}$, —$SOR^{45}$, —$SR^{45}$, —$NR^{46}SO_2R^{45}$, —$NR^{46}COR^{45}$, —$NR^{46}R^{47}$, —$SO_2NR^{46}R^{47}$, —$CONR^{46}R^{47}$, —$OR^{45}$, =O, $C_{1-4}$ alkyl, $C_{2-6}$ alkenyl, $C_{2-6}$ alkynyl, phenyl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, and S substituted with 0–3 $R^{33}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring selected from pyrrolyl, pyrrolidinyl, imidazolyl, piperidinyl, piperizinyl, methylpiperizinyl, and morpholinyl;

alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, and benztriazolyl; wherein said bicyclic heterocyclic ring system is substituted with 0–1 $R^{16}$;

$R^{14}$ is H, methyl, ethyl, propyl, or butyl;

$R^{15}$ is H, methyl, ethyl, propyl, or butyl;

$R^{16}$, at each occurrence, is independently selected from H, OH, F, Cl, CN, $NO_2$, methyl, ethyl, methoxy, ethoxy, trifluoromethyl, and trifluoromethoxy;

$R^{23}$, at each occurrence, is independently selected from H, OH, F, Cl, $CF_3$, $SO_2R^{45}$, $NR^{46}R^{47}$, CN, $NO_2$, methyl, ethyl, propyl, and butyl;

$R^{33}$, at each occurrence, is independently selected from H, OH, halo, —CN, —$NO_2$, —$CF_3$, —$OCF_3$, —$SO_2R^{35}$, —$S(=O)R^{35}$, —$SR^{35}$, —$NR^{36}R^{37}$, —$NHC(=O)R^{35}$, —$C(=O)NR^{36}R^{37}$, —$C(=O)H$, —$C(=O)R^{35}$, —$C(=O)OR^{35}$, —$OC(=O)R^{35}$, —$OR^{35}$, $C_{1-6}$ alkyl, $C_{2-6}$ alkenyl, $C_{2-6}$ alkynyl, $C_{1-4}$ haloalkyl, $C_{1-4}$ alkoxy, ($C_{1-4}$ haloalkyl)oxy, $C_{3-6}$ cycloalkyl, phenyl, aryl substituted with 0–2 $R^{34}$, $C_{1-6}$ alkyl substituted with $R^{34}$, and $C_{2-6}$ alkenyl substituted with $R^{34}$;

$R^{34}$, at each occurrence, is independently selected from OH, $C_{1-4}$ alkoxy, —$SO_2R^{35}$, —$NR^{36}R^{37}$, $NR^{36}R^{37}C(=O)$—, and ($C_{1-4}$ alkyl)$CO_2$—;

$R^{35}$, at each occurrence, is independently selected from $C_{1-14}$ alkyl, $C_{1-4}$ haloalkyl, $C_{3-6}$ cycloalkyl, ($C_{3-6}$ cycloalkyl)methyl-, and ($C_{3-6}$ cycloalkyl)ethyl-;

$R^{36}$, at each occurrence, is independently selected from H and $C_{1-4}$ alkyl;

$R^{37}$, at each occurrence, is independently selected from H, $C_{1-4}$ alkyl, —$C(=O)NH(C_{1-4}$ alkyl), —$SO_2(C_{1-4}$ alkyl), —$C(=O)O(C_{1-4}$ alkyl), —$C(=O)(C_{1-4}$ alkyl), and —$C(=O)H$;

$R^{45}$ is $C_{1-4}$ alkyl;

$R^{46}$, at each occurrence, is independently selected from H and $C_{1-4}$ alkyl;

$R^{47}$, at each occurrence, is independently selected from H, $C_{1-4}$ alkyl, —$C(=O)NH(C_{1-4}$ alkyl), —$SO_2(C_{1-4}$ alkyl), —$C(=O)O(C_{1-4}$ alkyl), —$C(=O)(C_{1-4}$ alkyl), and —$C(=O)H$;

m is 1 or 2.

4. A compound of claim 1 of Formula (Ic):

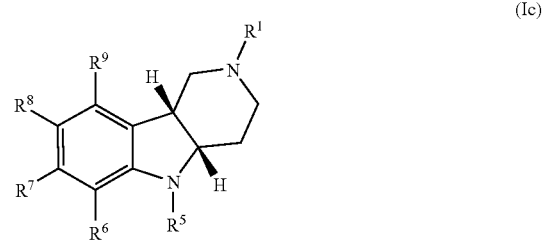

(Ic)

or a pharmaceutically acceptable salt thereof.

5. A pharmaceutical composition comprising a pharmaceutically acceptable carrier and a therapeutically effective amount of a compound of claim 1 or a pharmaceutically acceptable salt thereof.

* * * * *

UNITED STATES PATENT AND TRADEMARK OFFICE
CERTIFICATE OF CORRECTION

PATENT NO. : 7,109,339 B2
APPLICATION NO. : 10/743449
DATED : September 19, 2006
INVENTOR(S) : Taekyu Lee et al.

It is certified that error appears in the above-identified patent and that said Letters Patent is hereby corrected as shown below:

In the Claims: Column 160, Line 35 insert the following:
$C_{3-10}$ carbocyclic residue substituted with 0-3 $R^{41}$, and
5-6 membered heterocyclic ring system containing from 1-4 heteroatoms
selected from the group consisting of N, O, and S substituted with 0-3 $R^{41}$;

$R^{2a}$ is H, $C_{1-4}$ alkyl, (aryl)$C_{1-4}$ alkyl-, or
($C_{3-6}$ cycloalkyl)$C_{1-4}$ alkyl-;

$R^{4a}$ is H or $C_{1-4}$ alkyl;

$R^5$ is H, $C_{1-4}$ alkyl substituted with 0-2 $R^{20}$,
-C(=O)($C_{1-4}$ alkyl), -C(=O)O($C_{1-4}$ alkyl), or $C_{1-4}$ haloalkyl;

$R^6$ is selected from
-OCF$_3$, -SCH$_3$, -CF$_2$CF$_3$, -O-$R^{11}$,
-OCF$_2$CF$_3$, -OCF$_2$H, -OCF$_2$CH$_3$,
-S(=O)-$R^{11}$, -S(=O)$_2$-$R^{11}$, -S(=O)-NR$^{10}$-$R^{11}$,
-S(=O)$_2$-NR$^{10}$-$R^{11}$, -CH$_2$O-$R^{11}$, -CH$_2$S-$R^{11}$,
CH$_2$S(=O)-$R^{11}$, CH$_2$S(=O)$_2$-$R^{11}$, -CH$_2$NR$^{10}$-$R^{11}$, -C(=O)NR$^{10}$-$R^{11}$
$C_{1-4}$ haloalkyl, ($C_{1-4}$ haloalkyl)oxy;
$C_{2-4}$ alkenyl substituted with 0-2 $R^{20}$,
$C_{2-4}$ alkenyl substituted with 0-1 $R^{20}$, and
$C_{3-6}$ carbocyclic residue substituted with 0-3 $R^{21}$, $R^7$ and $R^9$ are independently selected from
-OCF$_3$, -CF$_2$CF$_3$, $C_{2-4}$ alkenyl, $C_{2-4}$ alkynyl, $C_{1-4}$ haloalkyl, and
($C_{1-4}$ haloalkyl)oxy;

UNITED STATES PATENT AND TRADEMARK OFFICE
CERTIFICATE OF CORRECTION

PATENT NO. : 7,109,339 B2
APPLICATION NO. : 10/743449
DATED : September 19, 2006
INVENTOR(S) : Taekyu Lee et al.

It is certified that error appears in the above-identified patent and that said Letters Patent is hereby corrected as shown below:

In the Claims: Claim 3, Column 166, Line 26 replace:

$R^4a$ with $R^{4a}$

Signed and Sealed this

Sixteenth Day of January, 2007

JON W. DUDAS
*Director of the United States Patent and Trademark Office*